(12) United States Patent
Cigan et al.

(10) Patent No.: US 12,338,444 B2
(45) Date of Patent: Jun. 24, 2025

(54) METHODS FOR PRODUCING A COMPLEX TRANSGENIC TRAIT LOCUS

(71) Applicants: PIONEER HI-BRED INTERNATIONAL, INC., Johnston, IA (US); E. I. DU PONT DE NEMOURS AND COMPANY, Wilmington, DE (US)

(72) Inventors: Andrew Mark Cigan, Madison, WI (US); Saverio Carl Falco, Wilmington, DE (US); Huirong Gao, Johnston, IA (US); Michael Lassner, Portland, OR (US); Derek Jantz, Durham, NC (US); Zhongsen Li, Hockessin, DE (US); Zhan-Bin Liu, Clive, IA (US); Sergei Svitashev, Johnston, IA (US); James Jefferson Smith, Durham, NC (US)

(73) Assignees: PIONEER HI-BRED INTERNATIONAL, INC., IA (US); CORTEVA AGRISCIENCE LLC, IN (US)

( * ) Notice: Subject to any disclaimer, the term of this patent is extended or adjusted under 35 U.S.C. 154(b) by 226 days.

(21) Appl. No.: 17/821,528

(22) Filed: Aug. 23, 2022

(65) Prior Publication Data

US 2023/0235342 A1 Jul. 27, 2023

Related U.S. Application Data

(63) Continuation of application No. 16/925,973, filed on Jul. 10, 2020, now Pat. No. 11,459,576, which is a continuation of application No. 16/007,529, filed on Jun. 13, 2018, now Pat. No. 10,822,610, which is a continuation of application No. 13/427,138, filed on Mar. 22, 2012, now Pat. No. 10,030,245.

(60) Provisional application No. 61/499,443, filed on Jun. 21, 2011, provisional application No. 61/466,602, filed on Mar. 23, 2011.

(51) Int. Cl.
*C12N 15/82* (2006.01)
*A01H 1/06* (2006.01)
*C12N 9/22* (2006.01)

(52) U.S. Cl.
CPC ........... *C12N 15/8202* (2013.01); *A01H 1/06* (2013.01); *C12N 9/22* (2013.01); *C12N 15/8213* (2013.01)

(58) Field of Classification Search
None
See application file for complete search history.

(56) References Cited

U.S. PATENT DOCUMENTS

| | | | |
|---|---|---|---|
| 5,036,006 A | 7/1991 | Sanford et al. |
| 5,380,831 A | 1/1995 | Adang et al. |
| 5,436,391 A | 7/1995 | Fujimoto et al. |
| 5,693,512 A | 12/1997 | Finer et al. |
| 5,929,301 A | 7/1999 | Baszcynski et al. |
| 5,959,177 A | 9/1999 | Hein et al. |
| 6,187,994 B1 | 2/2001 | Baszczynski et al. |
| 6,967,263 B2 | 11/2005 | Narvel |
| 7,223,601 B2 | 5/2007 | Baszczynski et al. |
| 7,262,055 B2 | 8/2007 | Choo et al. |
| 7,807,868 B2 | 10/2010 | Baszczynski et al. |
| 8,012,752 B2 | 9/2011 | Jayakumar et al. |
| 8,293,533 B2 | 10/2012 | Falco et al. |
| 8,574,910 B2 | 11/2013 | Falco et al. |
| 8,575,424 B2 | 11/2013 | Yau et al. |
| 8,581,036 B2 | 11/2013 | Samboju et al. |
| 8,586,361 B2 | 11/2013 | Tao et al. |
| 8,609,420 B2 | 12/2013 | Samuel et al. |
| 8,653,327 B2 | 2/2014 | Samboju et al. |
| 8,680,366 B2 | 3/2014 | Eudes et al. |
| 8,697,359 B1 | 4/2014 | Zhang |
| 8,722,410 B2 | 5/2014 | Samuel et al. |
| 8,771,945 B1 | 7/2014 | Zhang |
| 8,795,965 B2 | 8/2014 | Zhang |
| 8,802,921 B2 | 8/2014 | Ainley et al. |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |

(Continued)

FOREIGN PATENT DOCUMENTS

CN 101484581 A 7/2009
DE 102015006335 A1 11/2016

(Continued)

OTHER PUBLICATIONS

SEQ70 SNV genome data viewer Aug. 23, 2024 1 page (Year: 2024).*

(Continued)

*Primary Examiner* — Russell Kallis

(57) ABSTRACT

Methods for producing in a plant a complex transgenic trait locus comprising at least two altered target sequences in a genomic region of interest are disclosed. The methods involve the use of two or more double-strand-break-inducing agents, each of which can cause a double-strand break in a target sequence in the genomic region of interest which results in an alteration in the target sequence. Also disclosed are complex transgenic trait loci in plants. A complex transgenic trait locus comprises at least two altered target sequences that are genetically linked to a polynucleotide of interest. Plants, plant cells, plant parts, and seeds comprising one or more complex transgenic trait loci are also disclosed.

3 Claims, 14 Drawing Sheets

Figure 1:
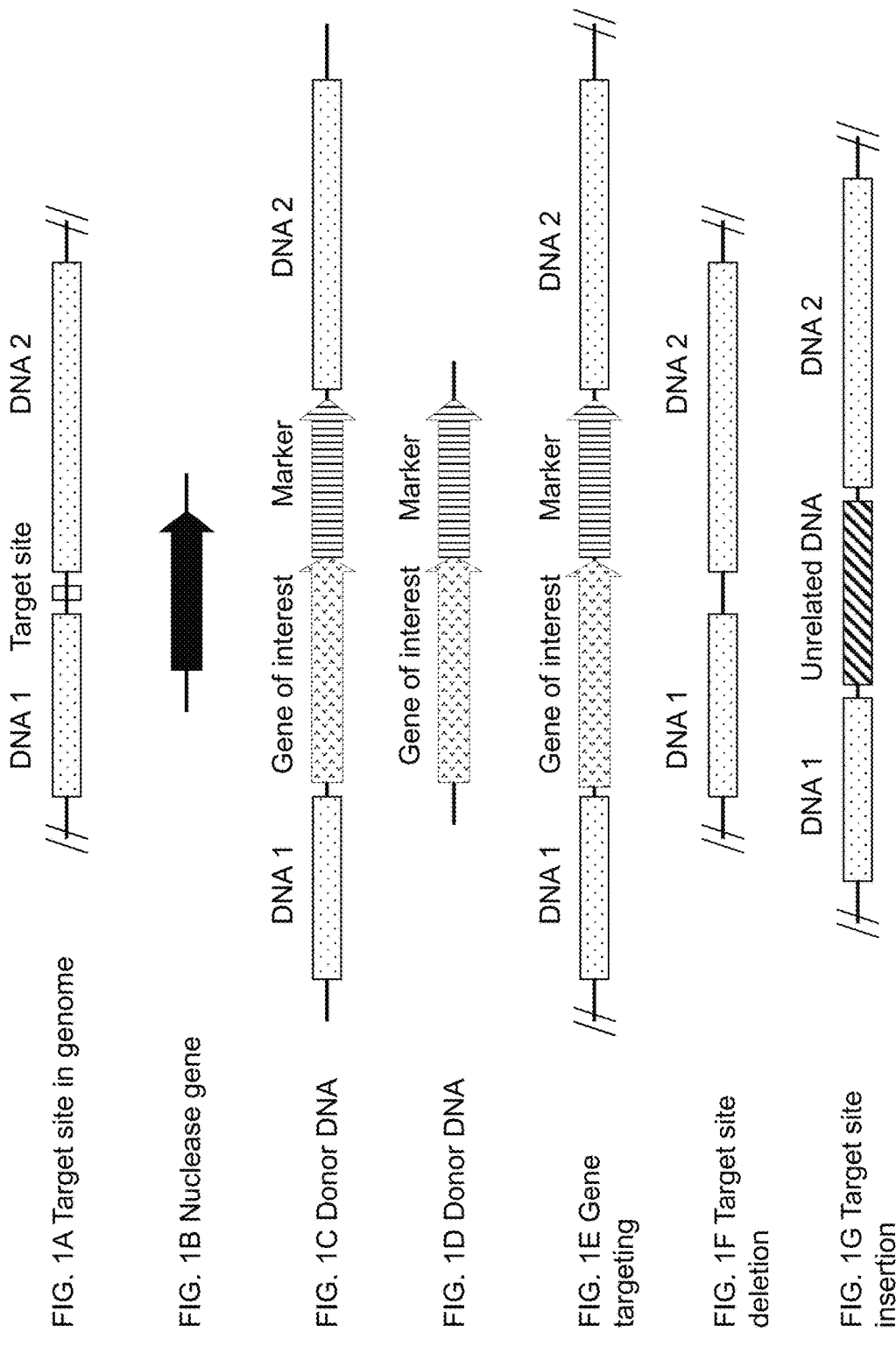

Specification includes a Sequence Listing.

(56) References Cited

U.S. PATENT DOCUMENTS

| | | |
|---|---|---|
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,163,284 B2 | 10/2015 | Liu et al. |
| 9,187,755 B2 | 11/2015 | Samuel et al. |
| 9,382,548 B2 | 7/2016 | Eudes et al. |
| 9,476,057 B2 | 10/2016 | Samuel et al. |
| 9,493,782 B2 | 11/2016 | Cigan et al. |
| 9,670,496 B2 | 6/2017 | D'Halluin et al. |
| 9,695,432 B2 | 7/2017 | Russell et al. |
| 9,719,108 B2 | 8/2017 | Samuel et al. |
| 9,738,908 B2 | 8/2017 | Wu |
| 9,840,713 B2 | 12/2017 | Zhang |
| 9,885,033 B2 | 2/2018 | Joung et al. |
| 9,909,131 B2 | 3/2018 | Sastry-Dent et al. |
| 10,030,245 B2 | 7/2018 | Lassner et al. |
| 10,435,699 B2 | 10/2019 | Falco et al. |
| 10,822,610 B2 | 11/2020 | Cigan et al. |
| 11,312,969 B2 | 4/2022 | Falco et al. |
| 11,459,576 B2 | 10/2022 | Michael et al. |
| 11,560,568 B2 | 1/2023 | Cigan et al. |
| 2002/0104117 A1 | 8/2002 | Derose et al. |
| 2003/0050258 A1 | 3/2003 | Calos |
| 2004/0231016 A1 | 11/2004 | Wang et al. |
| 2006/0253918 A1 | 11/2006 | Que |
| 2006/0282911 A1 | 12/2006 | Bull et al. |
| 2007/0083945 A1 | 4/2007 | Byrum et al. |
| 2007/0178593 A1 | 8/2007 | Miller et al. |
| 2007/0199095 A1 | 8/2007 | Allen et al. |
| 2008/0047031 A1 | 2/2008 | Tao et al. |
| 2009/0093059 A1 | 4/2009 | Baszczynski et al. |
| 2009/0104700 A1 | 4/2009 | Samuel et al. |
| 2009/0133152 A1 | 5/2009 | Lyznik et al. |
| 2010/0076057 A1 | 3/2010 | Sontheimer et al. |
| 2010/0100980 A1 | 4/2010 | Bull et al. |
| 2010/0159598 A1 | 6/2010 | Jayakumar et al. |
| 2010/0311168 A1 | 12/2010 | Samuel et al. |
| 2010/0313293 A1 | 12/2010 | Albertsen et al. |
| 2011/0035836 A1 | 2/2011 | Eudes et al. |
| 2011/0047655 A1 | 2/2011 | Tao et al. |
| 2011/0165679 A1 | 7/2011 | Gordon-Kamm et al. |
| 2011/0189775 A1 | 8/2011 | Ainley et al. |
| 2011/0191877 A1 | 8/2011 | Russell et al. |
| 2011/0191899 A1 | 8/2011 | Ainley et al. |
| 2011/0203012 A1 | 8/2011 | Dotson et al. |
| 2011/0247100 A1 | 10/2011 | Samboju et al. |
| 2012/0017292 A1 | 1/2012 | Kovalic et al. |
| 2012/0023619 A1 | 1/2012 | Samboju et al. |
| 2012/0023620 A1 | 1/2012 | Yau et al. |
| 2012/0047609 A1 | 2/2012 | Yu et al. |
| 2012/0244569 A1 | 9/2012 | Samuel et al. |
| 2013/0157369 A1 | 6/2013 | Miller |
| 2013/0198888 A1 | 8/2013 | Falco et al. |
| 2013/0263324 A1 | 10/2013 | Lassner et al. |
| 2013/0324408 A1 | 12/2013 | Cui et al. |
| 2013/0326645 A1 | 12/2013 | Cost et al. |
| 2014/0020131 A1 | 1/2014 | Bidney et al. |
| 2014/0068797 A1 | 3/2014 | Doudna et al. |
| 2014/0090113 A1 | 3/2014 | Cogan et al. |
| 2014/0096284 A1 | 4/2014 | Martin-Ortigosa et al. |
| 2014/0179006 A1 | 6/2014 | Zhang |
| 2014/0179770 A1 | 6/2014 | Zhang et al. |
| 2014/0182012 A1 | 6/2014 | Eudes et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0196169 A1 | 7/2014 | D'Halluin et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0242702 A1 | 8/2014 | Chen et al. |
| 2014/0242703 A1 | 8/2014 | Samuel et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0273235 A1 | 9/2014 | Voytas et al. |
| 2014/0310830 A1 | 10/2014 | Zhang et al. |
| 2014/0335620 A1 | 11/2014 | Zhang et al. |
| 2014/0342456 A1 | 11/2014 | Mali et al. |
| 2014/0357530 A1 | 12/2014 | Zhang et al. |
| 2014/0370558 A1 | 12/2014 | Mathis et al. |
| 2015/0040267 A1 | 2/2015 | Ainley et al. |
| 2015/0044191 A1 | 2/2015 | Liu et al. |
| 2015/0044772 A1 | 2/2015 | Zhao |
| 2015/0059010 A1 | 2/2015 | Cigan et al. |
| 2015/0067922 A1 | 3/2015 | Yang et al. |
| 2015/0079681 A1 | 3/2015 | Zhang |
| 2015/0082478 A1 | 3/2015 | Cigan et al. |
| 2015/0128307 A1 | 5/2015 | Sastry-Dent et al. |
| 2015/0128308 A1 | 5/2015 | Sastry-Dent et al. |
| 2015/0128309 A1 | 5/2015 | Sastry-Dent et al. |
| 2015/0128310 A1 | 5/2015 | Sastry-Dent et al. |
| 2015/0143588 A1 | 5/2015 | Sastry-Dent et al. |
| 2015/0167000 A1 | 6/2015 | Voytas et al. |
| 2015/0167009 A1 | 6/2015 | D'Halluin |
| 2015/0284727 A1 | 10/2015 | Kim et al. |
| 2015/0291967 A1 | 10/2015 | Mathis et al. |
| 2016/0024524 A1 | 1/2016 | Joung et al. |
| 2016/0032297 A1 | 2/2016 | Deschamps et al. |
| 2016/0201072 A1 | 7/2016 | Cigan et al. |
| 2016/0208271 A1 | 7/2016 | Cigan et al. |
| 2016/0208272 A1 | 7/2016 | Cigan et al. |
| 2016/0251667 A1 | 9/2016 | Cigan et al. |
| 2016/0257967 A1 | 9/2016 | Russell et al. |
| 2016/0272987 A1 | 9/2016 | Gil et al. |
| 2016/0304846 A1 | 10/2016 | Liu et al. |
| 2017/0022521 A1 | 1/2017 | Samuel et al. |
| 2017/0107527 A1 | 4/2017 | Dotson et al. |
| 2017/0166912 A1 | 6/2017 | Brower-Toland et al. |
| 2017/0183677 A1 | 6/2017 | Gao et al. |
| 2018/0002715 A1 | 1/2018 | Cigan et al. |
| 2018/0010200 A1 | 1/2018 | Sastry-Dent et al. |
| 2018/0057832 A1 | 3/2018 | Li |
| 2018/0142250 A1 | 5/2018 | Sastry-Dent et al. |
| 2018/0142263 A1 | 5/2018 | May et al. |
| 2018/0163203 A1 | 6/2018 | Bennett et al. |
| 2018/0230476 A1 | 8/2018 | Cigan et al. |
| 2018/0258417 A1 | 9/2018 | Cigan et al. |
| 2018/0258438 A1 | 9/2018 | Chaky et al. |
| 2018/0273960 A1 | 9/2018 | Cigan et al. |
| 2018/0282763 A1 | 10/2018 | Cigan et al. |
| 2018/0305706 A1 | 10/2018 | Cigan et al. |
| 2018/0327785 A1 | 11/2018 | Cigan et al. |
| 2018/0346895 A1 | 12/2018 | Cigan et al. |
| 2018/0371479 A1 | 12/2018 | Cigan et al. |
| 2019/0040405 A1 | 2/2019 | Cigan et al. |
| 2019/0100745 A1 | 4/2019 | Cigan et al. |
| 2019/0100762 A1 | 4/2019 | Cigan et al. |
| 2019/0136248 A1 | 5/2019 | Cigan et al. |
| 2022/0251586 A1 | 8/2022 | Falco et al. |
| 2023/0212595 A1 | 7/2023 | Cigan et al. |

FOREIGN PATENT DOCUMENTS

| | | |
|---|---|---|
| EP | 0359472 A2 | 3/1990 |
| EP | 0385962 A1 | 9/1990 |
| EP | 0359472 B1 | 12/1995 |
| EP | 0385962 B1 | 7/2001 |
| WO | 9116432 A1 | 10/1991 |
| WO | 9925821 A1 | 5/1999 |
| WO | 9925840 A1 | 5/1999 |
| WO | 9925854 A1 | 5/1999 |
| WO | 9925855 A1 | 5/1999 |
| WO | 0111058 A1 | 2/2001 |
| WO | 2005049842 A2 | 6/2005 |
| WO | 2007011733 A2 | 1/2007 |
| WO | 2007025097 A2 | 3/2007 |
| WO | 2007011733 A3 | 9/2007 |

(56) References Cited

FOREIGN PATENT DOCUMENTS

| | | | |
|---|---|---|---|
| WO | 2007134122 | A2 | 11/2007 |
| WO | 2008148559 | A1 | 12/2008 |
| WO | 2009006297 | A2 | 1/2009 |
| WO | 2009042164 | A1 | 4/2009 |
| WO | 2009114321 | A2 | 9/2009 |
| WO | 2010011961 | A2 | 1/2010 |
| WO | 2010077319 | A1 | 7/2010 |
| WO | 2010080430 | A1 | 7/2010 |
| WO | 2011117249 | A1 | 9/2011 |
| WO | 2011143124 | A2 | 11/2011 |
| WO | 2012129373 | A2 | 9/2012 |
| WO | 2012164565 | A1 | 12/2012 |
| WO | 2013019411 | A1 | 2/2013 |
| WO | 2013066423 | A2 | 5/2013 |
| WO | 2013068845 | A2 | 5/2013 |
| WO | 2013098244 | A1 | 7/2013 |
| WO | 2013112686 | A1 | 8/2013 |
| WO | 2013141680 | A1 | 9/2013 |
| WO | 2013142578 | A1 | 9/2013 |
| WO | 2013173535 | A2 | 11/2013 |
| WO | 2013176772 | A1 | 11/2013 |
| WO | 2014018423 | A2 | 1/2014 |
| WO | 2014065596 | A1 | 5/2014 |
| WO | 2014071006 | A1 | 5/2014 |
| WO | 2014089290 | A1 | 6/2014 |
| WO | 2014093479 | A1 | 6/2014 |
| WO | 2014093635 | A1 | 6/2014 |
| WO | 2014093694 | A1 | 6/2014 |
| WO | 2014093712 | A1 | 6/2014 |
| WO | 2014093768 | A1 | 6/2014 |
| WO | 2014144155 | A1 | 9/2014 |
| WO | 2014144761 | A2 | 9/2014 |
| WO | 2014150624 | A1 | 9/2014 |
| WO | 2014164466 | A1 | 10/2014 |
| WO | 2014165825 | A2 | 10/2014 |
| WO | 2014186686 | A1 | 11/2014 |
| WO | 2014194190 | A1 | 12/2014 |
| WO | 2015006294 | A2 | 1/2015 |
| WO | 2015026883 | A1 | 2/2015 |
| WO | 2015026885 | A1 | 2/2015 |
| WO | 2015026886 | A1 | 2/2015 |
| WO | 2015026887 | A1 | 2/2015 |
| WO | 2015071474 | A2 | 5/2015 |
| WO | 2015112896 | A2 | 7/2015 |
| WO | 2015131101 | A1 | 9/2015 |
| WO | 2015189693 | A1 | 12/2015 |
| WO | 2016007347 | A1 | 1/2016 |
| WO | 2016033298 | A1 | 3/2016 |
| WO | 2016040030 | A1 | 3/2016 |
| WO | 2016149352 | A1 | 9/2016 |
| WO | 2016186946 | A1 | 11/2016 |
| WO | 2017015015 | A1 | 1/2017 |
| WO | 2017034971 | A1 | 3/2017 |
| WO | 2017062855 | A1 | 4/2017 |
| WO | 2017066497 | A2 | 4/2017 |
| WO | 2017117395 | A1 | 7/2017 |
| WO | 2017155714 | A1 | 9/2017 |
| WO | 2017155715 | A1 | 9/2017 |
| WO | 2017155717 | A1 | 9/2017 |
| WO | 2017212264 | A1 | 12/2017 |
| WO | 2017218185 | A1 | 12/2017 |
| WO | 2018172556 | A1 | 9/2018 |

OTHER PUBLICATIONS

SEQ77 SNV genome data viewer Aug. 23, 2024 1 page (Year: 2024).*
SEQ70 SNV genome data viewer Aug. 23, 2024. (Year: 2024).*
SEQ77 SNV genome data viewer Aug. 23, 2024. (Year: 2024).*
Que Q., et al., "Trait Stacking in Transgenic Crops Challenges and Opportunities," GM Crops, Jul.-Oct. 2010, vol. 1, No. 4, pp. 220-229.
Sadowski P.D., "Site-specific Genetic Recombination: Hops, Flips, and Flops," Journal of FASEB, 1993, vol. 7, pp. 760-767.
Sanjana N.E., et al., "A Transcription Activator-Like Effector (TALE) Toolbox for Genome Engineering," Nature Protocols, 2012, vol. 7, No. 1, pp. 171-192, 39 pages.
Sauer B., "Site-Specific Recombination: Developments and Applications," Current Opinion in Biotechnology, 1994, vol. 5, pp. 521-527.
Schlake T., et al., "Use of Mutated FLP Recognition Target (FRT) Sites for the Exchange of Expression Cassettes at Defined Chromosomal Loci," Biochemistry, 1994, vol. 33, No. 43, pp. 12746-12751.
Shaikh A.C., et al., "The Cre Recombinase Cleaves the Lox Site in Trans," The Journal of Biological Chemistry, Feb. 28, 1997, vol. 272, No. 9, pp. 5695-5702.
Shan Q., et al., "Targeted Genome Modification of Crop Plants Using a CRISPR-Cas System," Nature Biotechnology, Aug. 1, 2013, vol. 31, No. 8, DOI: 10.1038/nbt.2650, ISSN 1087-0156, pp. 686-688, XP055153530.
Shuangyong Y., et al., "Construction of Rice T-DNA Insertion Mutant Library and Analysis of Mutation Types," Acta Genetics [X] 35-39, 1.2 Methods section, pp. 1389-1390.
Shukla V.K., et al., "Precise Genome Modification in the Crop Species Zea mays Using Zinc-finger Nucleases," Nature, May 21, 2009, vol. 459, No. 7245, pp. 437-441.
Song Q., et al., "Development and Evaluation of SoySNP50K, a High Density Genotyping Array for Soybean," PLoSONE, Jan. 25, 2013, vol. 8 No. 1, p. e54985, 12 pages.
Srivastava V., et al., "Biolistic Mediated Site-Specific Integration in Rice," Molecular Breeding, 2001, vol. 8, pp. 345-350.
Srivastava V., et al., "Cre-Mediated Site-Specific Gene Integration for Consistent Transgene Expression in Rice," Plant Biotechnology Journal, 2004, vol. 2 pp. 169-179.
Srivastava V., et al., "Marker-Free Site-Specific Integration in Plants," Trends in Biotechnology, Dec. 2004, vol. 22, No. 12, pp. 627-629.
Strauss A., et al., "Zinc Fingers, TAL Effectors, or Cas9-Based DNA Binding Proteins: What's Best for Targeting Desired Genome Loci?," Molecular Plant, Sep. 2013, vol. 6, No. 5, pp. 1384-1387.
Svitashev S., et al., "Targeted Mutagenesis, Precise Gene Editing, and Site-Specific Gene Insertion in Maize using Cas9 and Guide RNA," Plant Physiology, 2015, vol. 169, No. 2, pp. 931-945.
Thomson J.G., et al., "Site-Specific Recombination Systems for the Genetic Manipulation of Eukaryotic Genomes," Genesis, 2006, vol. 44, pp. 465-476.
Trinh K.R., et al., "Site-Specific and Directional Gene Replacement Mediated by Cre Recombinase," Journal of Immunological Methods, 2000, vol. 244, pp. 185-193.
Uniprot: Database Accession No. A0A1D6JPH3, Reference Sequence No. NM_001305818, 2 pages.
Uniprot: "SubName: Full=Glycerol-3-Phosphate Acyltransferase 5," Database Accession No. A0A1D6JPX5, Reference Sequence No. XM_008653185, 2015, 2 pages.
Vergunst A.C., et al., "Site-Specific Integration of Agrobacterium T-DNA in Arabidopsis thaliana Mediated by Cre Recombinase," Nucleic Acids Research, 1998, vol. 26, No. 11, pp. 2729-2734.
Voytas D.F., "Plant Genome Engineering with Sequence-Specific Nucleases," Annual Review of Plant Biology ,Mar. 1, 2013, vol. 64, pp. 327-350.
Watson A.T., et al., "Gene Tagging and Gene Replacement Using Recombinase-Mediated Cassette Exchange in Schizosaccharomyces Pombe," Gene Elsevier, 2008, vol. 407, pp. 63-74, (Supplemental).
Wei F., et al., "Physical and Genetic Structure of the Maize Genome Reflects Its Complex Evolutionary History," PLOS Genetics, Jul. 20, 2007, vol. 3, No. 7, pp. 1254-1263.
Whitelaw, C.A., et al., "Consortium for Maize Genomics," OGAHE59TC ZM2_0.7_1.5_KB Zea mays genomic clone ZMMBMa0060J21, Genomic Survey Sequence, GenBank: BZ526980. 1, 2002.
Wijnker E., et al., "Managing Meiotic Recombination in Plant Breeding," Trends in Plant Science, 2008, vol. 13, No. 12, pp. 640-646.

(56) References Cited

OTHER PUBLICATIONS

Wright D.A., et al., "High-Frequency Homologous Recombination in Plants Mediated by Zinc Finger Nucleases," The Plant Journal, 2005, vol. 44, pp. 693-705.

Xie K., et al., "RNA-Guided Genome Editing in Plants Using a CRISPR-Cas System," Molecular Plant, Nov. 2013, vol. 6, No. 6, pp. 1975-1983.

Xing H-L., e al., "A CRISPR/Cas9 Toolkit for Multiplex Genome Editing in Plants," BMC Plant Biology, 2014, vol. 14, No. 1, pp. 327-338, 12 Pages.

Xu K., et al., "Efficient Genome Engineering in Eukaryotes Using Cas9 from *Streptococcus thermophilus*," Cellular and Molecular Life Sciences, 2015, vol. 72, pp. 383-399, 40 Pages.

Yan S.Y., et al., "Generation and Identification of Rice T-DNA Insertional Mutant Lines," Acta Genetica Sinica, Dec. 2004, vol. 31, No. 12, pp. 1388-1394, 2001, Original 7 pages // with English language abstract 2 page).

"*Zea mays* Glutathione Reductase 1 (LOC541986), mRNA," Accession No. NM_001305818, Mar. 5, 2019, 2 Pages.

Zeevi V., et al., "Increasing Cloning Possibilities Using Artificial Zinc Finger Nucleases," Proceedings of the National Academy of Sciences of the United States of America, Sep. 2, 2008, vol. 105, No. 35, pp. 12785-12790.

Zhang H., et al., "The CRISPR/Cas9 System Produces Specific and Homozygous Targeted Gene Editing in Rice in One Generation," Plant Biotechnology Journal, 2014, vol. 12, No. 6, pp. 797-807.

Zhang Y., et al., "Transcription Activator-Like Effector Nucleases Enable Efficient Plant Genome Engineering1[W] [OA]," Plant Physiology, Nov. 2, 2012, vol. 161, No. 1, pp. 20-27, DOI:10.1104/pp.112.205179, ISSN 0032-0889, XP055070911.

Abate T., et al., "Characteristics of Maize Cultivars in Africa: How Modern are they and How Many Do Smallholder Farmers Grow?," Agriculture and Food Security, 2017, vol. 6:30, pp. 1-17.

Abrembski K., et al., "Bacteriophage P1 Site-specific Recombination," The Journal of Biological Chemistry, Feb. 10, 1984, vol. 259, No. 3, pp. 1509-1514.

Ainley W.M., et al., "Trait Stacking via Targeted Genome Editing," Plant Biotechnology Journal, Aug. 19, 2013, vol. 11, No. 9, pp. 1126-1134, DOI: 10.1111/pbi.12107, ISSN 1467-7644, XP055218224.

Albert H., et al., "Site-Specific Integration of DNA into wild-type and Mutant lox sites placed in the plant Genome," The Plant Journal, 1995, vol. 7, No. 4, pp. 649-659.

Ali Z., et al., "Efficient Virus-Mediated Genome Editing in Plants using the CRISPR/Cas9 system," Molecular Plant, Aug. 2015, vol. 8, pp. 1288-1291.

Baer A., et al., "Coping with Kinetic and Thermodynamic Barriers: RMCE, an Efficient Strategy for the Targeted Integration of Transgenes," Current Opinion in Biotechnology, 2001, vol. 12, pp. 473-480.

Baltes N.J., et al., "DNA Replicons for Plant Genome Engineering," The Plant Cell, Jan. 2014, vol. 26, No. 1, pp. 151-163.

Banerjee A., et al., "Markerless Multiple-Gene-Deletion System for *Streptococcus mutans*," Applied and Environmental Microbiology, Apr. 2008, vol. 74, No. 7, pp. 2037-2042.

Barrangou R., et al., "CRISPR Provides Acquired Resistance Against Viruses in Prokaryotes," Science, Mar. 23, 2007, vol. 315, pp. 1709-1712.

Barrangou R., "RNA-Mediated Programmable DNA Cleavage," Nature Biotechnology, Sep. 2012, vol. 30, No. 9, pp. 836-838.

Bashir K., et al., "Expression and Enzyme Activity of Glutathione Reductase is Upregulated by Fe-Deficiency in Graminaceous Plants," Plant Molecular Biology, 2007, vol. 65, pp. 277-284.

Belhaj K., et al. "Plant Genome Editing Made Easy: Targeted Mutagenesis in Model and Crop Plants Using the CRISPR/Cas System," Plant Methods, Oct. 2013, vol. 9 (39), pp. 1-10.

Bortesi L., et al., "The CRISPR/Cas9 System for Plant Genome Editing and Beyond," Biotechnology Advances, Jan. 1, 2015, vol. 33, No. 1, pp. 41-52, XP055217852.

Bottcher R., et al., "Efficient Chromosomal Gene Modification with CRISPR/Cas9 and PCR-Based Homologous Recombination Donors in Cultured *Drosophila* Cells," Nucleic Acids Research, Apr. 2014, vol. 42, No. 11, e89, 16 pages.

Buckner B., et al., "Cloning of the y1 Locus of Maize, a Gene Involved in the Biosynthesis of Carotenoids," The Plant Cell, Sep. 1990, vol. 2, pp. 867-876.

Cai C.Q., et al., Targeted Transgene Integration in Plant Cells Using Designed Zinc Finger Ucleases, Plant Mol Biol, Published on Dec. 27, 2008, vol. 69, No. 6, pp. 699-709.

Chawla R., et al., "Transgene Expression Produced by Biolistic-Mediated, Site-Specific Gene Integration Is Consistently Inherited by the Subsequent Generations," Plant Biotechnology Journal, 2006, vol. 4, pp. 209-218.

Chen L., et al., "Production and Characterization of Human 293 Cell Lines Expressing the Site-Specific Recombinase Cre," Somatic Cell and Molecular Genetics, 1996, vol. 22 No. 6, pp. 477-488.

Cho S.W., et al., "Analysis of Off-Target Effects of CRISPR/Cas-Derived RNA-Guided Endonucleases and Nickases," Genome Research, 2014, vol. 24, pp. 132-141.

Civardi L., et al., "The Relationship Between Genetic and Physical Distances in the Cloned a1-sh2 Interval of the *Zea mays* L. Genome," Proceedings of the National Academy of Sciences, Aug. 1994, USA, vol. 91, pp. 8268-8271.

Cong, et al., "Multiplex Genome Engineering Using CRISPR/Cas Systems," Science, 2013, vol. 339, Supplementary Material, 37 Total Pages.

Cox M., "The FLP Protein of the Yeast 2-µm Plasmid: Expression of a Eukaryotic Genetic Recombination System in *Escherichia coli*," Proceedings of the National Academy of Sciences of the United States of America, Jul. 1983, vol. 80, pp. 4223-4227.

Day C.D., et al., "Transgene Integration into the Same Chromosome Location can Produce Alleles that Express at a Predictable Level, or Alleles that are Differentially Silenced," Genes Development, Nov. 15, 2000, vol. 14, No. 22, pp. 2869-2880.

D'Halluin K., et al., "Targeted Molecular Trait Stacking in Cotton Through Targeted Double-strand Break Induction," Plant Biotechnology Journal, Jun. 18, 2013, vol. 11, pp. 933-941.

Djukanovic V., et al., "Gene Conversion in Transgenic Maize Plants Expressing FLP/FRT and Cre/loxP Site-Specific Recombinations Systems," Plant Biotechnology Journal, 2006, vol. 4, pp. 345-357.

Djukanovic V., et al.,"Male-Sterile Maize Plants Produced by Targeted Mutagenesis of the Cytochrome P450-like Gene (MS26) Using a Re-Designed I-Crel Homing Endonuclease," The Plant Journal, Nov. 5, 2013, vol. 76, No. 5, pp. 888-899.

Dow L.E., et al., "Inducible in Vivo Genome Editing with CRISPR-Cas9," Nature Biotechnology, Apr. 2005, vol. 33, No. 4, pp. 390-394, EPublished on Feb. 18, 2015.

Endo M., et al., "Toward Establishing an Efficient and Versatile Gene Targeting System in Higher Plants," Biocatalysis and Agricultural Biotechnology, 2014, vol. 3, pp. 2-6.

Esvelt K.M., et al., "Orthogonal Cas9 Proteins for RNA-guided Gene Regulation and Editing," Nature Methods, Sep. 29, 2013, vol. 10, No. 11, pp. 1116-1121.

Extended European Search Report for European Application No. 19206649.6, mailed Feb. 13, 2020, 11 Pages.

Feng Z., et al., "Efficient Genome Editing in Plants Using a CRISPR/Cas system," Cell Research, 2013, vol. 23, No. 10, pp. 1229-1232.

Fichtner F., et al., "Precision Genetic Modifications: a New Era in Molecular Biology and Crop Improvement," Planta, 2014, vol. 239, pp. 921-939.

Funke T., et al., "Structural Basis of Glyphosate Resistance Resulting from the Double Mutation Thr 97 Ile and Pro101 Ser in 5-Enolpyruvylshikimate-3-Phosphate Synthase from *Escherichia coli*," Journal of Biological Chemistry, Apr. 10, 2009, vol. 284, No. 15 pp. 9854-9860.

Gaj T., et al., "ZFN, TALEN, and CRISPR/Cas-Based Methods for Genome Engineering," Trends in Biotechnology, Elsevier Publications, Cambridge, GB, May 9, 2013, vol. 31, No. 7, pp. 397-405, DOI:10.1016/J.TIBTECH.2013.04.004, ISSN 0167-7799, XP028571313.

(56) References Cited

OTHER PUBLICATIONS

Ganal W.M., et al.; "A Large Maize (*Zea mays* L.) SNP Genotyping Array: Development and Germplasm Genotyping and Genetic Mapping to Compare with the B73 Reference Genome," PLOS One, Dec. 2011, vol. 6, Issue 12 (e28334), 15 Pages.

Gasiunas G., et al., "Cas9-crRNA Ribonucleoprotein Complex Mediates Specific DNA Cleavage for Adaptive Immunity in Bacteria," Proceedings of the National Academy of Sciences, National Academy of Sciences, Sep. 25, 2012, vol. 109, No. 39, pp. E2579-E2586, DOI:10.1073/pnas.1208507109, ISSN 0027-8424, XP055569955, EPublished on Sep. 4, 2012.

Gidoni D., et al., "Site-specific Excisional Recombination Strategies for Elimination of Undesirable Transgenes from Crop Plants," In Vitro Cellular Developmental Biology Plant, 2008, vol. 44, No. 6, pp. 457-467.

Gilbert L.A., et al., "CRISPR-Mediated Modular RNA-Guided Regulation of Transcription in Eukaryotes," Cell, Jul. 18, 2013, vol. 154, No. 2, pp. 442-451, 20 Pages.

Gilbertson L., "Cre-Lox Recombination: Cre-ative Tools for Plant Biotechnology," Trends in Biotechnology, Dec. 2003, vol. 21, No. 12, pp. 550-555.

Groth A.C., et al., "Phage Integrases: Biology and Applications," Journal of Molecular Biology, 2004, vol. 335, pp. 667-678.

Guo F., et al., "Structure of Cre Recombinase Complexed with DNA in a Site-Specific Recombination Synapse," Nature, Sep. 4, 1997, vol. 389, pp. 40-46, 28 pages.

Hale C.R., et al., "RNA-Guided RNA Cleavage by a CRISPR RNA-Cas Protein Complex," Cell, Nov. 25, 2009, vol. 139, pp. 945-956.

Horn C., et al., "Site-Specific Genomic Targeting in *Drosophila*," The Proceedings of the National Academy of Sciences, Aug. 30, 2005, vol. 102, No. 35, pp. 12483-12488.

Houching K.E., et al., "PZA03558-3872-B73 *Zea mays* ssp. *mays* B73 *Zea mays* Subsp. *mays* STS Genomic, Sequence Tagged Site," NCBI Accession No. BV687137, published Dec. 1, 2006, 2 Pages.

Hwang W.Y., et al., "Efficient In Vivo Genome Editing Using RNA-Guided Nucleases," Nature Biotechnology, Mar. 2013, vol. 31, No. 3, pp. 227-229, 12 Pages.

Hyten D.L., et al., "High-Throughput SNP Discovery Through Deep Resequencing of a Reduced Representation Library to Anchor and Orient Scaffolds in the Soybean Whole Genome Sequence," BMC Genomics, 2010, vol. 11, Article No. 38, 8 pages.

Hyun Y., et al., "Site-directed Mutagenesis in *Arabidopsis thaliana* Using Dividing Tissue-Targeted RGEN of the CRISPR/Cas System to Generate Heritable Null Alleles," Planta, Jan. 2015, vol. 241, No. 1, pp. 271-284.

Iida S., et al., "Modification of Endogenous Natural Genes by Gene Targeting in Rice and Other Higher Plants," Plant Molecular Biology, 2005, vol. 59, pp. 205-219.

International Preliminary Report on Patentability for International Application No. PCT/US2013/022891, mailed Aug. 7, 2014, 10 Pages.

International Preliminary Report on Patentability for International Application No. PCT/US2015/047706, mailed Mar. 23, 2017, 8 Pages.

Cameron P., et al., "Mapping the Genomic Landscape of CRISPR-Cas9 Cleavage," Nature Methods, Jun. 2017, vol. 14, No. 6, pp. 600-606 (Plus Supplemental).

International Preliminary Report on Patentability for International Application No. PCT/US2012/030061, mailed Oct. 3, 2013, 11 Pages.

International Search Report and Written Opinion for International Application No. PCT/US2012/030061, mailed Nov. 6, 2012, 16 Pages.

Townsend J.A., et al., "High-Frequency Modification of Plant Genes Using Engineered Zinc-Finger Nucleases," Nature, May 21, 2009, vol. 459, No. 7245, pp. 442-446.

Wilson R.K., "*Zea mays* Cultivar B73 Chromosome 1 Clone CH201-108H1, Sequencing in Progress, 7 Unordered Pieces," GenBank Accession No. AC205178.4, Sep. 23, 2013, 3 Pages, Selected Pages.

Wilson R.K., "*Zea mays* Cultivar B73 Chromosome 1 Clone CH201-1903, Sequencing in Progress, 3 Unordered Pieces," NCBI/GenBank Accession No. AC205142.5, Sep. 13, 2014, 2 Pages, Selected Pages.

International Preliminary Report on Patentability for International Application No. PCT/US2016/059093, mailed May 17, 2018, 10 Pages.

International Search Report and Written Opinion for International Application No. PCT/US2013/022891, mailed Apr. 25, 2013, 13 Pages.

International Search Report and Written Opinion for International Application No. PCT/US2015/047706, mailed Oct. 19, 2015, 13 Pages.

International Search Report and Written Opinion for International Application No. PCT/US2016/059093, mailed Feb. 8, 2017, 15 Pages.

Jacobs T.B., et al., "Targeted Genome Modifications in Soybean with CRISPR/Cas9," BMC Biotechnology, Mar. 2015, vol. 15, No. 16, 10 pages.

Jiang W., et al., "Demonstration of CRISPR/Cas9/sgRNA-Mediated Targeted Gene Modification in *Arabidopsis*, Tobacco, Sorghum and Rice," Nucleic Acids Research, Published Online Sep. 2, 2013, Nov. 1, 2013, vol. 41, No. 20, 12 pages, Oxford University Press, GB, doi:10.1093/nar/gkt780, ISSN 0305-1048, XP055219328.

Jiang W., et al., "Efficient CRISPR/Case9-Mediated Gene Editing in *Arabidopsis thaliana* and Inheritance of Modified Genes in the T2 and T3 Generations," PLOS ONE, Jun. 11, 2014, vol. 9, No. 6(e99225), pp. 1-10.

Kanchiswamy C.N., et al., "Non-GMO Genetically Edited Crop Plants," Trends in Biotechnology, Sep. 2015, vol. 33, No. 9, pp. 489-491, DOI: 10.1016/J.TIBTECH.2015.04.002, XP002765281.

Kim H., et al., "Targeted Genome Editing for Crop Improvement," Plant Breeding and Biotechnology, Dec. 30, 2015, vol. 3, No. 4, pp. 283-290, (Published on Nov. 30, 2015).

Kim K.S., et al., "Identification of Positive Yield QTL Alleles From Exotic Soybean Germplasm in Two Backcross Populations," Theoretical and Applied Genetics, 2012, vol. 125, pp. 1353-1369.

Kumar V., et al., "The CRISPR_Cas System for Plant Genome Editing: Advances and Opportunities," Journal of Experimental Botany, 2015, vol. 66, No. 1, pp. 47-57, Advance Access Publication Nov. 4, 2014.

Lauth M., et al., "Stable and Efficient Cassette Exchange under Non-Selectable Conditions by Combined Use of Two Site-Specific Recombinases," Nucleic Acids Research, 2002, vol. 30, No. 21(e115), pp. 1-7.

Li J.F., et al., "Multiplex and Homologous Recombination-Mediated Genome Editing in *Arabidopsis* and Nicotiana Benthamiana Using Guide RNA and Cas9," Nature Biotechnology, Aug. 2013, vol. 31, No. 8, pp. 688-691.

Li J-F., et al., "Multiplex and Homologous Recombination-Mediated Plant Genome Editing in *Arabidopsis* and Nicotiana Benthamiana using Guide RNA and Cas9," Nature Biotechnology, Aug. 2013, vol. 31, No. 8 (Supplemental), pp. 688-691, 15 Pages.

Li T., et al., "High-Efficiency TALEN-Based Gene Editing Produces Disease-Resistant Rice," Nature Biotechnology, May 7, 2012, vol. 30, No. 5, pp. 390-392, 25 Pages, Supplementary Information.

Li Z., et al., "A Cre/loxP-Mediated Self-activating Gene Excision System to Produce Marker Gene Free Transgenic Soybean Plants," Plant Molecular Biology, 2007, vol. 65, pp. 329-341.

Li Z., et al., "Cas9-Guide RNA Directed Genome Editing in Soybean," Plant Physiology, Aug. 20, 2015, Oct. 2015, vol. 169, No. 2, pp. 960-970.

Li Z., et al., "Site-Specific Integration of Transgenes in Soybean via Recombinase-Mediated DNA Cassette Exchange," Plant Physiology, Nov. 1, 2009, vol. 151, No. 3, pp. 1087-1095.

Li Z., et al., "Stacking Multiple Transgenes at a Selected Genomic Site via Repeated Recombinase-Mediated DNA Cassette Exchanges,"

(56) References Cited

OTHER PUBLICATIONS

Plant Physiology, Oct. 2010, vol. 154, pp. 622-631, DOI: 10.1104/pp.110.160093, ISSN 0032-0889, XP055067130, (Published Online on Aug. 18, 2010).
Liang Z., et al., "Targeted Mutagenesis in *Zea mays* using TALENs and the CRISPR/Cas System," Journal of Genetics and Genomics, Elsevier, BV, NL, 2014, vol. 41, No. 2, pp. 63-68, (Published Online on Dec. 14, 2013), DOI:10.1016/J.JGG.2013.12.001, ISSN 1673-8527, XP028661345.
Lieber M.R., et al., "The Mechanism of Double-Strand DNA Break Repair by the Nonhomologous DNA End Joining Pathway," Annual Review of Biochemistry, 2010, vol. 79, pp. 181-211, 34 Pages.
Louwerse J.D., et al., "Stable Recombinase-Mediated Cassette Exchange in *Arabidopsis* Using Agrobacterium Tumefaciens," Plant Physiology, Dec. 2007, vol. 145, pp. 1282-1293.
Luo S., et al., "Non-Transgenic Plant Genome Editing Using Purified Sequence-Specific Nucleases," Molecular Plant, Jun. 11, 2015, Sep. 2015, vol. 8, pp. 1425-1427.
Lyznik L.A., et al., "Activity of Yeast FLP Recombinase in Maize and Rice Protoplasts," Nucleic Acids Research, 1993, vol. 21, No. 4, pp. 969-975.
Lyznik L.A., et al., "Application of Site-Specific Recombination Systems for Targeted modification of Plant Genomes," Transgenic Plant Journal, 2007, vol. 1, No. 1, pp. 1-9.
Lyznik L.A., et al., "Double-strand Break-Induced Targeted Mutagenesis in Plants," In: Transgenic Plants: Methods and Protocols, Methods in Molecular Biology, 2012, vol. 847, pp. 399-416.
Ma M., et al., "A Guide RNA Sequence Design Platform for the CRISPR/Cas9 System for Model Organism Genomes," BioMed Research International, 2013, vol. 2013, Article ID 270805, 4 Pages.
Makarova K.S., et al., "Evolution and Classification of the CRISPR-Cas Systems," Nature Reviews Microbiology, Jun. 2011, vol. 9, No. 6, pp. 467-477, 23 Pages.
Mao Y., et al., "Application of the CRISPR-Cas System for Efficient Genome Engineering in Plants," Letter to the Editor, Molecular Plant, Nov. 2013, vol. 6, No. 6, pp. 2008-2011.
Mao Z., et al., "Comparison of Nonhomologous End Joining and Homologous Recombination in Human Cells," DNA Repair, 2008, vol. 7, pp. 1765-1771.
Marraffini L.A., et al., "CRISPR Interference: RNA-directed Adaptive Immunity in Bacteria and Archaea," Nature Review Genetics, Mar. 2010, vol. 11, No. 3, pp. 181-190, 23 Pages.
Martin-Ortigosa S., et al., "Mesoporous Silica Nanoparticle-Mediated Intracellular Cre Protein Delivery for Maize Genome Editing via loxP Site Excision 1'2[W][Open]," Plant Physiology, Feb. 2014, vol. 164, No. 2, pp. 537-547.
Martin-Ortigosa S., et al., "Proteolistics: A Biolistic Method for Intracellular Delivery of Proteins," Transgenic Resource, Oct. 2014, vol. 23, No. 5, pp. 743-756, DOI:10.1007/S11248-014-9807-Y, ISSN 0962-8819, XP035381272, (EPublished on Aug. 5, 2014).
Mian M.A.R., et al., "Molecular Markers Associated with Seed Weight in Two Soybean Populations," Theoretical and Applied Genetics, 1996, vol. 93, No. 7, pp. 1011-1016.
Miao J., et al., "Targeted Mutagenesis in Rice Using CRISPR-Cas System," Cell Research, Sep. 3, 2013, vol. 23, No. 10, pp. 1233-1236, doi:10.1038/cr.2013.123, ISSN 1001-0602, XP055153533.
Miller J.C., et al., "A TALE Nuclease Architecture for Efficient Genome Editing," Nature Biotechnology, Feb. 2011, vol. 29, No. 2, pp. 143-148.
Murray E.E., et al., "Codon Usage in Plant Genes," Nucleic Acids Research, 1989, vol. 17, No. 2, pp. 477-498.
Nanto K., et al., "Agrobacterium-Mediated RMCE Approach for Gene Replacement," Plant Biotechnology Journal, 2005, vol. 3, pp. 203-214.
Nekrasov V., et al., "Targeted Mutagenesis in the Model Plant *Nicotiana benthamiana* Using Cas9 RNA-Guided Endonuclease," Nature Biotechnology, Aug. 2013, vol. 31, No. 8, pp. 691-693.
Nelson W., et al., "Methylation-Sensitive Linking Libraries Enhance Gene-Enriched Sequencing of Complex Genomes and Map DNA Methylation Domains," BMC Genomics, Dec. 19, 2008, vol. 9, No. 621, 16 Pages.
Ow D.W., "Recombinase-Directed Plant Transformation for the Post-Genomic Era," Plant Molecular Biology, 2002, vol. 48, pp. 183-200.
Ow D.W., "Recombinase-Mediated Gene Stacking as a Transformation Operating System," Journal of Integrative Plant Biology, 2011, vol. 53, No. 7, pp. 512-519.
Patrick D.H., et al., "DNA Targeting Specificity of RNA-Guided Cas9 Nucleases," Nature Biotechnology, Sep. 2013, vol. 31, No. 9, pp. 827-834.
Perlak F.J., et al., "Modification of the Coding Sequence Enhances Plant Expression of Insect Control Protein Genes," Proceedings of the National Academy of Sciences of the United States of America, Apr. 1991, vol. 88, pp. 3324-3328.
Podevin N., et al., "Site-directed Nucleases: A Paradigm Shift in Predictable, Knowledge-based Plant Breeding," Trends in Biotechnology, Jun. 2013, vol. 31, No. 6, pp. 375-383, DOI:10.1016/j.tibtech.2013.03.004, XP028550365, (Epublished on Apr. 17, 2013).
Predicted: "*Zea mays* Glycerol-3-Phosphate 2-0-Acyltransferase 6 (LOC103631765), mRNA," Accession No. XM_008653185, Dec. 18, 2017, 1 Page.
Puchta H., et al., "Gene Replacement by Homologous Recombination in Plants," Plant Molecular Biology, 2002, vol. 48, pp. 173-182.
Puchta H., et al., "Synthetic Nucleases for Genome Engineering in Plants: Prospects for a Bright Future," The Plant Journal, 2014, vol. 78, pp. 727-741.
Qi L.S., et al., "Repurposing CRISPR as an RNA-Guided Platform for Sequence-Specific Control of Gene Expression," Cell, Feb. 28, 2013, vol. 152, No. 5, pp. 1173-1183, 22 pages.
Que Q., et al., "Maize Transformation Technology Development for Commercial Event Generation," Frontiers in Plant Science, Aug. 5, 2014, vol. 5, Article No. 379, 19 Pages, DOI:10.3389/fpls.2014.00379, XP055217826.

* cited by examiner

Genetic / physical Distance Between Target Sites and Transgene of Interest

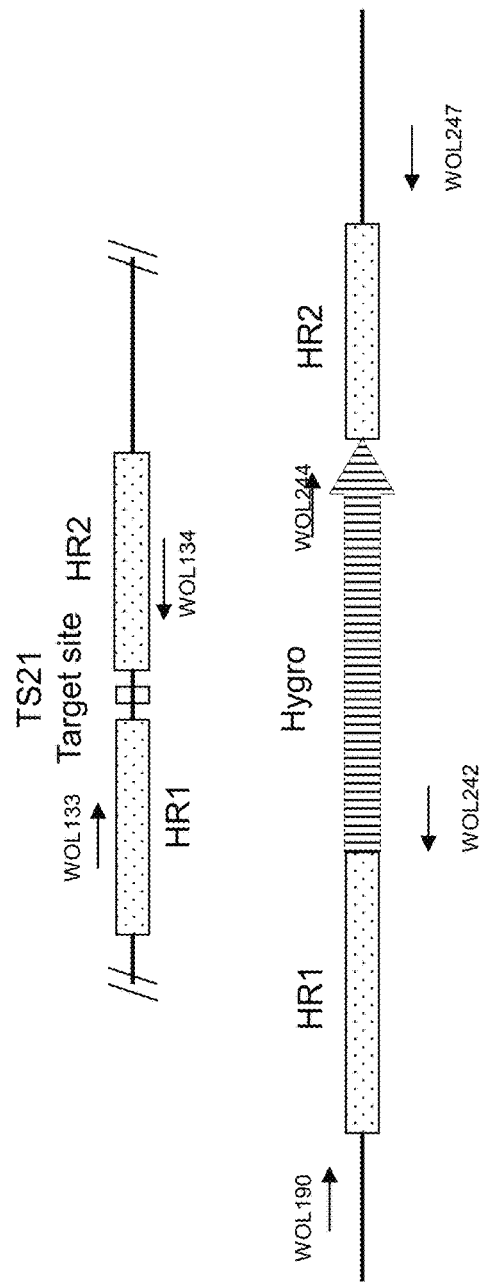

FIG. 4

FIG. 4A: Alignment of sequences of TS5 transgenic events (TS5 target sites underlined)

```
                                                       BssSI
SEQ ID                                                ┌─────────┐
NO:     Deletion/insertion event
124  WT    TAATGATCACATTTTTTTTTTTCTCACACTCACCTAAGTGCACGAGTAAGTCTTAGGTTAAAGTTTCATGCCCCCCCCCCCCAAAA
125  P2A6  TAATGATCACATTTTTTTTTTTCTCACACTCACCTAAGTGCACGAGTAGTGCACACGT......326bp deletion with 42bp filler DNA...........
126  P1B9  TAATGATCACATTTTTTTTTTTCTCACACTCACCTAAGTGCACGAGTACACGT▼GTAAGTCTTAGGTTAAAGTTTCATGCCCCCCCCCCCCAAAA
127  P2C5  TAATGATCACATTTTTTTTTTTCTCACACTCACCTAAGTGCACGAG......94bp deletion with 193bp filler DNA...........
```

▼ indicates a 161 bp insertion into the target site

FIG. 4B: Alignment of sequences of selected TS14 transgenic event (TS5 target sites underlined)

```
                                                       BsiWI
SEQ ID                                                ┌─────────┐
NO:     Deletion/insertion event
128  WT    TAATGATCACATTTTTTTTTTTCTCACACTCACCTAAGTGCAGACGTACGCAAGTAGCTTGTTACTTTCGTATTGACAATTCAAAATCGTCTTTTATTTTTATT
129  P4G10 TAATGATCACATTTTTTTTTTTCTCACACTCACCTAAGTGCAGACGTACGCAAGTAGCTTTGTTACT▼CAAGTAGCTTTGTTACTTTCGTATTGACAATTCAAAATCGTCTTTTATTTTTATT
```

HO Mega14 target sites are underlined with the cut sites in bold
▶ indicates a 115 bp insertion into the target site

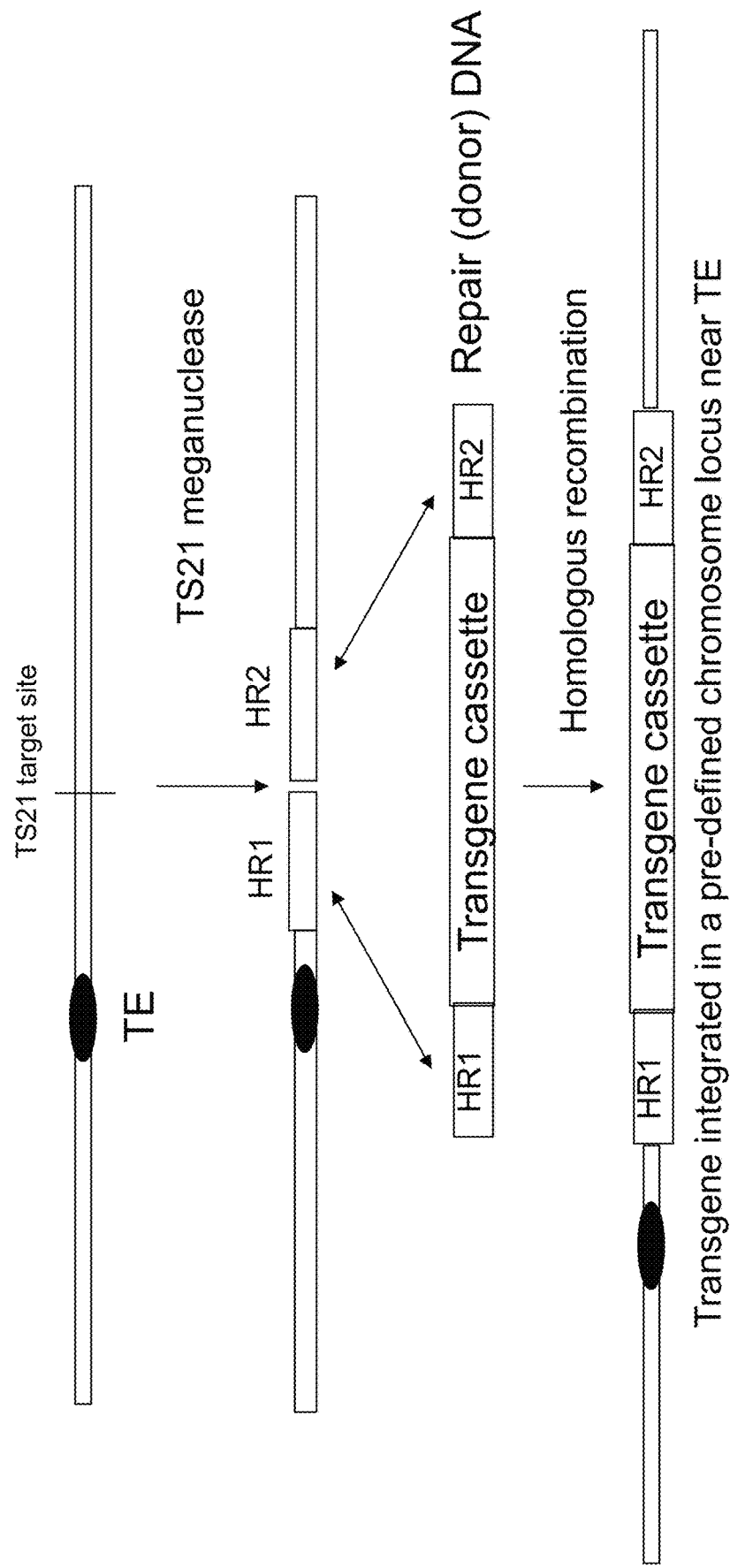

Location of Target Sites Near a Herbicide-Resistant Transgenic Event in Soybean

Cluster of Meganuclease Target Sites for Trait Stacking

FIG. 9
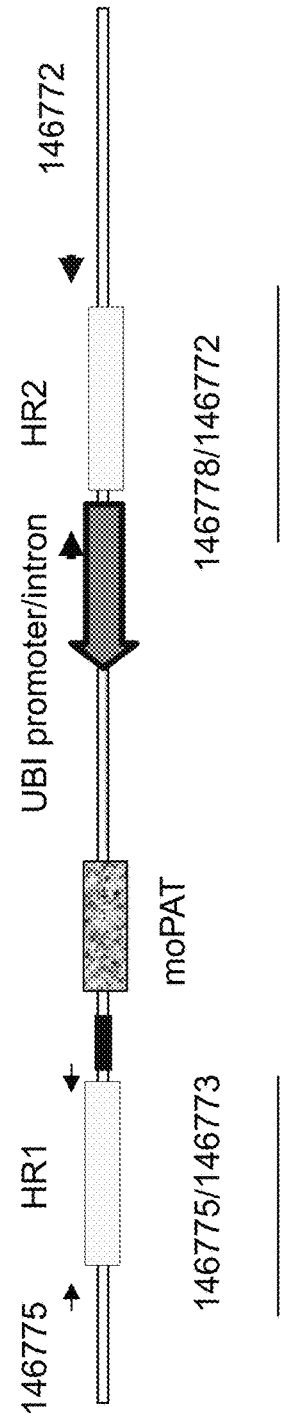
FIG. 9A
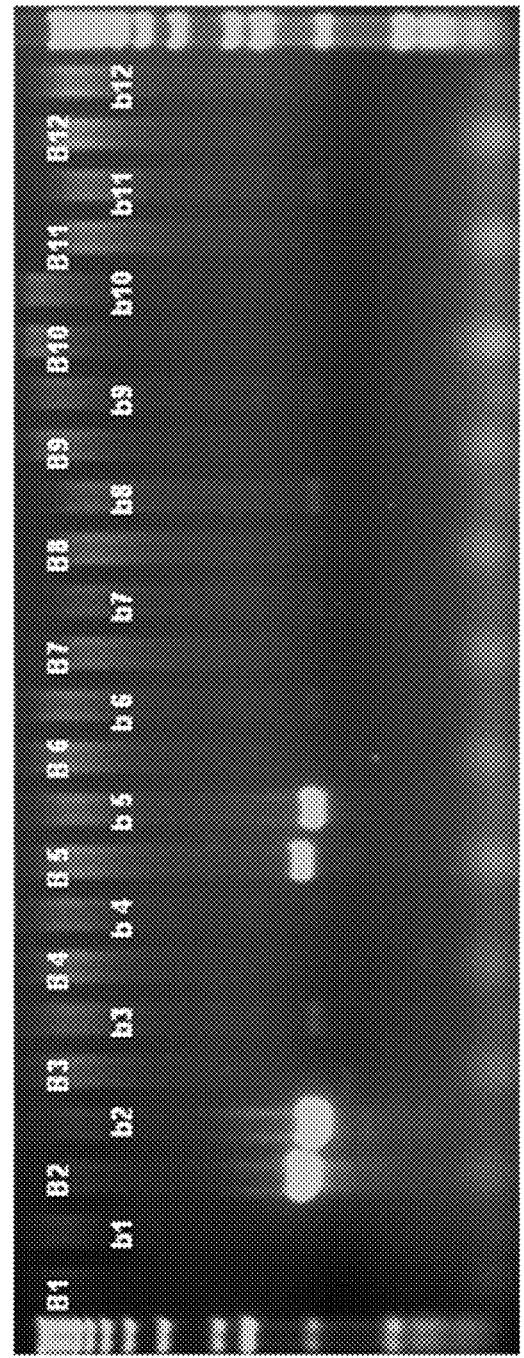
FIG. 9B

FIG. 10
FIG. 10A
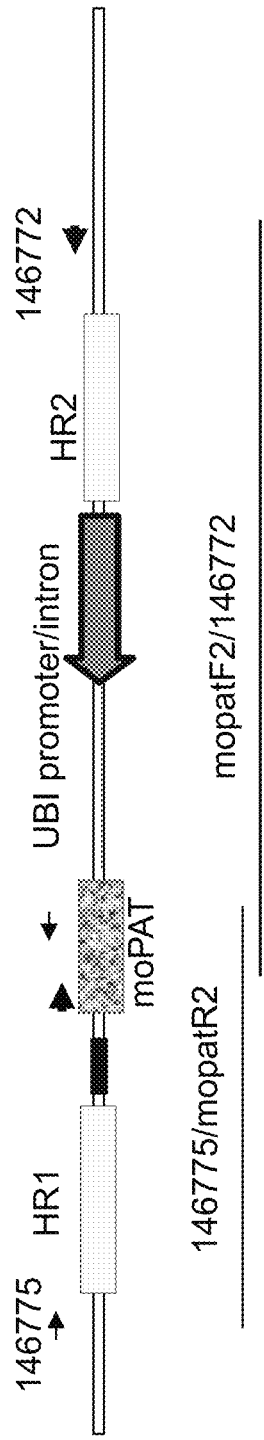
FIG. 10B

METHODS FOR PRODUCING A COMPLEX TRANSGENIC TRAIT LOCUS

CROSS-REFERENCE TO RELATED APPLICATIONS

This application is a continuation of U.S. patent application Ser. No. 16/925,973 filed on Jul. 10, 2020 (published as U.S. Patent Application No. 20210062201), which is a continuation of U.S. patent application Ser. No. 16/007,529 filed on Jun. 13, 1018 (now allowed as U.S. patent Ser. No. 10/822,610), which is a continuation of U.S. patent application Ser. No. 13/427,138 (now allowed as U.S. patent Ser. No. 10/030,245), which itself claims the benefit of U.S. Provisional Patent Application No. 61/499,443, filed Jun. 11, 2011 and U.S. Provisional Patent Application No. 61/466, 602, filed Mar. 23, 2011; all of which are hereby incorporated herein in their entirety by reference.

REFERENCE TO SEQUENCE LISTING

The Sequence Listing is submitted as a XML file named BB1990-US-CNT3.xml created on Feb. 23, 2023 having a size of 236 KB, and is hereby incorporated by reference pursuant to 37 C.F.R. § 1.52 (e) (5).

FIELD OF INVENTION

The invention relates to the field of plant molecular biology, in particular, to methods for altering the genome of a plant cell.

BACKGROUND

Recombinant DNA technology has made it possible to insert foreign DNA sequences into the genome of an organism, thus, altering the organism's phenotype. The most commonly used plant transformation methods are *Agrobacterium* infection and biolistic particle bombardment in which transgenes integrate into a plant genome in a random fashion and in an unpredictable copy number. Thus, efforts are undertaken to control transgene integration in plants.

One method for inserting or modifying a DNA sequence involves homologous DNA recombination by introducing a transgenic DNA sequence flanked by sequences homologous to the genomic target. U.S. Pat. No. 5,527,695 describes transforming eukaryotic cells with DNA sequences that are targeted to a predetermined sequence of the eukaryote's DNA. Specifically, the use of site-specific recombination is discussed. Transformed cells are identified through use of a selectable marker included as a part of the introduced DNA sequences.

It was shown that artificially induced site-specific genomic double-stranded breaks in plant cells were repaired by homologous recombination with exogenously supplied DNA using two different pathways. (Puchta et al., (1996) *Proc. Natl. Acad. Sci. USA* 93:5055-5060; U.S. Patent Application Publication No. 2005/0172365A1 published Aug. 4, 2005; U.S. Patent Application Publication No. 2006/0282914 published Dec. 14, 2006; WO 2005/028942 published Jun. 2, 2005).

Since the isolation, cloning, transfer and recombination of DNA segments, including coding sequences and non-coding sequences, is most conveniently carried out using restriction endonuclease enzymes. Much research has focused on studying and designing endonucleases such as WO 2004/067736 published Aug. 12, 2004; U.S. Pat. No. 5,792,632 issued to Dujon et al., Aug. 11, 1998; U.S. Pat. No. 6,610, 545 B2 issued to Dujon et al., Aug. 26, 2003; Chevalier et al., (2002) *Mol Cell* 10:895-905; Chevalier et al., (2001) *Nucleic Acids Res* 29:3757-3774; Seligman et al., (2002) *Nucleic Acids Res* 30:3870-3879.

Although a plethora of approaches have been developed to target a specific site for modification in the genome of a plant, there still remains a need for methods for producing a fertile plant, having an altered genome comprising two or more site-specific modifications in defined region of the genome of the plant.

BRIEF SUMMARY OF THE INVENTION

The present invention provides methods for producing in a plant a complex transgenic trait locus comprising at least two altered target sequences in a genomic region of interest. The methods involve selecting a genomic region in a plant that comprises a first target sequence and a second target sequence and then providing a first double-strand-break-inducing agent and a second double-strand-break-inducing agent. The first double-strand-break-inducing agent is capable of inducing a first double-strand break in DNA comprising the first target sequence, and the second double-strand-break-inducing agent is capable of inducing a second double-strand break in DNA comprising the second target sequence. The methods further involve contacting at least one plant cell with the first double-strand-break-inducing agent, identifying a cell comprising a first alteration at the first target sequence, and then recovering a first fertile plant from the cell comprising the first alteration. The first fertile plant also comprises the first alteration. Additionally, the methods involve contacting at least one plant cell with the second double-strand-break-inducing agent, identifying a cell comprising a second alteration at the second target sequence, and then recovering a second fertile plant from the cell comprising the second alteration. The methods further involve obtaining a fertile progeny plant from the second fertile plant, wherein the fertile progeny plant comprises both the first and second alterations in physical linkage.

In a first embodiment of the methods for producing in a plant a complex transgenic trait locus, the fertile progeny plant is obtained by crossing the first fertile plant and the second fertile plant and selecting the fertile progeny plant comprising both the first and second alterations in physical linkage.

In second embodiment, a cell of the first fertile plant, or progeny thereof comprising the first alteration, is contacted with the second double-strand-break-inducing agent.

In third embodiment, the complex transgenic trait locus further comprises at least one polynucleotide of interest in the genomic region of interest. Such a polynucleotide of interest can be, for example, a transgene, a native gene, and a gene that was a native gene prior to a targeted mutation therein.

In a fourth embodiment, the first alteration comprises insertion of a first DNA sequence of interest, or part thereof, into the first target sequence, and/or the second alteration comprises insertion of a second DNA sequence of interest, or part thereof, into the second target sequence. Such a first and/or a second DNA sequence of interest can be, for example, a DNA for gene silencing, a DNA encoding a phenotypic marker and a DNA encoding a protein providing an agronomic advantage.

In a fifth embodiment, the first and second double-strand-break-inducing agents are selected from the group consisting of an endonuclease, a zinc finger nuclease, or a TAL effector nuclease.

In a sixth embodiment, the endonuclease is modified to specifically cut at the first target sequence or at the second target sequence and no longer cuts at its wild-type endonuclease target sequence.

In a seventh embodiment, the first target sequence and the second target sequence are separated from each other by about 0.1, 0.2, 0.3, 0.4, 0.5, 0.6, 0.7, 0.8, 0.9, 1, 2, 3, 4, or 5 centimorgans (cM) in the genome of the plant.

In an eighth embodiment, the methods can involve crossing the fertile progeny plant with an additional fertile plant that comprises at least a third altered target sequence in the genomic region of interest and then selecting from the crossing a fertile progeny plant comprising the first alteration, the second and the at least third alteration in physical linkage. Like the first and second altered target sequences, the third altered target sequence originated from a third target sequence that is recognized and cleaved by a third double-strand-break-inducing agent.

Additionally provided are complex trait loci in plants produced by the methods of the invention and plants, plant cells, plant parts, and seeds thereof comprising at least one complex transgenic trait locus of the invention.

The present invention further provides a complex transgenic trait locus comprising at least two altered target sequences that are genetically linked in the genome of a plant to a polynucleotide of interest. Such altered target sequences originated from a corresponding target sequence that is recognized and cleaved by a double-strand-break-inducing agent. The altered target sequences comprise an alteration such as, for example, replacement of at least one nucleotide in the target sequence, a deletion of at least one nucleotide in the target sequence, an insertion of at least one nucleotide in the target sequence, or any combination thereof. The polynucleotide interest can be, for example, a transgene, a native gene, and a mutated gene. The present invention further provides plants, plant parts, plant cells, and seeds comprising at least one complex transgenic trait locus of the invention.

In an embodiment of the complex transgenic trait locus of the invention, at least one altered target sequence comprises a recombinant DNA molecule. Recombinant DNA molecules include, but are not limited to, a DNA for gene silencing, a DNA encoding a phenotypic marker, and a DNA encoding a protein providing an agronomic advantage.

In another embodiment, the two altered target sequences of the complex transgenic trait locus are located within about 0.1, 0.2, 0.3, 0.4, 0.5, 0.6, 0.7, 0.8, 0.9, 1, 2, 3, 4, 5, 6, 7, 8, 9, 10, 11 or up to 21 centimorgan (cM) of the polynucleotide of interest.

The invention provides plants, plant parts, plant cells, and seeds comprising at least one complex transgenic trait locus of the invention.

Additionally provided is an alternative method for producing in a plant a complex transgenic trait locus comprising at least two altered target sequences in a genomic region of interest. This method involves obtaining a first fertile plant comprising a first altered target sequence at the genomic region of interest and a second fertile plant comprising a second altered target sequence at the genomic region of interest. In this method, the first altered target sequence originated from a first target sequence that is recognized and cleaved by a first double-strand-break-inducing agent, and the second altered target sequence originated from a second target sequence that is recognized and cleaved by a second double-strand-break-inducing agent. The alternative method further involves crossing the first fertile plant and the second fertile plant, and then selecting from the crossing a fertile progeny plant comprising the first alteration and the second alteration in physical linkage.

Also provided are plants produced by the second method of the invention and plant cells, plant parts, and seeds thereof comprising at least one complex transgenic trait locus.

In another embodiment, the present invention provides a plant comprising an expression construct, which comprises a promoter operably linked to a nucleotide sequence encoding an endonuclease. The endonuclease is capable of specifically binding to and creating a double strand break in a target sequence selected from the group consisting of SEQ ID NO:1, 2, 3, 4, 5, 6, 7, 8, 68, 69, 70, 71, 72, 73, 74, 75, 76, and 77, wherein the promoter is capable of driving expression of an operably linked nucleotide sequence in a plant cell. The nucleotide sequence encoding the endonuclease can comprise a coding sequence of a DNA binding domain of an endonuclease, wherein the coding sequence comprises nucleotides 100-261 and nucleotides 850-1011 of SEQ ID NO:9, 10, 11, 12, 13, 14, 15, 16, 78, 79, 80, 81, 82 or 83; or a degenerate coding sequence thereof. Preferably, the nucleotide sequence encoding the endonuclease is a nucleotide sequence selected from the group consisting of SEQ ID NO:9, 10, 11, 12, 13, 14, 15, 16, 78, 79, 80, 81, 82, and 83.

In yet another embodiment of the invention, a plant of the invention comprises at least one altered target sequence, wherein the at least one altered target sequence originated from a corresponding target sequence that was recognized and cleaved by a double-strand break-inducing agent. In this embodiment, the altered target sequence is in a genomic region of interest that extends from: the target sequence set forth in SEQ ID NO: 4 to the target sequence set forth in SEQ ID NO: 2; the target sequence set forth in SEQ ID NO: 5 to the target sequence set forth in SEQ ID NO: 8; or the target sequence set forth in SEQ ID NO: 68 to the target sequence set forth in SEQ ID NO: 77. Such a plant of the invention can be produced by a method comprising providing at least one double-strand-break-inducing agent that is capable of inducing a double-strand break in DNA comprising a target sequence, wherein the target sequence is in a genomic region of interest that extends from: the target sequence set forth in SEQ ID NO: 4 to the target sequence set forth in SEQ ID NO: 2; the target sequence set forth in SEQ ID NO: 5 to the target sequence set forth in SEQ ID NO: 8; or the target sequence set forth in SEQ ID NO: 68 to the target sequence set forth in SEQ ID NO: 77. The method further comprises contacting at least one plant cell with the double-strand-break-inducing agent, identifying a cell comprising an alteration at the target sequence, and recovering a fertile plant comprising the alteration. In one embodiment of this method, the double-strand-break-inducing agent is encoded by a nucleotide sequence comprising a coding sequence of a DNA binding domain of an endonuclease, and wherein the coding sequence is selected from the group consisting of nucleotides 100-261 and nucleotides 850-1011 of SEQ ID NO: 9, 10, 11, 12, 13, 14, 15, 16, and 80, and degenerate coding sequences thereof. In another embodiment of this method, the double-strand-break-inducing agent is encoded by a nucleotide sequence comprising a coding sequence of a DNA binding domain of an endonuclease, and wherein the coding sequence is selected from the group consisting of nucleotides 100-261 and nucleotides 661-822 of SEQ ID NO: 78, 79, 81, 82 and 83, and degenerate coding sequences thereof. In another embodiment of this method, the double-strand-break-inducing agent is encoded by a nucleotide sequence is selected from the group consisting of SEQ ID NO: 9, 10, 11, 12, 13, 14, 15, 16, 78, 79, 80, 81, 82, and 83.

Additional embodiments of the methods and compositions of the present invention are disclosed below.

BRIEF DESCRIPTION OF THE DRAWINGS AND THE SEQUENCE LISTING

The invention can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§ 1.821-1.825. The sequence descriptions contain the three letter codes for amino acids as defined in 37 C.F.R. §§ 1.821-1.825, which are incorporated herein by reference.

FIGURES

FIG. 1. DNA double-strand break induced DNA alteration of an endogenous target site. FIG. 1A A generalized endogenous target site with flanking genomic DNA sequences designated as DNA 1 and DNA 2 which can be used as DNA exchange regions by homologous recombination. FIG. 1B A generalized DNA construct that can be used to express a DNA endonuclease to recognize and cleave the endogenous target site. The DNA endonuclease gene can be physically linked to the donor DNA described in FIG. 1C or FIG. 1D, or substituted by other double-strand break inducing agents. FIG. 1C A generalized donor DNA construct having two regions DNA1 and DNA 2 of homology to the genomic target which flank a polynucleotide of interest and/or marker gene. FIG. 1D A generalized donor DNA construct that does not have regions of homology to the genomic target to flank a polynucleotide of interest and/or marker gene. Insertion of the DNA fragment will produce an insertion of the polynucleotide of interest at or near the recognition site. FIG. 1E One expected outcome when the polynucleotide of interest and/or marker gene of donor construct described in FIG. 1C or FIG. 1D is inserted at the endogenous target site by homologous recombination or non-homologous recombination, respectively. FIG. 1F Another outcome when the endogenous target site is altered by a deletion during the repair of the DNA double-strand break cleaved by the DNA endonuclease. The polynucleotide of interest and/or marker gene of donor construct described in FIG. 1C or FIG. 1D can be inserted at unrelated sites by random DNA integration. FIG. 1G Another outcome when the endogenous target site is altered by the insertion of an unrelated DNA during the repair of the DNA double-strand breaks cleaved by the DNA endonuclease. The polynucleotide of interest and/or marker gene of donor construct described in FIG. 1C or FIG. 1D can be inserted at unrelated sites by random DNA integration.

Figure 2:
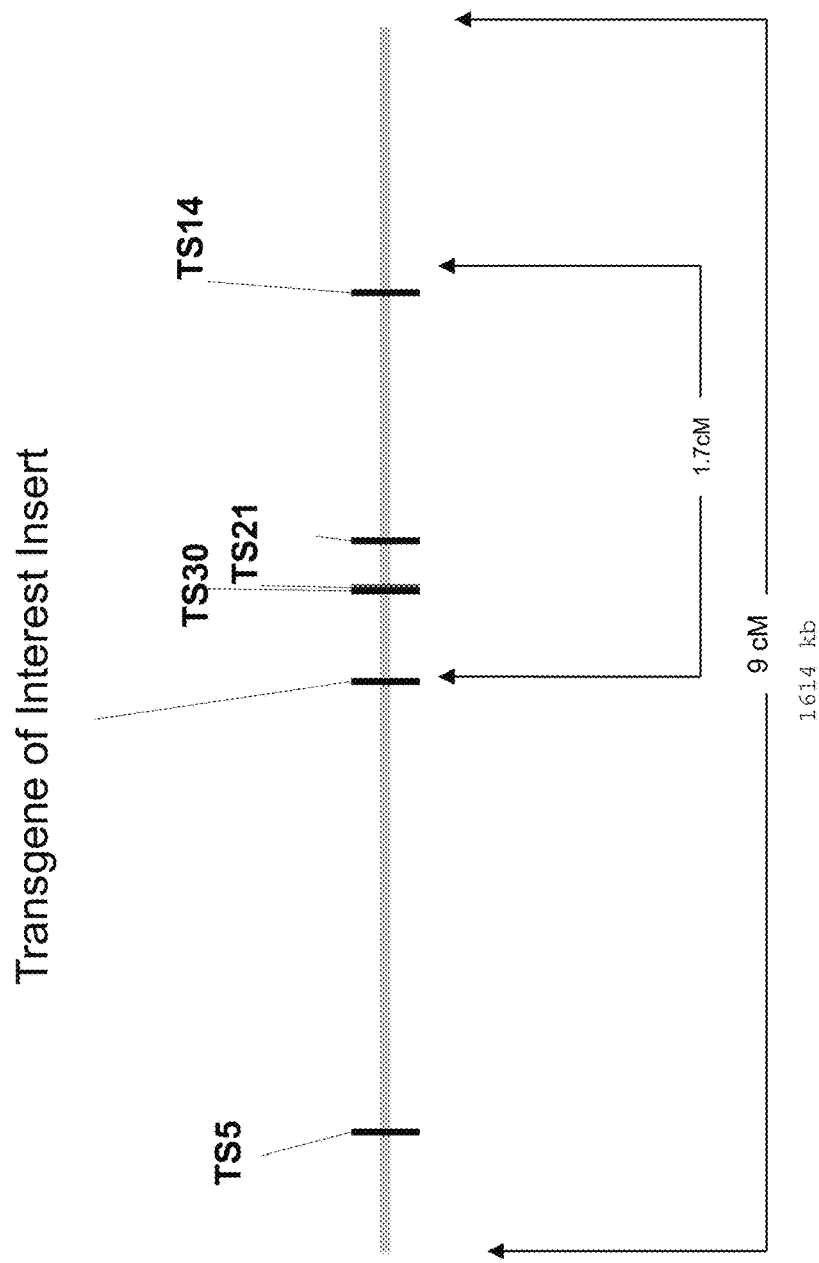

FIG. 2. Genetic distance between target sites and transgene of interest.

FIG. 3. FIG. 3A: Schematic diagram of PCR assays to detect TS21 target site modifications and transgenic integrations. FIG. 3B: Alignment of altered target sequences of selected TS21 transgenic event.

FIG. 4. FIG. 4A: Alignment of altered target sequences of selected TS5 transgenic events. FIG. 4B: Alignment of altered target sequences of selected TS14 transgenic events FIG. 5. Gene integration by homologous recombination enabled by double-strand breaks with custom designed meganuclease.

Figure 6:
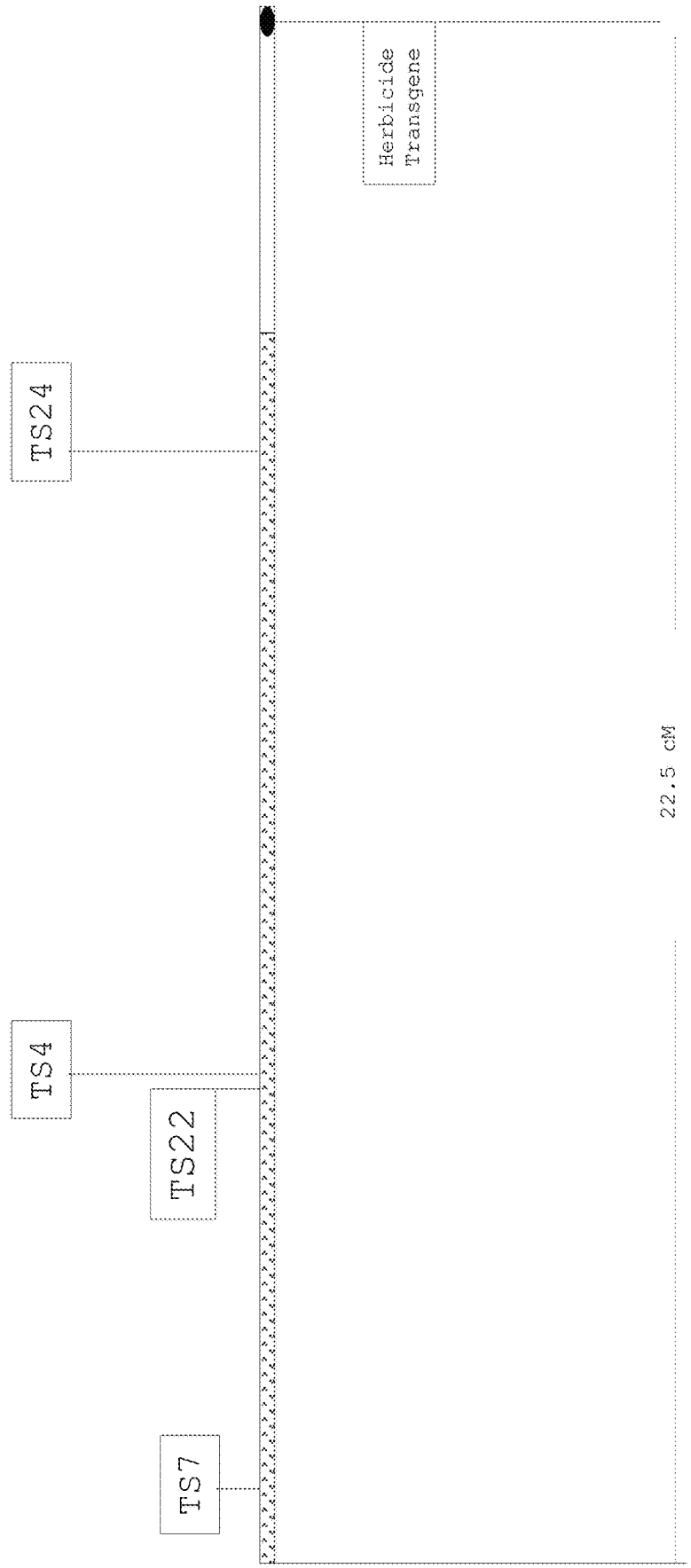

FIG. 6. Location of target sites near a herbicide resistant transgenic event in soybean.

Figure 7:
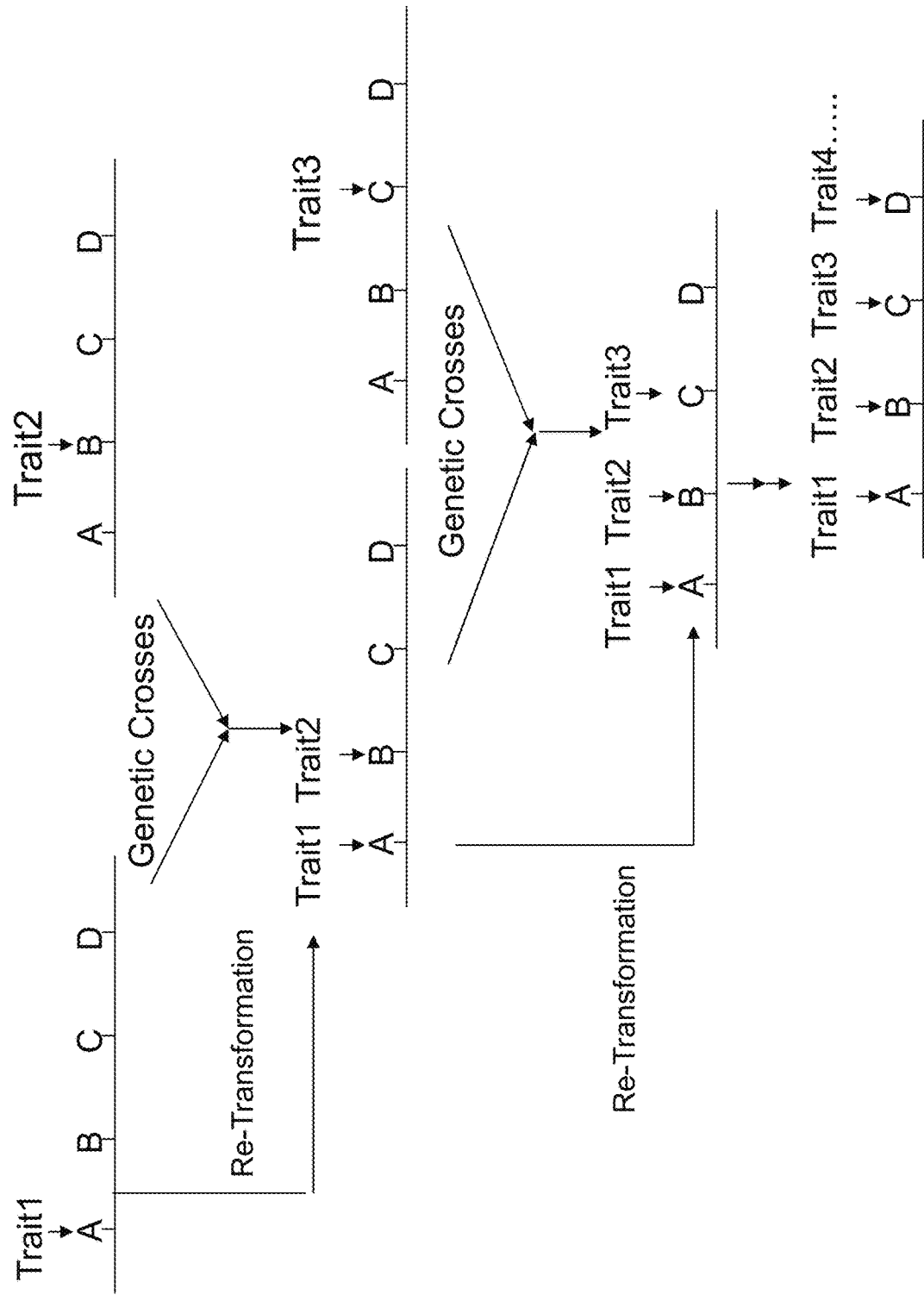

FIG. 7. Use of cluster of meganuclease target sites for stacking of multiple traits either by sequential transformation or genetic crosses.

Figure 8:
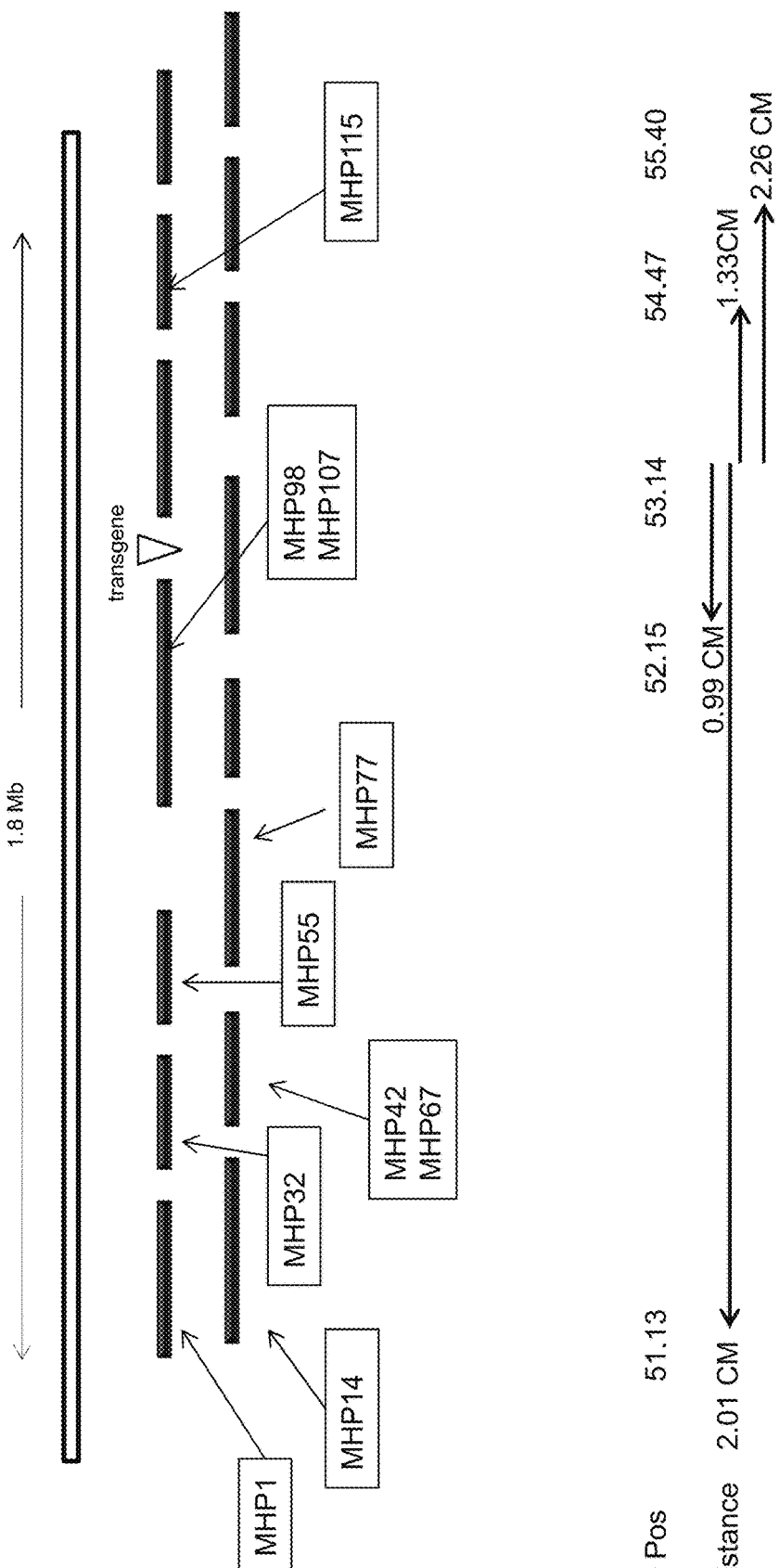

FIG. 8. The locations of various MHP target sites surrounding a transgenic DNA of interest integration site in a maize plant. Solid black rectangles represent BAC clones. Names and numbers in each box are the target sites. Arrows from box to BAC indicated the target site affiliated to BAC clones. Numbers and arrows on the bottom of the figure indicate the genetic distance of the target sites relative to the insertion location of the transgenic DNA of interest. As indicated at the top of the figure, the physical distance is about 1.8 Mb nucleotides in this region of the maize chromosome.

FIG. 9. FIG. 9A: Outline of PCR screening for integration of donor at MHP14 target site (donor was PHP44779) FIG. 9B: PCR of MHP14 events: B1-B12 junction PCR with primers 146773/146775; b1-b12 junction PCR with primers 146772/146778. Two events (B2 and B5) were positive for both junctions PCR. The arrows indicate the locations corresponding to the various primers used.

FIG. 10. FIG. 10A: Schematic outline of PCR to confirm ubi:mopat:pinII cassette integration at the endogenous MHP14 target. FIG. 10B: Long PCR on T0 plants from three events showed integration at the target site. The plant A5 was from event #1, A6-A8 event #2, and C4-C6 event #3. CKP: positive control from callus DNA. FIG. 10B: The left panel shows the results of junction PCR on the HR1 side using a genomic primer (146775) and a moPAT primer (mopatR2). The right panel shows the results of junction PCR on the HR2 side with a moPAT primer (mopatF2) a genomic primer (146772). The arrows on FIG. 10A indicate the locations corresponding to the various primers used.

Figure 11A:
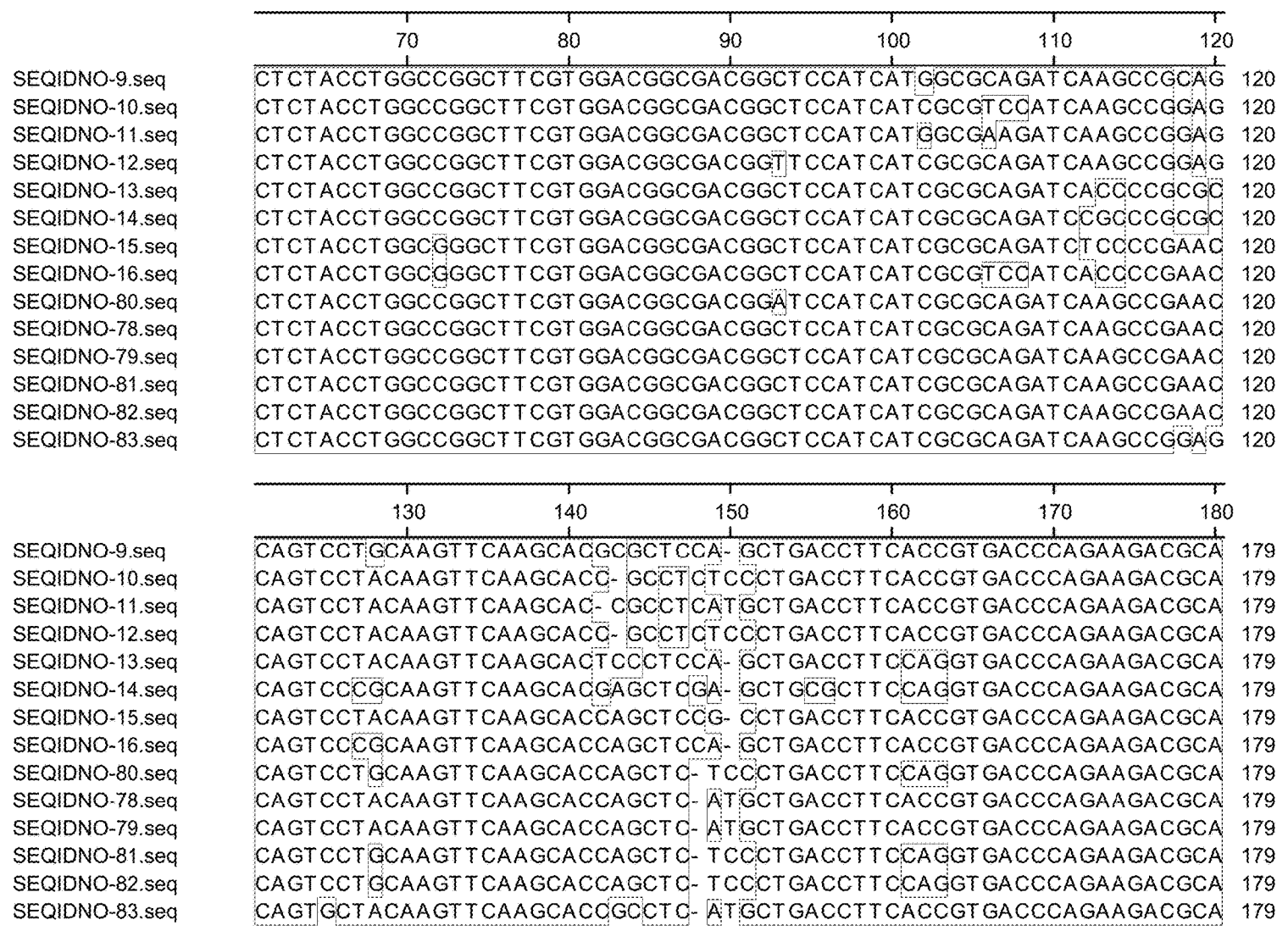
Figure 11B:
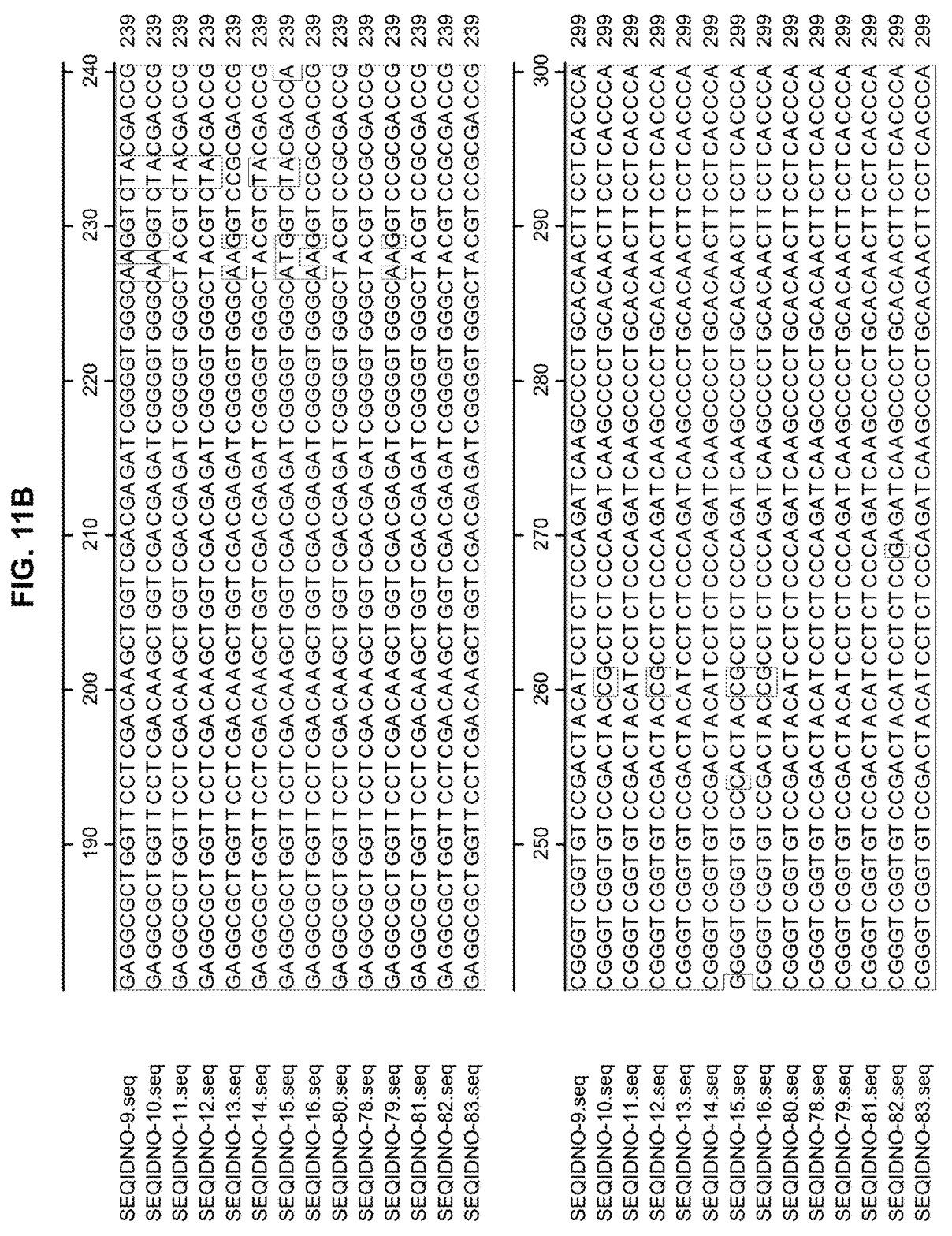
Figure 11C:
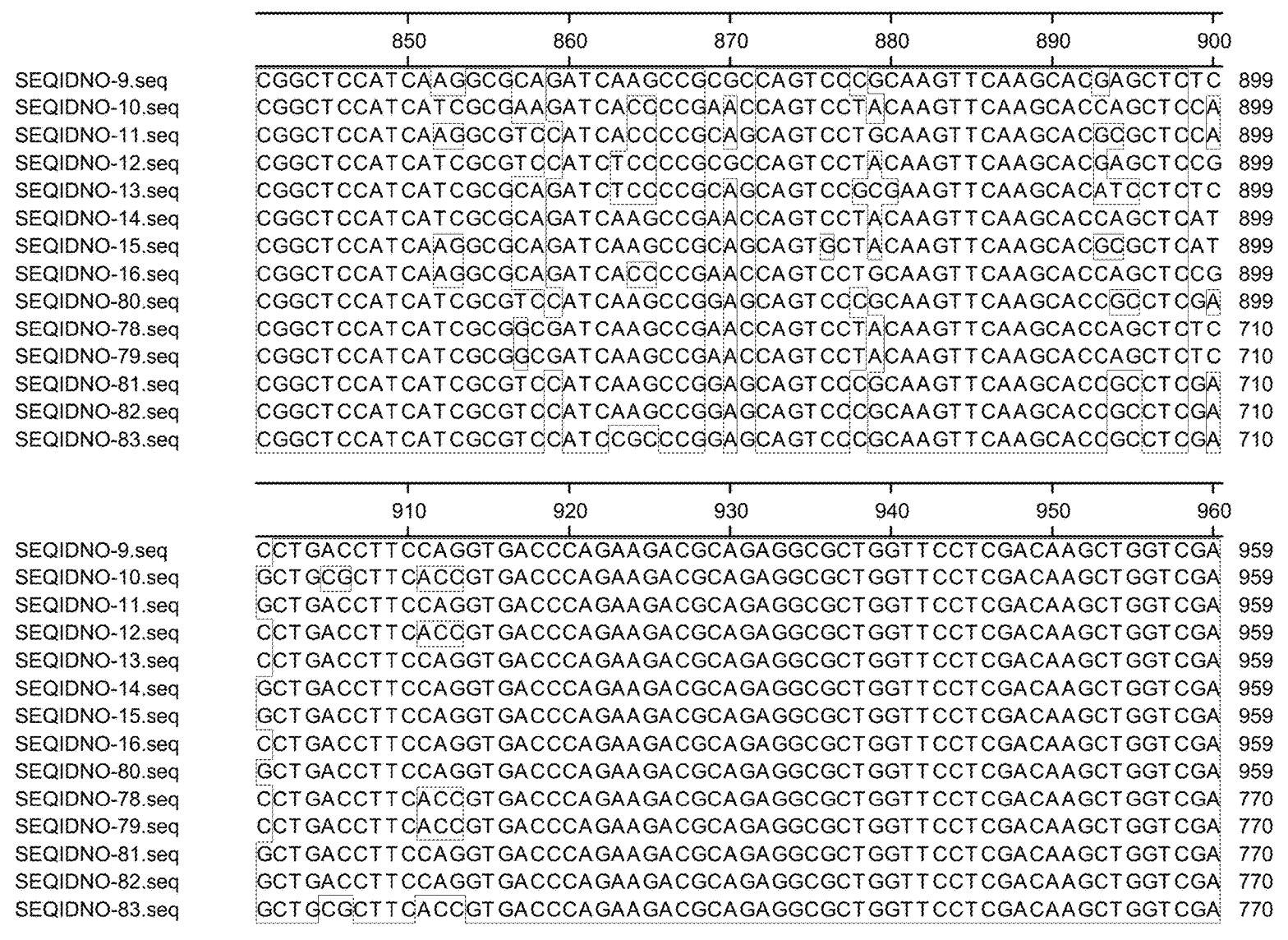
Figure 11D:
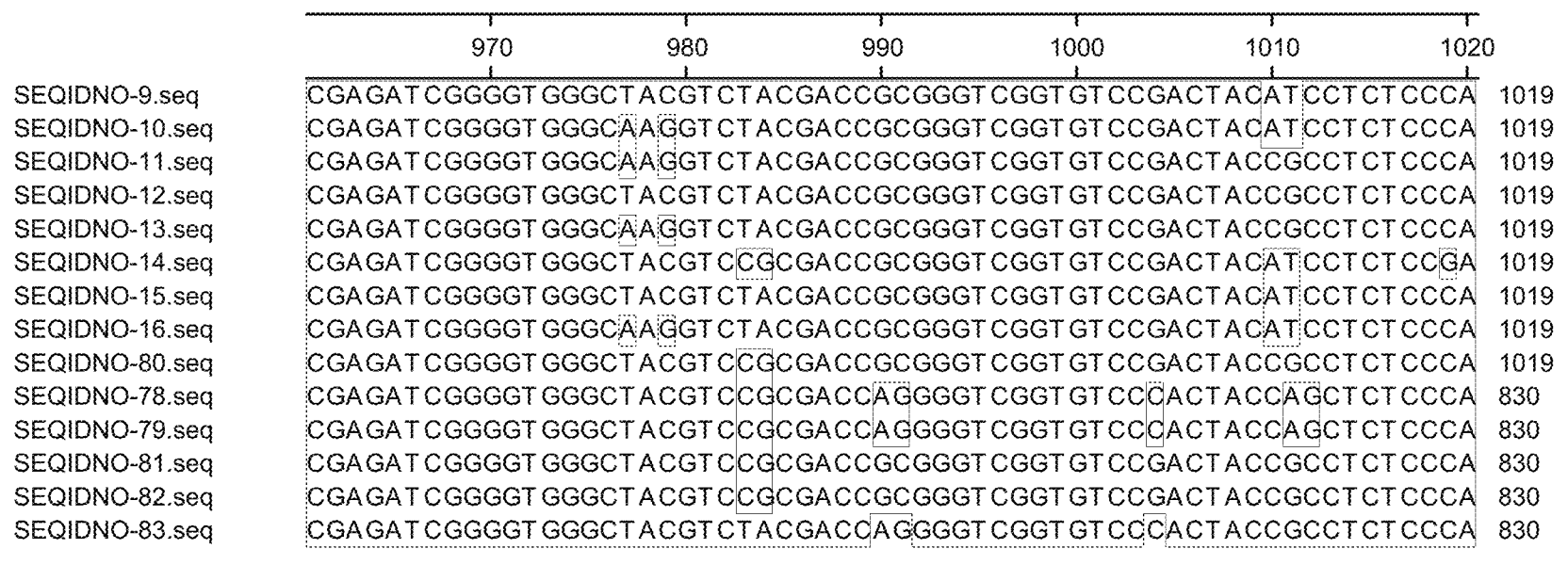

FIGS. 11A-11D. Alignment of fragments from the plant-optimized nucleotide sequences of meganucleases comprising the nucleotides 100-261 and nucleotides 850-1011 of SEQ ID NO: 9, 10, 11, 12, 13, 14, 15, 16, and 80, and the nucleotides 100-261 and nucleotides 661-822 of SEQ ID NO: 78, 79, 81, 82 and 83. FIG. 11A shows SEQ ID NOs: 9-16 and 78-80 sequence positions 60-180, FIG. 11B shows SEQ ID NOs: 9-16 and 78-80 sequence positions 180-300, FIG. 11C shows SEQ ID NOs: 9-16 and 78-80 sequence positions 840-960, and FIG. 11D shows SEQ ID NOs: 9-16 and 78-80 sequence positions 960-1020.

SEQUENCES

SEQ ID NO: 1 is the nucleotide sequence of the TS21 target site in soybean genome.

SEQ ID NO: 2 is the nucleotide sequence of the TS14 target site in soybean genome.

SEQ ID NO: 3 is the nucleotide sequence of the TS30 target site in soybean genome.

SEQ ID NO: 4 is the nucleotide sequence of the TS5 target site in soybean genome.

SEQ ID NO: 5 is the nucleotide sequence of the TS7 target site in soybean genome.

SEQ ID NO: 6 is the nucleotide sequence of the TS4 target site in soybean genome.

SEQ ID NO: 7 is the nucleotide sequence of the TS22 target site in soybean genome.

SEQ ID NO: 8 is the nucleotide sequence of the TS24 target site in soybean genome.

SEQ ID NO: 9 is the plant-optimized nucleotide sequence of the TS21 meganuclease containing a nuclear target site and an ST-LS1 intron.

SEQ ID NO: 10 is the plant-optimized nucleotide sequence of the TS14 meganuclease containing a nuclear target site and an ST-LS1 intron.

SEQ ID NO: 11 is the plant-optimized nucleotide sequence of the TS30 meganuclease containing a nuclear target site and an ST-LS1 intron.

SEQ ID NO: 12 is the plant-optimized nucleotide sequence of the TS5 meganuclease containing a nuclear target site and an ST-LS1 intron.

SEQ ID NO: 13 is the plant-optimized nucleotide sequence of the TS7 meganuclease containing a nuclear target site and an ST-LS1 intron.

SEQ ID NO: 14 is the plant-optimized nucleotide sequence of the TS4 meganuclease containing a nuclear target site and an ST-LS1 intron.

SEQ ID NO: 15 is the plant-optimized nucleotide sequence of the TS22 meganuclease containing a nuclear target site and an ST-LS1 intron.

SEQ ID NO: 16 is the plant-optimized nucleotide sequence of the TS24 meganuclease containing a nuclear target site and an ST-LS1 intron.

SEQ ID NO: 17 is the homologous region 1 (HR1) of the TS21 target site.

SEQ ID NO: 18 is the homologous region 2 (HR2) of the TS21 target site.

SEQ ID NO: 19 is the HR1 of the TS14 target site.

SEQ ID NO: 20 is the homologous region 2 of the TS14 target site.

SEQ ID NO: 21 is the HR1 of the TS30 target site.

SEQ ID NO: 22 is the homologous region 2 of the TS30 target site.

SEQ ID NO: 23 is the HR1 of the TS5 target site.

SEQ ID NO: 24 is the homologous region 2 of the TS5 target site.

SEQ ID NO: 25 is the HR1 of the TS7 target site.

SEQ ID NO: 26 is the homologous region 2 of the TS7 target site.

SEQ ID NO: 27 is the HR1 of the TS4 target site.

SEQ ID NO: 28 is the homologous region 2 of the TS4 target site.

SEQ ID NO: 29 is the HR1 of the TS22 target site.

SEQ ID NO: 30 is the homologous region 2 of the TS22 target site.

SEQ ID NO: 31 is the HR1 of the TS24 target site.

SEQ ID NO: 32 is the homologous region 2 of the TS24 target site.

SEQ ID NO: 33 is the plant-optimized nucleotide sequence of the TS21 meganuclease without a ST-LS1 intron.

SEQ ID NO: 34 is the amino acid sequence of the SV40 nuclear localization signal.

SEQ ID NO: 35: is the nucleotide sequences of expression cassette RTW317, comprising the TS21 meganuclease plant optimized sequence without an intron and operably linked to the soybean EF1A promoter.

SEQ ID NO: 36 is the nucleotide sequences of expression cassette RTW322, comprising the TS21 meganuclease plant optimized sequence with an intron and operably linked to the soybean EF1A promoter.

SEQ ID NO: 37 is the nucleotide sequence of RTW328A, which is the repair DNA fragment for TS21 meganuclease.

SEQ ID NO:38 is the nucleotide sequence of TS21 qPCR forward primer Mega21-190F.

SEQ ID NO:39 is the nucleotide sequence of TS21 qPCR reverse primer Mega21-301R.

SEQ ID NO:40 is the nucleotide sequence of TS21 qPCR probe mega21-250T. The fluorescent probe is labeled with FAM quenched with MGB.

SEQ ID NO:41 is the nucleotide sequence of TS14 qPCR forward primer Mega14-13F.

SEQ ID NO:42 is the nucleotide sequence of TS14 qPCR reverse primer Mega14-128R.

SEQ ID NO:43 is the nucleotide sequence of TS14 qPCR probe Mega14-85T. The fluorescent probe is labeled with FAM quenched with MGB.

SEQ ID NO:44 is the nucleotide sequence of TS30 qPCR forward primer Mega30-30F.

SEQ ID NO:45 is the nucleotide sequence of TS30 qPCR reverse primer Mega30-87R.

SEQ ID NO:46 is the nucleotide sequence of TS30 qPCR probe Mega30-52T. The fluorescent probe is labeled with FAM quenched with MGB.

SEQ ID NO:47 is the nucleotide sequence of TS5 qPCR forward primer Mega5-F1.

SEQ ID NO:48 is the nucleotide sequence of TS5 qPCR reverse primer Mega5-R1.

SEQ ID NO:49 is the nucleotide sequence of TS5 qPCR probe Mega5-T1. The fluorescent probe is labeled with FAM quenched with MGB.

SEQ ID NO:50 is the nucleotide sequence of the sense primer, WOL133, which is upstream of the TS21 target site in the soybean genome.

SEQ ID NO:51 is the nucleotide sequence of the antisense primer, WOL134, which is downstream of the TS21 target site in the soybean genome.

SEQ ID NO:52 is the nucleotide sequence of the sense primer, WOL190 which is further upstream of the TS21 target site beyond the TS21 HR1 fragment in the soybean genome.

SEQ ID NO:53 is the nucleotide sequence of the antisense primer, WOL242, which is specific to the hygromycin coding sequences.

SEQ ID NO:54 is the nucleotide sequence of the sense primer, WOL153, which is specific to the NOS Terminator.

SEQ ID NO:55 is the nucleotide sequence of the antisense primer, WOL247, which is further downstream of the TS21 target site beyond the TS21 HR2 fragment in the soybean genome.

SEQ ID NO:56 is the nucleotide sequence of the sense primer, WOL121, which is upstream of the TS14 target site in the soybean genome.

SEQ ID NO:57 is the nucleotide sequence of the antisense primer, WOL150, which is downstream of the TS21 target site in the soybean genome.

SEQ ID NO:58 is the nucleotide sequence of the sense primer, WOL192, which is further upstream of the TS14 target site beyond the TS14 HR1 fragment in the soybean genome.

SEQ ID NO:59 is the nucleotide sequence of the antisense primer, WOL193, which is further downstream of the TS14 target site beyond the TS14 HR2 fragment in the soybean genome.

SEQ ID NO:60 is the nucleotide sequence of the sense primer, WOL113, which is upstream of the TS30 target site in the soybean genome.

SEQ ID NO:61 is the nucleotide sequence of the antisense primer, WOL114, which is downstream of the TS30 target site in the soybean genome.

SEQ ID NO:62 is the nucleotide sequence of the sense primer, WOL194, which is further upstream of the TS30 target site beyond the TS30 HR1 fragment in the soybean genome.

SEQ ID NO:63 is the nucleotide sequence of the antisense primer, WOL195, which is further downstream of the TS30 target site beyond the TS30 HR2 fragment in the soybean genome.

SEQ ID NO:64 is the nucleotide sequence of the sense primer, WOL105, which is upstream of the TS5 target site in the soybean genome.

SEQ ID NO:65 is the nucleotide sequence of the antisense primer, WOL144, which is downstream of the TS5 target site in the soybean genome.

SEQ ID NO:66 is the nucleotide sequence of the sense primer, WOL196, which is further upstream of the TS5 target site beyond the TS5 HR1 fragment in the soybean genome.

SEQ ID NO:67 is the nucleotide sequence of the antisense primer, WOL197, which is further downstream of the TS5 target site beyond the TS5 HR2 fragment in the soybean genome.

SEQ ID NO:68 is the nucleotide sequence of the MHP1 target site in the maize genome.

SEQ ID NO:69 is the nucleotide sequence of the MHP14 target site sequence in the maize genome.

SEQ ID NO:70 is the nucleotide sequence of the MHP32 target site sequence in the maize genome.

SEQ ID NO:71 is the nucleotide sequence of the MHP42 target site sequence in the maize genome.

SEQ ID NO:72 is the nucleotide sequence of the MHP55 target site sequence in the maize genome.

SEQ ID NO:73 is the nucleotide sequence of the MHP67 target site sequence in the maize genome.

SEQ ID NO:74 is the nucleotide sequence of the MHP77 target site sequence in the maize genome.

SEQ ID NO:75 is the nucleotide sequence of the MHP98 target sit sequence in the maize genome.

SEQ ID NO:76 is the nucleotide sequence of the MHP107 target site sequence in the maize genome.

SEQ ID NO: 77 is the nucleotide sequence of the MHP115 target site sequence in the maize genome.

SEQ ID NO:78 is the plant-optimized nucleotide sequence of MHP14 comprising a nuclear localization signal and lacking an intron.

SEQ ID NO:79 is the plant-optimized nucleotide sequence of the MHP14+ comprising a nuclear localization signal and lacking an intron.

SEQ ID NO:80 is the plant-optimized nucleotide sequence of MHP55 comprising a nuclear localization signal and an intron.

SEQ ID NO:81 is the plant-optimized nucleotide sequence of MHP55 comprising a nuclear localization signal and lacking an intron.

SEQ ID NO:82 is the plant-optimized nucleotide sequence of MHP55-2 comprising a nuclear localization signal and lacking an intron.

SEQ ID NO:83 plant-optimized nucleotide sequence of MHP77 comprising a nuclear localization signal and lacking an intron.

SEQ ID NO:84 is the HR1 of the MHP14 target site.
SEQ ID NO:85 is the HR2 of the MHP14 target site.
SEQ ID NO:86 is the HR1 of the MHP55 target site.
SEQ ID NO:87 is the HR2 of the MHP55 target site.
SEQ ID NO:88 is the HR1 of the MHP77 target site.
SEQ ID NO:89 is the HR2 of the MHP77 target site.
SEQ ID NO: 90 is the HR1 of the MHP1 target site.
SEQ ID NO:91: is the HR2 of the MHP1 target site.
SEQ ID NO:92 is the HR1 of the MHP32 target site.
SEQ ID NO:93 is the HR2 of the MHP32 target site.
SEQ ID NO:94 is the HR1 of the MHP42 target site.
SEQ ID NO:95 is the HR2 of the MHP42 target site.
SEQ ID NO:96 is the HR1 of the MHP67 target site.
SEQ ID NO:97 is the HR2 of the MHP67 target site.
SEQ ID NO:98 is the HR1 of the MHP98 target site.
SEQ ID NO:99 is the HR2 of the MHP98 target site.
SEQ ID NO:100 is the HR1 of the MHP107 target site.
SEQ ID NO:101 is the HR2 of the MHP107 target site.
SEQ ID NO:102 is the HR1 of the MHP115 target site.
SEQ ID NO:103 is the HR2 of the MHP115 target site.

SEQ ID NO:104 is the nucleotide sequence of the plasmid PHP44285 (MHP14 and donor DNA).

SEQ ID NO:105 is the nucleotide sequence of the plasmid PHP44779 (MHP14+ and donor DNA).

SEQ ID NO:106 is the nucleotide sequence of the MHP14TS probe.

SEQ ID NO:107 is the nucleotide sequence of the MHPTS14TS_Forward_MGB primer.

SEQ ID NO:108 is the nucleotide sequence of the MHPTS14TS_Reverse_MGB primer.

SEQ ID NO:109 is the nucleotide sequence of the primer 146775 on genomic HR1 side.

SEQ ID NO:110 is the nucleotide sequence of the primer 146773 on vector HR1 side.

SEQ ID NO:111 is the nucleotide sequence of the primer 146772 on genomic HR2 side.

SEQ ID NO:112 is the nucleotide sequence of the primer 146778 on vector HR2 side.

SEQ ID NO:113 is the nucleotide sequence of the primer mopatF2.

SEQ ID NO:114 is the nucleotide sequence of the primer mopatR2.

SEQ ID NO:115 is the nucleotide sequence of the MHP55TS probe sequence.

SEQ ID NO:116 is the nucleotide sequence of the MHPTS55_Forward_MGB primer.

SEQ ID NO:117 is the nucleotide sequence of the MHP55TS_Reverse_MGB primer.

SEQ ID NO:118 is the nucleotide sequence of the MHP77TS probe.

SEQ ID NO:119 is the nucleotide sequence of the MHP77TS_Forward_MGB primer.

SEQ ID NO:120 is the nucleotide sequence of the MHP77TS_Reverse_MGB primer.

DETAILED DESCRIPTION OF THE INVENTION

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

In the context of this disclosure, a number of terms and abbreviations are used. The following definitions are provided.

As used herein a "complex transgenic trait locus" (plural: "complex transgenic trait loci") is a chromosomal segment within a genomic region of interest that comprises at least two altered target sequences that are genetically linked to each other and can also comprise one or more polynucleotides of interest as described hereinbelow. Each of the altered target sequences in the complex transgenic trait locus originates from a corresponding target sequence that was altered, for example, by a mechanism involving a double-strand break within the target sequence that was induced by a double-strand break-inducing agent of the invention. In certain embodiments of the invention, the altered target sequences comprise a transgene.

As used herein, a "genomic region of interest" is a segment of a chromosome in the genome of a plant that is desirable for producing a complex transgenic trait locus or the segment of a chromosome comprising a complex transgenic trait locus that was produced by the methods of the invention. The genomic region of interest can include, for example, one or more polynucleotides of interest prior to producing a complex transgenic trait locus therein. Generally, a genomic region of interest of the present invention comprises a segment of chromosome that is 0-15 cM.

The term "recognition sequence" or "recognition site" as used herein refers to a DNA sequence at which a double-strand break is induced in the plant cell genome by a double-strand break inducing agent. The terms "recognition sequence" and "recognition site" are used interchangeably herein.

The terms "target site", "target sequence", "target locus", "genomic target site", "genomic target sequence", and "genomic target locus" as used interchangeably herein refer to a polynucleotide sequence in the genome of a plant cell that comprises a recognition sequence for a double-strand break inducing agent.

An "artificial target sequence" is a target sequence that has been introduced into the genome of a plant. Such an artificial target sequence can be identical in sequence to an endogenous or native target sequence in the genome of a plant but be located in a different position (i.e., a non-endogenous or non-native position) in the genome of a plant.

The terms "endogenous target sequence" and "native target sequence" are used interchangeable herein to refer to a target sequence that is endogenous or native to the genome of a plant and is at the endogenous or native position of that target sequence in the genome of the plant.

An "altered target sequence" refers to a target sequence as disclosed herein that comprises at least one alteration of the invention when compared to non-altered target sequence. Such "alterations" of the invention include, for example: (i) replacement of at least one nucleotide, (ii) a deletion of at least one nucleotide, (iii) an insertion of at least one nucleotide, or (iv) any combination of (i)-(iii).

The term "double-strand-break-inducing agent" as used herein refers to any nuclease which produces a double-strand break in the target sequence. Producing the double-strand break in a target sequence or other DNA can be referred to herein as "cutting" or "cleaving" the target sequence or other DNA. In some embodiments of the invention, the double-strand-break-inducing agent has been engineered (or modified) to cut a specific endogenous target sequence, wherein the endogenous target sequence prior to being cut by the engineered double-strand-break-inducing agent was not a sequence that would have been recognized by a native (non-engineered or non-modified) double-strand-break-inducing agent.

As used herein, "physically linked," "in physical linkage", and "genetically linked" are used to refer to any two or more genes, transgenes, native genes, mutated genes, alterations, target sites, markers, and the like that are part of the same DNA molecule or chromosome.

As used herein, a "polynucleotide of interest" within a genomic region of interest is any coding and/or non-coding portion of the genomic region of interest including, but not limited to, a transgene, a native gene, a mutated gene, and a genetic marker such as, for example, a single nucleotide polymorphism (SNP) marker and a simple sequence repeat (SSR) marker.

"Open reading frame" is abbreviated ORF.

As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to polypeptide or nucleic acid fragments wherein changes in one or more amino acids or nucleotide bases do not affect the function of the molecule, such as the ability to mediate gene expression or to produce a certain phenotype. These terms also refer to modification(s) of nucleic acid fragments that do not substantially alter the functional properties of the resulting nucleic acid fragment relative to the initial, unmodified fragment. These modifications include deletion, substitution, and/or insertion of one or more nucleotides in the nucleic acid fragment.

Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence in an in vitro hybridization assay. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salt(s)) at pH 7.0 to 8.3, and at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth et al., (1984) *Anal Biochem* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology-Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120 or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, WI). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) *CABIOS* 5:151-153; Higgins et al., (1992) *Comput Appl Biosci* 8:189-191) and found in the MegAlign™ program of the LASERGENE bioinformatics computing suite (DNASTAR Inc., Madison, WI). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) *CABIOS* 5:151-153; Higgins et al., (1992) *Comput Appl Biosci* 8:189-191) and found in the MegAlign™ v6.1 program of the LASERGENE bioinformatics computing suite (DNASTAR Inc., Madison, WI). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, CA) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) *Proc. Natl. Acad. Sci. USA* 89:10915). GAP uses the algorithm of Needleman and Wunsch, (1970) *J Mol Biol* 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

BLAST® is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST® reports the identified sequences and their local alignment to the query sequence.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature, or at a different genetic locus than that found in nature. A "foreign" gene refers to a gene not normally found in the host organism, but that is introduced into the host organism by gene transfer. Foreign genes can comprise native genes inserted into a non-native organism, or chimeric genes.

A "mutated gene" is a native gene that has been altered through human intervention. Such a "mutated gene" has a sequence that differs from the sequence of the corresponding native gene by at least one nucleotide addition, deletion, or substitution. In certain embodiments of the invention, the mutated gene comprises an alteration that results from a double-strand-break-inducing agent as disclosed herein.

A "transgene" is a gene that has been introduced into the genome by a transformation procedure. A transgene can, for example encode one or more proteins or RNA that is not translated into protein. However, a transgene of the invention need not encode a protein and/or non-translated RNA. In certain embodiments of the invention, the transgene comprises one or more chimeric genes, including chimeric genes comprising, for example, a gene of interest, phenotypic marker, a selectable marker, and a DNA for gene silencing.

As used herein, a "targeted mutation" is mutation in a native gene that was made by altering a target sequence within the native gene using a method involving a double-strand-break-inducing agent that is capable of inducing a double-strand break in the DNA of the target sequence as disclosed herein or known in the art.

The term "genome" as it applies to a plant cells encompasses not only chromosomal DNA found within the nucleus, but organelle DNA found within subcellular components (e.g., mitochondria, or plastid) of the cell.

A "codon-modified gene" or "codon-preferred gene" or "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, 5' untranslated sequences, 3' untranslated sequences, introns, polyadenylation recognition sequences, RNA processing sites, effector binding sites, and stem-loop structures.

"A plant-optimized nucleotide sequence" is nucleotide sequence that has been optimized for increased expression in plants, particularly for increased expression in plants or in one or more plants of interest. For example, a plant-optimized nucleotide sequence can be synthesized by modifying a nucleotide sequence encoding a protein such as, for example, double-strand-break-inducing agent (e.g., an endonuclease) as disclosed herein, using one or more plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference. Additional sequence modifications are known to enhance gene expression in a plant host. These include, for example, elimination of: one or more sequences encoding spurious polyadenylation signals, one or more exon-intron splice site signals, one or more transposon-like repeats, and other such well-characterized sequences that may be deleterious to gene expression. The G-C content of the sequence may be adjusted to levels average for a given plant host, as calculated by reference to known genes expressed in the host plant cell. When possible, the sequence is modified to avoid one or more predicted hairpin secondary mRNA structures. Thus, "a plant-optimized nucleotide sequence" of the present invention comprises one or more of such sequence modifications.

"Promoter" refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro and Goldberg, (1989) *In The Biochemistry of Plants*, Vol. 115, Stumpf and Conn, eds (New York, NY: Academic Press), pp. 1-82.

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (e.g., Turner and Foster, (1995) *Mol Biotechnol* 3:225-236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook et al., *Molecular Cloning: A Laboratory Manual*; Cold Spring Harbor Laboratory:

Cold Spring Harbor, NY (1989). Transformation methods are well known to those skilled in the art and are described infra.

"PCR" or "polymerase chain reaction" is a technique for the synthesis of specific DNA segments and consists of a series of repetitive denaturation, annealing, and extension cycles. Typically, a double-stranded DNA is heat denatured, and two primers complementary to the 3' boundaries of the target segment are annealed to the DNA at low temperature, and then extended at an intermediate temperature. One set of these three consecutive steps is referred to as a "cycle".

The term "recombinant" refers to an artificial combination of two otherwise separated segments of sequence, e.g., by chemical synthesis, or manipulation of isolated segments of nucleic acids by genetic engineering techniques.

The terms "plasmid", "vector" and "cassette" refer to an extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for expression of that gene in a foreign host.

The terms "recombinant DNA molecule", "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not all found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) *EMBO J* 4:2411-2418; De Almeida et al., (1989) *Mol Gen Genetics* 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

The term "expression", as used herein, refers to the production of a functional end-product (e.g., an mRNA or a protein) in either precursor or mature form.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or other DNA-containing organelle, of a host organism resulting in gene expression without integration or stable inheritance. Host organisms containing the transformed nucleic acid fragments are referred to as "transgenic" organisms.

As used herein, "transgenic" refers to a plant or a cell which comprises within its genome a heterologous polynucleotide. Typically, the heterologous polynucleotide is stably integrated within the genome such that the polynucleotide is passed on to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant. The term "genome" refers to the entire complement of genetic material (genes and non-coding sequences) that is present in each cell of an organism, or virus or organelle; and/or a complete set of chromosomes inherited as a (haploid) unit from one parent. "Progeny" comprises any subsequent generation of a plant.

A "fertile plant" is a plant that is capable of producing a progeny plant. In certain embodiments of the invention, a fertile plant is a plant that produces viable male and female gametes and is self fertile. Such a self-fertile plant can produce a progeny plant without the contribution from any other plant of a gamete and the genetic material contained therein. Other embodiments of the invention can involve the use of a plant that is not self fertile because the plant does not produce male or female gametes that are viable or otherwise capable of fertilization. As used herein, a "male sterile plant" is a plant that does not produce male gametes that are viable or otherwise capable of fertilization. As used herein, a "female sterile plant" is a plant that does not produce female gametes that are viable or otherwise capable of fertilization. It is recognized that male and female sterile plants can be female and mail fertile, respectively. It is further recognized that a male fertile (but female sterile) plant can produce viable progeny when crossed with a female fertile plant and that a female fertile (but male sterile) plant can produce viable progeny when crossed with a male fertile plant.

A "centimorgan" (cM) or "map unit" is the distance between two linked genes, markers, target sites, loci, or any pair thereof, wherein 1% of the products of meiosis are recombinant. Thus, a centimorgan is equivalent to a distance equal to an 1% average recombination frequency between the two linked genes, markers, target sites, loci, or any pair thereof.

The present invention finds use in the breeding of plants comprising two to more transgenic traits. Currently, transgenic traits are randomly inserted throughout the plant genome as a consequence of transformation systems based on *Agrobacterium*, biolistics, or other commonly used procedures. More recently, gene targeting protocols have been developed that enable directed transgene insertion. One important technology, site-specific integration (SSI) enables the targeting of a transgene to the same chromosomal location as a previously inserted transgene. Custom-designed meganucleases and custom-designed zinc finger meganucleases allow researchers to design nucleases to target specific chromosomal locations, and these reagents allow the targeting of transgenes at the chromosomal site cleaved by these nucleases.

As disclosed herein, nuclease-mediated gene targeting can be used in methods for producing complex transgenic trait loci comprising multiple transgenes. In one embodiment of the invention, a complex transgenic trait locus is a locus that has multiple transgenes genetically linked to each other. By inserting independent transgenes within 1, 2 or even 5 centimorgans (cM) from each other, the transgenes can be bred as single genetic locus. FIG. 7 depicts the process of how two traits could be integrated into the genome at a genetic distance of, for example, 0.2 cM from each other in independent transformation runs or in sequential transformations (e.g., transformation and re-transformation). After selecting the events, plants containing the two events can be crossed to form an F1 that contains the events on different chromosomes. In progeny from these F1 (F2 or BC1) 1/500 progeny would have the two different transgenes recombined onto the same chromosome. The complex locus could then be bred as single genetic locus with both transgene traits. This process could be repeated to stack as many traits as desired.

The present invention provides methods for producing complex transgenic trait loci at selected genomic regions to simplify breeding with multiple transgenes. To initiate the development of a complex transgenic trait locus, a region of the genome is first selected. Second, the sequence of nearby genomic regions is compiled and nuclease reagents designed to facilitate targeting additional transgenes to those closely linked sites. Subsequently, algorithms for nuclease design such as, for example, those described in U.S. Patent Application Publication No. 2007/0117128 A1 are used to select potential target sites. Additional bioinformatic analysis such as, for example, copy number of the site in the target genome, location of the site relative to known gene coding regions and other factors could be used to filter the sites to a subset of preferred sites. Nucleases could then be used to target new transgenes to these preferred sites using published protocols See, for example, Halluin et al. (2008) *Plant Biotechnol. J.* 6:93-102; Shukla et al. (2009) *Nature* doi: 10.1038/nature07992; Wright et al. *Plant J.* (2005) 44:693-705; and WO 2009/006297); all of which are herein incorporated by reference.

In a first aspect, the present invention provides methods for producing in a plant a complex transgenic trait locus comprising at least two altered target sequences in a genomic region of interest. In one embodiment, the methods involve selecting a genomic region in a plant that comprises a first target sequence and a second target sequence. Generally, the first target sequence and the second target sequence are separated from each other by about 0.1, 0.2, 0.3, 0.4, 0.5, 0.6, 0.7, 0.8, 0.9, 1, 2, 3, 4, or 5 centimorgans (cM) in the genome of the plant. In certain embodiments of the invention, the first and second target sequences are physically linked to a polynucleotide of interest such as, for example, a transgene, native gene, or a gene with a targeted mutation, that is within about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, or 21 cM of the first and/or the second target sequence.

The methods of the invention further involve providing a first double-strand-break-inducing agent and a second double-strand-break-inducing agent. The first double-strand-break-inducing agent is capable of inducing a first double-strand break in DNA comprising the first target sequence, and the second double-strand-break-inducing agent is capable of inducing a second double-strand break in DNA comprising the second target sequence. The methods of the invention do not depend on a particular double-strand-break-inducing agent but only that the double-strand-break-inducing agent is capable of inducing a double-strand break in DNA in a target sequence of the invention. Any such double-strand-break-inducing agent that is disclosed herein or known in the art can be used in the methods of the present invention.

Additionally, the methods involve contacting at least one plant cell with the first double-strand-break-inducing agent, identifying a cell comprising a first alteration at the first target sequence, and then recovering a first fertile plant from the cell comprising the first alteration. The first fertile plant also comprises the first alteration. Additionally, the method involves contacting at least one plant cell with the second double-strand-break-inducing agent, identifying a cell comprising a second alteration at the second target sequence, and then recovering a second fertile plant from the cell comprising the second alteration. The method further involves obtaining a fertile progeny plant from the second fertile plant, wherein the fertile progeny plant comprises both the first and second alterations in physical linkage.

In one embodiment of this method, the fertile progeny plant is obtained by crossing the first fertile plant and the second fertile plant and selecting for a fertile progeny plant comprising both the first and second alterations in physical linkage. In another embodiment, a cell of the first fertile plant, or progeny thereof comprising the first alteration, is contacted with the second double-strand-break-inducing agent, and the second fertile plant comprises both the first and second alterations, which may or may not be physically linked. If necessary, the second fertile plant can be selfed and a fertile progeny plant selected comprising both the first and second alterations in physical linkage.

The first and second alterations are selected from the group consisting of (i) replacement of at least one nucleotide, (ii) a deletion of at least one nucleotide, (iii) an insertion of at least one nucleotide, and (iv) any combination of (i)-(iii). In one embodiment of the invention, the first and/or the second alterations comprise insertion of a DNA sequence of interest including, but not limited to, a DNA for gene silencing, a DNA encoding a phenotypic marker, and a DNA encoding a protein providing an agronomic advantage. In another embodiment, the first and/or the second alterations comprise a targeted mutation in a native gene.

In a like manner, the methods disclosed herein can be used to produce in a plant a complex transgenic trait locus comprising 1, 2, 3, 4, 5, 6, 7, 8, 9, 10, or more altered target sequences in physical linkage in a genomic region of interest comprising 1, 2, 3, 4, 5, 6, 7, 8, 9, 10, or more target sequences of interest. Each additional target sequence of interest in the genomic region of interest can be recognized and cleaved by a double-strand-break-inducing agent essentially as described above.

For example, a third DNA sequence of interest is inserted into a third target sequence by contacting at least one cell of a plant with a third double-strand-break-inducing agent and a third DNA molecule comprising the DNA sequence of interest, and then identifying a cell comprising the DNA sequence of interest. The method can further comprising recovering a fertile plant comprising the third DNA sequence of interest. In one embodiment, the cell comprising the third DNA sequence of interest comprises the first alteration, the second alteration, or both the first alteration and the second alteration. The method of the invention can further comprising producing a fertile plant comprising the first alteration, the second alteration, and the third DNA sequence of interest in physical linkage. In another embodiment, the fertile plant comprising the first alteration, the second alteration, and the third DNA sequence of interest is produced by crossing the fertile plant comprising the first and second alterations with a second fertile plant comprising the third DNA sequence of interest, and selecting a fertile progeny plant from the crossing, wherein the fertile progeny plant comprises the first alteration, the second alteration, and the third DNA sequence of interest in physical linkage.

The fertile plant comprising the first alteration, the second alteration, and the third DNA sequence of interest can be produced, for example, by: (i) contacting a cell comprising the first alteration and the second alteration with the third double-strand-break-inducing agent; (ii) identifying a cell from (i) comprising the third DNA sequence of interest, wherein the cell comprises the first alteration and the second alteration, and wherein the first alteration, the second alteration, and the third DNA sequence of interest are physically linked; and (iii) recovering a fertile plant comprising in physical linkage the first alteration, the second alteration, and the third DNA sequence of interest.

In another embodiment of the invention, the methods for producing in a plant a complex transgenic trait locus comprising at least two altered target sequences in a genomic region of interest that involve obtaining a first fertile plant comprising a first altered target site at the genomic region of interest and a second fertile plant comprising a second altered target site at the genomic region of interest. In this method, the first altered target sequence originated from a first target sequence that is recognized and cleaved by a first double-strand-break-inducing agent, and the second altered target sequence originated from a second target sequence that is recognized and cleaved by a second double-strand-break-inducing agent. The second method further involves crossing the first fertile plant and the second fertile plant, and then selecting from the crossing a fertile progeny plant comprising the first alteration and the second alteration in physical linkage.

The second method can optionally involve crossing the fertile progeny plant with an additional fertile plant that comprises at least a third altered target sequence in the genomic region of interest and then selecting from the crossing a fertile progeny plant comprising the first alteration, the second and the at least third alteration in physical linkage. Like the first and second altered target sequences, the third altered target sequence originated from a third target sequence that is recognized and cleaved by a third double-strand-break-inducing agent. In a like manner, a complex transgenic trait locus can be produced comprising 4, 5, 6, 7, 8, 9, 10, or more altered target sequences in physical linkage in the genomic region of interest.

In another aspect, the present invention provides complex transgenic trait loci in plants as well as plants, plant parts, plant cells, and seeds comprising at least one complex transgenic trait locus of the invention. A complex transgenic trait locus of the invention comprises at least two altered target sequences that are genetically linked to a polynucleotide of interest. Such altered target sequences originated from a corresponding target sequence that is recognized and cleaved by a double-strand-break-inducing agent using, for example, the methods disclosed herein. The altered target sequences comprise an alteration such as, for example, replacement of at least one nucleotide in the target sequence, a deletion of at least one nucleotide in the target sequence, an insertion of at least one nucleotide in the target sequence, or any combination thereof. The polynucleotide interest can be, for example, a transgene, a native gene, and a mutated gene. The present invention provides plants, plant parts, plant cells, and seeds comprising at least one complex transgenic trait locus of the invention.

In one embodiment, a complex transgenic trait locus of the invention comprises at least one altered target sequence comprising a recombinant DNA molecule. Recombinant DNA molecules of the invention include, but are not limited to, a DNA for gene silencing, a DNA encoding a phenotypic marker, and a DNA encoding a protein providing an agronomic advantage.

Generally, each of the altered target sites of the complex transgenic trait locus are located within about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, or 21 centimorgan (cM) of the polynucleotide of interest.

The methods of the present invention involve the use of one or more double-strand break inducing agents. A double-strand break inducing agent of the present invention is any agent that recognizes and/or binds to a specific polynucleotide recognition sequence to produce a break in the target sequence at or near the recognition sequence. Examples of double-strand break inducing agents include, but are not limited to, endonucleases, TAL effector nucleases, and zinc finger nucleases, and include modified derivatives, variants, and fragments thereof.

A recognition sequence is any polynucleotide sequence that is specifically recognized and/or bound by a double-strand break inducing agent. The length of the recognition site sequence can vary, and includes, for example, sequences that are at least 4, 6, 8, 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length.

It is possible that the recognition site could be palindromic, that is, the sequence on one strand reads the same in the opposite direction on the complementary strand. The nick/cleavage site could be within the recognition sequence or the nick/cleavage site could be outside of the recognition sequence. In another variation, the cleavage could occur at nucleotide positions immediately opposite each other to produce a blunt end cut or, in other cases, the incisions could be staggered to produce single-stranded overhangs, also called "sticky ends", which can be either 5' overhangs, or 3' overhangs. The recognition sequence can be endogenous or exogenous. When the recognition site is an endogenous sequence, it may be a recognition sequence recognized by a naturally-occurring, or native double-strand break inducing agent. Alternatively, an endogenous recognition site could be recognized and/or bound by a modified or engineered double-strand break inducing agent designed or selected to specifically recognize the endogenous recognition sequence to produce a double-strand break. A modified double-strand break inducing agent can be derived from a native, naturally-occurring double-strand break inducing agent or it could be artificially created or synthesized.

A variety of methods are available to identify those cells having an altered genome at or near the recognition sequence without using a screenable marker phenotype. Such methods can be viewed as directly analyzing a recognition sequence to detect any change in the recognition sequence, including but not limited to PCR methods, sequencing methods, nuclease digestion, Southern blots, and any combination thereof.

Proteins may be altered in various ways including amino acid substitutions, deletions, truncations, and insertions. Methods for such manipulations are generally known. For example, amino acid sequence variants of the protein(s) can be prepared by mutations in the DNA. Methods for mutagenesis and nucleotide sequence alterations include, for example, Kunkel, (1985) *Proc. Natl. Acad. Sci. USA* 82:488-92; Kunkel et al., (1987) *Meth Enzymol* 154:367-82; U.S. Pat. No. 4,873,192; Walker and Gaastra, eds. (1983) *Techniques in Molecular Biology* (MacMillan Publishing Company, New York) and the references cited therein. Guidance regarding amino acid substitutions not likely to affect biological activity of the protein is found, for example, in the model of Dayhoff et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double-strand-break-inducing activity are known and generally measure the overall activity and specificity of the agent on DNA substrates containing recognition sites.

Endonucleases are enzymes that cleave the phosphodiester bond within a polynucleotide chain, and include restriction endonucleases that cleave DNA as specific sites without damaging the bases. Restriction endonucleases include Type I, Type II, Type III, and Type IV endonucleases, which further include subtypes. In the Type I and Type III systems, both the methylase and restriction activities are contained in a single complex.

Type I and Type III restriction endonucleases recognize specific recognition sites, but typically cleave at a variable position from the recognition site, which can be hundreds of base pairs away from the recognition site. In Type II systems the restriction activity is independent of any methylase activity, and cleavage typically occurs at specific sites within or near to the recognition site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site.

Type IV restriction enzymes target methylated DNA. Restriction enzymes are further described and classified, for example in the REBASE database (webpage at rebase.neb.com; Roberts et al., (2003) *Nucleic Acids Res* 31:418-20), Roberts et al., (2003) *Nucleic Acids Res* 31:1805-12, and Belfort et al., (2002) in *Mobile DNA II*, pp. 761-783, Eds. Craigie et al., (ASM Press, Washington, DC).

Endonucleases also include meganucleases, also known as homing endonucleases (HEases), which like restriction endonucleases, bind and cut at a specific recognition sequence, however the recognition sites for meganucleases are typically longer, about 18 bp or more. Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. For example, intron-, intein-, and freestanding gene encoded meganuclease from *Saccharomyces cerevisiae* are denoted I-SceI, PI-SceI, and F-SceII, respectively. Meganuclease domains, structure and function are known, see for example, Guhan and Muniyappa (2003) *Crit Rev Biochem Mol Biol* 38:199-248; Lucas et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure et al., (2002) *Nat Struct Biol* 9:764. In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat et al., (2003) *Nucleic Acids Res* 31:2952-62; Chevalier et al., (2002) *Mol Cell* 10:895-905; Gimble et al., (2003) *Mol Biol* 334:993-1008; Seligman et al., (2002) *Nucleic Acids Res* 30:3870-9; Sussman et al., (2004) *J Mol Biol* 342:31-41; Rosen et al., (2006) *Nucleic Acids Res* 34:4791-800; Chames et al., (2005) *Nucleic Acids*

*Res* 33:e178; Smith et al., (2006) *Nucleic Acids Res* 34:e149; Gruen et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346.

Any meganuclease can be used as a double-strand break inducing agent including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, 1-PobIP, I-PorI, 1-PorIIP, I-PbpIP, I-SpBetaIP, I-ScaI, I-SexIP, I-SneIP, I-SpomI, I-SpomCP, 1-SpomIP, 1-SpomIIP, I-SquIP, I-Ssp68031, I-SthPhiJP, I-SthPhiST3P, I-SthPhiSTe3bP, I-TdeIP, I-TevI, 1-TevII, 1-TevIII, I-UarAP, I-UarHGPA1P, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any variant or derivative thereof.

The endonuclease can be a modified endonuclease that binds a non-native or exogenous recognition sequence and does not bind a native or endogenous recognition sequence. Modification of the endonuclease can be as little as one nucleotide. A modified endonuclease is not capable of making a double-strand break within a wild-type target sequence. A wild-type (i.e., prior to being modified) endonuclease is capable of making a double-strand break within the wild-type target sequence.

The endonuclease can be provided via a polynucleotide encoding the endonuclease. Such a polynucleotide encoding an endonuclease can be modified to substitute codons having a higher frequency of usage in a plant, as compared to the naturally occurring polynucleotide sequence. For example the polynucleotide encoding the endonuclease can be modified to substitute codons having a higher frequency of usage in a maize or soybean plant, as compared to the naturally occurring polynucleotide sequence.

A site-specific recombinase, also referred to as a recombinase, is a polypeptide that catalyzes conservative site-specific recombination between its compatible recombination sites, and includes native polypeptides as well as derivatives, variants and/or fragments that retain activity, and native polynucleotides, derivatives, variants, and/or fragments that encode a recombinase that retains activity.

One step in the recombination process involves polynucleotide cleavage at or near the recognition site. This cleaving activity can be used to produce a double-strand break. For reviews of site-specific recombinases and their recognition sites, see, Sauer (1994) *Curr Op Biotechnol* 5:521-7; and Sadowski (1993) *FASEB* 7:760-7. In some examples the recombinase is from the Integrase or Resolvase families.

The Integrase family of recombinases has over one hundred members and includes, for example, FLP, Cre, lambda integrase, and R. The Integrase family has been grouped into two classes based on the structure of the active sites, serine recombinases and tyrosine recombinases. The tyrosine family, which includes Cre, FLP, SSV1, and lambda (λ) integrase, uses the catalytic tyrosine's hydroxyl group for a nucleophilic attack on the phosphodiester bond of the DNA. Typically, members of the tyrosine family initially nick the DNA, which later forms a double-strand break. In the serine recombinase family, which includes phiC31 (ΦC31) integrase, a conserved serine residue forms a covalent link to the DNA target site (Grindley et al., (2006) *Ann Rev Biochem* 16:16). For other members of the Integrase family, see for example, Esposito et al., (1997) *Nucleic Acids Res* 25:3605-14 and Abremski et al., (1992) *Protein Eng* 5:87-91.

Other recombination systems include, for example, the streptomycete bacteriophage phiC31 (Kuhstoss et al., (1991) *J Mol Biol* 20:897-908); the SSV1 site-specific recombination system from *Sulfolobus shibatae* (Maskhelishvili et al., (1993) *Mol Gen Genet* 237:334-42); and a retroviral integrase-based integration system (Tanaka et al., (1998) *Gene* 17:67-76).

Sometimes the recombinase is one that does not require cofactors or a supercoiled substrate, including but not limited to Cre, FLP, and active derivatives, variants or fragments thereof. FLP recombinase catalyzes a site-specific reaction during DNA replication and amplification of the two-micron plasmid of *S. cerevisiae*. FLP recombinase catalyzes site-specific recombination between two FRT sites. The FLP protein has been cloned and expressed (Cox (1993) *Proc. Natl. Acad. Sci. USA* 80:4223-7). Functional derivatives, variants, and fragments of FLP are known (Buchholz et al., (1998) *Nat Biotechnol* 16:617-8, Hartung et al., (1998) *J Biol Chem* 273:22884-91, Saxena et al., (1997) *Biochim Biophys Acta* 1340:187-204, and Hartley et al., (1980) *Nature* 286:860-4).

The bacteriophage recombinase Cre catalyzes site-specific recombination between two lox sites (Guo et al., (1997) *Nature* 389:40-6; Abremski et al., (1984) *J Biol Chem* 259:1509-14; Chen et al., (1996) *Somat Cell Mol Genet* 22:477-88; Shaikh et al., (1977) *J Biol Chem* 272:5695-702; and Buchholz et al., (1998) *Nat Biotechnol* 16:617-8). Examples of site-specific recombinases that can be used to produce a double-strand break at a recognition sequence, including for example FLP, Cre, SSV1, lambda Int, phi C31, HK022, and R. Examples of site-specific recombination systems used in plants can be found in U.S. Pat. Nos. 5,929,301; 6,175,056; WO99/25821; U.S. Pat. No. 6,331,661; WO99/25855; WO99/25841, and WO99/25840, the contents of each are herein incorporated by reference.

Methods for modifying the kinetics, cofactor interaction and requirements, expression, optimal conditions, and/or recognition site specificity, and screening for activity of recombinases and variants are known, see for example Miller et al., (1980) *Cell* 20:721-9; Lange-Gustafson and Nash, (1984) *J Biol Chem* 259:12724-32; Christ et al., (1998) *J Mol Biol* 288:825-36; Lorbach et al., (2000) *J Mol Biol* 296:1175-81; Vergunst et al., (2000) *Science* 290:979-82; Dorgai et al., (1995) *J Mol Biol* 252:178-88; Dorgai et al., (1998) *J Mol Biol* 277:1059-70; Yagu et al., (1995) *J Mol Biol* 252:163-7; Sclimente et al., (2001) *Nucleic Acids Res* 29:5044-51; Santoro and Schultze, (2002) *Proc. Natl. Acad. Sci. USA* 99:4185-90; Buchholz and Stewart, (2001) *Nat Biotechnol* 19:1047-52; Voziyanov et al., (2002) *Nucleic Acids Res* 30:1656-63; Voziyanov et al., (2003) *J Mol Biol* 326:65-76; Klippel et al., (1988) *EMBO J* 7:3983-9; Arnold et al., (1999) *EMBO J* 18:1407-14; WO03/08045; WO99/25840; and WO99/25841. The recognition sites range from about 30 nucleotide minimal sites to a few hundred nucleotides.

Any recognition site for a recombinase can be used, including naturally occurring sites, and variants. Variant recognition sites are known, see for example Hoess et al., (1986) *Nucleic Acids Res* 14:2287-300; Albert et al., (1995) *Plant J* 7:649-59; Thomson et al., (2003) *Genesis* 36:162-7; Huang et al., (1991) *Nucleic Acids Res* 19:443-8; Siebler and Bode, (1997) *Biochemistry* 36:1740-7; Schlake and Bode, (1994) *Biochemistry* 33:12746-51; Thygarajan et al., (2001) *Mol Cell Biol* 21:3926-34; Umlauf and Cox, (1988) *EMBO J* 7:1845-52; Lee and Saito, (1998) *Gene* 216:55-65; WO01/23545; WO99/25821; WO99/25851; WO01/11058; WO01/07572 and U.S. Pat. No. 5,888,732.

A recombinase can be provided via a polynucleotide that encodes the recombinase or it can be provided via a modified polynucleotide encoding the recombinase. For example, the polynucleotide (encoding a recombinase) can be modified to substitute codons having a higher frequency of usage in a plant, as compared to the naturally occurring polynucleotide sequence or it can be modified to substitute codons having a higher frequency of usage in a maize or soybean plant, as compared to the naturally occurring polynucleotide sequence.

TAL effector nucleases are a new class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) *PNAS* 10.1073/pnas.1013133107; Scholze & Boch (2010) *Virulence* 1:428-432; Christian et al. *Genetics* (2010) 186:757-761; Li et al. (2010) *Nuc. Acids Res*. (2010) doi:10.1093/nar/gkq704; and Miller et al. (2011) *Nature Biotechnology* 29:143-148; all of which are herein incorporated by reference.

Transposases are polypeptides that mediate transposition of a transposon from one location in the genome to another. Transposases typically induce double-strand breaks to excise the transposon, recognize subterminal repeats, and bring together the ends of the excised transposon, in some systems other proteins are also required to bring together the ends during transposition.

Examples of transposons and transposases include, but are not limited to, the Ac/Ds, Dt/rdt, Mu-M1/Mn, and Spm(En)/dSpm elements from maize, the Tam elements from snapdragon, the Mu transposon from bacteriophage, bacterial transposons (Tn) and insertion sequences (IS), Ty elements of yeast (retrotransposon), Tal elements from *Arabidopsis* (retrotransposon), the P element transposon from *Drosophila* (Gloor et al., (1991) *Science* 253:1110-1117), the Copia, Mariner and Minos elements from *Drosophila*, the Hermes elements from the housefly, the PiggyBack elements from Trichplusia ni, Tc1 elements from *C. elegans*, and IAP elements from mice (retrotransposon). In some examples the transposase is provided via a polynucleotide that encodes the transposase.

It is possible to modify the polynucleotide encoding the transposase by substituting codons having a higher frequency of usage in a plant, as compared to the naturally occurring polynucleotide sequence of by substituting codons having a higher frequency of usage in a maize or soybean plant, as compared to the naturally occurring polynucleotide sequence.

DNA topoisomerases modulate DNA secondary and higher order structures and functions related primarily to replication, transcription, recombination and repair. Topoisomerases share two characteristics: (i) the ability to cleave and reseal the phosphodiester backbone of DNA in two successive transesterification reactions; and (ii) once a topoisomerase cleaved DNA intermediate is formed, the enzyme allows the severed DNA ends to come apart, allowing the passage of another single- or double-stranded DNA segment. DNA topoisomerases can be classified into three evolutionary independent families: type IA, type IB and type II.

Those that cleave one strand of DNA and allow single step changes in the linking number of circular DNA are defined as type I DNA topoisomerases. The *Escherichia coli* topoisomerase I and topoisomerase III, *Saccharomyces cerevisiae* topoisomerase III and reverse gyrase belong to the type IA or type 1-5' subfamily as the protein link is to a 5' phosphate in the DNA. The prototype of type IB or 1-3' enzymes are found in all eukaryotes and also in vaccinia virus topoisomerase I where the protein is attached to a 3' phosphate. Despite differences in mechanism and specificity between the bacterial and eukaryotic enzymes, yeast DNA topoisomerase I can complement a bacterial DNA topoisomerase I mutant (Bjornsti et al., (1987) *Proc. Natl. Acad. Sci. USA* 84:8971-5). Type IA topoisomerases relax negatively supercoiled DNA and require magnesium and a single-stranded region of DNA. Topoisomerases IB relax both positively and negatively supercoiled DNA with equal efficiency and do not require a single-stranded region of DNA or metal ions for function.

The type II family includes *E. coli* DNA gyrase, *E. coli* topoisomerase IV (par E), eukaryotic type II topoisomerases, and archaic topoisomerase VI. Type II enzymes are homodimeric (eukaryotic topoisomerase II) or tetrameric (gyrase), cleaving both strands of a duplex. Preferred cutting sites are known for available topoisomerases.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs consist of an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind a 18 nucleotide recognition sequence. A recognition sequence of 18 nucleotides is long enough to be unique in a mammalian genome ($4^{18}$=6.9×$10^{10}$).

To date, designer zinc finger modules predominantly recognize GNN and ANN triplets (Dreier et al., (2001) *J Biol Chem* 276:29466-78; Dreier et al., (2000) *J Mol Biol* 303:489-502; Liu et al., (2002) *J Biol Chem* 277:3850-6), but examples using CNN or TNN triplets are also known (Dreier et al., (2005) *J Biol Chem* 280:35588-97; Jamieson et al., (2003) *Nature Rev Drug Discov* 2:361-8). See also, Durai et al., (2005) *Nucleic Acids Res* 33:5978-90; Segal, (2002) *Methods* 26:76-83; Porteus and Carroll, (2005) *Nat Biotech-* nol 23:967-73; zinc-finger consortium (website at www.zincfinger.org); Pabo et al., (2001) *Ann Rev Biochem* 70:313-40; Wolfe et al., (2000) *Ann Rev Biophys Biomol Struct* 29:183-212; Segal and Barbas, (2001) *Curr Opin Biotechnol* 12:632-7; Segal et al., (2003) *Biochemistry* 42:2137-48; Beerli and Barbas, (2002) *Nat Biotechnol* 20:135-41; Carroll et al., (2006) *Nature Protocols* 1:1329; Ordiz et al., (2002) *Proc. Natl. Acad. Sci. USA* 99:13290-5; Guan et al., (2002) *Proc. Natl. Acad. Sci. USA* 99:13296-301; WO2002099084; WO00/42219; WO02/42459; WO2003062455; U.S. Patent Application Publication No. 20030059767; U.S. Patent Application Publication No. 2003/0108880; U.S. Pat. Nos. 6,140,466, 6,511,808 and 6,453,242.

Alternatively, engineered zinc finger DNA binding domains can be fused to other double-strand break inducing agents or derivatives thereof that retain DNA nicking/cleaving activity. For example, this type of fusion can be used to direct the double-strand break inducing agent to a different target site, to alter the location of the nick or cleavage site, to direct the inducing agent to a shorter target site, or to direct the inducing agent to a longer target site. In some examples a zinc finger DNA binding domain is fused to a site-specific recombinase, transposase, topoisomerase, or a derivative thereof that retains DNA nicking and/or cleaving activity.

It is possible to provide a zinc-finger nuclease via a polynucleotide that encodes the zinc-finger nuclease. This polynucleotide encoding the zinc-finger nuclease can be modified by substituting codons having a higher frequency of usage in a plant, as compared to the naturally occurring polynucleotide sequence or by substituting codons having a higher frequency of usage in a maize or soybean plant, as compared to the naturally occurring polynucleotide sequence.

Sufficient homology or sequence identity indicates that two polynucleotide sequences have sufficient structural similarity to act as substrates for a homologous recombination reaction. The structural similarity includes overall length of each polynucleotide fragment, as well as the sequence similarity of the polynucleotides.

Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bp. The amount of homology can also described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) *Molecular Cloning: A Laboratory Manual*, (Cold Spring Harbor Laboratory Press, NY); *Current Protocols in Molecular Biology*, Ausubel et al., Eds (1994) *Current Protocols*, (Greene Publishing Associates, Inc. and John Wiley & Sons, Inc); and, Tijssen (1993) *Laboratory Techniques in Biochemistry and Molecular Biology-Hybridization with Nucleic Acid Probes*, (Elsevier, New York).

Any means can be used to bring together the various components needed to alter the genome of a dicot plant cell. For example, in in vitro systems, the double-strand-break-inducing agent and the polynucleotide(s) comprising the recognition site(s) can be provided by contacting the components under the appropriate conditions for DNA cleavage.

Alternatively a variety of methods are known for the introduction of nucleotide sequences and polypeptides into an organism, including, for example, transformation, sexual crossing, and the introduction of the polypeptide, DNA, or mRNA into the cell.

Methods for contacting, providing, and/or introducing a composition into various organisms are known and include but are not limited to, stable transformation methods, transient transformation methods, virus-mediated methods, and sexual breeding. Stable transformation indicates that the introduced polynucleotide integrates into the genome of the organism and is capable of being inherited by progeny thereof.

Transient transformation indicates that the introduced composition is only temporarily expressed or present in the organism.

Protocols for introducing polynucleotides and polypeptides into plants may vary depending on the type of plant or plant cell targeted for transformation, such as monocot or dicot. Suitable methods of introducing polynucleotides and polypeptides into plant cells and subsequent insertion into the plant genome include microinjection (Crossway et al., (1986) *Biotechniques* 4:320-34 and U.S. Pat. No. 6,300,543), meristem transformation (U.S. Pat. No. 5,736,369), electroporation (Riggs et al., (1986) *Proc. Natl. Acad. Sci. USA* 83:5602-6, *Agrobacterium*-mediated transformation (U.S. Pat. Nos. 5,563,055 and 5,981,840), direct gene transfer (Paszkowski et al., (1984) *EMBO J* 3:2717-22), and ballistic particle acceleration (U.S. Pat. Nos. 4,945,050; 5,879,918; 5,886,244; 5,932,782; Tomes et al., (1995) "Direct DNA Transfer into Intact Plant Cells via Microprojectile Bombardment" in Plant Cell, Tissue, and Organ Culture: Fundamental Methods, ed. Gamborg & Phillips (Springer-Verlag, Berlin); McCabe et al., (1988) *Biotechnology* 6:923-6; Weissinger et al., (1988) *Ann Rev Genet* 22:421-77; Sanford et al., (1987) *Particulate Science and Technology* 5:27-37 (onion); Christou et al., (1988) *Plant Physiol* 87:671-4 (soybean); Finer and McMullen, (1991) *In Vitro Cell Dev Biol* 27P:175-82 (soybean); Singh et al., (1998) *Theor Appl Genet* 96:319-24 (soybean); Datta et al., (1990) *Biotechnology* 8:736-40 (rice); Klein et al., (1988) *Proc. Natl. Acad. Sci. USA* 85:4305-9 (maize); Klein et al., (1988) *Biotechnology* 6:559-63 (maize); U.S. Pat. Nos. 5,240,855; 5,322,783 and 5,324,646; Klein et al., (1988) *Plant Physiol* 91:440-4 (maize); Fromm et al., (1990) *Biotechnology* 8:833-9 (maize); Hooykaas-Van Slogteren et al., (1984) *Nature* 311:763-4; U.S. Pat. No. 5,736,369 (cereals);

Bytebier et al., (1987) *Proc. Natl. Acad. Sci. USA* 84:5345-9 (Liliaceae); De Wet et al., (1985) in The Experimental Manipulation of Ovule Tissues, ed. Chapman et al., (Longman, New York), pp. 197-209 (pollen); Kaeppler et al., (1990) *Plant Cell Rep* 9:415-8) and Kaeppler et al., (1992) *Theor Appl Genet* 84:560-6 (whisker-mediated transformation); D'Halluin et al., (1992) *Plant Cell* 4:1495-505 (electroporation); Li et al., (1993) *Plant Cell Rep* 12:250-5; Christou and Ford (1995) *Annals Botany* 75:407-13 (rice) and Osjoda et al., (1996) *Nat Biotechnol* 14:745-50 (maize via *Agrobacterium tumefaciens*).

Alternatively, polynucleotides may be introduced into plants by contacting plants with a virus or viral nucleic acids. Generally, such methods involve incorporating a polynucleotide within a viral DNA or RNA molecule. In some examples a polypeptide of interest may be initially synthesized as part of a viral polyprotein, which is later processed by proteolysis in vivo or in vitro to produce the desired recombinant protein. Methods for introducing polynucleotides into plants and expressing a protein encoded therein, involving viral DNA or RNA molecules, are known, see, for example, U.S. Pat. Nos. 5,889,191, 5,889,190, 5,866,785, 5,589,367 and 5,316,931. Transient transformation methods include, but are not limited to, the introduction of polypeptides, such as a double-strand break inducing agent, directly into the organism, the introduction of polynucleotides such as DNA and/or RNA polynucleotides, and the introduction of the RNA transcript, such as an mRNA encoding a double-strand break inducing agent, into the organism. Such methods include, for example, microinjection or particle bombardment. See, for example Crossway et al., (1986) *Mol Gen Genet* 202:179-85; Nomura et al., (1986) *Plant Sci* 44:53-8; Hepler et al., (1994) *Proc. Natl. Acad. Sci. USA* 91:2176-80; and, Hush et al., (1994) *J Cell Sci* 107:775-84.

Standard DNA isolation, purification, molecular cloning, vector construction, and verification/characterization methods are well established, see, for example Sambrook et al., (1989) *Molecular Cloning: A Laboratory Manual*, (Cold Spring Harbor Laboratory Press, NY). Vectors and constructs include circular plasmids, and linear polynucleotides, comprising a polynucleotide of interest and optionally other components including linkers, adapters, regulatory regions, introns, restriction sites, enhancers, insulators, selectable markers, nucleotide sequences of interest, promoters, and/or other sites that aid in vector construction or analysis. In some examples a recognition site and/or target site can be contained within an intron, coding sequence, 5' UTRs, 3' UTRs, and/or regulatory regions.

The present invention further provides expression constructs for expressing in a plant, plant cell, or plant part an endonuclease that is capable of binding to and creating a double strand break in a target site. The expression constructs of the invention comprise a promoter operably linked to a nucleotide sequence encoding an endonuclease of the present invention. The promoter is capable of driving expression of an operably linked nucleotide sequence in a plant cell. Any such promoter that is disclosed herein or known in the art can be used in the present invention. In one embodiment, the target site of the endonuclease is selected from the group consisting of TS21, TS14, TS30, TS5, TS7, TS4, TS22, and TS24 target sites of soybean, which have the nucleotide sequences set forth in SEQ ID NO:1, 2, 3, 4, 5, 6, 7, and 8, respectively. In another embodiment, the target site of the endonuclease is selected from the group consisting of MHP1, MHP14, MHP32, MHP42, MHP55, MHP67, MHP77, MHP98, MHP107, and MHP115 target sites of maize, which have the nucleotide sequences set forth in SEQ ID NO:68, 69, 70, 71, 72, 73, 74, 75, 76, and 77, respectively.

In certain embodiments, the expression constructs comprise a nucleotide sequence encoding the endonuclease that has been custom designed or engineered to cut at one the soybean target sites set forth above. Such nucleotide sequences include, for example, the nucleotide sequences set forth in SEQ ID NOS:9, 10, 11, 12, 13, 14, 15, and 16. Other nucleotide sequences of the invention include, but are not limited to, nucleotide sequences comprising a coding sequence of a DNA binding domain of an endonuclease, wherein the coding sequence is nucleotides 100-261 and nucleotides 850-1011 of SEQ ID NO:9, 10, 11, 12, 13, 14, 15 or 16 and degenerate coding sequences thereof. Such a degenerate coding sequence encodes the same amino acid sequence as that encoded by one of the coding sequences set forth in nucleotides 100-261 and nucleotides 850-1011 of SEQ ID NO:9, 10, 11, 12, 13, 14, 15 or 16 but differs in its nucleotide sequence due to the degeneracy of the genetic code.

In certain other embodiments, the expression constructs comprise a nucleotide sequence encoding the endonuclease that has been custom designed or engineered to cut at one the maize target sites set forth above. Such nucleotide sequences include, for example, the nucleotide sequences set forth in SEQ ID NOS: 78, 79, 80, 81, 82, and 83. Other nucleotide sequences of the invention include, but are not limited to, nucleotide sequences comprising a coding sequence of a DNA binding domain of an endonuclease, wherein the coding sequence comprises nucleotides 100-261 and nucleotides 850-1011 of SEQ ID NO: 80 and degenerate coding sequences thereof. Such a degenerate coding sequence encodes the same amino acid sequence as that encoded by one of the coding sequences set forth in nucleotides 100-261 and nucleotides 850-1011 of SEQ ID NO: 80 but differs in its nucleotide sequence due to the degeneracy of the genetic code. Other nucleotide sequences of the invention include, but are not limited to, nucleotide sequences comprising a coding sequence of a DNA binding domain of an endonuclease, wherein the coding sequence is nucleotides 100-261 and nucleotides 661-822 of SEQ ID NO: 78, 79, 81, 82 or 83 and degenerate coding sequences thereof. Such a degenerate coding sequence encodes the same amino acid sequence as that encoded by one of the coding sequences set forth in nucleotides 100-261 and nucleotides 661-822 of SEQ ID NO: 78, 79, 81, 82 or 83 but differs in its nucleotide sequence due to the degeneracy of the genetic code.

Any promoter can be used, and can be selected based on the desired outcome. A promoter is a region of DNA involved in recognition and binding of RNA polymerase and other proteins to initiate transcription. A plant promoter is a promoter capable of initiating transcription in a plant cell, for a review of plant promoters, see, Potenza et al., (2004) *In Vitro Cell Dev Biol* 40:1-22. Constitutive promoters include, for example, the core promoter of the Rsyn7 promoter and other constitutive promoters disclosed in WO99/43838 and U.S. Pat. No. 6,072,050; the core CaMV 35S promoter (Odell et al., (1985) *Nature* 313:810-2); rice actin (McElroy et al., (1990) *Plant Cell* 2:163-71); ubiquitin (Christensen et al., (1989) *Plant Mol Biol* 12:619-32; Christensen et al., (1992) *Plant Mol Biol* 18:675-89); pEMU (Last et al., (1991) *Theor Appl Genet* 81:581-8); MAS (Velten et al., (1984) *EMBO J* 3:2723-30); ALS promoter (U.S. Pat. No. 5,659,026), and the like. Other constitutive promoters are described in, for example, U.S. Pat. Nos. 5,608,149; 5,608,144; 5,604,121; 5,569,597; 5,466,785; 5,399,680;

5,268,463; 5,608,142 and 6,177,611. In some examples an inducible promoter may be used. Pathogen-inducible promoters induced following infection by a pathogen include, but are not limited to those regulating expression of PR proteins, SAR proteins, beta-1,3-glucanase, chitinase, etc.

Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize In2-2 promoter, activated by benzene sulfonamide herbicide safeners (De Veylder et al., (1997) *Plant Cell Physiol* 38:568-77), the maize GST promoter (GST-II-27, WO93/01294), activated by hydrophobic electrophilic compounds used as pre-emergent herbicides, and the tobacco PR-1a promoter (Ono et al., (2004) *Biosci Biotechnol Biochem* 68:803-7) activated by salicylic acid. Other chemical-regulated promoters include steroid-responsive promoters (see, for example, the glucocorticoid-inducible promoter (Schena et al., (1991) *Proc. Natl. Acad. Sci. USA* 88:10421-5; McNellis et al., (1998) *Plant J* 14:247-257); tetracycline-inducible and tetracycline-repressible promoters (Gatz et al., (1991) *Mol Gen Genet* 227:229-37; U.S. Pat. Nos. 5,814,618 and 5,789,156).

Tissue-preferred promoters can be utilized to target enhanced expression within a particular plant tissue. Tissue-preferred promoters include, for example, Kawamata et al., (1997) *Plant Cell Physiol* 38:792-803; Hansen et al., (1997) *Mol Gen Genet* 254:337-43; Russell et al., (1997) *Transgenic Res* 6:157-68; Rinehart et al., (1996) *Plant Physiol* 112:1331-41; Van Camp et al., (1996) *Plant Physiol* 112:525-35; Canevascini et al., (1996) *Plant Physiol* 112:513-524; Lam, (1994) *Results Probl Cell Differ* 20:181-96; and Guevara-Garcia et al., (1993) *Plant J* 4:495-505. Leaf-preferred promoters include, for example, Yamamoto et al., (1997) *Plant J* 12:255-65; Kwon et al., (1994) *Plant Physiol* 105:357-67; Yamamoto et al., (1994) *Plant Cell Physiol* 35:773-8; Gotor et al., (1993) *Plant J* 3:509-18; Orozco et al., (1993) *Plant Mol Biol* 23:1129-38; Matsuoka et al., (1993) *Proc. Natl. Acad. Sci. USA* 90:9586-90; Simpson et al., (1958) *EMBO J* 4:2723-9; Timko et al., (1988) *Nature* 318:57-8. Root-preferred promoters include, for example, Hire et al., (1992) *Plant Mol Biol* 20:207-18 (soybean root-specific glutamine synthase gene); Miao et al., (1991) *Plant Cell* 3:11-22 (cytosolic glutamine synthase (GS)); Keller and Baumgartner, (1991) *Plant Cell* 3:1051-61 (root-specific control element in the GRP 1.8 gene of French bean); Sanger et al., (1990) *Plant Mol Biol* 14:433-43 (root-specific promoter of *A. tumefaciens* mannopine synthase (MAS)); Bogusz et al., (1990) *Plant Cell* 2:633-41 (root-specific promoters isolated from *Parasponia andersonii* and *Trema tomentosa*); Leach and Aoyagi, (1991) *Plant Sci* 79:69-76 (*A. rhizogenes* rolC and rolD root-inducing genes); Teeri et al., (1989) *EMBO J* 8:343-50 (*Agrobacterium* wound-induced TR1' and TR2' genes); VfENOD-GRP3 gene promoter (Kuster et al., (1995) *Plant Mol Biol* 29:759-72); and rolB promoter (Capana et al., (1994) *Plant Mol Biol* 25:681-91; phaseolin gene (Murai et al., (1983) *Science* 23:476-82; Sengopta-Gopalen et al., (1988) *Proc. Natl. Acad. Sci. USA* 82:3320-4). See also, U.S. Pat. Nos. 5,837,876; 5,750,386; 5,633,363; 5,459,252; 5,401,836; 5,110,732 and 5,023,179.

Seed-preferred promoters include both seed-specific promoters active during seed development, as well as seed-germinating promoters active during seed germination. See, Thompson et al., (1989) *BioEssays* 10:108. Seed-preferred promoters include, but are not limited to, Cim1 (cytokinin-induced message); cZ19B1 (maize 19 kDa zein); and milps (myo-inositol-1-phosphate synthase); (WO00/11177; and U.S. Pat. No. 6,225,529). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, and nuc1. See also, WO00/12733, where seed-preferred promoters from END1 and END2 genes are disclosed.

A phenotypic marker is screenable or selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See for example, Yarranton, (1992) *Curr Opin Biotech* 3:506-11; Christopherson et al., (1992) *Proc. Natl. Acad. Sci. USA* 89:6314-8; Yao et al., (1992) *Cell* 71:63-72; Reznikoff, (1992) *Mol Microbiol* 6:2419-22; Hu et al., (1987) *Cell* 48:555-66; Brown et al., (1987) *Cell* 49:603-12; Figge et al., (1988) *Cell* 52:713-22; Deuschle et al., (1989) *Proc. Natl. Acad. Sci. USA* 86:5400-4; Fuerst et al., (1989) *Proc. Natl. Acad. Sci. USA* 86:2549-53; Deuschle et al., (1990) *Science* 248:480-3; Gossen, (1993) Ph.D. Thesis, University of Heidelberg; Reines et al., (1993) *Proc. Natl. Acad. Sci. USA* 90:1917-21; Labow et al., (1990) *Mol Cell Biol* 10:3343-56; Zambretti et al., (1992) *Proc. Natl. Acad. Sci. USA* 89:3952-6; Baim et al., (1991) *Proc. Natl. Acad. Sci. USA* 88:5072-6; Wyborski et al., (1991) *Nucleic Acids Res* 19:4647-53; Hillen and Wissman, (1989) *Topics Mol Struc Biol* 10:143-62; Degenkolb et al., (1991) *Antimicrob Agents Chemother* 35:1591-5; Kleinschnidt et al., (1988) *Biochemistry* 27:1094-104; Bonin, (1993) Ph.D. Thesis, University of Heidelberg; Gossen et al., (1992) *Proc. Natl. Acad. Sci. USA* 89:5547-51; Oliva et al., (1992) *Antimicrob Agents Chemother* 36:913-9; Hlavka et al., (1985) *Handbook of Experimental Pharmacology*, Vol. 78 (Springer-Verlag, Berlin); Gill et al., (1988) *Nature* 334:721-4.

The cells having the introduced sequence may be grown or regenerated into plants using conventional conditions, see for example, McCormick et al., (1986) *Plant Cell Rep* 5:81-4. These plants may then be grown, and either pollinated with the same transformed strain or with a different transformed or untransformed strain, and the resulting progeny having the desired characteristic and/or comprising the introduced polynucleotide or polypeptide identified. Two or more generations may be grown to ensure that the polynucleotide is stably maintained and inherited, and seeds harvested.

Any plant can be used, including moncot and dicot plants. Examples of monocot plants that can be used include, but are not limited to, corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), wheat (*Triticum aestivum*), sugarcane (*Saccharum* spp.), oats (*Avena*), barley (*Hordeum*), switchgrass (*Panicum virgatum*), pineapple (*Ananas comosus*), banana (Musa spp.), palm, ornamentals, turfgrasses, and other grasses. Examples of dicot plants that can be used include, but are not limited to, soybean (*Glycine max*), canola (*Brassica napus* and *B. campestris*), alfalfa (*Medicago sativa*), tobacco (*Nicotiana tabacum*), Arabidopsis (*Arabidopsis thaliana*), sunflower (*Helianthus annuus*), cotton (*Gossypium arboreum*), and peanut (*Arachis hypogaea*), tomato (*Solanum lycopersicum*), potato (*Solanum tuberosum*) etc.

The transgenes, recombinant DNA molecules, DNA sequences of interest, and polynucleotides of interest can comprise one or more genes of interest. Such genes of interest can encode, for example, a protein that provides agronomic advantage to the plant. Genes of interest, including, but not limited to, those that encode proteins that provide agronomic advantage, can be reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Illinois), pp. 497-502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene); glyphosate (e.g., the EPSPS gene and the GAT gene; see, for example, U.S. Publication No. 20040082770 and WO 03/092360); or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837-5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The transgenes, recombinant DNA molecules, DNA sequences of interest, and polynucleotides of interest can be comprise one or more DNA sequences for gene silencing. Methods for gene silencing involving the expression of DNA sequences in plant are known in the art include, but are not limited to, cosuppression, antisense suppression, double-stranded RNA (dsRNA) interference, hairpin RNA (hpRNA) interference, intron-containing hairpin RNA (ihpRNA) interference, transcriptional gene silencing, and micro RNA (miRNA) interference Cosuppression may be used to inhibit the expression of plant genes to produce plants having undetectable protein levels for the proteins encoded by these genes. See, for example, Broin et al. (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell et al. (1994) *Proc. Natl. Acad. Sci. USA* 91:3490-3496; Jorgensen et al. (1996) *Plant Mol. Biol.* 31:957-973; Johansen and Carrington (2001) *Plant Physiol.* 126:930-938; Broin et al. (2002) *Plant Cell* 14:1417-1432; Stoutjesdijk et al (2002) *Plant Physiol.* 129:1723-1731; Yu et al. (2003) *Phytochemistry* 63:753-763; and U.S. Pat. Nos. 5,034,323, 5,283,184, and 5,942,657; each of which is herein incorporated by reference. The efficiency of cosuppression may be increased by including a poly-dT region in the expression cassette at a position 3' to the sense sequence and 5' of the polyadenylation signal. See, U.S. Patent Publication No. 20020048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference.

Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550, or greater may be used. Methods for using antisense suppression to inhibit the expression of endogenous genes in plants are described, for example, in Liu et al (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, U.S. Patent Publication No. 20020048814, herein incorporated by reference.

Methods for using dsRNA interference to inhibit the expression of endogenous plant genes are described in Waterhouse et al. (1998) *Proc. Natl. Acad. Sci. USA* 95:13959-13964, Liu et al. (2002) *Plant Physiol.* 129:1732-1743, and WO 99/49029, WO 99/53050, WO 99/61631, and WO 00/49035; each of which is herein incorporated by reference.

Methods of hpRNA interference are described in Waterhouse and Helliwell (2003) *Nat. Rev. Genet.* 4:29-38 and the references cited therein. These methods are highly efficient at inhibiting the expression of endogenous genes. See, for example, Chuang and Meyerowitz (2000) *Proc. Natl. Acad. Sci. USA* 97:4985-4990; Stoutjesdijk et al. (2002) *Plant Physiol.* 129:1723-1731; and Waterhouse and Helliwell (2003) *Nat. Rev. Genet.* 4:29-38. Methods for using hpRNA interference to inhibit or silence the expression of genes are described, for example, in Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith et al. (2000) *Nature* 407:319-320. In fact, Smith et al. show 100% suppression of endogenous gene expression using ihpRNA-mediated interference. Methods for using ihpRNA interference to inhibit the expression of endogenous plant genes are described, for example, in Smith et al. (2000) *Nature* 407: 319-320; Wesley et al. (2001) *Plant J.* 27:581-590; Wang and Waterhouse (2001) *Curr. Opin. Plant Biol.* 5:146-150; Waterhouse and Helliwell (2003) *Nat. Rev. Genet.* 4:29-38; Helliwell and Waterhouse (2003) *Methods* 30:289-295, and U.S. Patent Publication No. 20030180945, each of which is herein incorporated by reference.

Transcriptional gene silencing (TGS) may be accomplished through use of hpRNA constructs wherein the inverted repeat of the hairpin shares sequence identity with the promoter region of a gene to be silenced. Processing of the hpRNA into short RNAs which can interact with the homologous promoter region may trigger degradation or methylation to result in silencing (Aufsatz et al. (2002) *PNAS* 99 (Suppl. 4):16499-16506; Mette et al. (2000) *EMBO J* 19(19):5194-5201).

The inhibition of the expression of a target protein may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier et al. (2003) *Nature* 425: 257-263, herein incorporated by reference. For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). miRNA molecules are highly efficient at inhibiting the expression of endogenous genes, and the RNA interference they induce is inherited by subsequent generations of plants.

The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events, the longer the region of homology, the greater the frequency. The length of the homology region needed to observe homologous recombination is also species-variable. In many cases, at least 5 kb of homology has been utilized, but homologous recombination has been observed with as little as 25-50 bp of homology. The minimum length of homology needed has been estimated at 20-50 bp in *E. coli* (Singer et al., (1982) *Cell* 31:25-33; Shen and Huang, (1986) *Genetics* 112:441-57; Watt et al., (1985) *Proc. Natl. Acad. Sci. USA* 82:4768-72), 63-89 bp in *Saccharomyces. cerevisiae* (Sugawara and Haber, (1992) *Mol Cell Biol* 12:563-75), and 163-300 bp in mammalian cells (Rubnitz and Subramani, (1984) *Mol Cell Biol* 4:2253-8; Ayares et al., (1986) *Proc. Natl. Acad. Sci. USA* 83:5199-203; Liskay et al., (1987) *Genetics* 115:161-7).

Homologous recombination has been demonstrated in insects. In *Drosophila*, Dray and Gloor found that as little as 3 kb of total template:target homology sufficed to copy a large non-homologous segment of DNA into the target with reasonable efficiency (Dray and Gloor, (1997) *Genetics* 147:689-99). Using FLP-mediated DNA integration at a target FRT in *Drosophila*, Golic et al., showed integration was approximately 10-fold more efficient when the donor and target shared 4.1 kb of homology as compared to 1.1 kb of homology (Golic et al., (1997) *Nucleic Acids Res* 25:3665). Data from *Drosophila* indicates that 2-4 kb of homology is sufficient for efficient targeting, but there is some evidence that much less homology may suffice, on the order of about 30 bp to about 100 bp (Nassif and Engels, (1993) *Proc. Natl. Acad. Sci. USA* 90:1262-6; Keeler and Gloor, (1997) *Mol Cell Biol* 17:627-34).

Homologous recombination has also been accomplished in other organisms. For example, at least 150-200 bp of homology was required for homologous recombination in the parasitic protozoan *Leishmania* (Papadopoulou and Dumas, (1997) *Nucleic Acids Res* 25:4278-86). In the filamentous fungus *Aspergillus nidulans*, gene replacement has been accomplished with as little as 50 bp flanking homology (Chaveroche et al., (2000) *Nucleic Acids Res* 28:e97). Targeted gene replacement has also been demonstrated in the ciliate Tetrahymena *thermophila* (Gaertig et al., (1994) *Nucleic Acids Res* 22:5391-8). In mammals, homologous recombination has been most successful in the mouse using pluripotent embryonic stem cell lines (ES) that can be grown in culture, transformed, selected and introduced into a mouse embryo. Embryos bearing inserted transgenic ES cells develop as genetically chimeric offspring. By interbreeding siblings, homozygous mice carrying the selected genes can be obtained. An overview of the process is provided in Watson et al., (1992) *Recombinant DNA,* 2nd Ed., (Scientific American Books distributed by WH Freeman & Co.); Capecchi, (1989) *Trends Genet* 5:70-6; and Bronson, (1994) *J Biol Chem* 269:27155-8. Homologous recombination in mammals other than mouse has been limited by the lack of stem cells capable of being transplanted to oocytes or developing embryos. However, McCreath et al., *Nature* 405:1066-9 (2000) reported successful homologous recombination in sheep by transformation and selection in primary embryo fibroblast cells.

Error-prone DNA repair mechanisms can produce mutations at double-strand break sites. The nonhomologous end-joining (NHEJ) pathways are the most common repair mechanism to bring the broken ends together (Bleuyard et al., (2006) *DNA Repair* 5:1-12). The structural integrity of chromosomes is typically preserved by the repair, but deletions, insertions, or other rearrangements are possible. The two ends of one double-strand break are the most prevalent substrates of NHEJ (Kirik et al., (2000) *EMBO J* 19:5562-6), however if two different double-strand breaks occur, the free ends from different breaks can be ligated and result in chromosomal deletions (Siebert and Puchta, (2002) *Plant Cell* 14:1121-31), or chromosomal translocations between different chromosomes (Pacher et al., (2007) *Genetics* 175: 21-9).

Episomal DNA molecules can also be ligated into the double-strand break, for example, integration of T-DNAs into chromosomal double-strand breaks (Chilton and Que, (2003) *Plant Physiol* 133:956-65; Salomon and Puchta, (1998) *EMBO J* 17:6086-95). Once the sequence around the double-strand breaks is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) *Plant Cell* 16:342-52). Ectopic and/or epigenic DNA sequences may also serve as a DNA repair template for homologous recombination (Puchta, (1999) *Genetics* 152: 1173-81).

Alteration of the genome of a plant cell, for example, through homologous recombination (HR), is a powerful tool for genetic engineering. Despite the low frequency of homologous recombination in higher plants, there are a few examples of successful homologous recombination of plant endogenous genes. The parameters for homologous recombination in plants have primarily been investigated by rescuing introduced truncated selectable marker genes. In these experiments, the homologous DNA fragments were typically between 0.3 kb to 2 kb. Observed frequencies for homologous recombination were on the order of $10^{-4}$ to $10^{-5}$. See, for example, Halfter et al., (1992) *Mol Gen Genet* 231:186-93; Offringa et al., (1990) *EMBO J* 9:3077-84; Offringa et al., (1993) *Proc. Natl. Acad. Sci. USA* 90:7346-50; Paszkowski et al., (1988) *EMBO J* 7:4021-6; Hourda and Paszkowski, (1994) *Mol Gen Genet* 243:106-11; and Risseeuw et al., (1995) *Plant J* 7:109-19.

An endogenous, non-selectable gene was targeted in *Arabidopsis* using a targeting vector containing a region of about 7 kb homologous to the target gene and the targeting frequency was estimated to be at least $3.9 \times 10^{-4}$ (Maio and Lam, (1995) *Plant J* 7:359-65). In another example, using a positive-negative selection scheme and a targeting vector containing up to 22.9 kb of sequence homologous to the target, homologous recombination was detected with a frequency less than $5.3 \times 10^{-5}$, despite the large flanking sequences available for recombination (Thykjr et al., (1997) *Plant Mol Biol* 35:523-30). In *Arabidopsis*, the AGL5 MADS-box gene was knocked out by homologous recombination using a targeting construct consisting of a kanamycin-resistance cassette inserted into the AGL5 sequence roughly 3 kb from the 5' end and 2 kb from the 3' end. Of the 750 kanamycin-resistant transgenic lines that were generated, one line contained the anticipated insertion (Kempin et al., (1997) *Nature* 389:802-3). Hanin et al., obtained homologous recombination events at a basal frequency of $7\times10^{-4}$ using 3 kb 5'-end and 2 kb 3'-end homology to the *Arabidopsis* PPO gene encoding protoporphyrinogen oxidase (Hanin et al., (2001) *Plant J* 28:671-7). Terada et al., targeted the Waxy locus in rice using an *Agrobacterium*-mediated transformation procedure. Negative selection, in the form of two copies of the diphteria toxin gene placed at both ends of T-DNA, was used to eliminate random integration of T-DNAs, allowing for enrichment of rare homologous recombination events in the selected material, and their transformation system generated thousands of events from just 150 rice seeds. The reported frequency of homologous recombination of the waxy gene in rice was $0.65\times10^{-3}$, without inclusion of elements to enhance homologous recombination (Terada et al., (2002) *Nat Biotech* 20:1030-4).

DNA double-strand breaks (DSBs) appear to be an effective factor to stimulate homologous recombination pathways in every organism tested to date (Puchta et al., (1995) *Plant Mol Biol* 28:281-92; Tzfira and White, (2005) *Trends Biotechnol* 23:567-9; Puchta, (2005) *J Exp Bot* 56:1-14). Using DNA-breaking agents, two- to nine-fold increase of homologous recombination was observed between artificially constructed homologous DNA repeats in plants (Puchta et al., (1995) *Plant Mol Biol* 28:281-92). In maize protoplasts, experiments with linear DNA molecules demonstrated enhanced homologous recombination between plasmids (Lyznik et al., (1991) *Mol Gen Genet* 230:209-18).

The effects of DSBs on homologous recombination have been investigated by using rare-cutting enzymes as well as transposons such as Ac and Mutator (Chiurazzi et al., (1996) *Plant Cell* 8:2057-66; Puchta et al., (1996) *Proc. Natl. Acad. Sci. USA* 93:5055-60; Xiao and Peterson, (2000) *Mol Gen Genet* 263:22-9; and Shalev and Levy (1997) *Genetics* 146:1143-51). Chiurazzi et al., (1996) *Plant Cell* 8:2057-66) introduced DSBs into an *Arabidopsis* chromosome using HO-endonuclease and observed 10-fold increase in the frequency of homologous recombination between repeats flanking the HO recognition site. Excision of Ac transposable elements also stimulated homologous recombination between repeats flanking the elements at an even higher frequency (Xiao and Peterson (2000) *Mol Gen Genet* 263: 22-9).

Puchta et al. reported that homologous recombination frequency at an artificial target locus was increased by up to two orders of magnitude when DSBs were generated using I-SceI (Puchta et al., (1996) *Proc. Natl. Acad. Sci. USA* 93:5055-60). In the experiment reported in Puchta et al., an I-SceI expression cassette was introduced into transgenic tobacco target lines together with targeting construct by co-inoculation with the two respective *Agrobacterium* strains. Homologous recombination between T-DNA containing the targeting construct and the target site reconstituted the kanamycin-resistance gene (nptII). There was an apparent correlation between frequency of homologous recombination and the amount of I-SceI expression cassette, suggesting that more DSBs yielded higher homologous recombination frequency.

High frequency of homologous recombination at a pre-introduced artificial target site was obtained using a zinc-finger nuclease (ZFN) in tobacco (Wright et al., (2005) *Plant J* 44:693-705). The zinc-finger nuclease expression cassette and donor DNA were introduced into protoplasts by co-electroporation and targeted modification was monitored by kanamycin resistance and GUS activity. One modified event was observed in approximately every 10 transformants, however, only 20% of the modified events contained the desired homologous recombination products as indicated by Southern blot analysis.

Zinc finger nucleases are engineered endonucleases with altered specificities, for example by fusion of an engineered DNA binding domain to an endonuclease, for example, FokI (Durai et al., (2005) *Nucleic Acids Res* 33:5978-90; Mani et al., (2005) *Biochem Biophys Res Comm* 335:447-57). Wright et al., and Lloyd et al., reported a high frequency mutagenesis at a DNA target site integrated into tobacco or *Arabidopsis* chromosomal DNA using zinc-finger nucleases (Wright et al., (2005) *Plant J* 44:693-705; Lloyd et al., (2005) *Proc. Natl. Acad. Sci. USA* 102:2232-7). Using a designed zinc-finger nuclease recognizing a tobacco endogenous acetolactate synthase (ALS) gene locus, a mutated ALS gene known to confer resistance to imidazolinone and sulphonylurea herbicides was introduced to replace the endogenous ALS gene at frequencies exceeding 2% of transformed cells (Townsend et al., (2009) *Nature* 459:442-5). The knock-out of an endogenous gene and the expression of a transgene can be achieved simultaneously by gene targeting. The IPK1 gene, which encodes inositol-1,3,4,5,6-pentakisphosphate 2-kinase needed in the final step of phytate biosynthesis in maize seeds, was targeted using a designed zinc-finger nuclease to insert via homologous recombination a PAT gene, which encodes phosphinothricin acetyl transferase tolerance to glufosinate ammonium herbicides such as bialaphos. The disruption of the IPK1 gene with the insertion of the PAT gene resulted in both herbicide tolerance and the expected alteration of the inositol phosphate profile in developing seeds (Shukla et al., (2009) *Nature* 459:437-41).

Members of the serine family of recombinases produce double-strand breaks at the recombination sites as a part of their catalytic activities (Grindley et al., (2006) *Ann Rev Biochem* 16:16). The R/RS system in sweet orange appeared to induce mutations of RS sites leading to chromosomal deletions not associated with site-specific recombination reactions per se (Ballester et al., (2006) *Plant Cell Rep* 26:39-45).

Another approach uses protein engineering of existing homing endonucleases to alter their target specificities. Homing endonucleases, such as I-SceI or I-CreI, bind to and cleave relatively long DNA recognition sequences (18 bp and 22 bp, respectively). These sequences are predicted to naturally occur infrequently in a genome, typically only 1 or 2 sites/genome. The cleavage specificity of a homing endonuclease can be changed by rational design of amino acid substitutions at the DNA binding domain and/or combinatorial assembly and selection of mutated monomers (see, for example, Arnould et al., (2006) *J Mol Biol* 355:443-58; Ashworth et al., (2006) *Nature* 441:656-9; Doyon et al., (2006) *J Am Chem Soc* 128:2477-84; Rosen et al., (2006) *Nucleic Acids Res* 34:4791-800; and Smith et al., (2006) *Nucleic Acids Res* 34:e149; Lyznik et al., (2009) U.S. Patent Application Publication No. 20090133152A1; Smith et al., (2007) U.S. Patent Application Publication No. 20070117128A1). Engineered meganucleases have been demonstrated that can cleave cognate mutant sites without broadening their specificity. An artificial recognition site specific to the wild type yeast I-SceI homing nuclease was introduced in maize genome and mutations of the recognition sequence were detected in 1% of analyzed F1 plants when a transgenic I-SceI was introduced by crossing and activated by gene excision (Yang et al., (2009) *Plant Mol Biol* 70:669-79). More practically, the maize liguleless locus was targeted using an engineered single-chain endonuclease designed based on the I-CreI meganuclease sequence. Mutations of the selected liguleless locus recognition sequence were detected in 3% of the TO transgenic plants when the designed homing nuclease was introduced by *Agrobacterium*-mediated transformation of immature embryos (Gao et al., (2010) *Plant J* 61:176-87).

EXAMPLES

The present invention is further defined in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Such modifications are also intended to fall within the scope of the appended claims.

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kb" means kilobase(s).

The DNA repair mechanisms of cells are the basis of transformation to introduce extraneous DNA or induce mutations on endogenous genes. DNA homologous recombination is a specialized way of DNA repair that the cells repair DNA damages using a homologous sequence. In plants, DNA homologous recombination happens at frequencies too low to be used in transformation until it has been found that the process can be stimulated by DNA double-strand breaks (Bibikova et al., (2001) *Mol. Cell Biol.* 21:289-297; Puchta and Baltimore, (2003) *Science* 300:763; Wright et al., (2005) *Plant J.* 44:693-705).

Example 1

DNA Double-Strand-Break-Induced Alteration of an Endogenous Target Site

When a DNA double-strand-break-inducing agent recognizes and cleaves the specific recognition sequence at a target site in the genome, a DNA double-strand break is formed triggering the cell DNA repair mechanisms to mobilize to repair the damage that could be fatal to the cell. The process can be utilized in plant transformation to introduce mutations specifically at the target site to knock out the gene residing at the target site or to insert a donor DNA of interest at the target site. Once the DNA double-strand break is formed, depending on the designs of the DNA constructs involved and the actual processes of DNA repair, different outcomes can be obtained serving different transformation purposes.

For simple site-specific gene mutations, a target site containing a recognition sequence (FIG. 1A) and a DNA double-strand break agent such as a endonuclease (FIG. 1B) that recognizes specifically the recognition sequence have to be present in the same cell. After the endonuclease recognizes and cuts the DNA, the two free ends can be repaired through end joining by the cell DNA repair machinery without the intervention of any external factors. The two ends can be repaired to its original state so no change can be detected or they can be altered before being repaired resulting detectable changes after they are connected again such as the deletion of one or more nucleotides of the recognition sequence and possibly extra surrounding sequences (FIG. 1F). Mutations are introduced at the target site by the latter process.

To achieve site-specific DNA insertions, a donor DNA containing the DNA of interest has to be simultaneously present in the cell in addition to the target site and the endonuclease. The donor DNA can contain the same DNA sequences that flank the target site to flank the gene of interest, i.e., the homologous sequences (FIG. 1C). The DNA of interest can be inserted at the target site by homologous recombination (FIG. 1E), a process that is stimulated by the DNA double-strand break at the target site. The donor DNA can also contain only the DNA of interest without any flanking homologous sequences (FIG. 1D). The DNA of interest can still be inserted at the target site though in a less predictable fashion through non-homologous recombination. Similarly, any unrelated DNA that happens to be present when the DNA ends are repaired can be inserted at the target site (FIG. 1G). The different outcomes (FIGS. 1E-G) can be obtained simultaneously in the same transformation experiment.

Any means to make a DNA double-strand break in vivo can be used as the DNA double-strand-break-inducing agent such as the most commonly used meganucleases which recognize >18 bp sequences, which are long enough to be unique in most genomes. Even numerous meganucleases have been found and characterized to recognize many different sequences, but such sequences are often not naturally present in important crops such as soybean or maize and even if similar sequences can be found in crop genomes, the limited numbers of these sequences are still too small to be useful. Certain meganucleases such as I-CreI can be modified by protein engineering in such a way that it will no longer preferentially recognize the recognition sequence of wild type I-CreI and instead will preferentially recognize specifically selected sequences of interest. Taking advantage of the flexibility of the I-CreI endonuclease, one can design and make a modified I-CreI to cleave a target site of our choice in the genome and subsequently introduce mutations or insert genes of interest at the selected target site. The precise genetic engineering that this methodology provides will solve many problems that traditional plant transformation methods such as *Agrobacterium* infection and biolistic bombardment currently face, such as unpredictable integration, unwanted endogenous gene interruption, unpredicted transgene expression, etc.

In one embodiment of the invention, we used engineered I-CreI-like meganucleases that recognize selected different endogenous target sites in the soybean genome and produced mutations and insertions at the selected target sites.

Example 2

Production of a Complex Trait Locus in the Soybean Genome Near a Transgenic Event for Oil Quality Using Engineered Meganucleases Soybean lines comprising an endogenous target recognition sequence in their genome were contacted with a custom designed meganuclease, derived from I CreI, which is designed to specifically recognize and create a double-strand break in the endogenous target sequence. Soybean embryos comprising an endogenous target site were contacted with the components described below, events selected and characterized.

A. TS21, TS14, TS30 and TS5 Target Sites

Sequence analyses were done for about 500000 bp genomic region in soybean near a transgenic event of interest (event DP-305423-1, U.S. Patent Application Publication No. 2008/0312082 A1, published Dec. 18, 2008). A series of soybean genomic endogenous target recognition sequences, referred to as TS21, TS14, TS30 and TS5, were selected for design of custom double-strand break inducing agents derived from I-CreI meganuclease. Each of these target recognition sequences is a unique 22 bp polynucleotide. The target recognition sites have the following sequences:

```
TS21 target
                                     (SEQ ID NO: 1)
GGCACTCTCGTGT▼GTGATTAAA TS14 target
                                     (SEQ ID NO: 2)
CAGACGTACGCAA▼GTAGCTTTG TS30 target
                                     (SEQ ID NO: 3)
GAGTCCCACGCAA▼GAGCATAAA TS5 target
                                     (SEQ ID NO: 4)
AAGACTTACGTGT▼GTACTCGTG
```

The double-strand break sites and overhang regions are shown in bold, the enzyme cuts after C13, as indicated by the solid triangle.

Within the soybean genome, TS5 is about 600 kbp upstream of, and on the same chromosome as, the transgenic event of interest. TS30, TS21 and TS14 are on the same chromosome as TS5 and are 120 kbp, 125 kbp and 500 kbp downstream of the transgenic event of interest (FIG. 2).

B. TS21, TS14, TS30, and TS5 Meganucleases

The I-CreI meganuclease was modified to produce the TS21, TS14, TS30 and TS5 meganucleases, which are designed to recognize their corresponding target sequences, under a contract with Precision Biosciences (Durham, NC USA). Wild-type I-CreI meganuclease is a homodimer. In order to recognize their target sequences, different substitutions were made to each monomer. The coding sequences for each monomer were joined by a linker sequence to produce single-chain fusion polypeptides. Genes encoding the designed meganucleases were optimized for expression in plants. SEQ ID NO: 9 is the plant-optimized nucleotide sequence of the TS21 meganuclease. SEQ ID NO: 10 is the plant-optimized nucleotide sequence of the TS14 meganuclease. SEQ ID NO: 11 is the plant-optimized nucleotide sequence of the TS30 meganuclease. SEQ ID NO: 12 is the plant-optimized nucleotide sequence of the TS5 meganuclease. These genes include a nucleus localization signal from the SV40 virus (SEQ ID NO: 34) and an intron from the potato ST-LS1 gene. The intron prevents expression of the genes in bacteria during the cloning process, but is not necessary for expression in plant cells. In these plant-optimized nucleotide sequences (SEQ ID NOs: 9-16) nucleotides 1-30 encode an SV40 nucleus localization amino acid sequence, nucleotides 100-261 and nucleotides 850-1011 encode the 1st half and 2nd half target site binding amino acid sequences, respectively, nucleotides 403-591 are the potato ST-LS1 intron, and nucleotides 685-798 encode the amino acid sequence of the polypeptide that links the two re-engineered I-CreI monomers into a single chain.

Plant optimized nucleotide sequences without the ST-LS1 intron encoding the engineered meganucleases were constructed as well (see, SEQ ID NO: 33 for example).

C. Vector Construction for Plant Expression Vectors of the Meganuclease Genes and Repair DNAs for Transgene Integration by Homologous Recombination Vectors comprising expression cassettes for the appropriate meganuclease were constructed using standard molecular biological techniques. All custom designed meganucleases were tested including TS21, TS14, TS30 and TS5. For each of the meganucleases, a plant expression vector comprising a polynucleotide encoding one of the meganuclease genes was operably linked to a soybean constitutive promoter.

The following meganuclease plant expression vectors were made:

RTW317 (SEQ ID NO: 35, GM-EF1A pro::TS21::pinII) expression cassette contains the TS21 meganuclease plant optimized sequence without an intron and driven by soybean EF1A promoter.

RTW322 (SEQ ID NO: 36, GM-EF1A pro::TS21 with ST-LS1 intron2::pinII) expression cassette contains the TS21 meganuclease plant optimized sequence with an intron and driven by soybean EF1A promoter. Other expression cassettes were made in a similar manner as RT317 and RTW322, but contained a different promoter, or meganuclease, such as: RTW319 (GM-EF1A pro::TS14::pinII), RTW324 (GM-EF1A pro::TS14 with ST-LS1 intron2::pinII), RTW323 (GM-EF1A pro::TS5 with ST-LS1 intron2::pinII), RTW325 (GM-EF1A pro::TS30 with ST-LS1 intron2::pinII), RTW345 (GM-UBQ pro::TS21::pinII), RTW334(GM-UBQ pro::TS21 with ST-LS1 intron2::pinII), RTW351 (GM-MTH1 pro::TS21::pinII), RTW339 (GM-MTH1 pro::TS21 with ST-LS1 intron2::pinII), wherein GM-ETF1A is the soybean ETF1A promoter, GM-UBQ is the soybean ubiquitin promoter, GM-MTH1 is the soybean MTH1 promoter, and pinII is the pinII terminator.

To achieve site-specific DNA insertions, a repair DNA (donor DNA) containing the gene of interest has to be simultaneously present in the cell in addition to the target site and the endonuclease. The gene of interest was flanked by two homologous recombination fragments (HR1 and HR2), which were 1 to 3 kb long genomic DNA sequences flanking the meganuclease target sites. The gene of interest can be inserted at the target site by DNA homologous recombination, a process that is stimulated by the DNA double-strand break at the target site.

A repair DNA (or donor DNA) fragment, Rep-RTW328A (SEQ ID NO: 37) was made for gene integration at TS21 target site in the soybean genome. The RTW328 repair DNA consists of a 1020 bp TS21 HR1 fragment (SEQ ID NO:17), a hygromycin selection marker cassette and a 1000 bp TS21 HR2 fragment (SEQ ID NO:18). The hygromycin selection marker was driven by a SCP1 promoter and a NOS terminator (U.S. Pat. No. 6,072,050; Suzuki et al., Gene (2000) 242(1-2):331-336). Similar repair DNA vectors were made for TS14, TS30, and TS5 target sites in soybean genome. The Rep-TS14 repair DNA vector consists of a 1000 bp TS14 HR1 fragment (SEQ ID NO:19, the same hygromycin selection marker cassette and a 928 bp TS14 HR2 fragment (SEQ ID NO:20). The Rep-TS30 repair DNA vector (consists of a 1000 bp TSO HR1 fragment (SEQ ID NO:21), the same hygromycin selection marker cassette and a 1009 bp TS30 HR2 fragment (SEQ ID NO:22). The Rep-TS5 repair DNA vector consists of a 1006 bp TS5 HR1 fragment (SEQ ID NO:23), the same hygromycin selection marker cassette and a 1007 bp TS5 HR2 fragment (SEQ ID NO:24).

A DNA double-strand break agent was simultaneously introduced with the repair DNA to facilitate homologous DNA recombination. It is convenient to transiently express the custom designed meganuclease by co-bombardment of a meganuclease expression vector with its corresponding repair DNA in soybean transformation. The presence or absence of an ST-LS1 intron in the DNA nucleotide sequence encoding a meganuclease did not affect the functionality of the meganuclease. Alterations at the target site were observed when expression of the meganuclease with both a DNA sequence that included or excluded the ST-LS1 intron in the expression cassette.

D. Genomic Sequence Modifications and Transgene Integration at Endogenous Target Sites with Custom Designed Meganucleases PCR and qPCR assays were done following established protocols using gene-specific primers and probes (Li et al., (2007) *Plant Mol Biol* 65:329-41; Li et al., (2009) *Plant Physiol* 151:1087-95). qPCR assays specific to the TS21, TS14, TS30, and TS5 target sequences were developed to identify sequence changes that happen in the region. The primers and probe were designed as below and tested.

TS21 qPCR:
Mega21-190F (SEQ ID NO:38)
Mega21-301R (SEQ ID NO:39)
Mega21-250T (SEQ ID NO:40)
TS14 qPCR:
Mega14-13F (SEQ ID NO:41)
Mega14-128R (SEQ ID NO:42)
Mega14-85T (SEQ ID NO:43)
TS30 qPCR:
Mega30-30F (SEQ ID NO:44)
Mega21-87R (SEQ ID NO:45)
Mega21-52T (SEQ ID NO:46)
TS5 qPCR:
Mega5-F1 (SEQ ID NO:47)
Mega5-R1 (SEQ ID NO:48)
Mega5-T1 (SEQ ID NO:49)

All hygromycin resistant soybean transgenic events were first analyzed by qPCR assays of the meganuclease target site. Changes in the meganuclease target sequence caused by DNA cleavage and repair result in the copy number reduction of the meganuclease target site from two copies in wild type soybean genome to either one or zero copies in the transgenic events. These "qPCR hit" events with reduced target site copy numbers were chosen for further genomic PCR and sequencing analyses. From qPCR analyses of the TS21, TS14, TS30 and TS5 target sites, it was shown that the copy numbers of the target sites in most of the positive transgenic events were reduced by half, indicating one allele of the target sites in soybean genome was disrupted by meganuclease cutting/DNA repair mechanism.

Two groups of genomic PCR amplifications were carried out to further characterize these candidate events from qPCR assay to understand the genomic sequence modifications and transgene integrations. The first group of genomic PCRs were designed to identify mutations in the meganuclease target sites, by amplifying genomic fragments containing the TS21 target site using a primer that anneals in HR1 and another primer that anneals in HR2. For example, for TS21, the primer set WOL133 and WOL134 (SEQ ID NO:50 and 51) were used to amplify genomic fragments containing the TS21 target site (FIG. 3A). The PCR products were cloned and sequenced to identify mutations at the TS21 target site. In some cases, a meganuclease in vitro cutting assay to cut the PCR product of an unmodified target site was used to test if the target site had been modified. In the in vitro cutting assay, the PCR products amplified using primers directed to the target site were digested with the meganuclease at 37° C. overnight. Samples with meganuclease enzyme were treated with proteinase K and SDS to denature the protein. The digestion products were separated on a 1.5 to 2% agarose gel. Undigested products indicate that the target site was modified. The undigested PCR products were then cloned and sequenced to verify the genome sequence modification. An example of the soybean genome sequence modification on TS21 target site is shown in FIG. 3B.

With this approach, soybean genome sequence modifications were detected at TS5, TS14 and TS30 target sites (FIG. 4 and Table 1).

TABLE 1 qPCR copy number analyses of TS30 target sites, pinII (representing the meganuclease cassette) and Hygro (representing the repair DNA cassette)

| Clone ID | TS30 qPCR Copy# | pinII qPCR copy# | Hygro qPCR copy# |
| --- | --- | --- | --- |
| A 7052.2.5 | 0.56 | 0.00 | 1.98 |
| A 7052.10.26 | 0.55 | 0.00 | 1.55 |
| A 7052.10.28 | 0.54 | 0.00 | 1.96 |
| A 7034.1.11 | 0.53 | 0.00 | 2.98 |
| A 7034.3.1 | 0.54 | 1.70 | 3.41 |
| A 7034.3.15 | 0.52 | 0.96 | 4.54 |
| WT control | 0.96 | 2.23 | 5.19 |

The copy numbers of the TS30 target sites in positive transgenic events were reduced by half, indicating one allele of the target sites in soybean genome was disrupted by meganuclease cutting/DNA repair mechanism. These results demonstrate that introduction of the meganuclease gene into the plant cell leads to modifications in the genomic region of interest.

Both wild type soybean and transgenic embryos have been used in the soybean transformation. The target modification rate (qPCR) with TS21 is the same in wild type soybean and the transgenic event. These results demonstrated that we can directly introduce genome modifications in the transgenic event or introduce genome modifications to the same locus in wild type soybean.

The second group of genomic PCR amplifications was more focused on transgene integration with border specific PCR. For example, for TS21 (FIG. 3A), the primer set WOL190 (SEQ ID NO:52) and WOL242 (SEQ ID NO:53) were designed and used to amplify the left border DNA fragment that results from transgene integration. WOL190 is a sequence specific primer located in soybean genome 5' beyond the TS21 HR1 region and WOL242 is a sequence specific primer to the 5' hygromycin-resistance marker gene coding sequence in the reverse orientation. An 1860 bp PCR product can only be obtained when the RTW328A repair DNA is integrated by homologous recombination facilitated by a double-strand break introduced at the genomic target site by TS21 meganuclease. Another set of primers, WOL153 (SEQ ID NO:54) and WOL247 (SEQ ID NO: 55), was also designed and used to amplify the right border DNA fragment that results from transgene integration. WOL153 is the sense primer from the NOS terminator and the WOL247 is a sequence specific primer located in soybean genome 3' beyond the TS21 HR2 region. A 1727 bp PCR product can only be obtained when the RTW328A repair DNA is integrated by homologous recombination facilitated by a double-strand break introduced at the genomic target site by TS21 meganuclease. Similar genomic PCR primers have been designed and tested for other custom designed meganuclease.

TS21 qPCR
Target site primers
WOL133 (SEQ ID NO:50)
WOL134 (SEQ ID NO:51)
Left border primers
WOL190 (SEQ ID NO:52)
WOL242 (SEQ ID NO:53)
Right border primers
WOL153 (SEQ ID NO:54)
WOL247 (SEQ ID NO:55)
TS14 qPCR
Target site primers
WOL121 (SEQ ID NO:56)
WOL150 (SEQ ID NO:57)
Left border primers
WOL192 (SEQ ID NO:58)
WOL242 (SEQ ID NO:53
Right border primers
WOL153 (SEQ ID NO:54)
WOL193 (SEQ ID NO:59)
TS30 qPCR
Target site primers
WOL113 (SEQ ID NO:60)
WOL114 (SEQ ID NO:61)
Left border primers
WOL194 (SEQ ID NO:62)
WOL242 (SEQ ID NO:53)
Right border primers
WOL153 (SEQ ID NO:54)
WOL195 (SEQ ID NO:63)
TS5 qPCR
Target site primers
WOL105 (SEQ ID NO:64)
WOL144 (SEQ ID NO:65)
Left border primers
WOL196 (SEQ ID NO:66)
WOL242 (SEQ ID NO:53)
Right border primers
WOL153 (SEQ ID NO:54)
WOL197 (SEQ ID NO:67)

Primer pairs were designed with one primer capable of annealing to either the 5' or 3' sequence flanking a target site and another primer capable of annealing to a sequence within the potential insert (i.e., the transgene). For the TS14 target site, 18 qPCR positive events were identified from total 68 events by qPCR analyses. Out of the 18 qPCR positive events, three events were confirmed to be perfect TS14 meganuclease mediated transgene integration events by homologous recombination.

These results demonstrate that soybean cells possess natural DNA repair machinery that can repair DNA double-strand break ends by simple end joining or by homologous recombination. It is thus expected that similar rates of site-directed mutagenesis and gene insertion via homologous recombination can be achieved at any target sites in the soybean genome using proper double-strand break inducing agents specific to the target recognition sequences. Using a simple PCR screening procedure described herein, it is practical to identify such insertion and mutation events. A perfect transgene integration event can be identified when both left border PCR and right border PCR indicate insertion at the target site. Transgene integration at the pre-defined target sites within a genomic region of interest provides a novel gene stacking technology. FIG. 5 is a schematic example of stacking new trait genes into a single target site in close proximity to a transgenic event of interest.

Example 3

Production of a Complex Trait Locus in the Soybean Genome Near a Herbicide Resistance Transgenic Event Using Engineered Meganucleases A. TS7, TS4, TS22 and TS24 Target Sites The transgene border analyses of a herbicide resistance transgenic event (Event 3560.4.3.5 described in U.S. Patent Application Publication Nos. 2010/0184079, 2009/0036308, and 2008/0051288) showed that the transgene was inserted in a soybean chromosome about 12 cM away from three disease resistance markers based on molecular marker analyses (FIG. 6). Sequence analyses were done for about 400000 bp in this genomic region of interest and four meganuclease target sites (TS7, TS4, TS22 and TS24) were identified with desirable genetic distances between these target sites and nearby disease resistance markers, and a herbicide resistance transgenic event. Each of these target recognition sequences is a unique 22 bp polynucleotide. The target recognition sites have the following sequences:

```
TS7 target
                                       (SEQ ID NO: 5)
GACATTGTCGTGA▼GAAAAGAGA TS4 target
                                       (SEQ ID NO: 6)
AAATCTGTCTTGC▼GAAACGGCA TS22 target
                                       (SEQ ID NO: 7)
TATTCTCTCATAA▼ATAAACTTT TS24 target
                                       (SEQ ID NO: 8)
GGAATGGACATAA▼GAGAACTGT
```

The double-strand break sites and overhang regions are shown in bold, the enzyme cuts after C13, as indicated by the solid triangle.

B. TS7, TS4, TS22 and TS24 Meganucleases

The I-CreI meganuclease was modified to produce the TS7, TS4, TS22 and TS24 meganucleases, which are designed to recognize their corresponding target sequences, under a contract with Precision Biosciences (Durham, NC USA). Wild-type I-CreI meganuclease is a homodimer. In order to recognize their target sequences, different substitutions were made to each monomer. The coding sequences for each monomer were joined by a linker sequence to produce single-chain fusion polypeptides All these target sites are about 1 to 10 cM away from the cluster of the three disease resistance markers.

The plant optimized nucleotide sequence encoding the TS7 meganuclease (SEQ ID NO: 13), TS4 meganuclease (SEQ ID NO:14), TS22 meganuclease (SEQ ID NO:15) and TS24 meganuclease (SEQ ID NO:16) includes a DNA fragment (from bp 1-30) encoding an SV40 nuclear localization signal (MAPKKKRKVH; SEQ ID NO: 34) as well as a ST-LS1 intron (from bp 403 to bp 591 of SEQ ID 13-16) in order to eliminate expression in *E. coli* and *Agrobacterium*. Nucleotides 685-798 of SEQ ID NOs:13-16 encode the amino acid sequence of the polypeptide that links the two engineered I-CreI monomers into a single chain. Nucleotides 100-261 of SEQ ID NOs:13-16 and nucleotides 850-1011 of SEQ ID NOs:13-16 encode the first half and the second half target site binding amino acid sequences, respectively.

C. Vector Construction for Plant Expression Vectors of the Meganuclease Genes and Repair DNAs for Transgene Integration by Homologous Recombination Vectors comprising expression cassettes for the appropriate meganuclease were constructed using standard molecular biological techniques. All custom designed meganucleases were tested including TS7, TS4, TS22 and TS24. For each of the meganucleases, a plant expression vector comprising a polynucleotide encoding one of the meganuclease genes was operably linked to a soybean constitutive promoter.

To achieve site-specific DNA insertions, a repair DNA (donor DNA) containing the DNA of interest has to be simultaneously present in the cell in addition to the target site and the endonuclease. The DNA of interest was flanked by two homologous recombination fragments (HR1 and HR2), which were 1 to 3 kb long genomic DNA sequences flanking the meganuclease target sites. The DNA of interest can be inserted at the target site by DNA homologous recombination, a process that is stimulated by the DNA double-strand break at the target site.

The HR1 and HR2 domains for TS7, TS4, TS22 and TS24 are SEQ ID NOs: 25 and 26, SEQ ID NOs: 27 and 28, SEQ ID NOs: 29 and 30 and SEQ ID NOs: 31 and 32, respectively.

Repair DNA vectors were made as described in Example 2 C.

A DNA double-strand break agent was simultaneously introduced with the repair DNA to facilitate homologous DNA recombination. It is convenient to transiently express the custom designed meganuclease by co-bombardment of a meganuclease expression vector with its corresponding repair DNA in soybean transformation.

Example 4

Cluster of Meganuclease Target Sites in a Short Region of the Soybean Genome for Stacking of Multiple Trait Genes As shown in FIG. 7, a series of meganuclease target sites can be identified with desirable genetic distances between these target sites. Custom designed meganucleases can be used to target a series of trait genes into this defined genome locus either by sequential transformation or by genetic crosses with individual trait genes. Using this method depicted in FIG. 7, multiple traits can be stacked in a genomic region of interest that comprises, for example, a transgene or native gene of interest, and other transgenic traits or native trait loci such as disease resistance markers.

Example 5

Production of a Complex Trait Locus at a Maize Endogenous Locus by Engineered Meganucleases
A. MHP Target Sites A genomic region encompassing about 1.8 million nucleotides and representing a genetic region of approximately 4.3 centimorgans (cM) on a maize chromosome was chosen as a target region for generation of a complex trait locus. The genomic region was scanned for 22-mer sequences that could serve as target sites containing recognition sequences for double-strand-break inducing meganucleases and be useful for insertion of additional transgenes in order to create a complex trait locus. A series of 35 putative target sites (SEQ ID NOs: 68-77) were selected in a 2 cM region (FIG. 8) in close proximity of the transgene insertion site for design of custom double-strand break inducing agents derived from I-CreI meganuclease. FIG. 8 show the genetic and physical location of the MHP target sites relative to each other and the transgene of interest.
B. MHP Meganucleases The I-CreI meganuclease was modified to produce endonucleases, which were designed to recognize their corresponding target sequences, (SEQ ID NOs: 68-77). The design of custom made meganucleases has been described in United States Patent Application Publication No. US 2007/0117128 A1.

Genes encoding the designed meganucleases were optimized for expression in plants. The engineered endonuclease expression cassettes contained the maize codon-optimized nucleotide sequences for better performance in maize cells. The endonuclease gene sequences were also supplemented with DNA sequences encoding a SV40 nuclear localization signal (SEQ ID NO: 34). The maize ubiquitin promoter and the potato proteinase inhibitor II gene terminator sequences completed the endonuclease gene designs. The MHP55 (SEQ ID NO:80) expression cassette was additionally modified by addition of the ST-LS1 intron to the coding sequence of the first monomer in order to eliminate its expression in *E. coli* and *Agrobacterium*. SEQ ID NO:82 is the plant-optimized nucleotide sequence of MHP55-2 containing a nuclear localization signal and without an intron. SEQ ID NO: 78 is the plant-optimized nucleotide sequence of the MHP14 meganuclease. A custom designed meganuclease, referred to as MHP14+ was made as well. SEQ ID NO: 79 is the plant-optimized nucleotide sequence of the MHP14+ meganuclease. SEQ ID NO: 83 is the plant-optimized nucleotide sequence of the MHP77 meganuclease C. Vector Construction for Plant Expression Vectors of the Meganuclease Genes and Repair (donor) DNAs for Transgene Integration by Homologous Recombination Vectors comprising expression cassettes for the appropriate meganuclease were constructed using standard molecular biological techniques. For each of the meganucleases, a plant expression vector comprising a polynucleotide encoding one of the meganuclease genes was operably linked to a maize constitutive promoter.

To achieve site-specific DNA insertions, a repair DNA (donor DNA) containing the gene of interest has to be simultaneously present in the cell in addition to the target site and the meganuclease. A vector (PHP44285,SEQ ID NO:104), or PHP44779, SEQ ID NO:105) containing a polynucleotide encoding the engineered meganuclease MHP14, or the optimized meganuclease MHP14+, and a donor DNA was constructed using standard molecular biology techniques. The donor DNA contained an herbicide resistance gene used as the selection marker for transformation. The herbicide resistance gene MoPAT encodes a phosphinothricin acetyltransferase, and was flanked by two homologous recombination fragments, HR1 (SEQ ID NO: 84) and HR2 (SEQ ID NO: 85), which were about 1 kb long genomic DNA sequences flanking the meganuclease target sites. Each vector PHP44285 or PHP44779 contained the meganuclease cassette, the donor DNA and the homology sequences HR1 and HR2.

Maize immature embryos 9-12 DAP (days after pollination, approximately 1.5-2.0 mm in size) from a maize transformable line were used for gene transformation by bombardment (Example 6). The immature embryos were placed on 560Y medium for 4 hours at 26° C. or alternatively, immature embryos were incubated at temperatures ranging from 26° C. to 37° C. for 8 to 24 hours prior to placing on 560Y preceding bombardment (as described in Example 6). Developmental genes ODP2 (AP2 domain transcription factor ODP2 (Ovule development protein 2); US20090328252 A1) and Wushel were included in the experiments through co-bombardment (Example 7). Maize immature embryos were transformed with the vectors PHP44285 or PHP44779.

D. Genomic Sequence Modifications and Transgene Integration at Endogenous Target Sites with Custom Designed Meganuclease Successful delivery of the MHP14 donor vector (PHP44285 or PHP44779) conferred bialaphos herbicide resistance, and was used to identify putative events by callus selection on herbicide containing media. Callus tissues and/or plants regenerated from stable transformants using standard culture and regeneration conditions were screened for modification of the endogenous MHP14 target site.

Real time PCR (qPCR) was used to determine the target site copy number. Two copies of the target site indicate that both alleles are wild type and that no modification occurred at the target site. One copy means one allele of the target site has changed during repair of the double strand break generated by the MHP14 or MHP14+, while absence of the target site (null) is the result of both alleles modified. The copy number can also be in between 1 and 2 due to chimeric nature of callus samples. The probe sequence for qPCR of MHP14 target site was CAGATTCACGTCAGATTT (SEQ ID NO: 106), the MHPTS14_forward primer was AGCGACATAGTGGTGTATAAAAGGAA (SEQ ID NO: 107) and MHPTS14_reverse primer was TGGATGTAATATGTGTACCTCATGCT (SEQ ID NO: 108). The amplicon was approximately 100 bp.

To examine whether increased temperature would increase the rate of target site modification, maize embryos were incubated at different temperatures following bombardment with several meganucleases. Table 2 shows the effect of temperature on the meganuclease activity of MHP14 as determined by target site modification. Table 2 indicates that increased temperature results in increased target site mutation rate.

TABLE 2

Effect of incubating maize embryos at increased temperature post-bombardment on target site mutation rate of meganucleases

| Meganuclease | Temperature (° C.) | Target Site Mutation Rate |
| --- | --- | --- |
| MHP14 | 28 | 14% |
| MHP14 | 32 | 46% |

Following bombardment, embryos were incubated on 560P (maintenance medium) for 12 to 48 hours at 28° C. or 32° C. and then placed at 28° C. Herbicide-resistant events were screened for modification at the target site by measuring target site copy-number using qPCR. Target site mutation rate indirectly measures the meganuclease activity. TSMutRate (target site mutation rate) indicated the modification rate of the MHP14 or LIG3/4 target site (#events with modification/#events100%). As shown in Table 2, target site mutation rate for both MHP14 and LIG34 was approximately 3× higher when embryos were placed at 32° C. for 48 hours after bombardment compared to no temperature elevation treatment.

Maize calli were also screened for integration of the transgene cassette from the donor DNA (PHP44285 or PHP44779) at the MHP14 target site through junction PCR and selected callus events were regenerated into T0 plants. FIG. 9A shows an outline of PCR screening for integration of the donor DNA fragment via homologous recombination at MHP14 target site (PHP44779 donor). Arrows indicate primer locations. FIG. 9B shows PCR of MHP14 callus events: B1-B12 Junction PCR with primers 146773/146775; b1-b12 Junction PCR with primers 146772/146778. Two events (B2 and B5) yielded the predicted 1-1.2 kb PCR fragments that result from integration by homologous recombination for both junctions. PCR products from T0 plants derived from these callus events were sequenced to verify the callus results. PCR screening revealed integration of the herbicide resistance transgene cassette at MHP14 target site. Primers were from the genomic region outside of the homology of donor vector and from the transgene cassette close to the end of the homology.

FIG. 10A shows a schematic outline of long fragment PCR reactions used to confirm UBI:moPAT:PinII cassette integration at the endogenous MHP14 target. FIG. 10B: shows the results of long fragment PCR on T0 plants from three events where integration occurred at the target site. The plant A5 was from event #1, A6-A8 event #2, and C4-C6 event #3. 10B-left shows the long junction fragment PCR on the HR1 side using genomic primer (146775) and moPAT primer (mopatR2); 10B-right shows the long junction fragment PCR on HR2 side (mopatF2/146772). Arrows indicated PCR primer locations. Primer set 146772/mopatF2 amplified a 4 kb fragment, spanning from moPAT gene through the UBI intron, UBI promoter, and the HR2 sequence to the adjacent genomic region. Primer set 146775/mopatR2 amplified a 2.2 kb fragment, spanning from the moPAT gene through the HR1 to the adjacent genomic region. These two fragments overlapped and covered the whole insert at MHP14 target site. The sizes of the two long PCR products indicate a perfect integration of the donor gene cassette at MHP14 target site To determine the segregation pattern of the integration events in progeny, T1 seeds from selfed T0 plants were planted in flats and T1 plants genotyped by using PCR and/or qPCR. The segregation ratio of integration genotypes fit 1:2:1 for wild type (no integration), heterozygous (one allele having integration and the other wild-type) and homozygous integration of the transgene at the MHP14 target site, demonstrating Mendelian inheritance. No visible phenotype was observed in the homozygous or heterozygous integration plants.

The entire inserted fragment of UBI:moPAT:PinII was obtained by using PCR on DNA from homozygous T1 plants with primers in the genomic region outside of the HR1 and HR2 (146772/146775). A PCR product of 5 kb was amplified from homozygous plants as expected. A 2 kb PCR product was amplified from the unmodified intact genomic sequence from wild-type plants.

Trait gene cassettes can be introduced at other target sites of the complex trait locus through homologous recombination mediated by engineered meganucleases. Engineered meganucleases were designed to direct double strand breaks a two other MHP target sites, MHP55 (SEQ ID NO: 72) and MHP77 (SEQ ID NO: 74) within the complex trait locus. Target site modification was determined using qPCR. The probe sequence for qPCR screening of the MHP55 target site was AACCGTCGTGAGACCT (SEQ ID NO: 115), the MHPTS55_Forward_MGBprimer sequence was AAGGCGCAGCCGTTGAG (SEQ ID NO: 116), and MHP55_reverse_MGB primer was CTACCGGTTTCGCGTGCTCT (SEQ ID NO: 117). The probe sequence for qPCR of MHP77 target site was TAGTATGACATACATACCGCC (SEQ ID NO: 118), the MHPTS77_Forward_MGB primer sequence was TCCTTAGGGCGGTATGTATGTCA (SEQ ID NO: 119), and MHP77_reverse_MGB primer was CATCGGT-CAAAAAACACATAAACTTT (SEQ ID NO: 120). The trait gene cassettes encoding MHP14, MHP55 and MHP77 were introduced into maize somatic embryos via transformation techniques using bombardment and following bombardment, embryos were incubated on 560P (maintenance medium) for 48 hours at. As shown in Table 3, maize callus containing the MHP55 target site bombarded with PHP45782 or PHP46924 which include genes encoding MHP55 or MHP55.2 meganucleases, respectively, also lead to an observed increase in the target site mutation rate modified MHP55.2 variant. In addition, maize callus containing a MHP77 target site bombarded with vectors PHP45970 or PHP50238 which include genes encoding MHP77 or MHP77.3 meganucleases, respectively, showed a higher frequency of mutated target sites from callus bombarded with the modified variant MHP77.3. Taken together, like MHP14, these meganucleases directed mutations to their corresponding target sites and modified versions lead to an increase in the target site mutation rate (approx 2 to 10-fold increase when compared to their original versions) suggesting the newly designed versions of the meganucleases were more active than the original nucleases.

TABLE 3

Meganuclease activity (defined as target site mutation rate) of original and modified meganucleases

| Meganuclease | Target Site Mutation Rate |
|---|---|
| MHP55 | 0% |
| MHP55-2 | 5% |
| MHP77 | 1% |
| MHP77-3 | 11% |
| MHP14 | 29% |
| MHP14+ | 40% |

The mutations observed at these target sites indicated that the engineered meganucleases were functional and that the target sites can be used for integration of additional trait genes.

E. Production of a Complex Trait Locus at a Maize Endogenous Locus by Crossing

A maize event obtained through random integration containing a transgene DNA of interest was identified and MHP14, MHP55 and MHP77 target sites surrounding the transgenic DNA of interest were identified as described above. Other maize events containing a modification at the MHP14, MHP55 and MHP77 target site (through addition of herbicide resistance gene as described above) were also identified.

Plants homozygous for the integration of a herbicide resistance gene at the MHP14 target site were crossed with homozygous maize plants containing the transgene DNA of interest. The cross resulted in fertile plants producing F1 seeds. The F1 seeds were planted and out-crossed with Elite inbred line plants and screened for the stacked phenotype. Additional trait genes can be added to the complex trait locus by crossing one transgenic event containing n-transgenes with other trangenic events containing the additional trait gene at the additional target site, and progeny can be screened for the presence of n+1 transgenes. This process can be repeated as many times as the amount of target sites are present in the complex trait locus.

F. Production of a Complex Trait Locus at a Maize Endogenous Locus by Serial Transformation A complex trait locus can be also be created by serial transformation. A first transformed line containing a first trait gene integrated at a first MHP target site can be used to supply embryos. The first transformed line can be retransformed with a second trait gene and a vector encoding a second engineered meganuclease; resulting in the second trait gene being integrated at a second MHP target site through homologous recombination mediated by the second engineered meganuclease. The homozygous integration plants containing a selectable marker at the MHP14 target site can be used to supply embryos. Two rounds of transformations will create two traits at the MHP locus. A transformed line that is homozygous for integration events with two trait genes at MHP target sites can be used to supply embryos for another retransformation, and a third trait gene can be introduced to a third target site.

Example 6

Transformation of Maize Immature Embryos

Transformation can be accomplished by various methods known to be effective in plants, including particle-mediated delivery, *Agrobacterium*-mediated transformation, PEG-mediated delivery, and electroporation.

a. Particle-Mediated Delivery

Transformation of maize immature embryos using particle delivery is performed as follows. Media recipes follow below.

The ears are husked and surface sterilized in 30% Clorox bleach plus 0.5% Micro detergent for 20 minutes, and rinsed two times with sterile water. The immature embryos are isolated and placed embryo axis side down (scutellum side up), 25 embryos per plate, on 560Y medium for 4 hours and then aligned within the 2.5-cm target zone in preparation for bombardment. Alternatively, isolated embryos are placed on 560L (Initiation medium) and placed in the dark at temperatures ranging from 26° C. to 37° C. for 8 to 24 hours prior to placing on 560Y for 4 hours at 26° C. prior to bombardment as described above.

A plasmid comprising the Zm-BBM (also referred to as Zm-ODP2) coding sequence (set forth in SEQ ID NO: 9) operably linked to a promoter is constructed. This could be a weak promoter such as nos, a tissue-specific promoter, such as globulin-1 or oleosin, an inducible promoter such as In2, or a strong promoter such as ubiquitin plus a plasmid containing the selectable marker gene phosphinothricin N-acetyltransferase (PAT; Wohlleben et al. (1988) *Gene* 70:25 37) that confers resistance to the herbicide bialaphos. Furthermore, plasmids containing the double strand brake inducing agent and donor DNA such as PHP44285 or PHP44779 are constructed as described above and co-bombareded with the plasmids containing the developmental genes ODP2 (AP2 domain transcription factor ODP2 (Ovule development protein 2); US20090328252 A1) and Wushel.

The plasmids are precipitated onto 1.1 μm (average diameter) tungsten pellets using a calcium chloride ($CaCl_2$)) precipitation procedure by mixing 100 μl prepared tungsten particles in water, 10 μl (1 μg) DNA in Tris EDTA buffer (1 μg total DNA), 100 μl 2.5 M $CaCl_2$, and 10 μl 0.1 M spermidine. Each reagent is added sequentially to the tungsten particle suspension, with mixing. The final mixture is sonicated briefly and allowed to incubate under constant vortexing for 10 minutes. After the precipitation period, the tubes are centrifuged briefly, liquid is removed, and the particles are washed with 500 ml 100% ethanol, followed by a 30 second centrifugation. Again, the liquid is removed, and 105 μl 100% ethanol is added to the final tungsten particle pellet. For particle gun bombardment, the tungsten/DNA particles are briefly sonicated. 10 μl of the tungsten/DNA particles is spotted onto the center of each macrocarrier, after which the spotted particles are allowed to dry about 2 minutes before bombardment.

The sample plates are bombarded at level #4 with a Biorad Helium Gun. All samples receive a single shot at 450 PSI, with a total of ten aliquots taken from each tube of prepared particles/DNA.

Following bombardment, the embryos are incubated on 560P (maintenance medium) for 12 to 48 hours at temperatures ranging from 26C to 37 C, and then placed at 26 C. After 5 to 7 days the embryos are transferred to 560R selection medium containing 3 mg/liter Bialaphos, and subcultured every 2 weeks at 26 C. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to a lighted culture room. Approximately 7-10 days later, developing plantlets are transferred to 272V hormone-free medium in tubes for 7-10 days until plantlets are well established. Plants are then transferred to inserts in flats (equivalent to a 2.5" pot) containing potting soil and grown for 1 week in a growth chamber, subsequently grown an additional 1-2 weeks in the greenhouse, then transferred to Classic 600 pots (1.6 gallon) and grown to maturity. Plants are monitored and scored for transformation efficiency, and/or modification of regenerative capabilities.

Initiation medium (560 L) comprises 4.0 g/l N6 basal salts (SIGMA C-1416), 1.0 ml/l Eriksson's Vitamin Mix (1000× SIGMA-1511), 0.5 mg/l thiamine HCl, 20.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I H2O); and 8.5 mg/l silver nitrate (added after sterilizing the medium and cooling to room temperature).

Maintenance medium (560P) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, 2.0 mg/l 2,4-D, and 0.69 g/l L-proline (brought to volume with D-I $H_2O$ following adjustment to pH 5.8 with KOH); 3.0 g/l Gelrite (added after bringing to volume with D-I H2O); and 0.85 mg/l silver nitrate (added after sterilizing the medium and cooling to room temperature).

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I H2O); and 8.5 mg/l silver nitrate (added after sterilizing the medium and cooling to room temperature).

Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I H2O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I H2O); and 1.0 mg/l indoleacetic acid and 3.0 mg/l bialaphos (added after sterilizing the medium and cooling to 60° C.).

Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H2O), 0.1 g/l myo-inositol, and 40.0 g/l sucrose (brought to volume with polished D-I $H_2O$ after adjusting pH to 5.6); and 6 g/l bacto-agar (added after bringing to volume with polished D-I H2O), sterilized and cooled to 60° C.

b. *Agrobacterium*-Mediated Transformation

*Agrobacterium*-mediated transformation was performed essentially as described in Djukanovic et al. (2006) *Plant Biotech J* 4:345-57. Briefly, 10-12 day old immature embryos (0.8-2.5 mm in size) were dissected from sterilized kernels and placed into liquid medium (4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 68.5 g/L sucrose, 36.0 g/L glucose, pH 5.2). After embryo collection, the medium was replaced with 1 ml *Agrobacterium* at a concentration of 0.35-0.45 OD550. Maize embryos were incubated with *Agrobacterium* for 5 min at room temperature, then the mixture was poured onto a media plate containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 30.0 g/L sucrose, 0.85 mg/L silver nitrate, 0.1 nM acetosyringone, and 3.0 g/L Gelrite, pH 5.8. Embryos were incubated axis down, in the dark for 3 days at 20° C., then incubated 4 days in the dark at 28° C., then transferred onto new media plates containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.69 g/L L-proline, 30.0 g/L sucrose, 0.5 g/L MES buffer, 0.85 mg/L silver nitrate, 3.0 mg/L Bialaphos, 100 mg/L carbenicillin, and 6.0 g/L agar, pH 5.8. Embryos were subcultured every three weeks until transgenic events were identified. Somatic embryogenesis was induced by transferring a small amount of tissue onto regeneration medium (4.3 g/L MS salts (Gibco 11117), 5.0 ml/L MS Vitamins Stock Solution, 100 mg/L myo-inositol, 0.1 μM ABA, 1 mg/L IAA, 0.5 mg/L zeatin, 60.0 g/L sucrose, 1.5 mg/L Bialaphos, 100 mg/L carbenicillin, 3.0 g/L Gelrite, pH 5.6) and incubation in the dark for two weeks at 28° C. All material with visible shoots and roots were transferred onto media containing 4.3 g/L MS salts (Gibco 11117), 5.0 ml/L MS Vitamins Stock Solution, 100 mg/L myo-inositol, 40.0 g/L sucrose, 1.5 g/L Gelrite, pH 5.6, and incubated under artificial light at 28° C. One week later, plantlets were moved into glass tubes containing the same medium and grown until they were sampled and/or transplanted into soil.

Example 7

Transient Expression of BBM Enhances Transformation

Parameters of the transformation protocol can be modified to ensure that the BBM activity is transient. One such method involves precipitating the BBM-containing plasmid in a manner that allows for transcription and expression, but precludes subsequent release of the DNA, for example, by using the chemical PEI. In one example, the BBM plasmid is precipitated onto gold particles with PEI, while the transgenic expression cassette (UBI::moPAT-GFPm::PinII; moPAT is the maize optimized PAT gene) to be integrated is precipitated onto gold particles using the standard calcium chloride method.

Briefly, gold particles were coated with PEI as follows. First, the gold particles were washed. Thirty-five mg of gold particles, 1.0 in average diameter (A.S.I. #162-0010), were weighed out in a microcentrifuge tube, and 1.2 ml absolute EtOH was added and vortexed for one minute. The tube was incubated for 15 minutes at room temperature and then centrifuged at high speed using a microfuge for 15 minutes at 4° C. The supernatant was discarded and a fresh 1.2 ml aliquot of ethanol (EtOH) was added, vortexed for one minute, centrifuged for one minute, and the supernatant again discarded (this is repeated twice). A fresh 1.2 ml aliquot of EtOH was added, and this suspension (gold particles in EtOH) was stored at −20° C. for weeks. To coat particles with polyethylimine (PEI; Sigma #P3143), 250 µl of the washed gold particle/EtOH mix was centrifuged and the EtOH discarded. The particles were washed once in 100 µl ddH2O to remove residual ethanol, 250 µl of 0.25 mM PEI was added, followed by a pulse-sonication to suspend the particles and then the tube was plunged into a dry ice/EtOH bath to flash-freeze the suspension, which was then lyophilized overnight. At this point, dry, coated particles could be stored at −80° C. for at least 3 weeks. Before use, the particles were rinsed 3 times with 250 µl aliquots of 2.5 mM HEPES buffer, pH 7.1, with 1× pulse-sonication, and then a quick vortex before each centrifugation. The particles were then suspended in a final volume of 250 µl HEPES buffer. A 25 µl aliquot of the particles was added to fresh tubes before attaching DNA. To attach uncoated DNA, the particles were pulse-sonicated, then 1 µg of DNA (in 5 µl water) was added, followed by mixing by pipetting up and down a few times with a Pipetteman and incubated for 10 minutes. The particles were spun briefly (i.e. 10 seconds), the supernatant removed, and 60 µl EtOH added. The particles with PEI-precipitated DNA-1 were washed twice in 60 µl of EtOH. The particles were centrifuged, the supernatant discarded, and the particles were resuspended in 45 µl water. To attach the second DNA (DNA-2), precipitation using TFX-50 was used. The 45 µl of particles/DNA-1 suspension was briefly sonicated, and then 5 µl of 100 ng/µl of DNA-2 and 2.5 µl of TFX-50 were added. The solution was placed on a rotary shaker for 10 minutes, centrifuged at 10,000 g for 1 minute. The supernatant was removed, and the particles resuspended in 60 µl of EtOH. The solution was spotted onto macrocarriers and the gold particles onto which DNA-1 and DNA-2 had been sequentially attached were delivered into scutellar cells of 10 DAP Hi-II immature embryos using a standard protocol for the PDS-1000. For this experiment, the DNA-1 plasmid contained a UK:RFP::pinII expression cassette, and DNA-2 contained a UBI::CFP::pinII expression cassette. Two days after bombardment, transient expression of both the CFP and RFP fluorescent markers was observed as numerous red & blue cells on the surface of the immature embryo. The embryos were then placed on non-selective culture medium and allowed to grow for 3 weeks before scoring for stable colonies. After this 3-week period, 10 multicellular, stably-expressing blue colonies were observed, in comparison to only one red colony. This demonstrated that PEI-precipitation could be used to effectively introduce DNA for transient expression while dramatically reducing integration of the PEI-introduced DNA and thus reducing the recovery of RFP-expressing transgenic events. In this manner, PEI-precipitation can be used to deliver transient expression of BBM and/or WUS2.

For example, the particles are first coated with UBI::BBM::pinII using PEI, then coated with UBI::moPAT-YFP using TFX-50, and then bombarded into scutellar cells on the surface of immature embryos. PEI-mediated precipitation results in a high frequency of transiently expressing cells on the surface of the immature embryo and extremely low frequencies of recovery of stable transformants (relative to the TFX-50 method). Thus, it is expected that the PEI-precipitated BBM cassette expresses transiently and stimulates a burst of embryogenic growth on the bombarded surface of the tissue (i.e. the scutellar surface), but this plasmid will not integrate. The PAT-GFP plasmid released from the Ca++/gold particles is expected to integrate and express the selectable marker at a frequency that results in substantially improved recovery of transgenic events. As a control treatment, PEI-precipitated particles containing a UBI::GUS::pinII (instead of BBM) are mixed with the PAT-GFP/Ca++ particles. Immature embryos from both treatments are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

As an alternative method, the BBM plasmid is precipitated onto gold particles with PEI, and then introduced into scutellar cells on the surface of immature embryos, and subsequent transient expression of the BBM gene elicits a rapid proliferation of embryogenic growth. During this period of induced growth, the explants are treated with *Agrobacterium* using standard methods for maize (see Example 1), with T-DNA delivery into the cell introducing a transgenic expression cassette such as UBI::moPAT-GFPm::pinII. After co-cultivation, explants are allowed to recover on normal culture medium, and then are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

It may be desirable to "kick start" callus growth by transiently expressing the BBM and/or WUS2 polynucleotide products. This can be done by delivering BBM and WUS2 5'-capped polyadenylated RNA, expression cassettes containing BBM and WUS2 DNA, or BBM and/or WUS2 proteins. All of these molecules can be delivered using a biolistics particle gun. For example 5'-capped polyadenylated BBM and/or WUS2 RNA can easily be made in vitro using Ambion's mMessage mMachine kit. RNA is co-delivered along with DNA containing a polynucleotide of interest and a marker used for selection/screening such as Ubi::moPAT-GFpm::PinII. It is expected that the cells receiving the RNA will immediately begin dividing more rapidly and a large portion of these will have integrated the agronomic gene. These events can further be validated as being transgenic clonal colonies because they will also express the PAT-GFP fusion protein (and thus will display green fluorescence under appropriate illumination). Plants regenerated from these embryos can then be screened for the presence of the polynucleotide of interest.

Although the foregoing invention has been described in some detail by way of illustration and example for purposes of clarity of understanding, it will be obvious that certain changes and modifications may be practiced within the scope of the appended claims.

That which is claimed:

1. A method to produce a maize plant comprising a complex transgenic trait locus in a plant, the trait locus comprising at least first and second altered target sequences, wherein the first altered target sequence originated from a first endogenous target sequence that is recognized and cleaved by a first engineered double-strand-break-inducing agent and the second altered target sequence originated from a second endogenous target sequence that is recognized and cleaved by a second engineered double-strand-break-inducing agent, wherein each of said altered target sequences differ from their corresponding endogenous target sequence, wherein the first and second endogenous target sequences are located on the same arm of the same chromosome, wherein each of the alterations comprises a heterologous polynucleotide, and wherein at least one of the engineered double-strand-break-inducing agents cleaves a target sequence selected from the group consisting of SEQ ID NO: 77 or SEQ ID NO:70.

2. The method to produce the maize plant of claim 1 wherein the heterologous polynucleotide is selected from the group consisting of: DNA for gene silencing, DNA encoding a phenotypic marker, and DNA encoding a protein providing an agronomic advantage.

3. The method to produce the maize plant of claim 1, the method comprising obtaining a seed from the maize plant comprising said complex transgenic trait locus of claim 1.

* * * * *

SEQUENCE LISTING

```
Sequence total quantity: 129
SEQ ID NO: 1              moltype = DNA   length = 22
FEATURE                   Location/Qualifiers
source                    1..22
                          mol_type = genomic DNA
                          organism = Glycine max
SEQUENCE: 1
ggcactctcg tgtgtgatta aa                                                  22

SEQ ID NO: 2              moltype = DNA   length = 22
FEATURE                   Location/Qualifiers
source                    1..22
                          mol_type = genomic DNA
                          organism = Glycine max
SEQUENCE: 2
cagacgtacg caagtagctt tg                                                  22

SEQ ID NO: 3              moltype = DNA   length = 22
FEATURE                   Location/Qualifiers
source                    1..22
                          mol_type = genomic DNA
                          organism = Glycine max
SEQUENCE: 3
gagtcccacg caagagcata aa                                                  22

SEQ ID NO: 4              moltype = DNA   length = 22
FEATURE                   Location/Qualifiers
source                    1..22
                          mol_type = genomic DNA
                          organism = Glycine max
SEQUENCE: 4
aagacttacg tgtgtactcg tg                                                  22

SEQ ID NO: 5              moltype = DNA   length = 22
FEATURE                   Location/Qualifiers
source                    1..22
                          mol_type = genomic DNA
                          organism = Glycine max
SEQUENCE: 5
gacattgtcg tgagaaaaga ga                                                  22

SEQ ID NO: 6              moltype = DNA   length = 22
FEATURE                   Location/Qualifiers
source                    1..22
                          mol_type = genomic DNA
                          organism = Glycine max
SEQUENCE: 6
aaatctgtct tgcgaaacgg ca                                                  22

SEQ ID NO: 7              moltype = DNA   length = 22
FEATURE                   Location/Qualifiers
source                    1..22
                          mol_type = genomic DNA
                          organism = Glycine max
SEQUENCE: 7
tattctctca taaataaact tt                                                  22

SEQ ID NO: 8              moltype = DNA   length = 22
FEATURE                   Location/Qualifiers
source                    1..22
                          mol_type = genomic DNA
                          organism = Glycine max
SEQUENCE: 8
ggaatggaca taagagaact gt                                                  22

SEQ ID NO: 9              moltype = DNA   length = 1272
FEATURE                   Location/Qualifiers
misc_feature              1..1272
                          note = synthetic construct; plant optimized nucleotide
                           sequence of TS21 meganuclease
source                    1..1272
                          mol_type = other DNA
                          organism = synthetic construct
SEQUENCE: 9
atggcaccga agaagaagcg caaggtgcat atgaacacca agtacaacaa ggagttcctg          60
ctctacctgg ccggcttcgt ggacggcgac ggctccatca tggcgcagat caagccgcag         120
cagtcctgca gttcaagca cgcgctccag ctgaccttca ccgtgaccca gaagacgcag         180
aggcgctggt tcctcgacaa gctggtcgac gagatcgggg tgggcaaggt ctacgaccgc         240
```

```
gggtcggtgt ccgactacat cctctcccag atcaagcccc tgcacaactt cctcacccag    300
ctccagccgt tcctcaagct gaagcagaag caggcgaacc tcgtcctgaa gatcatcgag    360
cagctcccct cggccaagga gtccccggac aagttcctgg aggtaagttt ctgcttctac    420
cttttgatata tatataataa ttatcattaa ttagtagtaa tataatattt caaatatttt    480
tttcaaaata aaagaatgta gtatatagca attgcttttc tgtagtttat aagtgtgtat    540
attttaattt ataacttttc taatatatga ccaaaacatg gtgatgtgca ggtgtgcacg    600
tgggtcgacc agatcgcggc cctcaacgac agcaagaccc gcaagacgac ctcggagacg    660
gtgcgggcgg tcctggactc cctcccagga tccgtgggag gtctatcgcc atctcaggca    720
tccagcgcg catcctcggc ttcctcaagc ccgggttcag gatctccga agcactcaga    780
gctggagcaa ctaagtccaa ggaattcctg ctctacctgg ccggcttcgt ggacggcgac    840
ggctccatca aggcgcagat caagccgcgc cagtcccgca agttcaagca cgagctctcc    900
ctgaccttcc aggtgaccca gaagacgcag aggcgctggt tcctcgacaa gctggtcgac    960
gagatcgggg tgggctacgt ctacgaccgc gggtcggtgt ccgactacat cctctcccag   1020
atcaagcccc tgcacaactt cctcacccag ctccagccgt tcctcaagct gaagcagaag   1080
caggcgaacc tcgtcctgaa gatcatcgag cagctcccct cggccaagga gtccccggac   1140
aagttcctgg aggtgtgcac gtgggtcgac cagatcgcgg ccctcaacga cagcaagacc   1200
cgcaagacga cctcggagac ggtgcgggcg gttctagact ccctcagcga agaagaag    1260
tcgtcccct ga                                                        1272

SEQ ID NO: 10          moltype = DNA   length = 1272
FEATURE                Location/Qualifiers
misc_feature           1..1272
                       note = synthetic construct; plant optimized nucleotide
                       sequence of TS14 meganuclease
source                 1..1272
                       mol_type = other DNA
                       organism = synthetic construct
SEQUENCE: 10
atggcaccga agaagaagcg caaggtgcat atgaacacca agtacaacaa ggagttcctg     60
ctctacctgg ccggcttcgt ggacggcgac ggctccatca tcgcgtccat caagccggag    120
cagtcctaca agttcaagca ccgcctctcc ctgaccttca ccgtgaccca gaagacgcag    180
aggcgctggt tcctcgacaa gctggtcgac gagatcgggg tgggcaaggt ctacgaccgc    240
gggtcggtgt ccgactaccg cctctcccag atcaagcccc tgcacaactt cctcacccag    300
ctccagccgt tcctcaagct caagcagaag caggccaacc tcgtgctgaa gatcatcgag    360
cagctgccct ccgccaagga atccccggac aagttcctgg aggtaagttt ctgcttctac    420
cttttgatata tatataataa ttatcattaa ttagtagtaa tataatattt caaatatttt    480
tttcaaaata aaagaatgta gtatatagca attgcttttc tgtagtttat aagtgtgtat    540
attttaattt ataacttttc taatatatga ccaaaacatg gtgatgtgca ggtgtgcacg    600
tgggtggacc agatcgcggc cctcaacgac agcaagaccc gcaagacgac ctcggagacg    660
gtgcgggcgg tcctggactc cctcccagga tccgtgggag gtctatcgcc atctcaggca    720
tccagcgccg catcctcggc ttcctcaagc ccgggttcag gatctccga agcactcaga    780
gctggagcaa ctaagtccaa ggaattcctg ctctacctgg ccggcttcgt ggacggcgac    840
ggctccatca tcgcgaagat caccccgaac cagtcctaca agttcaagca ccagctccga    900
ctgcgcttca ccgtgaccca gaagacgcag aggcgctggt tcctcgacaa gctggtcgac    960
gagatcgggg tgggcaaggt ctacgaccgc gggtcggtgt ccgactacat cctctcccag   1020
atcaagcccc tgcacaactt cctcacccag ctccagccgt tcctcaagct gaagcagaag   1080
caggcgaacc tcgtcctgaa gatcatcgag cagctcccct cggccaagga gtccccggac   1140
aagttcctgg aggtgtgcac gtgggtcgac cagatcgcgg ccctcaacga cagcaagacc   1200
cgcaagacga cctcggagac ggtgcgggcg gttctagact ccctcagcga agaagaag    1260
tcgtcccct ga                                                        1272

SEQ ID NO: 11          moltype = DNA   length = 1272
FEATURE                Location/Qualifiers
misc_feature           1..1272
                       note = synthetic construct; plant optimized nucleotide
                       sequence of TS30 meganuclease
source                 1..1272
                       mol_type = other DNA
                       organism = synthetic construct
SEQUENCE: 11
atggcaccga agaagaagcg caaggtgcat atgaacacca agtacaacaa ggagttcctg     60
ctctacctgg ccggcttcgt ggacggcgac ggctccatca tggcgaagat caagccggag    120
cagtcctaca agttcaagca ccgcctcatg ctgaccttca ccgtgaccca gaagacgcag    180
aggcgctggt tcctcgacaa gctggtcgac gagatcgggg tgggctacgt ctacgaccgc    240
gggtcggtgt ccgactacat cctctcccag atcaagcccc tgcacaactt cctcacccag    300
ctccagccgt tcctcaagct gaagcagaag caggcgaacc tcgtcctgaa gatcatcgag    360
cagctcccct cggccaagga gtccccggac aagttcctgg aggtaagttt ctgcttctac    420
cttttgatata tatataataa ttatcattaa ttagtagtaa tataatattt caaatatttt    480
tttcaaaata aaagaatgta gtatatagca attgcttttc tgtagtttat aagtgtgtat    540
attttaattt ataacttttc taatatatga ccaaaacatg gtgatgtgca ggtgtgcacg    600
tgggtcgacc agatcgcggc cctcaacgac agcaagaccc gcaagacgac ctcggagacg    660
gtgcgggcgg tcctggactc cctcccagga tccgtgggag gtctatcgcc atctcaggca    720
tccagcgccg catcctcggc ttcctcaagc ccgggttcag gatctccga agcactcaga    780
gctggagcaa ctaagtccaa ggaattcctg ctctacctgg ccggcttcgt ggacggcgac    840
ggctccatca aggcgccat cacccccgcag cagtcctgca agttcaagca cgcgctccag    900
ctgaccttcc aggtgaccca gaagacgcag aggcgctggt tcctcgacaa gctggtcgac    960
gagatcgggg tgggcaaggt ctacgaccgc gggtcggtgt ccgactaccg cctctcccag   1020
atcaagcccc tgcacaactt cctcacccag ctccagccgt tcctcaagct gaagcagaag   1080
caggcgaacc tcgtcctgaa gatcatcgag cagctcccct cggccaagga gtccccggac   1140
```

```
aagttcctgg aggtgtgcac gtgggtcgac cagatcgcgg ccctcaacga cagcaagacc   1200
cgcaagacga cctcggagac ggtgcgggcg gttctagact ccctcagcga agaagaag    1260
tcgtcccct ga                                                       1272

SEQ ID NO: 12           moltype = DNA  length = 1272
FEATURE                 Location/Qualifiers
misc_feature            1..1272
                        note = synthetic construct; Plant optimized nucleotide
                        sequence of TS5 meganuclease
source                  1..1272
                        mol_type = other DNA
                        organism = synthetic construct
SEQUENCE: 12
atggcaccga agaagaagcg caaggtgcat atgaacacca agtacaacaa ggagttcctg   60
ctctacctgg ccggcttcgt ggacggcgac ggttccatca tcgcgcagat caagccggag   120
cagtcctaca agttcaagca ccgcctctcc ctgaccttca ccgtgaccca gaagacgcag   180
aggcgctggt tcctcgacaa gctggtcgac gagatcgggg tgggctacgt ctacgaccgc   240
gggtcggtgt ccgactaccg cctctcccag atcaagcccc tgcacaactt cctcacccag   300
ctccagccgt tcctgaagct caagcagaag caggccaacc tcgtgctgaa gatcatcgag   360
cagctgccct ccgccaagga atccccggac aagttcctgg aggtaagttt ctgcttctac   420
cttttgatata tatataataa ttatcattaa ttagtagtaa tataatattt caaatatttt   480
tttcaaaata aaagaatgta gtatatagca attgcttttc tgtagtttat aagtgtgtat   540
attttaattt ataacttttc taatatatga ccaaaacatg gtgatgtgca ggtgtgcacg   600
tgggtcgacc agatcgcggc cctcaacgac agcaagaccc gcaagacgac ctcggagacg   660
gtgcgggcgg tcctggactc cctcccagga tccgtgggag gtctatcgcc atctcaggca   720
tccagccgcg catcctcggc ttcctcaagc ccggggtcag ggatctccga agcactcaga   780
gctggagcaa ctaagtccaa ggaattcctg ctctacctgg ccggcttcgt ggacggcgac   840
ggctccatca tcgcgtccat ctccccgcgc cagtcctaca agttcaagca cgagctccgc   900
ctgaccttca ccgtgaccca gaagacgcag aggcgctggt tcctcgacaa gctggtcgac   960
gagatcgggg tgggctacgt ctacgaccgc gggtcggtgt ccgactaccg cctctcccag   1020
atcaagcccc tgcacaactt cctcacccag ctccagccgt tcctcaagct gaagcagaag   1080
caggcgaacc tcgtcctgaa gatcatcgag cagctcccct cggccaagga gtccccggac   1140
aagttcctgg aggtgtgcac gtgggtcgac cagatcgcgg ccctcaacga cagcaagacc   1200
cgcaagacga cctcggagac ggtgcgggcg gttctagact ccctcagcga agaagaag    1260
tcgtcccct ga                                                       1272

SEQ ID NO: 13           moltype = DNA  length = 1272
FEATURE                 Location/Qualifiers
misc_feature            1..1272
                        note = synthetic construct; Plant optimized nucleotide
                        sequence of TS7 meganuclease
source                  1..1272
                        mol_type = other DNA
                        organism = synthetic construct
SEQUENCE: 13
atggcaccga agaagaagcg caaggtgcat atgaacacca agtacaacaa ggagttcctg   60
ctctacctgg ccggcttcgt ggacggcgac ggctccatca tcgcgcagat caccccgcgc   120
cagtcctaca agttcaagca ctccctccag ctgaccttcc aggtgaccca gaagacgcag   180
aggcgctggt tcctcgacaa gctggtcgac gagatcgggg tgggcaaggt ccgcgaccgc   240
gggtcggtgt ccgactacat cctctcccag atcaagcccc tgcacaactt cctcacccag   300
ctccagccgt tcctcaagct gaagcagaag caggcgaacc tcgtcctgaa gatcatcgag   360
cagctcccct tcggccaagga gtccccggac aagttcctgg aggtaagttt ctgcttctac   420
cttttgatata tatataataa ttatcattaa ttagtagtaa tataatattt caaatatttt   480
tttcaaaata aaagaatgta gtatatagca attgcttttc tgtagtttat aagtgtgtat   540
attttaattt ataacttttc taatatatga ccaaaacatg gtgatgtgca ggtgtgcacg   600
tgggtcgacc agatcgcggc cctcaacgac agcaagaccc gcaagacgac ctcggagacg   660
gtgcgggcgg tcctggactc cctcccagga tccgtgggag gtctatcgcc atctcaggca   720
tccagccgcg catcctcggc ttcctcaagc ccggggtcag ggatctccga agcactcaga   780
gctggagcaa ctaagtccaa ggaattcctg ctctacctgg ccggcttcgt ggacggcgac   840
ggctccatca tcgcgcagat ctccccgcag cagttcaagca catcctcgc               900
ctgaccttcc aggtgaccca gaagacgcag aggcgctggt tcctcgacaa gctggtcgac   960
gagatcgggg tgggcaaggt ctacgaccgc gggtcggtgt ccgactaccg cctctcccag   1020
atcaagcccc tgcacaactt cctcacccag ctccagccgt tcctcaagct gaagcagaag   1080
caggcgaacc tcgtcctgaa gatcatcgag cagctcccct cggccaagga gtccccggac   1140
aagttcctgg aggtgtgcac gtgggtcgac cagatcgcgg ccctcaacga cagcaagacc   1200
cgcaagacga cctcggagac ggtgcgggcg gttctagact ccctcagcga agaagaag    1260
tcgtcccct ga                                                       1272

SEQ ID NO: 14           moltype = DNA  length = 1272
FEATURE                 Location/Qualifiers
misc_feature            1..1272
                        note = synthetic construct; Plant optimized nucleotide
                        sequence of TS4 meganuclease
source                  1..1272
                        mol_type = other DNA
                        organism = synthetic construct
SEQUENCE: 14
atggcaccga agaagaagcg caaggtgcat atgaacacca agtacaacaa ggagttcctg   60
ctctacctgg ccggcttcgt ggacggcgac ggctccatca tcgcgcagat ccgcccgcgc   120
```

```
cagtcccgca agttcaagca cgagctcgag ctgcgcttcc aggtgaccca gaagacgcag    180
aggcgctggt tcctcgacaa gctggtcgac gagatcgggg tgggctacgt ctacgaccgc    240
gggtcggtgt ccgactacat cctctcccag atcaagcccc tgcacaactt cctcacccag    300
ctccagccgt tcctcaagct gaagcagaag caggcgaacc tcgtcctgaa gatcatcgag    360
cagctcccct cggccaagga gtccccggac aagttcctgg aggtaagttt ctgcttctac    420
ctttgatata tatataataa ttatcattaa ttagtagtaa tataatattt caaatatttt    480
tttcaaaata aaagaatgta gtatatagca attgcttttc tgtagtttat aagtgtgtat    540
attttaattt ataactttc taatatatga ccaaaacatg gtgatgtgca ggtgtgcacg    600
tgggtcgacc agatcgcggc cctcaacgac agcaagaccc gcaagacgac ctcggagacg    660
gtgcgggcgg tcctggactc cctcccagga tccgtgggag gtctatcgcc atctcaggca    720
tccagcgccg catcctcggc ttcctcaagc ccggggttcag ggatctccga agcactcaga    780
gctggagcaa ctaagtccaa ggaattcctg ctctacctgg cgggcttcgt ggacggcgac    840
ggctccatca tcgcgcagat caagccgaac cagtcctaca agttcaagca ccagctcatg    900
ctgaccttcc aggtgaccca gaagacgcag aggcgctggt tcctcgacaa gctggtcgac    960
gagatcgggg tgggctacgt ccgcgaccgc gggtcggtgt ccgactacat cctctcccag   1020
atcaagcccc tgcacaactt cctcacccag ctccagccgt tcctcaagct gaagcagaag   1080
caggcgaacc tcgtcctgaa gatcatcgag cagctcccct cggccaagga gtccccggac   1140
aagttcctgg aggtgtgcac gtgggtcgac cagatcgcgg ccctcaacga cagcaagacc   1200
cgcaagacga cctcggagac ggtgcgggcg gttctagact ccctcagcga gaagaagaag   1260
tcgtccccct ga                                                       1272

SEQ ID NO: 15           moltype = DNA  length = 1272
FEATURE                 Location/Qualifiers
misc_feature            1..1272
                        note = synthetic construct; Plant optimized nucleotide
                          sequence of TS22 meganuclease
source                  1..1272
                        mol_type = other DNA
                        organism = synthetic construct
SEQUENCE: 15
atggcaccga agaagaagcg caaggtgcat atgaacacca agtacaacaa ggagttcctg     60
ctctacctgg cgggcttcgt ggacggcgac ggctccatca tcgcgcagat ctccccgaac    120
cagtcctaca agttcaagca ccagctccgc ctgaccttca ccgtgaccca gaagacgcag    180
aggcgctggt tcctcgacaa gctggtcgac gagatcgggg tgggcatggt ctacgaccag    240
gggtcggtgt cccactaccg cctctcccag atcaagcccc tgcacaactt cctcacccag    300
ctccagccgt tcctcaagct gaagcagaag caggcgaacc tcgtcctgaa gatcatcgag    360
cagctcccct cggccaagga gtccccggac aagttcctgg aggtaagttt ctgcttctac    420
ctttgatata tatataataa ttatcattaa ttagtagtaa tataatattt caaatatttt    480
tttcaaaata aaagaatgta gtatatagca attgcttttc tgtagtttat aagtgtgtat    540
attttaattt ataactttc taatatatga ccaaaacatg gtgatgtgca ggtgtgcacg    600
tgggtcgacc agatcgcggc cctcaacgac agcaagaccc gcaagacgac ctcggagacg    660
gtgcgggcgg tcctggactc cctcccagga tccgtgggag gtctatcgcc atctcaggca    720
tccagcgccg catcctcggc ttcctcaagc ccggggttcag ggatctccga agcactcaga    780
gctggagcaa ctaagtccaa ggaattcctg ctctacctgg cgggcttcgt ggacggcgac    840
ggctccatca aggcgcagat caagccgcag cagtgctaca agttcaagca cgcgctcatg    900
ctgaccttcc aggtgaccca gaagacgcag aggcgctggt tcctcgacaa gctggtcgac    960
gagatcgggg tgggctacgt ctacgaccgc gggtcggtgt ccgactacat cctctcccag   1020
atcaagcccc tgcacaactt cctcacccag ctccagccgt tcctcaagct gaagcagaag   1080
caggcgaacc tcgtcctgaa gatcatcgag cagctcccct cggccaagga gtccccggac   1140
aagttcctgg aggtgtgcac gtgggtcgac cagatcgcgg ccctcaacga cagcaagacc   1200
cgcaagacga cctcggagac ggtgcgggcg gttctagact ccctcagcga gaagaagaag   1260
tcgtccccct ga                                                       1272

SEQ ID NO: 16           moltype = DNA  length = 1272
FEATURE                 Location/Qualifiers
misc_feature            1..1272
                        note = synthetic construct; Plant optimized nucleotide
                          sequence of TS24 meganuclease
source                  1..1272
                        mol_type = other DNA
                        organism = synthetic construct
SEQUENCE: 16
atggcaccga agaagaagcg caaggtgcat atgaacacca agtacaacaa ggagttcctg     60
ctctacctgg cgggcttcgt ggacggcgac ggctccatca tcgcgtccat ggccccgaac    120
cagtcccgca agttcaagca ccagctccag ctgaccttca ccgtgaccca gaagacgcag    180
aggcgctggt tcctcgacaa gctggtcgac gagatcgggg tgggcaaggt ccgcgaccgc    240
gggtcggtgt ccgactaccg cctctcccag atcaagcccc tgcacaactt cctcacccag    300
ctccagccgt tcctcaagct gaagcagaag caggcgaacc tcgtcctgaa gatcatcgag    360
cagctcccct cggccaagga gtccccggac aagttcctgg aggtaagttt ctgcttctac    420
ctttgatata tatataataa ttatcattaa ttagtagtaa tataatattt caaatatttt    480
tttcaaaata aaagaatgta gtatatagca attgcttttc tgtagtttat aagtgtgtat    540
attttaattt ataactttc taatatatga ccaaaacatg gtgatgtgca ggtgtgcacg    600
tgggtcgacc agatcgcggc cctcaacgac agcaagaccc gcaagacgac ctcggagacg    660
gtgcgggcgg tcctggactc cctcccagga tccgtgggag gtctatcgcc atctcaggca    720
tccagcgccg catcctcggc ttcctcaagc ccggggttcag ggatctccga agcactcaga    780
gctggagcaa ctaagtccaa ggaattcctg ctctacctgg cgggcttcgt ggacggcgac    840
ggctccatca aggcgcagat caccccgaac cagtcctgca agttcaagca ccagctccgc    900
ctgaccttcc aggtgaccca gaagacgcag aggcgctggt tcctcgacaa gctggtcgac    960
gagatcgggg tgggcaaggt ctacgaccgc gggtcggtgt ccgactacat cctctcccag   1020
```

```
atcaagcccc tgcacaactt cctcacccag ctccagccgt tcctcaagct gaagcagaag   1080
caggcgaacc tcgtcctgaa gatcatcgag cagctcccct cggccaagga gtccccggac   1140
aagttcctgg aggtgtgcac gtgggtcgac cagatcgcgg ccctcaacga cagcaagacc   1200
cgcaagacga cctcggagac ggtgcgggcg gttctagact ccctcagcga gaagaagaag   1260
tcgtcccct ga                                                        1272

SEQ ID NO: 17           moltype = DNA   length = 1020
FEATURE                 Location/Qualifiers
source                  1..1020
                        mol_type = genomic DNA
                        organism = Glycine max
SEQUENCE: 17
ttatttatcc cctataaagg gcaccagtta gttcaatctg atgtctaacc taatttggat   60
acatgccttt tattgcagct gccgtccgtg cacagaggag tcttaggagg aacaactgta   120
gagaaaagga tctgccaaat tcgctagaaa attcaccaga aacaccaccc gttatccaat   180
taaacaagat ttttggatca cttgtgaagt tgaattgcta tccaactgct attcccattt   240
ctaaaccttg ttacacgagc atcttgatca atggtctaga aagggaaata gcagttagt   300
ggtgcttcaa cgataagtta ttggatttag tatttatctt agcctgtttt cgtgtacttt   360
gttttgccgg atggaggtat gtgattttgt ctatgattct taatacaata acctacactt   420
actctcattg atagtttgtg cagatctaat agctatgaag caccgatacc ggacatgaca   480
cggtcaggtg gacacatgta atgtctaaaa tattaaaata tagaacgtag tacgagtgtc   540
gtgtcggtgt tagatactga tagggacgcg tgtcggacac gtgcatgac aaaggactga   600
agtgcttaga attgtttatg tttgagatct tgttgatgag aggcagatag aggtcaactt   660
gccaagataa cctacagttc tatattagat gctttgtgca aaaacgatca tccaaaggct   720
attggattat tcaagaaaac taagaccaa ggagttcaaa accgcctatg tacacatgca   780
ctatacttat ggatggattg tgcgaagtgg aagacttcaa aatgcaaaaa tgattttca   840
ggatctactg attaaaaggct atcaactaag tgtctgtctg tactctgtat aatgttatga   900
ttcataggct ttgtaaagag ggatttttg atgaagcatt gatctagaaa tctaaaatgg   960
aaaacagatc ttaaagaaga tacactgtgt aaatgtgtaa tggcactggc actctcgtgt   1020

SEQ ID NO: 18           moltype = DNA   length = 1000
FEATURE                 Location/Qualifiers
source                  1..1000
                        mol_type = genomic DNA
                        organism = Glycine max
SEQUENCE: 18
gtgtgtgatt aaaagtcata tatggtttaa gatacttttt tttataaaga tagtagtggt   60
caattttcg atattacaca agtgtttctt tttcttctca ttgtactgta gatctgattt   120
actttcaatg attgtttaag tcactggtgt aattgtttgt gtttcaaata tcaaaccaag   180
ctgaaactga gatgatgatg atttgaaatg ctttatctca tgtagtcgac tcaattttcc   240
tgtatatttc ttgttctttt taagaaaaca ggagcttta agatttaaaa caccagcata   300
ttttgtttgc ataatccaaa ttgtcttagg tgtaaagttg ctgacatttc ccttgatgtc   360
attgctgcat aattaattgg agcctttca aaacctatgg ttatttttgt tggggattaa   420
tcaaggaacg cgtgtctcag tctcaagtgt tatgattgct gatatcagtg atatattgct   480
gcacaatgaa gtgaactat tttaaatttc aattgatgat tctgcattca atttatcatc   540
tgacctttt atcttttacc tcatctggca tttttagtctt ttaccagata aaaggaccaa   600
acacatgaga tataatcacc aaatgaaaag aatgaaagac gagatataaa gatgtggttt   660
ttctttttat tcctggaaga tttagatgat gtttcaatt aagttgtttg tggatgcttt   720
tagatgattt tgtttgcat acatatgttt actttttgt tctcaacttc tcattcattt   780
tccatgagtt catcccgtga aaagtgatt tagcagaaaa cgttttcc ctgttgtctt   840
tgtcctaaac ttttggattc taagttttt tatatgaaaa ttagatcatt tggcactagg   900
ttttccaaag acacaagtag actctttcta tgaaatcaat cttaaatccc ttttagagga   960
aaaacatttt aaaggaggtg aacatgttgt ggagtgggaa                         1000

SEQ ID NO: 19           moltype = DNA   length = 1000
FEATURE                 Location/Qualifiers
source                  1..1000
                        mol_type = genomic DNA
                        organism = Glycine max
SEQUENCE: 19
attttgtcag tcttgtaact tttgaaaact tttttttctt ttttttataga ccaataatat   60
aatatattat attaaaaaaa ccaaacttat aacaacatgt aacacgttag caaacagtag   120
atctcaacca aacgttcgaa aacttttgga tattatatat gtggctgttg gcactgctaa   180
actcagcagt atatctccat tattgatgag tctctcctaa aattatcttt ccaagtctta   240
ttttttattt aattggttag atattaaatt gaaaaataaa ataaaagttg tgttgttgtg   300
tagttttcgt cacttttact cataagaaaa tatatatact acgtttagca tctttaaact   360
gaaaactttt cagttgaaat gcataacaaa atattggcca agtaattagt acacaaaatc   420
ttgctcaaag tgtttgccac catagattta ggttgtgttt aggacgatta cttaaaatat   480
cattaattga taattgaaac ttcaaataaa attaaaagt ttaaaagtta aatagttaaa   540
aatgaaagct gaaataaat aagctaatgg attcaatttg aagtatttaa tagtatcaac   600
tagtgaaatt tattcataaa ttctcttta aatataacc gatttatta gttaatataa   660
aaaaaaaata gtatgaacta ataaaattga tcaaagtaa attaatataa atataaaatt   720
ttatatgatg aataatcagt agaaaataata aaaaagttag ctctagaaaa gataaattga   780
tttaattagg gtcatgacaa aattttgcta gcttctattt tagtctgctt tgcctttagaa   840
tatttacatt caaatagctc tttttatagca taacaaacat aaaaaaagct attgattcta   900
cataaaaaaa aaagattaat tatgctattc tttgggacaa aacttttaga tgaatgccaa   960
tttaaaataa ttattaaggt attcaagcag acgtacgcaa                         1000

SEQ ID NO: 20           moltype = DNA   length = 928
```

| FEATURE | Location/Qualifiers |
|---|---|
| source | 1..928<br>mol_type = genomic DNA<br>organism = Glycine max |

SEQUENCE: 20

```
gcaagtagct tgttactttt cgtattgaca attcaaaatc gtctttatt tttatttgt    60
tttgtttaat tagaggactt tttgaagtcg tccatcatgt gtttcttatt ttgtcagttt   120
tgtcacttat gaacactttt tttacagaca ataatatat tatattaaaa aaaccatact   180
tataacaaca acatgtaaca cgttggcaaa cagttaatct caaccaaacg ctcgaaaact   240
tttggatatt atatatatat atgcatggct attggcagtg ctaaagtcat cattatcatt   300
ctaaagtcat cagtatcatt ctaattctca tattgagtgg attcatttca tcaatcactt   360
tgcctttctc atcataacca ccaaaatgcc aaccattaat ccagttggtt tgaaattcat   420
ggaaggcata ataacattta tgatgatgat gttgcaggtt gttgtttctg ctcaagacca   480
tattatgtgc attcagactg agagagaagc actcctccaa ttcaaggctg cacttctgga   540
tcactatggc atgctctctt cttggaccac ttctgattgc tgccaatggc aagggattcg   600
ctgctccaac ctcaccgccc atgttctaat gctcgacctt cacagtttag gcctcagagg   660
agagatccac cagtcgttga tggagttgca acaattaaac tatttaaacc tcagttggaa   720
ttcttttcaa ggcagaggaa tcccagagtt tcttggttct ctcaccaact tgagataccc   780
tgatctgtca cattctgatt tgaaggaaa aattccaact cagtttggct ctctttctca   840
tttgaaatac ttaaatcttg ctgggaatta ttatctggag ggtcaatcc cacgtcaact   900
tggaaatctc tcccagttgc agcatctt                                     928
```

| SEQ ID NO: 21 | moltype = DNA length = 1000 |
|---|---|
| FEATURE | Location/Qualifiers |
| source | 1..1000<br>mol_type = genomic DNA<br>organism = Glycine max |

SEQUENCE: 21

```
tcatgccagc ctcagccagc ttccaaatca tttccctcgt attggtagaa ggtccaatgg    60
tgcacactat cttcgtcttg cgcctaaacg ttggcttaga ccacattcca acagagttct   120
caccaaatgg ctgcacccca cgtaaatgtt gcaaatgctc ctcaatctaa acaccaaaac   180
acaaaaaggg tcacaagaat tatcccttaa aaactcaaaa aatgcaaaaa acacgaactt   240
ttggatcatc ttcgggtgac atggggatga cttcagaagg ggcagatttc cttgcactga   300
tctgaaggct tctgagcctg agtttggagc gtttgttatt gttctctccc aaagggaaca   360
ccttggaagc aaaagatgga ggctttaaca ggttttgggt tctgtcacgt gcagatccga   420
aagtggggca aatggggtg ctttgaatgg atcgtgaagc cacgacctga gccattgtta   480
gaaagagaga gaaatggggt ggatgaggaa gagagagtg tgaggggtat aagaagaagg   540
tgaggggga aatggaagtt ggaaaaatcg ccgctaagtt tggcggaggt tctgagaagg   600
aagccttgtt cgtatcgaaa cacaaaggac actactgtgt ttgaattctg ttcaacgtgt   660
ttgttgttgt aatttattg aaatggactg tacttctttt ctgttttttt ttttcacagt   720
aaaaatgcac tgtatttcct taaatctgct cataaacaat tacacatatt ttattagcta   780
aaatttaata taaattacaa aatatttaca aatatgttga tcaataaaa agtgaaacac   840
ataattttat tattctaac aaatttatct tatgataaag tgtagtatttg aaagattatt   900
attaagggac aatttctgtt gttgtggaca actttcataa gtgatccatg aaacaccaca   960
ttttatagtc accagattga tctcagattt atgctcttgc                       1000
```

| SEQ ID NO: 22 | moltype = DNA length = 1009 |
|---|---|
| FEATURE | Location/Qualifiers |
| source | 1..1009<br>mol_type = genomic DNA<br>organism = Glycine max |

SEQUENCE: 22

```
ttgcgtggga ctcagatcct gagggaggac atgaagatg tgtcgaaccc aacaagtggt    60
gctactcatg gcagctccaa caagaagagc tttaaaacta agttcatgca ggaacaaaag   120
gacaggatga aagatgcacc accagagtgt cctgcaggag ttttgttccc aaagtgacgt   180
tcaacgccac gtcatgagtt tgaatgctca acacaactaa cacacccttg ctaagaagtc   240
ctagaaaaat aaaaatctaa ggttagaaa tggactaatg atgtacatgt aaaaataata   300
tgctgaagcc ccttgagtta aaagatgtgg attctaacga ctttgataat tttaatggg   360
attttttata agttaattta ttgattattt ttaatatttt tcttatattt tttattcac   420
aaaactaaaa tctaaaatct tatttatagg aataaggaat tgagttaat aacaccgata   480
tgttgataat gatttaaatc atgggaatct gtgtttataa atagagaaaa aaaaaccctt   540
atgatataaa accttcctta gtctaaactc cctagctttg tgttaattgg attgtccaaa   600
aggaggctag ctagttgtt ccttcctcgt ccttactcct aaatgcatgg attaaggaaa   660
gaagcttctt tttgtttggt gttatatgtt tttgggtca ttatagtatg ggcaacttaa   720
cactcactct aagaggtgtt accttggcta ttcctagatg gctagacatc aaaactttga   780
atacaaaatt attaaagatc aataaaat gatttattta taatactgag attaaattg   840
aattttaatc tctctttaat tcatggtatg caattttaga ttttattttt tcatgtaatt   900
ttaatcatca cattttaaaa aattcataat tttaaattga ttttaattt tgtatatgtt   960
ttattttaa tttttatcta gttaaactgt atatttaaca tattgattt                1009
```

| SEQ ID NO: 23 | moltype = DNA length = 1006 |
|---|---|
| FEATURE | Location/Qualifiers |
| source | 1..1006<br>mol_type = genomic DNA<br>organism = Glycine max |

SEQUENCE: 23

```
attgaaagat tctatttgc ttgtttggtt gtcattggga taaatgaatg agtactataa    60
actttgaaaa acatatatac tttgagcagt tctatgacct aattttgctt gtttgattag   120
aattttgaat gaatacaaac gaattgcttt gataaatgtg ttatgaattg aacagataat   180
```

```
ttcaatgaaa atagatcaaa attagatcgg tttcaattta tatatatata tatatatata    240
tatatatata tatatatata tatattggta taaaatattt ttacacaaaa tttaataaag    300
ttttaacatt ttataatatt attttgttca ttaatataag gtaatacagt ataaattcct    360
attatgtgtt tatataaatt tctattttta gtccttaatt ttgataattg tcaattaatt    420
ataatttagt cttcaaaatt tgatattact agtcaactta aacttaaata ttaataaatt    480
agtcaattta atttaaaaat ttgactatat atatatataa atcaaaaggg ttaaacaatt    540
catttatcat aaaactcggg ttaagatcac atgatagcaa agcaattcgt ttgacaattt    600
aaaaattcgg maaatatagt cttagtcata aaacaaaatc aaaagggtta agattaaatc    660
ataaaactat attttttta aatgatatcr tgtgatcaat taaaaaagac aacttttaatt    720
ataatmatct attcactaaa aaaacctaac tcatttgatt gagtagaata tatatrttat    780
tgtactttrt ttatcttttga ttcctaccaa taattaaaaa caaataatca tctatctatt    840
ttatatagtc tagtttttatt cttctcataa cactaaaaaa ttatttaatg atgatatgat    900
cacttaaaaa aattacataa tttatatttc tatatcgtaa ccattcatgt gatataatga    960
tcacattttt tttttctcac actcacctaa gtgcacgagt acacac                  1006

SEQ ID NO: 24           moltype = DNA   length = 1007
FEATURE                 Location/Qualifiers
source                  1..1007
                        mol_type = genomic DNA
                        organism = Glycine max
SEQUENCE: 24
acacgtaagt cttaggttaa agtttcatgc cccccccccc cccccccccc aaaattacat     60
ttttttccat taaaataact ccaaactact ctacttctct cgctttggcg gaaccaccat    120
tgctctatga aaaggccatt ttattttcaa ccgcattgtt ttggaactat acaacgcaaa    180
agccttccat cctctatcat tgagctactt caaatcttgg tttctcttcg tcttctacca    240
gttatgtaag ctttcttcct ttcctctttt tggttgagca gcacgaaatt attttttcttc    300
ttgttattag ctagaagcac tattctagaa caagcttgca aaaaggactc aagttatctt    360
tggtaaggga agctttagac ctcaagtcta gcttggagac ttttgatttt gaagctttgt    420
attttgtatc ttggctaaag aatatatgtt ggaaaaagtc ttcttgaaga gctcttaaag    480
tgttgatttt gatgaaagtt cgttcaaaca taaattgttg gcttgaata ttttttctat    540
ttatttgcac caaaaacgtt atgtttatta tgttccacta taatttattg ttttgaggac    600
gggaaaagga tcggagttgg ttaagcttga tcttgagaat atatgtcttt tgtatttgaa    660
gtctttctga tggtgattct agatgacatg tcttatgggt ggagtaatag cgtaagtatc    720
tagagtatgt gagttgtaat gatctctaaa aactactcgtg gaagtaatga tcttttacttg    780
aagaaaagac tattatgtga aagagactta tacttgaaga agattattga aatacaagtg    840
tggagtaaag ttttacttta aataaaaata aaaaagttaa atacaagtaa aaaaatactc    900
ataaatttaa ctttaaaatt ttaaattaag atgtaatgta atattcactt atatggttac    960
tcataattca tgaatataac tctcctcggt tacatagtcg ttaaatg                  1007

SEQ ID NO: 25           moltype = DNA   length = 993
FEATURE                 Location/Qualifiers
source                  1..993
                        mol_type = genomic DNA
                        organism = Glycine max
SEQUENCE: 25
agccgataac ttatagataa cgttacagat aacattaact taaagataat tgtaccttgt     60
agataatgtg tagtcctgta gataattgaa tatatatcaa gagataaagg gatgacaaca    120
tattcaaata ataaaagtta gagataactt gtggtttggg gagttcaact gcgaagggtt    180
ggacgtctgt gctcctacac caggattgac atggaggatt gacgtgtgtc ttggagtgtc    240
acatggtatg atacatgtat tttgtggatt atgaacaaca caattgctta aagttctact    300
caatttactt attacttcag gtgatgtctt ggtagttcac agatataagt ttttgtctgc    360
tatctttcat gtggacacac aagtatgtgt aaatagagat ttttttttgaa agtttgagat    420
ccagggggcgc accaatgtat aggggagggg accttggcgg tttaaatcac cataaaattt    480
taaaaatctt ttaaaaaaat ttaagccaaa caaattttga ctttttttaca tcacctaaaa    540
atgaaccact agaaagtata atattgtcag atcctaattc tttttgggca aaaaaaaaca    600
aaaaaaaaga aggaaagaaa aagtattaag aaaaagaaaa caaaaaaata aacaaaaaaa    660
caaaagaata aaaacaaaa aaagagaaga aaacaaaaca aaaaaaaaag aagaaaaat    720
aaaacaaaaa agtattaaga aaaaaaaaga acagtaaaaa aacaaaagaa agaaaatgta    780
aaaaaagaa aaaaatagaa gaaaaaagga aaagttaaaa aaaagattt tgtgacctat    840
tggcttctca aggagagccc attaggtcaa gaggagaaca ttgtataaaa aaataaagaa    900
ggaaagtctg tgcaattaag gcacatagga ggcaacatga atcccaagga gaacaatgga    960
ccaatcttgtt ggcgtcattt gacattgtcg tga                                993

SEQ ID NO: 26           moltype = DNA   length = 1118
FEATURE                 Location/Qualifiers
source                  1..1118
                        mol_type = genomic DNA
                        organism = Glycine max
SEQUENCE: 26
gtgagaaaag agagagggat cactaggtaa cccctcattt cctcactctc tcagtttccc     60
tctagtcttt tcttctttct ttcttttctt ccccctttct ttcttcttttc tttatgtttt    120
caatctactg cttcgttatg tcccatctcg tcggtgggca ccttggccgt cggcgatgtt    180
tttgtgaatt gaattgggat tttctttttcg tggggttttc acgcattcct tcatctcctt    240
tgttcttctt cttttttcgt ttgcgccacc gtcgtgcctc cttcgcatca tcgctatcgt    300
ggtcgtgcca tcgctgtccc cgtgcggcc tcgcaccgtt ggatcttgga tcaatggtgt    360
cgaggacggg gcgccaccct ctgtgctggt tcacccttttt atcgtgtcgt ttggaggcta    420
ggacatctag ggttttcaa ccctgttgtc taattgcggg ttgggtcagg tcaccctgac    480
cgagttccaa cccccacaaaaa aatggaattt tttttttacta tttacaccac cttttcaaat    540
atgcaccatt ttctcatttt gggtctagcc cgttttttatg aagtatgaaa taaaataaaa    600
```

```
aacactattt gcaccaattt tttacacatc accttctttc atgttatgcc tagcccgttt    660
ttgtgaagtc taaagtaaaa taataaccgt tattacactt ttttctttaa tacaagcacc    720
ttcttctatt ttgggcataa catgtattt ttagtctgaa agaaaataaa aagtgctact    780
cacagctgct ttttcaacac atgcaccttc ttttgttttg ggcctagcgt gtgtttttt    840
tattattaag tccgaagtaa aataaaactg atgattacac cacttttttt atatatgcac    900
ccctgaaact taggatgatg actaggtcca ccatgtctgc actccgttag tgttaattaa    960
gtcaaagtca atcctttga ctttgaaaaa aaatataaat attagtggat gaatctttat   1020
tttatttaat ttctttattg tttatatcat ttatttcatt cttcaatgtg attttatttt   1080
tattattgcc tagttagtta gtttaattaa taatgtat                           1118

SEQ ID NO: 27         moltype = DNA   length = 1002
FEATURE               Location/Qualifiers
source                1..1002
                      mol_type = genomic DNA
                      organism = Glycine max
SEQUENCE: 27
cctctcacga aacggaagcc tctatcagac ttagcttgcc tgataactct ttgtatatat     60
attctcaggg gttaaaatta aaatagtgtt ttgatacttg ttttgttttc catgttgtta    120
tttatattga tgagggaacc aatcttggtg aaaatgtggg agatatatgc catggttagt    180
tttgtgaaat taagttgctt acaatgtgtt taacgaaatg cccttgaatg cattctctcg    240
ttagtcattt aaattatgag ctatcatgaa ttttagtttta aagttcattt aaattatgct    300
atttgttaca gactttaatt taaattatgc taagagtctt ttgttatgct ataattggtg    360
tggtttctaa catttatgtt ggaatagaag taatgtcaat tataattagc ttaatcagcc    420
caaaacattc actgtatttg tgtgcaaatt aagtgagctt aaccttggtt ttgtgaatga    480
tataccttac ctctaatcat gttaaaatag aacctaagtg tagattattt aaatcctaag    540
ttctacatat taatacacta tgcaagttat gcaatataggg tgcttatata tgttgctgaa    600
aacatgttac acttctgctc tgtgatacga gctgcattgt gattgacgca gatcttagtt    660
tttaatgacc tgtggaattg ttgtaggctt gtgtgtactc tttgtgaaac aattgatccc    720
atttcatttc aattttttgta cattttttta tgatttttat agtgtaacat gctctgctga    780
gtgattact gtgtggctgc tgtaataaag caataaaatg ctatgttttg aaatatcttga    840
cacttggttt gtatttttagt tgaaaataga cttaaaaagg gttctataga atttggaact    900
actcaaattg cttttatctt caatttatac caatgtcatc tttaaggcat gttaatcata    960
tatcttaaca agcggtaatc tatatcttga aatctgtctt gc                       1002

SEQ ID NO: 28         moltype = DNA   length = 1001
FEATURE               Location/Qualifiers
source                1..1001
                      mol_type = genomic DNA
                      organism = Glycine max
SEQUENCE: 28
ttgcgaaacg gcagataaaa tttgctttgt cttagaacaa ttcatgaaaa cagcccctag     60
tgagtcaaag tatcccctt tgtttcaatt taaaaaatta atttctcact attcttattg    120
tgtaaatttt ttaaggaaat tgtgtaatct ttattcatat gttaagttta atttgatata    180
taatatttaa tagaattata ttgttgatgt cataatgtta atcatgctaa tatagatgtt    240
ttaatcttaa tttatttatt aataaatgtt aaatgttaat tattgttagc aaagacaaat    300
tcaaggaagg acaagaaagg atcttgcact cccttcctaa ggatccttta tatacatgtg    360
aaaaaagaaa aaataataga agaaaatgaa ttaaagaaat aagttgttga atttatgttt    420
gtttaatatt tttattctca gtaatggatc tatcttaatt tttcatacaa attttctca    480
caaaattaat aatgttttat ttttataaaa cttattttt attaagggtt agatataaat    540
aattgcacaa aaaagaaag aaaaatagtt cccttttaaaa atgttttggg atttgttctt    600
cattgttagt aagaggattt gaacccataa tttttttcct ttttttatta ctaagttaat    660
cttataagtc ttagttaact tgaatgtcaa tcataccaat agagtattat gtgaatattt    720
ttcataaaat attaattatc aagtctatgg atgtagaaaa atagtttaat taaaaaatg    780
acgataataa aaatgttcaa ttatgtgttg attatactac acctcactta ttaaaaaaaa    840
ataccacaca tcacattttt ttcgcttaat tgacatcaag aatgagaatg caaacaaaaa    900
atatgaatta gaccagaaaa caatccatcc atcgtatgcc atatagatca tctcataaac    960
cacctgtgta aggaaaattt ttattgtcaa ttgggcttag c                       1001

SEQ ID NO: 29         moltype = DNA   length = 1002
FEATURE               Location/Qualifiers
source                1..1002
                      mol_type = genomic DNA
                      organism = Glycine max
SEQUENCE: 29
acaaatacga atcatgtacc tgcatggaag aaataaccac acaacacaca atgatcagaa     60
taagcaaatg catataatta agcatgatac aaatatcaata tcatggaag taacaatgac    120
ttgtcaaaaa tttggatgaa attcaatatg taaatcaaag ctttgtccct gaaaccctct    180
atataaatca aagctttgtc cctgaaaccc tctatgtaaa tgtgacagtc tcatgtctcc    240
cttcctgaaa acccactaaa aactgcctaa ccccccctgct gttactccat aatttattct    300
acaataactg cttaaggcag ttacatatgg tcctaaatca ctacacattc agttacgatt    360
aaccctttgt gcctaactac ggtttcgaaa catcacaaca gagacagacc attgaacaat    420
ggattttcat cattaacata caacagagac ataccttcga tggaagcgta gacacgaact    480
ccacaaacgc gaactcgaca atgtggttgc agttacagaa gcatagccca gtttgcgaca    540
aacacgaact caggcagaag gagaaacaac aataaagcc tggttaaaa gcgaaacgc    600
ctaatgttaa aacgacgaac gcctaatgtt aaaacgaaag gacgtacctc aatggataag    660
tgccaaagac gatctccaca aacacaatct ccacaatgtg gttgcagtca cagaagcaca    720
agatcaagag atcaagagaa aagattcacg ttagtccatt atttgttaaa agaatctctt    780
aatggttgaa aaggtttggc cttaaaaata actaaaaata attgtgtaat cgattatcaa    840
agatctataa tcgattacta atgagaaaat ttcaaaaata actctgaaaa gtcacatccc    900
```

| | | |
|---|---|---|
| tttatgagtt | tttgaaaagc caccaaggt ctatatatat gtgaattgtg ttcgaaaatc | 960 |
| tttagaattt | tttcaaaact tctttgtctt attctctcat aa | 1002 |

SEQ ID NO: 30      moltype = DNA   length = 1000
FEATURE           Location/Qualifiers
source            1..1000
                      mol_type = genomic DNA
                      organism = Glycine max
SEQUENCE: 30

| | | |
|---|---|---|
| ataaataaac | ttttggtcaa acacttgcaa atcaattaaa gattcttta agtttttcaa | 60 |
| tttgtattat | acttctctag aagagagaaa aacttttgta cttcaaaaag aaaactatta | 120 |
| ttgtgatcaa | gaggtagtga gtctcttgat ttgtgagttt ttctgaacac aagagaaatg | 180 |
| tatccctagg | tggttcagaa gttgtaaagg aatttacaag aacaatagaa atctcaaatg | 240 |
| agttgcttga | agattgaacg taaactgagt ttgcaattct ctctttcctt aattatctca | 300 |
| tttacataat | tgcaatttaa ttttgtcttg tgcatttaaa gagtgtcaat taaattgttc | 360 |
| gttgtttctt | attctgcata ttaagtttgc atatatcatt taagagaga attaaaattt | 420 |
| gttaggggaa | aattttaaaa cttaattcac ctcgctctta aattattgat gccacttgtt | 480 |
| taaccatatg | ttatcaattg aaataaatta attttttaat agaaatatga aaataattaa | 540 |
| ataacaaaaa | aaaccaaaaa aaagaagaaa ataatcaata tattatcgac aactactatt | 600 |
| atcatattat | taacataaaa aatatcaaca tattattaac aactatttta aattaatatg | 660 |
| aaaacaatta | tataactaaa aaaataataa gaaagtaatg aaaaaaatca aatatattata | 720 |
| aactaatcca | atatattaaa actactattt tgactgatca acataagaga caacaaaaaa | 780 |
| tttcatatta | ttaacaagag tgtggctcaa gttgtcaatc cataatttat agaataaattt | 840 |
| attaaagcaa | actacgaatg aatatggttt aagcagatac taacataagt ttacaaaact | 900 |
| taacaaaatg | catgcatttt ctttactcta gaaatataaa agcctatttt aaaagacagt | 960 |
| aataaaatta | ctaagaacta caccattcaa aatagtgccg | 1000 |

SEQ ID NO: 31      moltype = DNA   length = 1002
FEATURE           Location/Qualifiers
source            1..1002
                      mol_type = genomic DNA
                      organism = Glycine max
SEQUENCE: 31

| | | |
|---|---|---|
| agctttaatt | ttgttccgta catagtggcc acctattcta tccatgtcat aaccaataag | 60 |
| gtccaacata | attgacagat aactgaattt tttaaatata ttaggagttc gattactgat | 120 |
| catgtgcata | cagaagattt tgagaaagac aaaactcact ttagtgatat ctatgtttcg | 180 |
| aaagaaatta | attttcgact acccattaga agatatcttt ggtacaaaca aaaaagaaga | 240 |
| aaaaaattct | atcaatatca tagatattat actcaaatta taagactcat atattccacc | 300 |
| attcatccac | ttgcttttgt gatgcccctt gaaaaagaga ttggttgcaa tctcttatgt | 360 |
| tgttctgatt | cctactcgga agacgtcatg tgctcctcac gagactaaga aaaggtcatg | 420 |
| aagataaagg | atctatactc taaattgcta accaatgttg tggttggtaa attctgttct | 480 |
| tatataatgt | tagatatttc tgaagagtca tggttcagaa tcgggatcc atcacatgcc | 540 |
| cctatgctaa | taggttatat acaatgcttt tcgttgagga tgcttacaat atttttacgta | 600 |
| agagcacaat | taaaataaaa aaagtaattg ttagaagatg catagttaaa gttaaagtat | 660 |
| gaggacagac | aacatggata aatactcctt ctgtgtccgc acaaatgcag agcatcgaat | 720 |
| atagaacctc | ggttgatatg actaatgtat gtagaacaca tactaagtaa taatagatta | 780 |
| gtctaagttt | gatggatttt ttttattca taggaaatga aaatagtgtc aggagattta | 840 |
| taatataata | gtttatgtat tctacttaac catttaaatt agatctcttg acaagttaca | 900 |
| atagttaaga | gaacaaaact ctcctcatgt ttttttattt ttttatttac atacaagatt | 960 |
| cggacaagac | aacttaaaga aaaagccttg gaatggacat aa | 1002 |

SEQ ID NO: 32      moltype = DNA   length = 1002
FEATURE           Location/Qualifiers
source            1..1002
                      mol_type = genomic DNA
                      organism = Glycine max
SEQUENCE: 32

| | | |
|---|---|---|
| ataagagaac | tgtttttat attattatta tttcctttct aattcataga gaacccagta | 60 |
| tgttgaccat | atcaccctga aatgaaattt aaataccctca accaataatt actaaaataa | 120 |
| ccttgaaatg | gctaaattgc tagctactct tttatatgta actgaggtgt tacttcatca | 180 |
| aaaggatata | tattgagatc actcactaat tactagtaca ttgtaacatt gtaacactat | 240 |
| ggatgtgttt | gaataagtat ttttcatcta gtttcacttg acaatgggaa cagcagcatt | 300 |
| gagttgtatt | gattggatga gatcagagtc tagcaagtta agtggtggca gagagaaagg | 360 |
| gctctctgtg | gaactacctt ttcggatttc ttgcattgta agcaaagccg caactgtgtt | 420 |
| tctgaaaatc | ccttctcctg ccacagttat tgcatctttt gcttcctttg ctctctcagc | 480 |
| ttcttcctct | gccgggaaca ctgcatcgat tatgctctca cactccttca ccagctttga | 540 |
| gatcaaatct | gttgtgaaaa atggctgctc caacactttc tggatgaatg gcaaacgcag | 600 |
| aagcccccct | gtcctcttgt cgtatttctt cagaatttct agcaaccctg caaaattcag | 660 |
| tgttgtcact | tgttcaaggt agcatcaaat tctgtagaga aagctgcatc aaagtctatg | 720 |
| gcaatgcatt | tcctagcctt tttatcaata gcaaaccatg ttttaacatt ggagtttaat | 780 |
| tttcatgcac | tgtaaagagt tttatgggtg aaacacgaga aattattaga tggtttaaga | 840 |
| ctgttacatt | catggtcccc attagtttct acattatata tatattga ttttctgaa | 900 |
| aactcaatta | tgtctcgtgt aaaattatt aatttgagac tgtaatctta tattatgtaa | 960 |
| taatttcacg | tcaatcaatt agaaattacc ttagatataa ag | 1002 |

SEQ ID NO: 33      moltype = DNA   length = 1083
FEATURE           Location/Qualifiers
misc_feature      1..1083
                      note = synthetic construct; Plant optimized nucleotide

|  |  |
|---|---|
| source | sequence of TS21 meganuclease<br>1..1083<br>mol_type = other DNA<br>organism = synthetic construct |

SEQUENCE: 33

```
atggcaccga agaagaagcg caaggtgcat atgaacacca agtacaacaa ggagttcctg   60
ctctacctgg ccggcttcgt ggacggcgac ggctccatca tggcgcagat caagccgcag  120
cagtcctgca agttcaagca cgcgctccag ctgaccttca ccgtgaccca gaagacgcag  180
aggcgctggt tcctcgacaa gctggtcgac gagatcgggg tgggcaaggt ctacgaccgc  240
gggtcggtgt ccgactacat cctctcccag atcaagcccc tgcacaactt cctcacccag  300
ctccagccgt tcctcaagct gaagcagaag caggcgaacc tcgtcctgaa gatcatcgag  360
cagctcccct cggccaagga gtccccggac aagttcctgg aggtgtgcac gtgggtcgac  420
cagatcgcgg ccctcaacga cagcaagacc cgcaagacga cctcggagac ggtgcgggcg  480
gtcctggact ccctcccagg atccgtggga ggtctatcgc catccaggc atccagcgcc  540
gcatcctcgg cttcctcaag cccgggttca gggatctccg aagcactcag agctggagca  600
actaagtcca aggaattcct gctctacctg gccggcttcg tggacggcga cggctccatc  660
aaggcgcaga tcaagccgcg ccagtccgc aagttcaagc acgagctctc cctgaccttc  720
caggtgaccc agaagacgca gaggcgctgg ttcctcgaca agctggtcga cgagatcggg  780
gtgggctacg tctacgaccg cgggtcggtg tccgactaca tcctctccca gatcaagccc  840
ctgcacaact tcctcaccca gctccagccg ttcctcaagc tgaagcagaa gcaggcgaac  900
ctcgtcctga gatcatcga gcagctcccc tcggccaagg agtccccgga caagttcctg  960
gaggtgtgca cgtgggtcga ccagatcgcg gccctcaacg acagcaagac ccgcaagacg 1020
acctcggaga cggtgcgggc ggttctagac tccctcagcg agaagaagaa gtcgtccccc 1080
tga                                                                1083
```

| | |
|---|---|
| SEQ ID NO: 34<br>FEATURE<br>source | moltype = AA length = 10<br>Location/Qualifiers<br>1..10<br>mol_type = protein<br>organism = Simian virus 40 |

SEQUENCE: 34
MAPKKKRKVH                                                           10

| | |
|---|---|
| SEQ ID NO: 35<br>FEATURE<br>misc_feature | moltype = DNA length = 5937<br>Location/Qualifiers<br>1..5937<br>note = synthetic construct; Expression cassette RTW317, comprising the TS21 meganuclease plant optimized nucleotide sequence without an intron and operably linked to the soybean EF1A promoter |
| source | 1..5937<br>mol_type = other DNA<br>organism = synthetic construct |

SEQUENCE: 35

```
cacatggtta acctagactt gtccatcttc tggattggcc aacttaatta atgtatgaaa   60
taaaaggatg cacacatagt gacatgctaa tcactataat gtgggcatca agttgtgtg   120
ttatgtgtaa ttactagtta tctgaataaa agagaaagat atcatccata tttcttatcc  180
taaatgaatg tcacgtgtct ttataattct ttgatgaacc agatgcattt cattaaccaa  240
atccatatac atataaatat taatcatata taattaatat caattgggtt agcaaaacaa  300
atctagtcta ggtgtgtttt gcgaatgcgg ccgccaccgc ggtggagctc gaattctagt  360
ggccggccca gctgatatcc atcacactgg cggccgacct cgactgaatt gttccgcgg  420
ccagcctgct ttttgtaca agttggcat tataaaaag cattgcttat caatttgttg  480
caacgaacag gtcactatca gtcaaaataa aatcattatt tggggcccga gcttaagtaa  540
ctaactaaca ggaagagttt gtagaaacgc aaaaaggcca tccgtcagga tggccttctg  600
cttagtttga tgcctggcag tttatggcgg gcgtcctgcc cgccaccctc cgggccgttg  660
cttcacaacg ttcaaatccg ctcccggcgg atttgtccta ctcaggagag cgttccacga  720
caaacaacag ataaaacgaa aggcccagtc ttccgactga cctttcgtt tattttgatg  780
cctggcagtt ccctactctc gcttagtagt tagacgtccc cgagatccat gctagcggta  840
atacggttat ccacagaatc aggggataac gcaggaaaga acatgtgagc aaaaggccag  900
caaaaggcca ggaaccgtaa aaaaggccgc ttgctggcgt ttttccatag gctccgcccc  960
cctgacgagc atcacaaaaa tcgacgctca agtcagaggt ggcgaaaccc gacaggacta 1020
taaagatacc aggcgtttcc ccctggaagc tccctcgtgc gctctcctgt tccgaccctg 1080
ccgcttaccg gatacctgtc cgcctttctc ccttcggaa gcgtggcgct ttctcatagc 1140
tcacgctgta ggtatctcag ttcggtgtag gtcgttcgct ccaagctggg ctgtgtgcac 1200
gaacccccg ttcagcccga ccgctgcgcc ttatccggta actatcgtct tgagtccaac 1260
ccggtaagac acgacttatc gccactggca gcagccactg gtaacaggat tagcagagcg 1320
aggtatgtag gcggtgctac agagttcttg aagtggtggc ctaactacgg ctacactaga 1380
agaacagtat ttggtatctg cgctctgctg aagccagtta ccttcggaaa aagagttggt 1440
agctcttgat ccggcaaaca aaccaccgct ggtagcggtg gtttttttgt ttgcaagcag 1500
cagattacgc gcagaaaaaa aggatctcaa gaagatcctt tgatcttttc tacgggtct 1560
gacgctcagt ggaacggggc caatctgaa taatgttaca accaattaac caattctgat 1620
tagaaaaact catcgagcat caaatgaaac tgcaatttat tcatatcagg attatcaata 1680
ccatattttt gaaaagccg tttctgtaat gaaggagaaa actcaccgag gcagttccat 1740
aggatggcaa gatcctggta tcggtctgcg attccgactc gtccaacatc aatacaacct 1800
attaatttcc cctcgtcaaa aataaggtta tcagtgaga atcaccatg agtgacgact 1860
gaatccggtg agaatggcaa aagtttatgc atttcttttcc agacttgttc aacaggccag 1920
ccattacgct cgtcatcaaa atcactcgca tcaaccaaac cgttattcat tcgtgattgc 1980
gcctgagcga cgcgaaatac gcgatcgctg ttaaaaggac aattacaaac aggaatcgaa 2040
tgcaaccggc gcaggaacac tgccagcgca tcaacaatat tttcacctga atcaggatat 2100
```

```
tcttctaata cctggaatgc tgttttcccg gggatcgcag tggtgagtaa ccatgcatca 2160
tcaggagtac ggataaaatg cttgatggtc ggaagaggca taaattccgt cagccagttt 2220
agtctgacca tctcatctgt aacatcattg gcaacgctac ctttgccatg tttcagaaac 2280
aactctggcg catcgggctt cccatacaag cgatagattg tcgcacctga ttgcccgaca 2340
ttatcgcgag cccattata cccatataaa tcagcatcca tgttggaatt taatcgcggc 2400
ctcgacgttt cccgttgaat atggctcata acaccccttg tattactgtt tatgtaagca 2460
gacagtttta ttgttcatga tgatatattt ttatcttgtg caatgtaaca tcagagattt 2520
tgagacacgg gccagagctg cagctggatg gcaaataatg atttattt gactgatagt 2580
gacctgttcg ttgcaacaaa ttgataagca atgctttctt ataatgccaa ctttgtacaa 2640
gaaagctggg tctagatatc tcgacccggg caatcaaatt atatatgtaa agcaattaca 2700
gtttatcaaa ctttatttat ggaaataatt tattatcaca tttattttgg tttataaatt 2760
ttaaattaaa atatccccta aataaaaata attttttaaca tgacttattg tcctaaaataa 2820
attatttccg taaattaaat aaaatgaagt ttttttcttt caaagaatct aaatggtcat 2880
aatgagaatt ctctaaaaaa atacataatg agaataatta tggaatttat ttattaataa 2940
aaattaatag cattttgata gacaattaat aaaattttaa aaataaccat atagaaataa 3000
taattttttt actatcggtt ccaattaaaa taatgataaa aaataaaata gattattaat 3060
tgatattgat atgaaattta aataaagaat ataatcatat atttttattga tatatgatat 3120
gatatagatt aattgatatt gattttgata tggaatttaa aaataatata ataattgtt 3180
ttattttatta atacgtgtaa tcaaataatt ctcactttt gaatcaatca gtgtacttaa 3240
agataatatc agttgaatat ttttatcct tttacgtgtg ctgtgagaca ttatcatcaa 3300
ttgtgttgta tatgatatat agatatagat atataaaatat atagattgag tgatataata 3360
tatttaaaat ataaattata tatatgtttt aaatatttt tgcatatata tatatatttg 3420
taaaaactag aagtatttt tcatgagata attattatcg agttgaataa gtctattatt 3480
tgtgagagcc aaccatattt atatatgtga ttaaatttta tctttgtgaa attaaaaata 3540
ataaaaaata ccttaaaatc ataataatag aaaaacttat atttataatt taccattata 3600
cttaaaaaaa attaaataaa tattataaat aaaatacta tcgagtaatg gccgcgctag 3660
ggttttttgag aaaaaatctt cccacgcact caactgcact gtacggcgtc gttttcacag 3720
ccgcataata gaagccgcgt tccccaaccc ttcctcacaa cattctcgga ccctccagca 3780
ccgtcaccca aacaaatatc cacgcggtag taggcgcgtg aaacaaactc taatccgaac 3840
tacgagacgt gagaagcacg cgctttagcg agcgtttcaa ttgtcgctac gaaagcagag 3900
aaggatacaa acggaactag ggtaaattag taagggtaat ttcgtaaaca gaagaaaaga 3960
gttgtagcta taaataaacc ctcaaccct cgtcgcatta cttctcttca cacctttgtt 4020
cactcttctt ctcttgcggc tagggtttta gcgcagcttc ttctaggtc gttatctacc 4080
accgttctat ggatttttatt cctcttattc gtgttattc tattgttta tgttgcttgc 4140
aatatgttt ttctgaatct gtcgtcgttg tcttcaattt tatccatgtt tcagagatca 4200
attttgtttg tgtagtatgt gcttattctt cttcttttcg ttcgagttgt taataacggt 4260
gctatggtgt ttcaaaagt gttttttta ttacttttga tttaaagttt ttttggtaag 4320
gcttttattt gcttgttata ttcaaatctt tggatccaga tcttatataa gttttggtt 4380
caagaaagtt tttggttact gatgaataga tcattaact gtacttaa tcgattcaag 4440
ctaaagttt tttggttactg atgaatagat ctattatctg ttacttttaa tcggttcaag 4500
ctcaagttt tggttactg atgaatagat ctatatacgt cacagtgtgc taaacatgcc 4560
cttgttttat ctcgatcta tgtatggag tgccataaat tttgttatgt ctattttttt 4620
atctgttgga atcatactga gtttgatgcg ttacgattga gcatacctat ttttgggctt 4680
gttgtatggt gggtatttag atcttaatct ttttatgcttt atgaaaggtt ttgtaatgac 4740
aaaggtctta atgttgttaa acttttatttt ttactttata tggtgtgttg atgtgttatg 4800
gtttgacaa ctttttttt ttctggattt ttgcagattt aaggaagcca tggcaccgaa 4860
gaagaagcgc aaggtgcata tgaacaccaa gtacaacaag gtttcctgc tctacctggc 4920
cggcttcgtg gacggcgacg gctccatcat ggcgcagatc aagccgcagc agtcctgcaa 4980
gttcaagcac gcgctccagc tgaccttcac cgtgacccag aagacgcaga ggcgctggtt 5040
cctcgacaag ctggtcgacg agatcggggt gggcaaggtc tacgaccgcg gtcggtgtc 5100
cgactacatc ctctcccaga tcaagccct gcacaacttc ctcacccagc tccagccgtt 5160
cctcaagctg aagcagaagc aggcgaacct cgtcctgaag atcatcgagc agctcccctc 5220
ggccaaggag tccccggaca agttcctgga ggtgtgcacg tgggtcgacc agatcgcggc 5280
cctcaacgac agcaagaccc gcaagacgac ctcggagacg gtgcgggcgg tcctggactc 5340
cctcccagga tccgtgggag gtctatcgcc atctcaggca tccagcgccg catcctcggc 5400
ttcctcaagc ccgggttcag ggatctccga agcactcaga gctggagcaa ctaagtccaa 5460
ggaattcctg ctctacctgg ccggcttcgt ggacggcgac ggctccatca aggcgcagat 5520
caagccgcgc cagtcccgca agttcaagca cgagctctcc ctgaccttcc aggtgacccca 5580
gaagacgcag aggcgctggt tcctcgacaa gctggtcgac gagatcgggg tgggctacgt 5640
ctacgaccgc gggtcggtgt ccgactacat cctctcccag atcaagcccc tgcacaactt 5700
cctcacccag ctccagccgt tcctcaagct gaagcagaag caggcgaacc tcgtcctgaa 5760
gatcatcgag cagctcccct cggccaagga gtccccggac aagttcctgg aggtgtgcac 5820
gtgggtcgac cagatcgcgg ccctcaacga cagcaagacc cgcaagacga cctcggagac 5880
ggtgcgggcg gttctagact ccctcagcga gaagaagaag tcgtccccct gaggtac     5937
```

```
SEQ ID NO: 36          moltype = DNA   length = 6126
FEATURE                Location/Qualifiers
misc_feature           1..6126
                       note = synthetic construct; Expression cassette RTW322,
                         comprising the TS21 meganuclease plant optimized
                         nucleotide sequence ST-LS1 intron2 and operably linked to
                         the soybean EF1A promoter
source                 1..6126
                       mol_type = other DNA
                       organism = synthetic construct
SEQUENCE: 36
cacatggtta acctagactt gtccatcttc tggattggcc aacttaatta atgtatgaaa   60
taaaaggatg cacacatagt gacatgctaa tcactataat gtgggcatca aagttgtgtg  120
ttatgtgtaa ttactagtta tctgaataaa agagaaagag atcatcccata tttcttatcc 180
```

```
taaatgaatg tcacgtgtct ttataattct ttgatgaacc agatgcattt cattaaccaa    240
atccatatac atataaatat taatcatata taattaatat caattgggtt agcaaaacaa    300
atctagtcta ggtgtgtttt gcgaatgcgg ccgccaccgc ggtggagctc gaattctagt    360
ggccggccca gctgatatcc atcacactgg cggccgcact cgactgaatt ggttccggcg    420
ccagcctgct tttttgtaca aagttggcat tataaaaaag cattgcttat caatttgttg    480
caacgaacag gtcactatca gtcaaaataa aatcattatt tggggcccga gcttaagtaa    540
ctaactaaca ggaagagttt gtagaaacgc aaaaaggcca tccgtcagga tggccttctg    600
cttagtttga tgcctggcag tttatggcgg gcgtcctgcc cgccaccctc cgggccgttg    660
cttcacaacg ttcaaatccg ctcccggcgg atttgtccta ctcaggagag cgttcaccga    720
caaacaacag ataaaacgca aggcccagtc ttccgactga gcctttcgtt ttatttgatg    780
cctggcagtt ccctactctc gcttagtagt tagacgtccc cgagatccat gctagcggta    840
atacggttat ccacagaatc aggggataac gcaggaaaga acatgtgagc aaaaggccag    900
caaaaggcca ggaaccgtaa aaaggccgcg ttgctggcgt ttttccatag gctccgcccc    960
cctgacgagc atcacaaaaa tcgacgctca agtcagaggt ggcgaaaccc gacaggacta   1020
taaagatacc aggcgtttcc ccctggaagc tccctcgtgc gctctcctgt tccgaccctg   1080
ccgcttaccg gatacctgtc cgcctttctc ccttcgggaa gcgtggcgct ttctcatagc   1140
tcacgctgta ggtatctcag ttcggtgtag gtcgttcgct ccaagctggg ctgtgtgcac   1200
gaaccccccg ttcagcccga ccgctgcgcc ttatccggta actatcgtct tgagtccaac   1260
ccggtaagac acgacttatc gccactggca gcagccactg gtaacaggat tagcagagcg   1320
aggtatgtag gcggtgctac agagttcttg aagtggtggc ctaactacgg ctacactaga   1380
agaacagtat ttggtatctg cgctctgctg aagccagtta ccttcggaaa aagagttggt   1440
agctcttgat ccggcaaaca aaccaccgct ggtagcggtg gtttttttgt ttgcaagcag   1500
cagattacgc gcagaaaaaa aggatctcaa gaagatcctt tgatcttttc tacgggtct   1560
gacgctcagt ggaacggggc caatctgaa taatgttaca accaattaac caattctgat   1620
tagaaaaact catcgagcat caaatgaaac tgcaatttat tcatatcagg attatcaata   1680
ccatattttt gaaaaagccg tttctgtaat gaaggagaaa actcaccgag gcagttccat   1740
aggatggcaa gatcctggta tcggtctgcg attccgactc gtccaacatc aatacaacct   1800
attaatttcc cctcgtcaaa aataaggtta tcaagtgaga atcaccatg agtgacgact   1860
gaatccggta agaatggcaa aagtttatgc atttctttcc agacttgttc aacaggccag   1920
ccattacgct cgtcatcaaa atcactcgca tcaaccaaac cgttattcat tcgtgattgc   1980
gcctgagcga gacgaaatac gcgatcgctg ttaaaaggac aattacaaac aggaatcgaa   2040
tgcaaccggc gcaggaacac tgccagcgca tcaacaatat tttcacctga atcaggatat   2100
tcttctaata cctggaatgc tgttttttccg gggatcgcag tggtgagtaa ccatgcatca   2160
tcaggagtac ggataaaatg cttgatggtc ggaagaggca taaattccgt cagccagttt   2220
agtctgacca tctcatctgt aacatcattg gcaacgctac ctttgccatg tttcagaaac   2280
aactctggcg catcgggctt cccatacaag cgatagattg tcgcacctga ttgcccgaca   2340
ttatcgcgag cccatttata cccatataaa tcagcatcca tgttggaatt taatcgcggc   2400
ctcgacgttt cccgttgaat atggctcata acccccttg tattactgtt tatgtaagca   2460
gacagtttta ttgttcatga tgatatattt ttatcttgtg caatgtaaca tcagagattt   2520
tgagacacgg gccagagctg cagctggatg gcaaataatg attttatttt gactgatagt   2580
gacctgttcg ttgcaacaaa ttgataagca atgcttttct ataatgccaa ctttgtacaa   2640
gaaagctggg tctagatatc tcgacccggg caatcaaatt atatatgtaa agcaattaca   2700
gtttatcaaa ctttatttat ggaaataatt tattatcaca tttatttttg ttatttaatt   2760
ttaaattaaa atatcaccta aataaaaata attttttaaca tgacttattg tcctaaataa   2820
attatttccg taaattaaat aaaatgaagt tttttttcttt caaagaatct aaatggtcat   2880
aatgagaatt ctctaaaaaa atacataatg agaataatta tggaatttat ttattaataa   2940
aaattaatag cattttgata gacaattaat aaaaattttaa ataaccat atagaaataa   3000
taattttttt actatcggtt ccaattaaaa taatgataaa aaataaaata gattattaat   3060
tgatattgat atgaaattta aataaagaat ataatcatat attttattga tatatgatat   3120
gatatagatt aattgatatt gattttgata tggaatttaa aaataatata ataattgttt   3180
ttatttatta atacgtgtaa tcaaataatt ctcactttt gaatcaatca gtgtacttaa   3240
agataatatc agttgaatat ttttttatcct tttacgtgtg ctgtgagaca ttatcatcaa   3300
ttgtgttgta tatgatatat agatatagat atataaatat atagattgag tgatataata   3360
tatttaaaat ataattata tatatgtttt aatatatttt tgcatatata tatatatttg   3420
taaaaactag aagtatttt tcatgagata attattacg agttgaataa gtctattatt   3480
tgtgagagcc aaccatttt atatatgtga ttaaatttta tctttgtgaa attaaaaata   3540
ataaaaaata ccttaaaatc ataataatag aaaaacttat atttataatt taccattata   3600
cttaaaaaaa attaaataaa tattataaat ataaatacta tcgagtaatg gccgcgctag   3660
ggtttttgag aaaaaatctt cccacgcact caactgcact gtacggcgtc gttttcacag   3720
ccgcataata gaagccgcgt tccccaaccc ttcctcacaa cattctcgga ccctccagca   3780
ccgtcaccca aacaaatatc cacgcggtag taggcgcgtg aaacaaactc taatccgaac   3840
tacgagacgt gagaagcacg cgctttagcg agcgtttcaa ttgtcgctac gaaagcagag   3900
aaggatacaa acggaactag ggtaaattag taagggtaat ttcgtaaaca gaagaaaaga   3960
gttgtagcta taaataaacc ctctaaccct cgtcgcatta cttctcttca caccttgtt   4020
cactcttctt ctcttgcggc tagggttta gcgcagcttc ttctaggttc gttatctacc   4080
accgttctat ggatttatt ccttctattc gtgtttattc tattggttta tgttgcttgc   4140
aatatgtttt ttctgaatct gtcgtcgttg tcttcaattt tatccatgtt tcagagatca   4200
atttgtttg tgtagtatgt gcttattctt cttcttttcg ttcgagttgt taataacggt   4260
gctatggtgt tttcaaaagt gtttttttta ttacttttga tttaaagttt ttttggtaag   4320
gcttttattt gcttgttata ttcaaatctt tggatccaga tcttatataa gttttttggtt   4380
caagaaagtt tttggttact gatgaataga tctattaact gttactttaa tcgattcaag   4440
ctaaagtttt ttggttactg atgaatagat ctattatctg ttacttttaa tcggttcaag   4500
ctcaagtttt ttggttactg atgaatagat ctatatacgt cacagtgtgc taaacatgcc   4560
cttgttttat ctcgatctta tgtatggag tgcataaat tgtttatgt ctattttttt   4620
atctgttgga atcatactga gtttgatgcg ttacgattga gcatacctat ttttgggctt   4680
gttgtatggt gggtatttag atcttaatct tttatgcttt atgaaaggtt tgtaatgac    4740
aaaggtctta atgttgttaa acttttattt ttacttata tggtgtgttg atgtgttatg   4800
gttttgacaa cttttttttt ttctggattt ttgcagattt aaggaagcca tggcaccgaa   4860
gaagaagcgc aaggtgcata tgaacaccaa gtacaacaag gagttcctgc tctacctggc   4920
```

```
cggcttcgtg gacggcgacg gctccatcat ggcgcagatc aagccgcagc agtcctgcaa    4980
gttcaagcac gcgctccagc tgaccttcac cgtgacccag aagacgcaga ggcgctggtt    5040
cctcgacaag ctggtcgacg agatcggggt gggcaaggtc tacgaccgcg gtcggtgtc    5100
cgactacatc ctctcccaga tcaagcccct gcacaacttc ctcacccagc tccagccgtt    5160
cctcaagctg aagcagaagc aggcgaacct cgtcctgaag atcatcgagc agtcccctc    5220
ggccaaggag tccccggaca agttcctgga ggtaagtttc tgcttctacc tttgatatat    5280
atataataat tatcattaat tagtagtaat ataatatttc aaatatttt ttcaaaataa    5340
aagaatgtag tatatagcaa ttgctttct gtagtttata agtgtgtata ttttaattta    5400
taactttct aatatatgac caaaacatgg tgatgtgcag gtgtgcacgt gggtcgacca    5460
gatcgcggcc ctcaacgaca gcaagacccg caagacgacc tcggagacgg tgcgggcggt    5520
cctggactcc ctcccaggat ccgtgggagg tctatcgcca tctcaggcat ccagcgccgc    5580
atcctcggct tcctcaagcc cgggttcagg gatctccgaa gcactcagag ctggagcaac    5640
taagtccaag gaattcctgc tctacctggc cggcttcgtg gacggcgacg gctccatcaa    5700
ggcgcagatc aagccgcgcc agtcccgcaa gttcaagcac gagctctccc tgaccttcca    5760
ggtgacccag aagacgcaga ggcgctggtt cctcgacaag ctggtcgacg agatcggggt    5820
gggctacgtc tacgaccgcg gtcggtgtc cgactacatc ctctcccaga tcaagcccct    5880
gcacaacttc ctcacccagc tccagccgtt cctcaagctg aagcagaagc aggcgaacct    5940
cgtcctgaag atcatcgagc agctcccctc ggccaaggag tccccggaca agttcctgga    6000
ggtgtgcacg tgggtcgacc agatcgcggc cctcaacgac agcaagaccc gcaagacgac    6060
ctcggagacg gtgcgggcgg ttctagactc cctcagcgag aagaagagt cgtcccctg    6120
aggtac                                                              6126

SEQ ID NO: 37          moltype = DNA   length = 5056
FEATURE                Location/Qualifiers
misc_feature           1..5056
                       note = synthetic construct; Nucleotide sequence of RTW328A,
                       which is the repair DNA fragment for TS21 meganuclease
source                 1..5056
                       mol_type = other DNA
                       organism = synthetic construct
SEQUENCE: 37
cgcgcctcta gttgaagaca cgttcatgtc ttcatcgtaa gaagcactc agtagtcttc      60
ggccagaatg gccatctgga ttcagcaggc ctagaaggcc atttaaatcc tgaggatctg    120
gtcttcctaa ggaccgggga tatcgctatc aactttgtat agaaaagttg ggccgaattc    180
gagctcggta cggccagaat ccggtaagtc acgtgaccta cgtcacttaaa              240
ttcggccaga atgccatct ggattcagca ggcctagaag gcccggaccg attaaacttt    300
aattcggtcc gggttaccttc gagttattta tccctataa agggcaccag ttagttcaat    360
ctgatgtcta acctaatttg gatacatgcc ttttattgca gctgccgtcc gtgcacagag    420
gagtcttagg aggaacaact gtagagaaa ggatctgcca aattcgctag aaaattcgac    480
agaaacacca cccgttatcc aattaaacaa gattttggga tcacttgtga agttgaattg    540
ctatccaact gctattccca tttctaaacc ttgttacacg agcatcttga tcaatggtct    600
agaaagggaa atagcagttg agtggtgctt caacgataag ttattggatt tagtatttat    660
cttagcctgt tttcgtgtac tttgtttgc cggatggagga tatgtgattt tgtctatgat    720
tcttaataca ataacctaca cttactctca ttgatagtttt gtgcagatct aatagctatg    780
aagcaccgat accggacatg acacggtcag gtggacacat gtaatgtcta aaatattaaa    840
atatagaacg tagtacgagt gtcgtgtcgg tgttagatac tgatagggac gcgtgtcgga    900
caccggacat gacaaaggac tgaagtgctt agaattgtt atgtttgaga tcttgttgat    960
gagaggcaga tagaggtcaa cttgccaaga taacctacag ttctatatta gatgcttgt   1020
gcaaaacga tcatccaaag gctattggat tattcaagaa aactaagac caaggagttc   1080
aaaaccgcct atgtacacat gcactatact tatggatgga ttgtgcgaag tggaagactt   1140
cagaatgcaa aaatgatttt tcaggatcta ctgattaaga gctatcaact aagtgctcgt   1200
ctgtactctg tataatgtta tgattcatag gctttgtaaa gagggatttt ttgatgaagc   1260
attgatctag aaatctaaaa tggaaaacag atcttaaaga agatacactg tgtaaatgtg   1320
taatggcact ggcactctcg tgtactagtg gtcacctaag tgactagggt cacgtgaccc   1380
tagtcactta ttcccaacag aagttcctat tccgaagttc ctattctcta gaaagtatag   1440
gaacttccac tagtacccaa caagcttgca tgcctgcagg tttaaacagt cgactctaga   1500
gatccgtcaa catggtggag cacgacactc tcgtctactc caagaatatc aaagatacag   1560
tctcagaaga ccaaagggct attgagactt ttcaacaaag ggtaatatcg ggaaaacctcc   1620
tcggattcca ttgcccagct atctgtcact tcatcaaaag gacagtagaa aaggaaggtg   1680
gcacctacaa atgccatcat tgcgataaag gaaaggctat cgttcaagat gcctctgccg   1740
acagtggtcc caaagatgga cccccaccca cgaggagcat cgtggaaaaa gaagacgttc   1800
caaccacgtc ttcaaagcaa gtggattgat gtgatgatcc tatgcgtatg gtatgacgtg   1860
tgttcaagat gatgacttca aacctaccta tgacgtatgg tatgacgtgt gtcgactgat   1920
gacttagatc cactcgagcg gctataaata cgtacctacg caccctgcgc taccatccct   1980
agagctgcag cttatttta caacaattac caacaacaac aaacaacaaa caacattaca   2040
attactattt acaattacag tcgacccta gtccatgaaa aagcctgaac tcaccgcgac   2100
gtctgtcgag aagtttctga tcgaaaagtt cgacagcgtc tccgacctga tgcagctctc   2160
ggagggcgaa gaatctcgtg ctttcagctt cgatgtagga gggcgtggat atgtcctgcg   2220
ggtaaatagc tgcgccgatg gtttctacaa agatcgttat gtttatcggc actttgcatc   2280
ggccgcgctc ccgattccgg aagtgcttga cattggggaa ttcagcgaga gcctgaccta   2340
ttgcatctcc cgccgtgcac agggtgtcac gttgcaagac ctgcctgaaa ccgaactgcc   2400
cgctgttctg cagccggtcg cggaggccat ggatgcgatc gctgcggccg atcttagcca   2460
gacgagcggg ttcggcccat tcggaccgca aggaatcggt caatacacta catggcgtga   2520
tttcatatgc gcgattgctg atccccatgt gtatcactgg caaactgtga tggacgacac   2580
cgtcagtgcg tccgtcgcgc aggctctcga tgagctgatg ctttgggccg aggactgccc   2640
cgaagtccgg cacctcgtgc acgcggattt cggctccaac aatgtcctga cggacaatgg   2700
ccgcataaca gcggtcattg actggagcga ggcgatgttc ggggattccc aatacgaggt   2760
cgccaacatc ttcttctgga ggccgtggtt ggcttgtatg gagcagcaga cgcgctactt   2820
cgagcggagg catccggagc ttgcaggatc gccgcggctc cgggcgtata tgctccgcat   2880
```

```
tggtcttgac caactctatc agagcttggt tgacggcaat ttcgatgatg cagcttgggc    2940
gcagggtcga tgcgacgcaa tcgtccgatc cggagccggg actgtcgggc gtacacaaat    3000
cgcccgcaga agcgcggccg tctggaccga tggctgtgta gaagtactcg ccgatagtgg    3060
aaaccgacgc cccagcactc gtccgagggc aaaggaatag tgaggtacct aaagaaggag    3120
tgcgtcgaag cagatcgttc aaacatttgg caataaagtt tcttaagatt gaatcctgtt    3180
gccggtcttg cgatgattat catataaatt ctgttgaatt acgttaagca tgtaataatt    3240
aacatgtaat gcatgacgtt atttatgaga tgggttttta tgattagagt cccgcaatta    3300
tacatttaat acgcgataga aaacaaaata tagcgcgcaa actaggataa attatcgcgc    3360
gcggtgtcat ctatgttact agatcgatgt cgacccggga tcatggctag cgaagttcct    3420
attccgaagt tcctattctc tagaaagtat aggaacttca gatcctctag agtcgacctg    3480
caggcatgcc cgcggatatc gatgggcccc ggccgaagct tcaagtttgt acaaaaaagc    3540
aggctccggc cagaatccgg taagtgacta gggtcacgtg accctagtca cttaaattcg    3600
gccagaatgg ccatctggat tcagcaggcc tagaaggccc ggaccgatta aactttaatt    3660
cggtccggaa gcttggatcc gtcgacgaat tcactagtgt taccagagct ggtcacctaa    3720
gtgactaggg tcacgtgacc ctagtcactt attcccgggc acccagcttt cttgtacaaa    3780
gtggccgtta acgatcggc cagaatccgg taagtgacta gggtcacgtg accctagtca    3840
cttaaattcg gccagaatgg ccatctggat tcagcaggcc tagaaggccc ggaccgatta    3900
aactttaatt cggtccgggt tacctctaga aagcttgtcg acctgcaggt gtgtgattaa    3960
aagtcatata tggtttaaga acttttttt tataaagata gtagtggtca attttcgat    4020
attacacaag tgttctttt tcttctcatt gtactgtaga tctgatttac tttcaatgat    4080
tgtttaagtc actggtgtaa ttgttgtgt ttcaaatatc aaaccaagct gaaactgaga    4140
tgatgatgat ttgaaatgct ttatctcatg tagtcgactc aattttcctg tatattcctt    4200
gttcttttta aagaaacagg agcttttaag atttaaaaca ccagcatatt ttgtttgcat    4260
aatccaaatt gtcttaggtg taaagttgct gacatttccc ttgatgtcat tgctgcataa    4320
ttaattggag ccttttcaaa acctatggtt tattttgttg gggattattc aaggaacgcg    4380
tgtctcagtc tcaagtgtta tgattgctga tatcagtgat atattgctgc acaatgaagt    4440
ggaactattt taaatttcaa ttgatgattc tgcattcaat ttatcatctg accttttat    4500
cttttacctc atctggcatt ttagtctttt accagataaa aggaccaaac acatgagata    4560
taatcaccaa atgaaaagaa tgaaagacga gatataaaga tgtggttttt cttttattc    4620
ctggaagatt tagatgatgt tttcaattaa gttgttttga tgatcttta gatgattttg    4680
ttttgcatac atatgtttac tttttttgttc tcaacttctc attcattttc catgatttca    4740
tcccgtgaaa aagtgattta gcagaaaacg ttttcccct gttgtctttg tcctaaactt    4800
ttggattcta agtttttta tatgaaaatt agatcattg gcacatggtt ttccaaagac    4860
acaagtagac tctttctatg aaatcaatct taaatccctt ttagaggaaa aacatttaa    4920
aggaggtgaa catgttgtgg agtgggaagg atccggtcac ctaagtgact agggtcacgt    4980
gaccctagtc acttattccc gggcaacttt attatacaaa gttgatagat ctcgaattca    5040
ttccgattaa tcgtgg                                                    5056

SEQ ID NO: 38         moltype = DNA   length = 24
FEATURE               Location/Qualifiers
misc_feature          1..24
                      note = synthetic construct; Primer Mega21-190F
source                1..24
                      mol_type = other DNA
                      organism = synthetic construct
SEQUENCE: 38
ggcactctcg tgtgtgatta aaag                                           24

SEQ ID NO: 39         moltype = DNA   length = 27
FEATURE               Location/Qualifiers
misc_feature          1..27
                      note = synthetic construct; Primer Mega21-301R
source                1..27
                      mol_type = other DNA
                      organism = synthetic construct
SEQUENCE: 39
caatgagaag aaaagaaac acttgtg                                         27

SEQ ID NO: 40         moltype = DNA   length = 16
FEATURE               Location/Qualifiers
misc_feature          1..16
                      note = synthetic construct; Probe mega21-250T
source                1..16
                      mol_type = other DNA
                      organism = synthetic construct
SEQUENCE: 40
agtagtggtc aatttt                                                    16

SEQ ID NO: 41         moltype = DNA   length = 23
FEATURE               Location/Qualifiers
misc_feature          1..23
                      note = synthetic construct; Primer Mega14-13F
source                1..23
                      mol_type = other DNA
                      organism = synthetic construct
SEQUENCE: 41
aacacatgat ggacgacttc aaa                                            23

SEQ ID NO: 42         moltype = DNA   length = 23
```

-continued

```
FEATURE                 Location/Qualifiers
misc_feature            1..23
                        note = synthetic construct; Primer Mega14-128R
source                  1..23
                        mol_type = other DNA
                        organism = synthetic construct
SEQUENCE: 42
caagcagacg tacgcaagta gct                                              23

SEQ ID NO: 43           moltype = DNA  length = 19
FEATURE                 Location/Qualifiers
misc_feature            1..19
                        note = synthetic construct; Probe Mega14-85T
source                  1..19
                        mol_type = other DNA
                        organism = synthetic construct
SEQUENCE: 43
ttgtcaatac gaaagtaac                                                   19

SEQ ID NO: 44           moltype = DNA  length = 21
FEATURE                 Location/Qualifiers
misc_feature            1..21
                        note = synthetic construct; Primer Mega30-30F
source                  1..21
                        mol_type = other DNA
                        organism = synthetic construct
SEQUENCE: 44
tgccatgagt agcaccactt g                                                21

SEQ ID NO: 45           moltype = DNA  length = 23
FEATURE                 Location/Qualifiers
misc_feature            1..23
                        note = synthetic construct; Primer Mega30-87R
source                  1..23
                        mol_type = other DNA
                        organism = synthetic construct
SEQUENCE: 45
ctcagattta tgctcttgcg tgg                                              23

SEQ ID NO: 46           moltype = DNA  length = 16
FEATURE                 Location/Qualifiers
misc_feature            1..16
                        note = synthetic construct; Probe Mega30-52T
source                  1..16
                        mol_type = other DNA
                        organism = synthetic construct
SEQUENCE: 46
tgggttcgac acatct                                                      16

SEQ ID NO: 47           moltype = DNA  length = 28
FEATURE                 Location/Qualifiers
misc_feature            1..28
                        note = synthetic construct; Primer Mega5-F1
source                  1..28
                        mol_type = other DNA
                        organism = synthetic construct
SEQUENCE: 47
tcgtaaccat tcatgtgata taatgatc                                         28

SEQ ID NO: 48           moltype = DNA  length = 22
FEATURE                 Location/Qualifiers
misc_feature            1..22
                        note = synthetic construct; Primer Mega5-R1
source                  1..22
                        mol_type = other DNA
                        organism = synthetic construct
SEQUENCE: 48
tgcttacgtg tgtactcgtg ca                                               22

SEQ ID NO: 49           moltype = DNA  length = 18
FEATURE                 Location/Qualifiers
misc_feature            1..18
                        note = synthetic construct; Probe Mega5-T1
source                  1..18
                        mol_type = other DNA
                        organism = synthetic construct
SEQUENCE: 49
ttctcacact cacctaag                                                    18
```

```
SEQ ID NO: 50            moltype = DNA   length = 32
FEATURE                  Location/Qualifiers
misc_feature             1..32
                         note = synthetic construct; Primer WOL133
source                   1..32
                         mol_type = other DNA
                         organism = synthetic construct
SEQUENCE: 50
gttgatgaga ggcagataga ggtcaacttg cc                                    32

SEQ ID NO: 51            moltype = DNA   length = 33
FEATURE                  Location/Qualifiers
misc_feature             1..33
                         note = synthetic construct; Primer WOL134
source                   1..33
                         mol_type = other DNA
                         organism = synthetic construct
SEQUENCE: 51
ttatgcagca atgacatcaa gggtaatgtc agc                                   33

SEQ ID NO: 52            moltype = DNA   length = 27
FEATURE                  Location/Qualifiers
misc_feature             1..27
                         note = synthetic construct; Primer WOL190
source                   1..27
                         mol_type = other DNA
                         organism = synthetic construct
SEQUENCE: 52
ctaatgacac gtgtatcaag taactgg                                          27

SEQ ID NO: 53            moltype = DNA   length = 27
FEATURE                  Location/Qualifiers
misc_feature             1..27
                         note = synthetic construct; Primer WOL242
source                   1..27
                         mol_type = other DNA
                         organism = synthetic construct
SEQUENCE: 53
tcgaactttt cgatcagaaa cttctcg                                          27

SEQ ID NO: 54            moltype = DNA   length = 34
FEATURE                  Location/Qualifiers
misc_feature             1..34
                         note = synthetic construct; Primer WOL153
source                   1..34
                         mol_type = other DNA
                         organism = synthetic construct
SEQUENCE: 54
gattagagtc ccgcaattat acatttaata cgcg                                  34

SEQ ID NO: 55            moltype = DNA   length = 27
FEATURE                  Location/Qualifiers
misc_feature             1..27
                         note = synthetic construct; Primer WOL247
source                   1..27
                         mol_type = other DNA
                         organism = synthetic construct
SEQUENCE: 55
aactgagaga ctgagcgaca atcacag                                          27

SEQ ID NO: 56            moltype = DNA   length = 31
FEATURE                  Location/Qualifiers
misc_feature             1..31
                         note = synthetic construct; Primer WOL121
source                   1..31
                         mol_type = other DNA
                         organism = synthetic construct
SEQUENCE: 56
gctaatggat tcaatttgaa gtatttaata g                                     31

SEQ ID NO: 57            moltype = DNA   length = 34
FEATURE                  Location/Qualifiers
misc_feature             1..34
                         note = synthetic construct; Primer WOL150
source                   1..34
                         mol_type = other DNA
                         organism = synthetic construct
SEQUENCE: 57
actttagaat gataatgatg actttagcac tgcc                                  34
```

```
SEQ ID NO: 58            moltype = DNA   length = 27
FEATURE                  Location/Qualifiers
misc_feature             1..27
                         note = synthetic construct; Primer WOL192
source                   1..27
                         mol_type = other DNA
                         organism = synthetic construct
SEQUENCE: 58
gtacgcaaac agcttgttta cctttcg                                        27

SEQ ID NO: 59            moltype = DNA   length = 28
FEATURE                  Location/Qualifiers
misc_feature             1..28
                         note = synthetic construct; Primer WOL193
source                   1..28
                         mol_type = other DNA
                         organism = synthetic construct
SEQUENCE: 59
ttccaatttg agagggtata tttccttc                                       28

SEQ ID NO: 60            moltype = DNA   length = 30
FEATURE                  Location/Qualifiers
misc_feature             1..30
                         note = synthetic construct; Primer WOL113
source                   1..30
                         mol_type = other DNA
                         organism = synthetic construct
SEQUENCE: 60
ggaagccttg ttcgtatcga aacacaaagg                                     30

SEQ ID NO: 61            moltype = DNA   length = 29
FEATURE                  Location/Qualifiers
misc_feature             1..29
                         note = synthetic construct; Primer WOL114
source                   1..29
                         mol_type = other DNA
                         organism = synthetic construct
SEQUENCE: 61
ccacatcttt taactcaagg ggcttcagc                                      29

SEQ ID NO: 62            moltype = DNA   length = 28
FEATURE                  Location/Qualifiers
misc_feature             1..28
                         note = synthetic construct; Primer WOL194
source                   1..28
                         mol_type = other DNA
                         organism = synthetic construct
SEQUENCE: 62
ccaagtcaat aactttctga tgagaagc                                       28

SEQ ID NO: 63            moltype = DNA   length = 29
FEATURE                  Location/Qualifiers
misc_feature             1..29
                         note = synthetic construct; Primer WOL195
source                   1..29
                         mol_type = other DNA
                         organism = synthetic construct
SEQUENCE: 63
ggttaggcaa attagatagt gtttgattt                                      29

SEQ ID NO: 64            moltype = DNA   length = 29
FEATURE                  Location/Qualifiers
misc_feature             1..29
                         note = synthetic construct; Primer WOL105
source                   1..29
                         mol_type = other DNA
                         organism = synthetic construct
SEQUENCE: 64
ctcgggttaa gatcacatga tagcaaagc                                      29

SEQ ID NO: 65            moltype = DNA   length = 31
FEATURE                  Location/Qualifiers
misc_feature             1..31
                         note = synthetic construct; Primer WOL144
source                   1..31
                         mol_type = other DNA
                         organism = synthetic construct
SEQUENCE: 65
```

```
cttaaccaac tccgatcctt ttcccgtcct c                                          31

SEQ ID NO: 66          moltype = DNA   length = 27
FEATURE                Location/Qualifiers
misc_feature           1..27
                       note = synthetic construct; Primer WOL196
source                 1..27
                       mol_type = other DNA
                       organism = synthetic construct
SEQUENCE: 66
attctatgaa aaggatgtct tgtggcg                                               27

SEQ ID NO: 67          moltype = DNA   length = 25
FEATURE                Location/Qualifiers
misc_feature           1..25
                       note = synthetic construct; Primer WOL197
source                 1..25
                       mol_type = other DNA
                       organism = synthetic construct
SEQUENCE: 67
acaccaagcc caatcgccat acatc                                                 25

SEQ ID NO: 68          moltype = DNA   length = 22
FEATURE                Location/Qualifiers
source                 1..22
                       mol_type = genomic DNA
                       organism = Zea mays
SEQUENCE: 68
tggattgact tgcgagataa ac                                                    22

SEQ ID NO: 69          moltype = DNA   length = 22
FEATURE                Location/Qualifiers
source                 1..22
                       mol_type = genomic DNA
                       organism = Zea mays
SEQUENCE: 69
caaacagatt cacgtcagat tt                                                    22

SEQ ID NO: 70          moltype = DNA   length = 22
FEATURE                Location/Qualifiers
source                 1..22
                       mol_type = genomic DNA
                       organism = Zea mays
SEQUENCE: 70
ttacatgacg taggacatta cg                                                    22

SEQ ID NO: 71          moltype = DNA   length = 22
FEATURE                Location/Qualifiers
source                 1..22
                       mol_type = genomic DNA
                       organism = Zea mays
SEQUENCE: 71
gtttctcacg cgtgagagcc tt                                                    22

SEQ ID NO: 72          moltype = DNA   length = 22
FEATURE                Location/Qualifiers
source                 1..22
                       mol_type = genomic DNA
                       organism = Zea mays
SEQUENCE: 72
ccaaccgtcg tgagacctgc cc                                                    22

SEQ ID NO: 73          moltype = DNA   length = 22
FEATURE                Location/Qualifiers
source                 1..22
                       mol_type = genomic DNA
                       organism = Zea mays
SEQUENCE: 73
agatcggacg caagagggtt ta                                                    22

SEQ ID NO: 74          moltype = DNA   length = 22
FEATURE                Location/Qualifiers
source                 1..22
                       mol_type = genomic DNA
                       organism = Zea mays
SEQUENCE: 74
gggcggtatg tatgtcatac ta                                                    22

SEQ ID NO: 75          moltype = DNA   length = 22
```

```
FEATURE              Location/Qualifiers
source               1..22
                     mol_type = genomic DNA
                     organism = Zea mays
SEQUENCE: 75
caagctctcg cgaaaagggc ag                                                      22

SEQ ID NO: 76        moltype = DNA   length = 22
FEATURE              Location/Qualifiers
source               1..22
                     mol_type = genomic DNA
                     organism = Zea mays
SEQUENCE: 76
ctagtatacg tgagagacct tg                                                      22

SEQ ID NO: 77        moltype = DNA   length = 22
FEATURE              Location/Qualifiers
source               1..22
                     mol_type = genomic DNA
                     organism = Zea mays
SEQUENCE: 77
aagaaataca tgcgagccag tc                                                      22

SEQ ID NO: 78        moltype = DNA   length = 1083
FEATURE              Location/Qualifiers
misc_feature         1..1083
                     note = synthetic construct; Plant optimized nucleotide
                       sequence of MHP14 containing a nuclear localization signal
                       and no intron
source               1..1083
                     mol_type = other DNA
                     organism = synthetic construct
SEQUENCE: 78
atggcaccga agaagaagcg caaggtgcat atgaacacca agtacaacaa ggagttcctg    60
ctctacctgg ccggcttcgt ggacggcgac ggctccatca tcgcgcagat caagccgaac   120
cagtcctaca agttcaagca ccagctcatg ctgaccttca ccgtgaccca gaagacgcag   180
aggcgctggt tcctcgacaa gctggtcgac gagatcgggg tgggctacgt ccgcgaccgc   240
gggtcggtgt ccgactacat cctctcccag atcaagcccc tgcacaactt cctcacccag   300
ctccagccgt tcctcaagct gaagcagaag caggcgaacc tcgtcctgaa gatcatcgag   360
cagctcccct cggccaagga gtccccggac aagttcctgg aggtgtgcac gtgggtcgac   420
cagatcgcgg ccctcaacga cagcaagacc cgcaagacga cctcggagac ggtgcgggcg   480
gtcctggact ccctcccagg atccgtggga ggtctatcgc catctcaggc atccagcgcc   540
gcatcctcgg cttcctcaag cccggggttca gggatctccg aagcactcag agctggagca   600
actaagtcca aggaattcct gctctacctg gccggcttcg tggacggcga cggctccatc   660
atcgcggcga tcaagccgaa ccagtcctac aagttcaagc accagctctc cctgaccttc   720
accgtgaccc agaagacgca gaggcgctgg ttcctcgaca gctggtcga cgagatcggg   780
gtgggctacg tccgcgacca ggggtcggtg tcccactacc agctctccca gatcaagccc   840
ctgcacaact tcctcaccca gctccagccg ttcctcaagc tgaagcagaa gcaggcgaac   900
ctcgtcctga agatcatcga gcagctcccc tcggccaagg agtccccgga caagttcctg   960
gaggtgtgca cgtgggtcga ccagatcgcg gccctcaacg acagcaagac ccgcaagacg  1020
acctcggaga cggtgcgggc ggttctagac tcccctcagc agaagaagaa gtcgtccccc  1080
tga                                                                1083

SEQ ID NO: 79        moltype = DNA   length = 1083
FEATURE              Location/Qualifiers
misc_feature         1..1083
                     note = synthetic construct; Plant plant optimized
                       nucleotide sequence of MHP14+ containing a nuclear
                       localization signal and no intron
source               1..1083
                     mol_type = other DNA
                     organism = synthetic construct
SEQUENCE: 79
atggcaccga agaagaagcg caaggtgcat atgaacacca agtacaacaa ggagttcctg    60
ctctacctgg ccggcttcgt ggacggcgac ggctccatca tcgcgcagat caagccgaac   120
cagtcctaca agttcaagca ccagctcatg ctgaccttca ccgtgaccca gaagacgcag   180
aggcgctggt tcctcgacaa gctggtcgac gagatcgggg tgggcaaggt ccgcgaccgc   240
gggtcggtgt ccgactacat cctctcccag atcaagcccc tgcacaactt cctcacccag   300
ctccagccgt tcctcaagct gaagcagaag caggcgaacc tcgtcctgaa gatcatcgag   360
cagctcccct cggccaagga gtccccggac aagttcctgg aggtgtgcac gtgggtcgac   420
cagatcgcgg ccctcaacga cagcaagacc cgcaagacga cctcggagac ggtgcgggcg   480
gtcctggact ccctcccagg atccgtggga ggtctatcgc catctcaggc atccagcgcc   540
gcatcctcgg cttcctcaag cccggggttca gggatctccg aagcactcag agctggagca   600
actaagtcca aggaattcct gctctacctg gccggcttcg tggacggcga cggctccatc   660
atcgcggcga tcaagccgaa ccagtcctac aagttcaagc accagctctc cctgaccttc   720
accgtgaccc agaagacgca gaggcgctgg ttcctcgaca gctggtcga cgagatcggg   780
gtgggctacg tccgcgacca ggggtcggtg tcccactacc agctctccca gatcaagccc   840
ctgcacaact tcctcaccca gctccagccg ttcctcaagc tgaagcagaa gcaggcgaac   900
ctcgtcctga agatcatcga gcagctcccc tcggccaagg agtccccgga caagttcctg   960
```

```
gaggtgtgca cgtgggtcga ccagatcgcg gccctcaacg acagcaagac ccgcaagacg   1020
acctcggaga cggtgcgggc ggttctagac tccctcagcg agaagaagaa gtcgtccccc   1080
tga                                                                 1083

SEQ ID NO: 80           moltype = DNA  length = 1273
FEATURE                 Location/Qualifiers
misc_feature            1..1273
                        note = synthetic construct; Plant optimized nucleotide
                         sequence of MHP55 containing a nuclear localization signal
                         and an intron
source                  1..1273
                        mol_type = other DNA
                        organism = synthetic construct
SEQUENCE: 80
atggcaccga agaagaagcg caaggtgcat atgaacacca agtacaacaa ggagttcctg   60
ctctacctgg ccggcttcgt ggacggcgac ggatccatca tcgcgcagat caagccgaac   120
cagtcctgca agttcaagca ccagctctcc ctgaccttcc aggtgaccca agagacgcag   180
aggcgctggt tcctcgacaa gctggtcgac gagatcgggg tgggctacgt ccgcgaccgc   240
gggtcggtgt ccgactacat cctctcccag atcaagcccc tgcacaactt cctcacccag   300
ctgcagccgt tcctcaagct gaagcagaag caggcgaacc tcgtcctgaa gatcatcgag   360
cagctcccct cggccaagga gtccccggac aagttcctgg aggtaagttt ctgcttctac   420
ctttgatata tataataataa ttatcattaa ttagtagtaa taatattttt caaatatttt   480
tttcaaaata aaagaatgta gtatatagca attgcttttc tgtagtttat aagtgtgtat   540
attttaattt ataactttcc taatatatga ccaaaacatg gtgatgtgca ggtgtgcacg   600
tgggtcgacc agatcgcggc cctcaacgac agcaagaccc gcaagacgac ctcggagacg   660
gtgcgggcgg tcctggactc cctcccagga tccgtgggaa gtctatcgcc atctcaggca   720
tccagcgccg catcctcggc ttcctcaagc ccggggttca ggatctccga agcactcaga   780
gctggagcaa ctaagtccaa ggaattcctg ctctacctgg ccggcttcgt ggacggcgac   840
ggctccatca tcgcgtccat caagccggag cagtcccgca agttcaagca ccgcctcgag   900
ctgaccttcc aggtgaccca agagacgcag aggcgctggt tcctcgacaa gctggtcgac   960
gagatcgggg tgggctacgt ccgcgaccgc gggtcggtgt ccgactaccg cctctcccag   1020
atcaagcccc tgcacaactt cctcacccag ctccagccgt tcctcaagct taagcagaag   1080
caggcgaacc tcgtcctgaa gatcatcgag cagctcccct cggccaagga gtccccggac   1140
aagttcctgg aggtgtgcac gtgggtcgac cagatcgcgg ccctcaacga cagcaagacc   1200
cgcaagacga cctcggagac ggtgcgggcg gttctagact ccctcagcga agaagaagaa   1260
tcgtccccct gaa                                                     1273

SEQ ID NO: 81           moltype = DNA  length = 1083
FEATURE                 Location/Qualifiers
misc_feature            1..1083
                        note = synthetic construct; Plant optimized nucleotide
                         sequence of MHP55 containing a nuclear localization signal
                         and without an intron
source                  1..1083
                        mol_type = other DNA
                        organism = synthetic construct
SEQUENCE: 81
atggcaccga agaagaagcg caaggtgcat atgaacacca agtacaacaa ggagttcctg   60
ctctacctgg ccggcttcgt ggacggcgac ggctccatca tcgcgcagat caagccgaac   120
cagtcctgca agttcaagca ccagctctcc ctgaccttcc aggtgaccca agagacgcag   180
aggcgctggt tcctcgacaa gctggtcgac gagatcgggg tgggctacgt ccgcgaccgc   240
gggtcggtgt ccgactacat cctctcccag atcaagcccc tgcacaactt cctcacccag   300
ctccagccgt tcctcaagct gaagcagaag caggcgaacc tcgtcctgaa gatcatcgag   360
cagctcccct cggccaagga gtccccggac aagttcctgg aggtgtgcac gtgggtcgac   420
cagatcgcgg ccctcaacga cagcaagacc cgcaagacct cggagacggt gcgggcgg    480
gtcctggact ccctcccagg atccgtggga ggtctatcgc catctcaggc atccagcgcc   540
gcatcctcgg cttcctcaag cccggggttca gggatctccg aagcactcag agctggagca   600
actaagtcca aggaattcct gctctacctg gccggcttcg tggacggcga cggctccatc   660
atcgcgtcca tcaagccgga gcagtcccgc aagttcaagc accgcctcga gctgaccttc   720
caggtgaccc agagacgca gaggcgctgg ttcctcgacg agctggtcga cgagatcggg   780
gtgggctacg tccgcgaccg cgggtcggtg tccgactacc gcctctccca gatcaagccc   840
ctgcacaact tcctcaccca gctccagccg ttcctcaagc tgaagcagaa gcaggcgaac   900
ctcgtcctga agatcatcga gcagctcccc tcggccaagg agtccccgga caagttcctg   960
gaggtgtgca cgtgggtcga ccagatcgcg gccctcaacg acagcaagac ccgcaagacg   1020
acctcggaga cggtgcgggc ggttctagac tccctcagcg agaagaagaa gtcgtccccc   1080
tga                                                                 1083

SEQ ID NO: 82           moltype = DNA  length = 1083
FEATURE                 Location/Qualifiers
misc_feature            1..1083
                        note = synthetic construct; Plant optimized nucleotide
                         sequence of MHP55-2 containing a nuclear localization
                         signal and without an intron
source                  1..1083
                        mol_type = other DNA
                        organism = synthetic construct
SEQUENCE: 82
atggcaccga agaagaagcg caaggtgcat atgaacacca agtacaacaa ggagttcctg   60
ctctacctgg ccggcttcgt ggacggcgac ggctccatca tcgcgcagat caagccgaac   120
```

```
cagtcctgca agttcaagca ccagctctcc ctgaccttcc aggtgaccca gaagacgcag    180
aggcgctggt tcctcgacaa gctggtcgac gagatcgggg tgggctacgt ccgcgaccgc    240
gggtcggtgt ccgactacat cctctcccag atcaagcccc tgcacaactt cctcacccag    300
ctccagccgt tcctcaagct gaagcagaag caggcgaacc tcgtcctgaa gatcatcgag    360
cagctcccct cggccaagga gtccccggac aagttcctgg aggtgtgcac gtgggtcgac    420
cagatcgcgg ccctcaacga cagcaagacc cgcaagacga cctcggagac ggtgcgggcg    480
gtcctggact ccctcccagg atccgtggga ggtctatcgc catctcaggc atccagcgcc    540
gcatcctcgg cttcctcaag cccggggttca gggatctccg aagcactcag agctggagca    600
actaagtcca aggaattcct gctctacctg gccggcttcg tggacggcga cggctccatc    660
atcgcgtcca tcaagccgga gcagtcccgc aagttcaagc accgcctcga gctgaccttc    720
caggtgaccc agaagacgca gaggcgctgg ttcctcgaca agctggtcga cgagatcggg    780
gtgggctacg tccgcgaccg cgggtcggtg tccgactacc gcctctccca gatcaagccc    840
ctgcacaact tcctcaccca gctccagccg ttcctcaagc tgaagcagaa gcaggcgaac    900
ctcgtcctga agatcatcga gcagctcccc tcggccaagg agtccccgga caagttcctg    960
gaggtgtgca cgtgggtcga ccagatcgcg gccctcaacg acagcaagac ccgcaagacg    1020
acctcggaga cggtgcgggc ggttctagac tccctcagcg agaagaagaa gtcgtccccc    1080
tga                                                                 1083

SEQ ID NO: 83            moltype = DNA   length = 1083
FEATURE                  Location/Qualifiers
misc_feature             1..1083
                         note = synthetic construct; Plant ooptimized nucleotide
                           sequence of MHP77 containing a nuclear localization signal
                           and without an intron
source                   1..1083
                         mol_type = other DNA
                         organism = synthetic construct SEQUENCE: 83
atggcaccga agaagaagcg caaggtgcat atgaacacca agtacaacaa ggagttcctg     60
ctctacctgg ccggcttcgt ggacggcgac ggctccatca tcgcgcagat caagccgagg    120
cagtgctaca agttcaagca ccgcctcatg ctgaccttca ccgtgaccca gaagacgcag    180
aggcgctggt tcctcgacaa gctggtcgac gagatcgggg tgggctacgt ccgcgaccgc    240
gggtcggtgt ccgactacat cctctcccag atcaagcccc tgcacaactt cctcacccag    300
ctccagccgt tcctcaagct gaagcagaag caggcgaacc tcgtcctgaa gatcatcgag    360
cagctcccct cggccaagga gtccccggac aagttcctgg aggtgtgcac gtgggtcgac    420
cagatcgcgg ccctcaacga cagcaagacc cgcaagacga cctcggagac ggtgcgggcg    480
gtcctggact ccctcccagg atccgtggga ggtctatcgc catctcaggc atccagcgcc    540
gcatcctcgg cttcctcaag cccggggttca gggatctccg aagcactcag agctggagca    600
actaagtcca aggaattcct gctctacctg gccggcttcg tggacggcga cggctccatc    660
atcgcgtcca tccgcccgga gcagtcccgc aagttcaagc accgcctcga gctgcgcttc    720
accgtgaccc agaagacgca gaggcgctgg ttcctcgaca agctggtcga cgagatcggg    780
gtgggctacg tctacgacca ggggtcggtg tccactacc gcctctccca gatcaagccc    840
ctgcacaact tcctcaccca gctccagccg ttcctcaagc tgaagcagaa gcaggcgaac    900
ctcgtcctga agatcatcga gcagctcccc tcggccaagg agtccccgga caagttcctg    960
gaggtgtgca cgtgggtcga ccagatcgcg gccctcaacg acagcaagac ccgcaagacg    1020
acctcggaga cggtgcgggc ggttctagac tccctcagcg agaagaagaa gtcgtccccc    1080
tga                                                                 1083

SEQ ID NO: 84            moltype = DNA   length = 1041
FEATURE                  Location/Qualifiers
source                   1..1041
                         mol_type = genomic DNA
                         organism = Zea mays SEQUENCE: 84
gtgaatctgt ttggaattga aaaacaagtg cttccttta tacaccacta tgtcgcttca      60
atgtttgcga accaaggtaa agaaatgtaa aatcttacaa tttccgtgca tccgacataa    120
atctgtggtc acatagctat tgttaaacgg ttgcaaatcc taaggaggac cattattgtg    180
caacaactac atatggtaga agcgcttgtt ttgatgtgtg cacattttgt tgctaaaagg    240
atcacgatgc ccaagagggg ggtgaattgg gcttttctaa aaatcaacac taattaaaac    300
ctaagcaaga gcccaacttc accccgacaa ctagcaataa gagaatatga aagggaaata    360
ggatcaaacc ttttcctaaa tgattttggt ggttgaattg cccaacacaa ataattggac    420
taactagttt gctctagatc atacattcta caggtgccaa aggttcaaca caaaccaatc    480
aaaagaacaa gttaggcttc aaaagaaagg agcaaaaagg aaaccgaagt gtgcctggtc    540
tgccgcaccg ggctgtccgg tgtgccacca gacagtgtcg ggtgcaccag gtgaatcag    600
ctcaagctcc tcaacttcgg gtttcccaga cgcagctcca ctataattca ttggactgtc    660
cggtgcaccc gcagagcaac ggctacttgc gcgcaacggt cgactctgca aagtgaacag    720
tgcaattcag aagtcagagc agatggtcag aggggcaccg gattgtccgg tgtagcaccg    780
gactgtccgg tgccgcatga ggacaaagcc tccaacggtc gaccagctcc aagccctaac    840
tacaagatga cgtggcggcg caccggacac tgtccggtcg tgcaccgac tgttcggtgc    900
gcccatcgcc agtagccttc tccaaccggct acaatttggt tggtggctat aaataccacc    960
ccaaccggcc actttaaggt gtgggagccc aagcaacatt ccaagtcata tagttgacat    1020
attcaagcca tcccaaccac c                                              1041

SEQ ID NO: 85            moltype = DNA   length = 906
FEATURE                  Location/Qualifiers
source                   1..906
                         mol_type = genomic DNA
                         organism = Zea mays

SEQUENCE: 85
```

```
tcactttccc ccctattttt ctccctattt tttcatctcc cgcagcggtt ccccctaaat  60
actcctatat accccaatac aactataaaa tatcattttc tatatcaact atcaattttt  120
tatctactaa caattactcg tggacccaca tcacaatgtt tagggtgatg aacagtgaca  180
cgctagatct gaggggagag agaaaagggt cggcgcgtag ggggcgctgt agggggcacc  240
gctgcggctg tggagtgccc cctacagccc ccatgcaagg gcagggggat actgaggggg  300
ctgcgttgcg tacagcctga caggctctc ttcgcatttg cgcgggacag aaatgacttg  360
ccgaggatga aagcagagag acggatttgg ccgagcgcac agcagctcgc caaagacggc  420
gtcgaagcag cagtgaccgc ggtcgagtga gggagtcatc ctggattcgc ggtttatcga  480
ctcggcacgg gggcaaccat ggcgttgaag gtaggcaaca tgaggagcca tcgattgaca  540
ccggtcttcg gaatcggcgg atctcgacga tggtgacaag gaggaggcca cgaagcgtcg  600
tcgagcagag cgcgacaagc aaatcgagtc ggccacgagc gtggatttgg atctgacccc  660
caagtttttg tatggatcct attcccaat ttgtagatct tcaatttcct tactttaatt  720
ttccatagca caaacgatgt ttgcatgcac gattcggaca atcttgactt gttcgtccac  780
ggttggagtt tagggttgga atgtgtaaaa cacgtgataa actgtgtaca actcgagaac  840
tagataattc attttggatt gtaatatgtg tacctcatgc tatagttttg gttaaatctg  900
acgtga                                                              906

SEQ ID NO: 86            moltype = DNA   length = 979
FEATURE                  Location/Qualifiers
source                   1..979
                         mol_type = genomic DNA
                         organism = Zea mays
SEQUENCE: 86
tcacgacggt tgggctggag agccggctgg tagggagga cctcaacggc tgcgccttcg  60
tctactgctc cctcagcttc ctggacaaga tcttctgcgg gatcgccctg tttgccctgg  120
aatcgtacga aggtaagtga cgccgagatc ggcagagatg cttgaaaatt tgtgttttc  180
cttctgctgc gaaggccggc aactgatcgg gcgggcgcaa caccgtcgtc ttccgctgca  240
gatacgatga gctgcggcga gacgggggc ctcaacacgg tgagcaggta cggaacgggc  300
ctgatccccc ctcctgcttc gccgtcctta ctccgagagc cactgcactg gaagcccgc  360
tgcttgtctg acggactgaa gaaaccggtg gatgtgctga gggtggggag aagaaatgcg  420
catcctcttc aattagattt gatttgaaga ggaacatgtc actcgctttt tttttcaatt  480
agaatcctct tcgattaggt ttgaagaggg gggaaatgcc actagttttt tttccaatta  540
gatttgaaag caggccactt tgtaataata ttcgccatgc cgtcgtgttg gcacatcaca  600
tatgcatagt tttggtgtgc taatagatga cattaagttg tgtacgtat aactcgaatt  660
tctgcgaagt ttgtgtgcat gtcatcagat tattgtacta agagcaggaa cagcatatgg  720
tcgaggctga aacagaagac tagtatacag atccgtgtag gaaagaaaaa aaaaactagc  780
tttgaacacg ctgaaaacga cctgacact gaatgcaaac atcacccgcc gcggcgggct  840
ctcctcacag ctcgtcctcc gactccgacc ggtacttgtc cacgtccgcc ctccggtgct  900
tcccccttgcc gtcgacggcg gcgacgtcgg gcccagcgac cctctccttc acctcctcca  960
gcctctcctt ggccgtgtc                                                979

SEQ ID NO: 87            moltype = DNA   length = 734
FEATURE                  Location/Qualifiers
source                   1..734
                         mol_type = genomic DNA
                         organism = Zea mays
SEQUENCE: 87
tagagtatga gtcctgctgc ggtgcgtgga gtcgcttgag agcgttggcg gcgagaagtc  60
cgccaacggc actgtggatc tcggccacgg aagagaaaaa gaaaaggcaa aaattgcatt  120
gtcgaatacg tgaacaggaa aatccaattt tcgtatcatg acctctgtat atgtatccat  180
atatataaaa aaaattctaa tatataaaca gactcaatat tttgtaaaaa atgccattt  240
aaatttgtat taatatatgt tggaaaatgt aaagaatgag atatagaaa cgaaatttag  300
agaaggttgc tgaagatata aaagattaaa tcttttagag tgtgctataa aggatagaga  360
atatttgttt aatggatgaa atttagaaa cgttattgga gataggctaa aaaatatact  420
gcattgcaaa attcagcctt cccttcactc acccatctct ggaactgcct gcctgcctcg  480
aacgtaggag atcaagtgga acgaccggcg cctcaagtcc ctcctcaccg tcggcgcgac  540
gctctgggtc atctccggcg tcaccgtctt cgtcttcccg agccagatgc acaacaccct  600
ctcgccatgt tcatccggcg ctgccaacgcg ctcgtcatgg taaaacgcgg gcgcctagct  660
agcacgccac gctgcacgtc caaatcctac cggtttcgcg tgctctggct ttacattaca  720
tgggcaggtc tcac                                                     734

SEQ ID NO: 88            moltype = DNA   length = 1016
FEATURE                  Location/Qualifiers
source                   1..1016
                         mol_type = genomic DNA
                         organism = Zea mays
SEQUENCE: 88
atacataccg ccctaaggac ctagatagtg tgttggtcca aaaaccaac atagaaacat  60
caaagttttt gccattaata gaaaagattg atggacaact catttccaaa gccatacagt  120
caattgtaat catcttcaac ccaatcaaaa actcatagtt tataaccgtt ctttggccag  180
cttcacggat agtctgtccc tctgagactg aaagtagcct agaagtgggt gaataggcta  240
aacctaaaat ttccaccaca aactttgaaa taatgtcaaa taagcagttc aactggtgca  300
ggccagttca accgctatta aggccggttg aaccactcta aaccggccca accgtgagag  360
aggatcaagg ctatgaacaa cgcagagact aatgagagat tccttttaaga aaagagctca  420
cgggataaat taggcataaa tagggaaaat ttgtgtggat aagatccaca cacaagacaa  480
ctcgatcgat gtccttctttg ctaaagataa ttcacaacga tttgaattaa agcaaagaca  540
caaagacgca aggatttatc ctgaggttcg gccacaccat aaaggtgccc tactccctgt  600
tgaggagccc acaaaggacc aagtcttttc caactctaat cctccacaaa tcgaccacaa  660
aggtcaaggc aaactctttc tcaactttgc tcaacgagtg agtgaaacaa acttcttggg  720
```

```
gtcgtccaca aatttggaga ctcccaagca acctcaaact gccaaggaac tcgaaggttc    780
caagggcaac aaatctgcac aagaagtgtt tgcagtgggc tcaagagatg agaaagggg     840
gggagagaaa actaagtcta aaagtgaaaa actcaaactt acaccaagg  gcccttcaat    900
caagcgatga gggagcgatt tggggtgtga gagagttggg agcttttatc tcaagttagg    960
tcagcaatga atgcgtggag caaccataat gaatgaggag agagacatga ggggt        1016

SEQ ID NO: 89          moltype = DNA   length = 898
FEATURE                Location/Qualifiers
source                 1..898
                       mol_type = genomic DNA
                       organism = Zea mays
SEQUENCE: 89
ctttggcaag caattgcatg cgagtaaaca agtaattaag agtaaggttc accggttagg     60
ttccttacct cggtgtaaag cttggaacat ggttgttgag gttagttagg ttccttaccc    120
acaagtcaca ctctcccaca tggtgtgctc ataccctaagt tatacttgat cagcctagac   180
cacttggcgc tcttcacacc ccactctact aatgtgctct tcgtgtctcc tgtggggcga    240
gcacggtacc ccttacaatg cctcctttag agccacacac gatttcatgc aggattccat    300
ggagccataa cctccaaggc acctaggagg tggaaacctc taaaagtaac aagacaatga    360
tcttcctagt gataacttga taatgtgagt tagtaagagg tttggggcga aggctcaagc    420
atgctcaaca agtgctccta ttgctcagct tagggagcac acatttacac tcctactttt    480
tatagcccca cttcccacaa ctagacacta taacactttt tgagaaaact acacattagt    540
ggacactcca taatacaacc cacggatagc ccatatttga attccgatga ctatatttca    600
attaaatgcg tgttagtcgt catagaaagt gtttagtgaa cagtctatct gttaattttt    660
aacatgtcta taaacttcct aatttatgtc ccctttaaag aatgtgcgac agatagtctg    720
cctttgaggc ccatatagta caccgaccaa atatttgcat tcaccgaaac tcccaagttt    780
ctatccacta tctaaaacag tgtagagaca gtctacatga ggggcccaa  tagtccatcg    840
gtcaaaaaac acataaactt taagtttttt gtccatcact tgaattagta tgacatac      898

SEQ ID NO: 90          moltype = DNA   length = 260
FEATURE                Location/Qualifiers
source                 1..260
                       mol_type = genomic DNA
                       organism = Zea mays
SEQUENCE: 90
agggcaagtc aatccatgca acaccactca cgaatatgtt acgttaatac caaaaccata     60
tattgacaca catgcacaac atcatatatt atgttaatca ctttataaat ccaattttaa    120
tctaaaacaa tgttttatca cacacgattt cgcaatatac atcggtgata aagatacgcc    180
ggttgaccat gtaagtcaac aaagggtcga taacgtcgtg acacttaaaa ggaggcgagt    240
cacacatcta tatgggtgct                                                260

SEQ ID NO: 91          moltype = DNA   length = 900
FEATURE                Location/Qualifiers
source                 1..900
                       mol_type = genomic DNA
                       organism = Zea mays
SEQUENCE: 91
cgtacaactt taggaatcac accagccgcc tactctaagc ttgggcctca cttctgtggt     60
ccctatcagg ttctggagga aattgggaca gtatcttaca ggcttgccct gccatctcac    120
gcccgcatcc ataatgtgtt tcatgtctct ttactaaaga aatatattgg ggctcccccg    180
gctgcaatag ttcctctacc cccaatatta catggcagag tcctgcctca gcctgagaag    240
gttactaagg cacgcaagaa ccgaggcgtg tgggaactgc ttgtgcaatg gctgggacaa    300
tcagccgctg atgcaacgtg ggttcagctg gaggactttc gtcgccgttt tcctggtgtc    360
caggtcgcgg acgacttgtt tttggggag  ggggaaatg  ataccgatgc atttgtagga    420
aaggtatacc agagaaggaa tcgccaggaa taaaggaaac aacagataag gaataaaaga    480
gacaacagat aattttctat attttagtcag tcagcagatt aggaataaaa gagacagcag    540
ataagtttct atatttagtc agtctatttt ctagcaagtt gagagtgata tgatttgttt    600
ctatattaac ctgggctcag tctataagag accaggggta gtttgtacta gggattatca    660
aaagaagaaa atctcctagt cctaggaggt tgcctgggcc cctggggtgc actgaggaa     720
ctctccagcg tccggaacgc caccaggaat cctcctcccc cttccactc  ctatttcctg    780
cgttcattgt ccacaacctc ctgctgagcc cccaacgaaa gcagggagtt tgcgtcactc    840
gaccccaac tgataagggt ttaaggtcgg gaaatctcac ccgtgaagtt tatctcgcaa    900

SEQ ID NO: 92          moltype = DNA   length = 931
FEATURE                Location/Qualifiers
source                 1..931
                       mol_type = genomic DNA
                       organism = Zea mays
SEQUENCE: 92
ctacgtcatg taagtttcta gtggttgtat tgctctgggt ttgaagatta taggtgattg     60
ttgaaggtag aatatgaaag tagcctacga gtcaatggaa gtctcccgtt tcagcattat    120
atggccaaat gaagagataa ccctgtatag atcataatcc tatatgcatc taaccacttt    180
cactatagac gcaacgcatt ttccggcgtt cggttggttc cctgcgaggc ttgtgtacgg    240
ctgcatgcat gggacatgcc ttcgaagatc ccttgactc  ggtgtgtgac cgctttactc    300
ggcttcggtt gcatggacta gaggcccacg atgcaccctg ttgacgaccc atcaggggcc    360
ttataagcgt cacatggagc gcatccatgc atggtgacct aggggatatc catgtaacac    420
cccaggtgtt agctagaagt aataacccaa ccacttggac cattatcaca tgtggataac    480
ttaaggtaaa agtcactaaa attaatgacc atattcctaa taaggtgaaa acacccctag    540
aagaattaac ttacccaccc catggtgatc aaaggaaagg ggagtaacca accccctaaa    600
cctactctct tgagcccaag agcaccaata caaagtgtca agagaaagtt aaccaaaatc    660
```

-continued

```
cttaaccaca agtggaccct taacaaaagt tatagctaac taaataccta acaaaagttc    720
ttgagggtta agcaccaaaa gggggtgctag agtcccaatc aagtcacaca tgtgggagaa    780
ggggagagaa atcaagattt tttcataaat ccaaaaacag ccctatccca aaaacataaa    840
atctccaatt atgaaatgtg tgcctaattg tcctaggaac accctcgtaa agtttgaact    900
cgagccctca ctgtttgaca tgacaagtca t                                   931
```

SEQ ID NO: 93        moltype = DNA   length = 922
FEATURE              Location/Qualifiers
source               1..922
                      mol_type = genomic DNA
                      organism = Zea mays
SEQUENCE: 93

```
cgccgcatta aatgcgcggc agagagccgt tggcgcggag atgaccgttg cttcggagtc    60
gcaccggaca gtccggtgaa ttatagcgga ctagccgttg gagtttcccg aagctggcga   120
gttcctgagg ccgtcctccc ttggcgcacc ggacactgtc cggtgtacac cggacagtcc   180
ggtgaattat agccgagtcg cctctgcgaa ttcccgaagg tgacgagatt gagtctgagt   240
cccccctagtg caccggacat gtccggtggc gcaccggaca gtccggtgcg ccagaccagg   300
ggtgccttcg gttgccctt tgcttctttg ttgaatccaa aactcggtct ttttattggc   360
tgagtgtgaa cctttacac ctgtataatc tatacacttg ggcaaactag ttagtccaaa   420
gatttgtgtt gggcaactca accaccaaaa ttatttagga actaggtgta agcctaattc   480
cctttcaagg cttcacttcg gaccactcta gaagtctatg gatggtctag cctcttagca   540
tgaacgatcc acgacaatga tacttagccc acttttcaaa acacgctttt gaaaatattt   600
taactcacga attcagaaga attgttaata atcttgctaa tgcatcatct aaaagctcta   660
tgaggcatta agtttcacat aagaaattgt cattgactcc tcttgacagt atggctatct   720
atccgactaa cccagacaat tttcttctct aaacaccttg tgactggtgt cggtgtttgg   780
taccaatggc gcactatggg atataccatg tagtgctttt ggggaggatag cgatgtcgat   840
caaaacttga tggttcatgc caggcacgat ggaacagagc agattatata ggtttgaacc   900
acctagaggc gtaatgtcct ac                                            922
```

SEQ ID NO: 94        moltype = DNA   length = 994
FEATURE              Location/Qualifiers
source               1..994
                      mol_type = genomic DNA
                      organism = Zea mays
SEQUENCE: 94

```
acgcgtgaga aactgagaat cgcctgcggg ccgcgaatgg cgagcgagca cggcttgaga    60
atctgacgat ggaggaagct tggatagtgg aagggtattt ttggagatca atttgtagat   120
gctggtggaa gcgttttctt tcctatactg gccttctcga aacctgtagg agttgctcta   180
acaggtaagc atcatcagcc cctccttgtc cctcagtttg taatacagca atttcagata   240
tggacataga aaaactctag gtccaccact gatagtaatc ctctaccatc aaaatatatt   300
ttatttgttt tcgaaaataa ataagacaat gttaagagta catgtagaac cttctaaaca   360
tctgaacttc agattcaaca ccaaatcaac atgatgagtt tcaacatgtg agttaaatga   420
caaagtgggt tgcttttagaa agcaaacaca gttacctagt tagggcttaa gcagacaatt   480
attttttggg tagtgattta caaaataatt tattttccga ttgcaactat gtgttacact   540
caattttaaaa aaatatgttt tataatcaga ccacacatcg aagtacaggt gtgtattatc   600
gaggtacatg attatttcaa tatttgagag agccttttca acttggtaca attgggacac   660
ccaaatggaa agaaacagta tgatcaaagg acctgaattag gtgggcacaa taactgaagt   720
tatctggcca attattaagt aacactttt tagaattcct ggggcctggt cagcatgtac   780
gattgaccat aaaattgttct ggtcagcata gttattgaca actccggaaa ctatctgata   840
agacatactt gggacctgtt tgtttgagat tataaatatg tttagattat aaccccaaac   900
aaacaaaccc ttcatattcc taaaacaagt ctaaaattta attaaatata taataaatgt   960
tacatatgct atttgtcacc taggtgcgac tggg                               994
```

SEQ ID NO: 95        moltype = DNA   length = 1048
FEATURE              Location/Qualifiers
source               1..1048
                      mol_type = genomic DNA
                      organism = Zea mays
SEQUENCE: 95

```
ctgccgatgc tatataagtt gagtcgccct gccgatcgtt gacgctcgaa cgtcgaccct    60
cctgaagaat aggctcctgt tgcgtgtctc ctaaccacgg ccacctcgac ttcggctaac   120
tcggcatcca ggggctatcg ccttatcaga atccacaccg gtctcttctc cagccacaac   180
attggcaccc tcacgacgct gcgaccgcag gggggttcaa cccgtcgact cctaccttcg   240
gcctctactc cagtttcatc gtgtgtggtg ccccgttgc gactgcgggg atgttagact   300
gtgtgtgtag gccggcacca ctgttgggct gccggcccat tagggttagg gttgtgagtc   360
tatatattat acccccatctc ttatcaatac aaccaccact tgatacttct acatagagga   420
tagaggtagg agcagcccct aatcttcagc tttcatagcc aactgcccaa gaatatccat   480
aaacctagcc aattcacttc tccaatcgcc ttagtctagt aaaagcaaat gccctatgca   540
tgtaacttta ccttgcactt tcttttccac ttctgcactt ccatccatca tcttcacatg   600
ttgagcactt gcacttcatg gtccttgcca tctccacttc acggttctat atatgtggct   660
caactatctt gtacactaaa tcgcctattc atctcacatg aaataaatta gtctggcatt   720
caattatcaa agccaaatca ggtctttcac tccagagctc ctgcttgact agttgccgct   780
cttccgtgat gtttgccacc tcttccaccc ccagactgca gtggtatact ttcccccaat   840
ctattttag tgctaaaatt ggggcttcct caaattgaat tatttgctta tccatatgcg   900
catcttactg taaatcgcgg tggtggccta tgaccgccag gatgtgtcta caacgcagta   960
cctatggcta taagttgcag cttcctccac aactggtagg ccaatctccc ccatgcaggc  1020
gcgcacagga gagggaaggc tctcacgc                                     1048
```

SEQ ID NO: 96        moltype = DNA   length = 901

| FEATURE | Location/Qualifiers |
|---|---|
| source | 1..901<br>mol_type = genomic DNA<br>organism = Zea mays |

SEQUENCE: 96

```
ttgcgtccga tctcatccac ccgctcctga tccaacgacc cagatccttg gataccggtt   60
cgagcgcgcg cccctacccc taggccccac acgttgccgc ctgcgcccct gatgctaggc  120
ctgaactgtc agtccaccct ccaccctggc cgctgaccgc tctgtcaccg cttgctcgcg  180
ccccgtgcg cttgcccgca gatctgatct cggcagttga tctgtgatcg gatggccgag  240
agcgcccgat accccttcat ttggaaattt tgttaaagag atccccggtt tcttagaaat  300
caacccgcag tctagtttta ttgcgcctga gtccctggtt ttttgcagag agacccagta  360
actttatttt tatcacaaaa attggtttaa tttagggttt tgaattccaa aacttgtaaa  420
tttcatatct tttgcatatg aactccaaat tgggtggttc aaattgcaaa atgttcataa  480
tgttattctc tatgtgttta aattatattc atttactatt ttcatgtctc aattttgtgg  540
ctaatcccta ggttaattta aagtgataga atatttatta aagggtaaaa taaaaggtaa  600
agccctaatg aatgtccatg tgcttaactt tgtaaactta atttcattta atgtaatccc  660
atccctagaa tctgtttatt taagtaagta atttattgag atagacttag ttagaaaata  720
gtagacctt aaacatagtg atctaccta ataccatgg ttcacttgtg tgtttgtact  780
tttctactga acctttgtt gatcggttgc acatgtttgg tgtgctgttc tttgttgttc  840
cccaagtgtg ttgaatgaat gattgctttg cgtacacaac gagcaatccg aggttccgag  900
t                                                                  901
```

| SEQ ID NO: 97 | moltype = DNA   length = 1083 |
|---|---|
| FEATURE | Location/Qualifiers |
| source | 1..1083<br>mol_type = genomic DNA<br>organism = Zea mays |

SEQUENCE: 97

```
atggcaccga agaagaagcg caaggtgcat atgaacacca agtacaacaa ggagttcctg   60
ctctacctgg ccggcttcgt ggacggcgac ggctccatca tcgcgtccat caagccgaac  120
cagtcccgca agttcaagca ccagctcatg ctgaccttca ccgtgaccca gaagacgcag  180
aggcgctggt tcctcgacaa gctggtcgac gagatcgggg tgggcaaggt ccgcgaccgc  240
gggtcggtgt ccgactaccg cctctgccag atcaagcccc tgcacaactt cctcacccag  300
ctccagccgt tcctcaagct gaagcagaag caggcgacc tcgtcctgaa gatcatcgag  360
cagctccct cggccaagga gtccccggac aagttcctgg aggtgtgcac gtgggtcgac  420
cagatcgcgg ccctcaacga cagcaagacc cgcaagacga cctcggagac ggtgcgggcg  480
gtcctggact ccctcccagg atccgtggga ggtctatcgc catctcaggc atccagcgcc  540
gcatcctcgg cttcctcaag cccgggttca gggatctccg aagcactcag agctggagca  600
actaagtcca aggaattcct gctctacctg gccggcttcg tggacggcga cggctccatc  660
aaggcgcaga tcaagccgaa ccagtcctac aagttcaagc accagctctc cctgaccttc  720
caggtgaccc agaagacgca gaggcgctgg ttcctcgaca agctggtcga cgagatcggg  780
gtgggctacg tctacgaccg cgggtcggtg tccgactaca tcctctccca gatcaagccc  840
ctgcacaact tcctcaccca gctccagccg ttcctcaagc tgaagcagaa gcaggcgaac  900
ctcgtcctga gatcatcga gcagctcccc tcggccaagg agtccccgga caagttcctg  960
gaggtgtgca cgtgggtcga ccagatcgcg gccctcaacg acagcaagac ccgcaagacg 1020
acctcggaga cggtgcgggc ggttctagac tccctcagcg agaagaagaa gtcgtccccc 1080
tga                                                               1083
```

| SEQ ID NO: 98 | moltype = DNA   length = 1026 |
|---|---|
| FEATURE | Location/Qualifiers |
| source | 1..1026<br>mol_type = genomic DNA<br>organism = Zea mays |

SEQUENCE: 98

```
tcgcgagagc ttgggggggcc ttgacgactg agtgagtgtc tttcgtgctc ggccttcctg   60
ctctcgtttg cgtcttcgcg caaggaaacg ggaagagaaa aagagggacc gtcccgtccg  120
tgcggacgtt gtcgtgcatg ggtgggtctt gcatgatttg tgcctgccgt cctgtggtcg  180
acgggaagcg acgcgagtc ggcgaagccc agctggagcg tagagccaag agcccgtgct  240
gtgcgcgctg tgtgctgtag ctgtgccgtt gcagttgcag ttgcagttgc agttgcagcg  300
acgggttctc acttgatcac ttcggagttc aggcaaagct ctcgtggtgg ctgccatgcc  360
accactggct gatagcgtgt ggacccattc caggcccata cccactttac ctacccgggc  420
acccaaaggc cgaagcctgc tattgtagta ttgtcggcct gcgcagcaga gcgctgagtg  480
tctactgatt ataccgctga aattaaatgc ggtattcgct tttcagacca aaccagacca  540
gatcagccag tgcaaagccc gcagtgggat ccaggcaaac gttttctcca ctgcaatcga  600
tctgctgcta cgtagaggcc ggtagtctac tgagcgcaac gcgtacaagt tgctgttgct  660
ggatcgctag ctcacatacc tctcgacgca ctcggttgtt ggcttcacat gcatggccgc  720
ccaccaccaccttt ctcggtgacc acctacatgg tctctctagc agaccccgtc agtgccgcgc  780
gcattccggtg catgcatgcc tgtatggaca tgacgtgcgt tctcgagcaa taattagatc  840
catgttggca ccagagatgg gtagaccgtg cgtgcacgaa ataactggta ccatcagtga  900
acaaaacaag cattcctcgt ggcgttcatg gcggtgatgg cagtgggaat gtacaactga  960
cttcagggac cgtgacggac cgtgggataa agacgcagta gagcaggaaa gatacttcct 1020
accaaa                                                            1026
```

| SEQ ID NO: 99 | moltype = DNA   length = 856 |
|---|---|
| FEATURE | Location/Qualifiers |
| source | 1..856<br>mol_type = genomic DNA<br>organism = Zea mays |

SEQUENCE: 99

```
caaaggagtc aaggacagac actgtcgatg atatgagaca acaacaacaa aagcacactc   60
cgtttcaata aaaagaagat tatcggactc cctcatacca gccctaccta cgacacgtgt  120
aacgcctcag gggaggaacg ggacacaccc atgcatgcgg atgcgggcgc agcatatcct  180
gacacgcgcg gcgtgacccg cctgtcagtg agtctgcacc gtccgatcga gccgcgcggg  240
tcacgtcgag gccgcgctgg tcggtccttt tttcttcgtt ccccccggtcc ctcctgcccc  300
tggtatgtaa tattttctct gccctcgtgg agtaccgacc gcgagaaagg aacggccgtg  360
ggaagaaagc gacgggaggg ggcgggcgct tggatcggcg gcatctgtag aaagatggga  420
atcctcctgc aggacaacta gacaagtgtc caccggaaca gaagaccttta tctagtagta  480
gcagaagagt ggtagcagta caccttttcta aagtttgatt taaaaaaaat tgaaagtatc  540
aaatatctat ttaacaatat gtaatgcttc tactacaaag tatttttttgt aatgagaat  600
ttagtaaatac tcattttatt tataagtact aaaatttcat ataaattagg ttaaaccttta  660
aaataacttg actgagtcga cgctctatta taaaattttt ttctcagac cgagggagta  720
aataaaacta aacaaagcga ggagctgcgc ggaggacatg tcaacgaggg agacgacgac  780
gagagaaacc aacgagattt tttgccagac atgaaagcga gagaggcctt gtatgttcct  840
cgcctgccct tttcgc                                                 856

SEQ ID NO: 100           moltype = DNA  length = 1068
FEATURE                  Location/Qualifiers
source                   1..1068
                         mol_type = genomic DNA
                         organism = Zea mays
SEQUENCE: 100
tcacgtatac tagctgaccc atggagccca ttgccagtag ctgctcccgc tttacgctcg   60
gatcaggtga ctcaatagaa tccggctgag atcctcgcta gtgaccgtta ccttcctcta  120
gggggaacctg cctctctatg tatataagaa accacgcccct ctcgcctcct aatcctaccc  180
atgttgagcg tcaccgaaag ctgagagcct cgccatcgac tgagggggggg gggggagat   240
tgccgccacg gtcaacccat tagtgtgccg catccccgcc ttcggagcat ggtctagggg  300
catccacggg tcgtggcgga gctatccgtg gcattatcaa gcaggatggg tcctcggacc  360
aatgggaatt tctcgccgta gtccttcgcc atagatccgc ctgcaccgtg gtcggaggac  420
atcacctact tcatcgctgg tacataaccc ctataccgtt agctagggtc ccctatccat  480
gtagctctcc tccgatcaag atctaaagca tcaaagcgct aacctgaaag ggaaatggtt  540
aaccatttcc tataatcgat tttggtgttt gacgactatc acaaaccata tggactaact  600
agtttgccta gtcaatattt ttccttaggt gcataaagtt catatacaca ttgtcgggta  660
ccgtaattag gggtacccccc aacactccta aacagacctt gtaaacacct tcaaagcaaa  720
ccatgaagac caacagttcg ggtcaaagtc aaagcttcgt ctaccaaggg acacgatctc  780
gcctcggccg agcccgaccc caggcgggaa cagtagtccc ggacggattc acgtctcgcc  840
cgagggtctc ctcaggcagt gagcacaccc tcggctcagc caaaggcaag ccttgtcgtg  900
caagcgaccc tggccaaatc gccttaccag tcgaccgtat tgcatgcgca tttaatgctg  960
ggatccgcctg acaccttatc ctgacacgcg tgcctcagtt gacaaggtcg aagtgaccgc 1020
agtcgcttcg cccttccact gaccgatctg acagaaaaat agcaccgc              1068

SEQ ID NO: 101           moltype = DNA  length = 982
FEATURE                  Location/Qualifiers
source                   1..982
                         mol_type = genomic DNA
                         organism = Zea mays
SEQUENCE: 101
tttctgacag cccaacgaat ttcgttgatg aaatatgcaa ctttcatgat ctctgaagtc   60
gtaaatgcat cttcatatat cttcaagcct ttcacgacat agcaaaaggg tattgtcggt  120
accttataac taagtatcct cttctactgt attaagatag agacctccgc ggttaacttt  180
aaacgcgtac taaggtaatg agtggccggt cctacggacc tggacctgtc tgtcaggacc  240
cctggcttca agttccgctc ttcacctcga atttgtaaca cccaaaaatc ataattttttg  300
gatttagaaa aaatatatta tcctgaaatc taaataagaa tattttctca taaaagattt  360
aagtaaaagt atttcataaa agagattata tattagaaag tatttcctcg taaaacaaaa  420
caagtaataa atattaaagt tttttttaatg aacttttaat gtgactacac attcaaaata  480
ttttcgtaaa ataaaatatta tgtgtgttgc atattgaaaa cattgcctaa ataaataaat  540
aaggtaataa attaatgaat aaacttaata cacaaaccttt gcattcatgc tggatatttt  600
tttgtgcaaa ttagaacttt gtttgaatct aaatctaatt ggaattggaa aatagaaaat  660
agaaaaagaa taaaaaagga aaaggaaact ttacatgcat cgtgggccga gtaacgcagc  720
acgctccacc cgcggtctct tttccttttc tactagtcac tgacacgcga gccccacagt  780
gcagcctcac catctcgcac tcgaatgggc tctagaagtc gctcccaaat ggggcccagg  840
tgccaacacc ttcttctcta aatcaatggg gatcacaatg aatcctttcg taaccgccat  900
gtaacggcct ccatagatcc cgaccaccag tactttctct attcgtgcgc gcctgcccga  960
gggaccgttg tggcaaggtc tc                                          982

SEQ ID NO: 102           moltype = DNA  length = 1052
FEATURE                  Location/Qualifiers
source                   1..1052
                         mol_type = genomic DNA
                         organism = Zea mays
SEQUENCE: 102
agaatgacga ttgctggact gggagacatt gggttggcgt aactgttcag gacttcgggt   60
acccgtgggt caccgtgggt gaagtgaga aacccggacc cgaacccgaa aaggtgcggg  120
tcgggttcgg gtcacacccg tgggtgaaaa aacacacccg cgccgcacc cgtcgggtcg  180
ggtacccgac gggtacccga acctgtgggt gaaattgcca tgcctacagc tggctgtggc  240
gtcaggctcg ggagcccatg ccaattgggc taaaagccca aaattttcca atgcacgcca  300
ttggggctgc acagttctag cactagactg gcttttcttc agtgaaactg aggctgcact  360
ttgcaactgc ttcttcaggc aaacactaca tatgattgga cgtccagctc gtgggcgcaa  420
ggctcgcggg ggcctggatg cgcagggatg ctccctcttc gtatctccat gcgtacaaac  480
```

```
tgacacaaca aaaagccatt gagttgcatc ggtgcgtgca ggctcgtctc cattcataca    540
gcgcccacca atcaccggct aagtgcggtc aacggaacgt ggagagcctg acgcacgcg     600
cctaggtatc caatcacgcg gagtactgtg tccagccgaa gccttccaca gcggccgagg    660
accgaggtat agttcaacgg aacgttgccg tgctcgatcc ggcagtgaga ctccggcctg    720
catcgttgtc gtctttgctt cagaactgac aaaacgtgta tgtggacctg gcctagaagg    780
tcatacaata caaaactaga attatttttag aattgacagt ggcagagtat taggaatcat    840
cagctgcgat aacataaccg acagttaata ctccatccat ttcaatttat aattcactta    900
tcttttttat cctaaatttg ataggttcgt cttattcaaa aaaaattata attatcatta    960
atttttactg tgatatagtt taacatataa tacatttttaa gcgtggtttt caattttttta   1020
ttttttcacaa aacatggta agaaatacat gc                                  1052

SEQ ID NO: 103          moltype = DNA   length = 792
FEATURE                 Location/Qualifiers
source                  1..792
                        mol_type = genomic DNA
                        organism = Zea mays
SEQUENCE: 103
atgcgagcca gtcaaacttg ttaagaaaaa tcaaacgaat tagaaattag gacagtggga     60
gtatacaaac gggagtatat aaacgactat cactattaat ttagtgttga gtgagcaatt    120
atcggttcgt gtctatcact atcactcatg atatgaatca acggtgataa ctgctaagca    180
taaatggttt ataattttc atatgagatc gaacgaagat atactctata ttgaaattat     240
ttagtttaaa ggaatctaaa acttacagt cgataacttc ttaattaatt cgagatggtt     300
tacccgtgta aatattcaat atgatttttg aatcatattt gacatgatta acaatgtcaa    360
attcgcaata tcgaatgaag acaaactcaa cattaaagtt gtgctagtat aatgctcgtg    420
tgttgtgaca aaacataaat atttgatagt ataacgatta catgaaaatg aacaatagat    480
atattaccat cgatcgacct taatatctga caaattattt gtcaacaacc aatacaaaac    540
taaacttgga attcagaacg cctcctcctc tcccttagct gttcagtcac gcatcacggg    600
tggcagagcc tcctcctcct atccaggaa ggtcgatgtt ctttatggtg gtgcggactg    660
cggaagaatc tgggtgaaga aggtggagac gagaaagaga tgagaagtta gagggttaat    720
aacttaatat acgatgacaa gagcgatgaa gaggaggatg aagcgcttat ggtggtgcat    780
gattggttgc at                                                        792

SEQ ID NO: 104          moltype = DNA   length = 15574
FEATURE                 Location/Qualifiers
misc_feature            1..15574
                        note = synthetic construct; plasmid PHP44285
source                  1..15574
                        mol_type = other DNA
                        organism = synthetic construct
SEQUENCE: 104
gtttaccccgc caatatatcc tgtcaaacac tgatagttta aactgaaggc gggaaacgac     60
aatctgatca tgagcggaga attaagggag tcacgttatg accccgccg atgacgcggg    120
acaagccgtt ttacgtttgg aactgacaga accgcaacgt tgaaggagcc actcagcaag    180
ctggtacgat tgtaatacga ctcactatag ggcgaattga gcgctgttta aacgctcttc    240
aactggaaga gcggttacta ccggctggat ggcggggcct tgatcgtgca ccgcggcgt     300
ccggactaac taactagtcg agctagttac cctatgaggt gacatgaagc gctcacggtt    360
actatgacgg ttagcttcac gactgttggt ggcagtagta tacgacttag ctatagttcc    420
ggacttaccc ttaagataac ttcgtatagc atacattata cgaagttatg ggcccaccgg    480
tggtaccgag ctcgttttaaa cgctcttcaa ctggaagagc ggttaccaga gctggtcacc    540
tttgtccacc aagatggaac tggcgcgcct cattaattaa gtcagcggcc gctctagttg    600
aagacacgtt catgtcttca tcgtaagaag cactcagtc tcttcggcc agaatggcca    660
tctggattca gcaggcctag aaggccattt aaatcctgag gatctggtct tcctaaggac    720
ccgggatagc ttgcatgcct gcagtgcagc gtgacccgt cgtgccctcc tctagagata    780
atgagcattg catgtctaag ttataaaaaa ttaccacata ttttttttgt cacacttgtt    840
tgaagtgcag tttatctatc tttatacata tatttaaact ttactctacg aataaataaa    900
tctatagtac tacaataata tcagtgtttt agagaatcat ataaatgaac agttagacat    960
ggtctaaagg acaattgagt attttgacaa caggactcta cagttttatc tttttagtgt   1020
gcatgtgttc tcctttttt ttgcaaatag cttcacctat ataatacttc atccatttta   1080
ttagtacatc catttagggt ttaggttaa tggttttta tggttttata aggtacta tttttagtaca   1140
tctattttat tctatttag cctctaaatt aagaaaacta aaactctatt ttagtttttt   1200
tatttaataa tttagatata aaatagaata aaataaagtg actaaaaatt aaacaaatac   1260
cctttaagaa attaaaaaaa ctaaggaaac attttttcttg tttcgagtag ataatgccag   1320
cctgttaaac gccgtcgacg agtctaacgg acaccaacca gcgaaccagc agcgtcgcgt   1380
cgggccaagc gaagcagacg gcacggcatc tctgtcgctg cctctgaccc cctctcgaga   1440
gttccgctcc accgttggac ttgctccgct gtcggcatcc agaaattgcg tggcggagcg   1500
gcagacgtga gccggcacgg caggcggcct cctcctcctc tcacggcacc ggcagctacg   1560
ggggattcct ttcccaccgc tccttcgctt tccttcctc gcccgccgta ataaatagac   1620
accccctcca caccctcttt ccccaacctc gtgttgttcg gagcgcacac acacacaacc   1680
agatctcccc caaatccacc cgtcggcacc tccgcttcaa ggtacgccgc tcgtcctccc   1740
ccccccccct ctctacccttc tctagatcgg cgttccggtc catgcatggt tagggcccgg   1800
tagttctact tctgttcatg tttgtgttag atccgtgttt gtgttagatc cgtgctgcta   1860
gcgttcgtac acgatgcga cctgtacgtc agacacgttc tgattgctaa cttgccagtg   1920
tttctctttg gggaatcctg ggatggctct agccgttccg cagacgggat cgatttcatg   1980
atttttttgg ttcgttcga taggttttgg tttgcccttt tccttattt caatatatgc   2040
cgtgcacttg tttgtcgggt catctttca tgctttttt tgtcttggtt gtgatgatgt   2100
ggtctggttg ggcggtcgtt ctagatcgga gtagaattct gtttcaaact acctggtgga   2160
tttattaatt ttggatctgt atgtgtgtgc catacatatt catagttacg aattgaagat   2220
gatggatgga aaatatcgatc taggataggt atacatgttg atgcgggttt tactgatgca   2280
tatacagaga tgctttttgt tcgcttggtt gtgatgatgt ggtgtggttg ggcggtcgtt   2340
```

```
cattcgttct agatcggagt agaatactgt ttcaaactac ctggtgtatt tattaatttt   2400
ggaactgtat gtgtgtgtca tacatcttca tagttacgag tttaagatgg atggaaatat   2460
cgatctagga taggtataca tgttgatgtg ggttttactg atgcatatac atgatggcat   2520
atgcagcatc tattcatatg ctctaacctt gagtacctat ctattataat aaacaagtat   2580
gttttataat tattttgatc ttgatatact tggatgatgg catatgcagc agctatatgt   2640
ggatttttttt agccctgcct tcatacgcta tttatttgct tggtactgtt tcttttgtcg   2700
atgctcaccc tgttgtttgg tgttacttct gcaggtcgac tctagaggat ccatggcacc   2760
gaagaagaag cgcaaggtgc atatgaacac caagtacaac aaggagttcc tgctctacct   2820
ggccggcttc gtggacggcg acggctccat catcgcgcag atcaagccga accagtccta   2880
caagttcaag caccagctca tgctgacctt caccgtcgac cagaagacgc agaggcgctg   2940
gttcctcgac aagctggtcg acgagatcgg ggtgggctac gtccgcgacc gcgggtcggt   3000
gtccgactac atcctctccc agatcaagcc cctgcacaac ttcctcaccc agctccagcc   3060
gttcctcaag ctgaagcaga agcaggcgaa cctcgtcctg aagatcatcg agcagctccc   3120
ctcggccaag gagtcccgg acaagttcct ggaggtgcc acgtgggtcg accagatcgc   3180
ggccctcaac gacagcaaga cccgcaagac gacctcggag acggtgcggg cggtcctgga   3240
ctccctccca ggatccgtgg gaggtctatc gccatctcag gcatccagcg ccgcatcctc   3300
ggcttcctca agcccgggtt cagggatctc cgaagcactc agagctggag caactaagtc   3360
caaggaattc ctgctctacc tggccggctt cgtggacggc gacggctcca tcatcgcggc   3420
gatcaagccg aaccagtcct acaagttcaa gcaccagctc tccctgacct tcaccgtgac   3480
ccagaagacg cagaggcgct ggttcctcga caagctggtc gacgagatcg gggtgggcta   3540
cgtccgcgac caggggtcgg tgtcccacta ccagctctcc cagatcaagc cctgcacaa   3600
cttcctcacc cagctccagc cgttcctcaa gctgaagcag aagcaggcga acctcgtcct   3660
gaagatcatc gagcagctcc cctcggccaa ggagtcccg gacaagttcc tggaggtgtg   3720
cacgtgggtc gaccagatcg cggccctcaa cgacagcaag acccgcaaga cgacctcgga   3780
gacggtgcgg gcggttctag actccctcag cgagaagaag aagtcgtccc cctgaggtac   3840
cacatggtta acctagactt gtccatcttc tggattggcc aacttaatta atgtatgaaa   3900
taaaaggatg cacacatagt gacatgctaa tcactataat gtgggcatca aagttgtgtg   3960
ttatgtgtaa ttactagtta tctgaataaa agagaaagag atcatccata tttcttatcc   4020
taaatgaatg tcacgtgtct ttataattct ttgatgaacc agatgcattt cattaaccaa   4080
atccatatac atataaatat taatcatata taattaatat caattgggtt agcaaaacaa   4140
atctagtcta ggtgtgtttt gcgaatgcgg ccatcggacc gattaaactt taattcggtc   4200
cgataacttc gtatagcata cattatacga agttatacct ggtggcgtca ctttccccc   4260
tatttttctc cctattttt catctcccgc agcggttccc cctaaatact cctatatacc   4320
ccaatacaac tataaaatat catttttctat atcaactatc aatttttttat ctactaacaa   4380
ttactcgtgg acccacatca caatgtttag ggtgatgaac agtgacacgc tagatctgag   4440
gggagagaga aaagggtcgg cgcgtagggg gcgctgtagg gggcaccgct gcggctgtgg   4500
agtgccccct acagccccca tgcaagggga ggggatact gaggggggctg cgttgcgtac   4560
agcctgacag gctctccttc gcatttgcgc gggacagaaa tgacttgccg aggatggaag   4620
cagagacg gatttggccg agcgcacagc agctcgccaa agacgcgtc gaagcagcag   4680
tgaccgcggt cgagtgaggg agtcatcctg gattcgcggt ttatcgactc ggcacggggg   4740
caaccatggc gttgaaggta ggcaacatga ggagccatcg attgacaccg gtcttcggaa   4800
tcggcggatc tcgacgatgg tgacaaggag gaggccacga agcgtcgtcg agcagagcgc   4860
gacaagcaaa tcgagtcggc cacgagcgtg gatttggatc tgaccccaa gttttttgtat   4920
ggatcctatt ccccaatttg tagatcttca atttccttac tttaatttc catagcacaa   4980
acgatgtttg catgcacgat tcggacaatc ttgacttgtt cgtccacggt tggagtttag   5040
ggttggaatg tgtaaaacac gtgataaact gtgtacaact cgagaactag ataattcatt   5100
ttggattgta atatgtgtac ctcatgctat agttttggtt aaatctgacg tgaaagggcg   5160
aattcgccgc tagcctgcag tgcagcgtga cccggtcgtg cccctctcta gagataatga   5220
gcattgcatg tctaagttat aaaaaattac cacatatttt ttttgtcaca cttgtttgaa   5280
gtgcagttta tctatctta tacatatatt taaactttac tctacgaata atataatcta   5340
tagtactaca ataatatcag tgttttagag aatcatataa atgaacagtt agacatgtgt   5400
taaaggacaa ttgagtattt tgacaacagg actctacagt tttatctttt tagtgtgcat   5460
gtgttctcct ttttttttgc aaatagcttc acctatataa tacttcatcc atttattag   5520
tacatccatt tagggtttag ggttaatggt ttttatagac taatttttt agtacatcta   5580
ttattccta tttagcctc taaattaaga aactaaaac tctattttag ttttttttatt   5640
taataattta gatataaaat agaataaaat aaagtgacta aaaattaaac aaataccctt   5700
taagaaatta aaaaaactaa ggaaacattt tccttgtttc gagtagataa tgccagcctg   5760
ttaaacgccg tcgacgagtc taacggacac caaccagcga accagcagcg tcgcgtcggg   5820
ccaagcgaag cagacggcac ggcatctctg tcgctgcctc tggacccctc tcgagagttc   5880
cgctccaccg ttggacttgc tccgctgtcg gcatccagaa attgcgtggc ggagcagcag   5940
acgtgagccg gcacgcagg cggcctcctc ctcctctcac ggcaccggca gctacggggg   6000
attccttcc caccgctcct tcgctttccc ttcctgccc gccgtaataa atagacaccc   6060
cctccacacc ctctttcccc aacctcgtgt tgttcggagc gcacacacac acaaccagat   6120
ctccccaaa tccacccgtc ggcaccctcg cttcaaggta ccgcgctcgt cctcccccc   6180
cccctctct accttctcta gatcggcgtt ccgtccatg catggttagg gcccggtagt   6240
tctacttctg ttcatgtttg tgttagatcc gtgtttgtgt tagatccgtg ctgctagcgt   6300
tcgtacacgg atgcgacctg tacgtcagac acgttctgat tgctaacttg ccagtgtttc   6360
tctttgggga atcctgggat ggctctagcc gttccgcaga cgggatcgat ttcatgattt   6420
tttttgtttc gttgcatagg gtttggtttg cccttttcct ttattcaat atatgccgtg   6480
cacttgtttg tcgggtcatc ttttcatgct tttttttgtc ttggttgtga tgatggtc   6540
tggttgggcg gtcgttctag atcggagtag aattctgttt caaactacct ggtggattta   6600
ttaattttgg atctgtatgt gtgtgccata catattcata gttacgaatt gaagatgatg   6660
gatggaaata tcgatctagg ataggtatac atgttgatgc gggttttact gatgcatata   6720
cagagatgct tttttgttcgc ttggttgtga tgatggtggtg tggttgggcg gtcgttcatt   6780
cgttctagat cggagtagaa tactgtttca aactaccctgg tgtatttatt aattttggaa   6840
ctgtatgtgt gtgtcataca tcttcatagt tacgagttta agatggatgg aaatatcgat   6900
ctaggatagg tatacatgtt gatgtgggtt ttactgatgc atatacatga tggcatatgc   6960
agcatctatt catatgctct aaccttgagt acctatctat taataaaac aagtatgttt   7020
tataattatt ttgatcttga tacttggga tgatggcata tgcagcagct atatgtggat   7080
```

```
tttttagcc ctgccttcat acgctattta tttgcttggt actgtttctt ttgtcgatgc 7140
tcaccctgtt gtttggtgtt acttctgcag gtcgactcta gaggatcaat tcgctagcga 7200
agttcctatt ccgaagttcc tattctctag aaagtatagg aacttcagat ccaccgggat 7260
ccacacgaca ccatgtcccc cgagcgccgc cccgtcgaga tccgcccggc caccgccgcc 7320
gacatggccg ccgtgtgcga catcgtgaac cactacatcg agacctccac cgtgaacttc 7380
cgcaccgagc cgcagacccc gcaggagtgg atcgacgacc tggagcgcct ccaggaccgc 7440
tacccgtggc tcgtggccga ggtggagggc gtggtggccg gcatcgccta cgccggcccg 7500
tggaaggccc gcaacgccta cgactggacc gtggagtcca ccgtgtacgt gtcccaccgc 7560
caccagcgcc tcggcctcgg ctccaccctc tacacccacc tcctcaagag catggaggcc 7620
cagggcttca agtccgtggt ggccgtgatc ggcctcccga acgacccgtc cgtgcgcctc 7680
cacgaggccc tcggctacac cgcccgcggc accctccgcg ccgccggcta caagcacggc 7740
ggctggcacg acgtcggctt ctggcagcgc gacttcgagc tgccgccccc gccgcgcccg 7800
gtgcgccgcg tgacgcagat ctgagtcgaa acctagactt gtccatcttc tggattggcc 7860
aacttaatta atgtatgaaa taaaaggatg cacacatagt gacatgctaa tcactataat 7920
gtgggcatca aagttgtgtg ttatgtgtaa ttactagtta tctgaataaa agagaaagag 7980
atcatccata tttcttatcc taaatgaatg tcacgtgtct ttataattct ttgatgaacc 8040
agatgcattt cattaaccaa atccatatac atataaatat taatcatata taattaatat 8100
caattgggtt agcaaaacaa atctagtcta ggtgtgtttt gcgaatgcgg ccctagcgta 8160
tacgaagttc ctattccgaa gttcctattc tccagaaagt ataggaactt ctgtacacct 8220
gagctgattc cgatgacttc gtaggttcct agctcaagcc gctcgtgtcc aagcgtcact 8280
tacgattagc taatgattac ggcatctagg accgactagc taactaacta gtacaattcg 8340
cccttgtgaa tctgtttgga attgaaaaac aagtgcttcc ttttatacac cactatgtcg 8400
cttcaatgtt tgcgaaccaa ggtaaagaaa tgtaaaatct tacaatttcc gtgcatccga 8460
cataaatctg tggtcacata gctattgtta acggttgca aatcctaagg aggaccatta 8520
ttgtgcaaca actacatatg gtagaagcgc ttgttttgat gtgtgcacat tttgttgcta 8580
aaaggatcac gatgcccaag aggggggtga atttgggctt tctaaaaatc aacactaatt 8640
aaaacctaag caagagccca acttcacccc gacaactagc aataagagaa tatgaaaggv 8700
aaataggatc aaacctttc ctaaatgatt ttggtggttg aattgcccaa cacaaataat 8760
tggactaact agtttgctct agatcataca ttctacaggt gccaaggtt caacacaaac 8820
caatcaaaag aacaagttag gcttcaaaag aaaggagcaa aaaggaaacc gaagtgtgcc 8880
tggtctggcg caccgggctg tccggtgtgc caccagacag tgtccggtgc accagggtga 8940
atcagctcaa gctcctcaac ttcgggtttc ccagacgcag ctccactata attcattgga 9000
ctgtccggtg caccgcaga gcaacggcta cttgcgcgca acggtcgact ctgcaaagtg 9060
aacagtgcaa ttcagaagtc agagcagatg gtcgacgggg caccggattg tccggtgtag 9120
caccggactg tccggtgccg catgaggaca aagcctccaa ccggtcgacca gctccaagcc 9180
ctaactacaa gatgacgtgg cggcgcaccg gacactgtcc ggtggtgcac cggactgttc 9240
ggtgcgccca tcgccagtag ccttctccaa cggctacaat ttggttggtg gctataaata 9300
ccaccccaac cggcactttt aaggtgtggg agcccaagca acattccaag tcatatagtt 9360
gacatattca agccatccca accaccgtag aattaattca ttccgattaa tcgtggcctc 9420
ttgctcttca ggatgaagag ctatgtttaa acgtgcaagc gctactagac aattcagtac 9480
attaaaaacg tccgcaatgt gttattaagt tgtctaagcg tcaatttgtt tacaccacaa 9540
tatatcctgc caccagccag ccaacagctc cccgaccggc agctcggcac aaaatcacca 9600
ctcgatacag gcagcccatc agtccgggac ggcgtcgggc ggagagccgt tgtaaggcgg 9660
cagactttgc tcatgttacc gatgctattc ggaagaacgg caactaagct gccgggtttg 9720
aaacacggat gatctcgcgg agggtagcat gttgattgta acgatgacag agcgttgctg 9780
cctgtgatca aatatcatct ccctcgcaga gatccgaatt atcagccttc ttattcattt 9840
ctcgcttaac cgtgacaggc tgtcgatctt gagaactatg ccgacataat aggaaatcgc 9900
tggataaagc cgctgaggaa gctgagtggc gctatttctt tagaagtgaa cgttgacgat 9960
cgtcgaccgt accccgatga attaattcgg acgtacgttc tgaacacagc tggatactta 10020
cttgggcgat tgtcatacat gacatcaaca atgtacccgt ttgtgtaacc gtctcttgga 10080
ggttcgtatg acactagtgg ttcccctcag cttgcgacta gatgttgagg cctaacattt 10140
tattagagag caggctagtt gcttagatac atgatcttca ggccgttatc tgtcagggca 10200
agcgaaaatt ggccatttat gacgaccaat gccccgcaga agctcccatc tttgccgcca 10260
tagacgccgc gccccccttt tggggtgtag aacatccttt tgccagatgt ggaaaagaag 10320
ttcgttgtcc cattgttggc aatgacgtag tagccggcga aagtgcgaga cccatttgcg 10380
ctatatataa gcctacgatt tccgttgcga ctattgtcgt aattggatga actattatcg 10440
tagttgctct cagagttgtc gtaatttgat ggactattgt cgtaattgct tatgagttg 10500
tcgtagttgc ttggagaaat gtcgtagttg gatggggagt agtcataggg aagacgagct 10560
tcatccacta aaacaattgg caggtcagca agtgcctgcc ccgatgccat cgcaagtacg 10620
aggcttagaa ccaccttcaa cagatcgcgc atagtcttcc ccagctctct aacgcttgag 10680
ttaagccgcg ccgcgaagcg gcgtcggctt gaacgaattg ttagacatta tttgccgact 10740
accttggtga tctcgccttt cacgtagtga acaaattctt ccaactgatc tgcgcgcgag 10800
gccaagcgat cttcttgtcc aagataagcc tgcctagctt caagtatgac gggctgatac 10860
tgggccggca ggcgctccat tgcccagtcg gcagcgacat ccttcggccg gattttgccg 10920
gttactgcgc tgtaccaaat gcgggacaac gtaagcacta catttcgctc atcgccagcc 10980
cagtcgggcg gcgagttcca tagcgttaag gtttcattta gcgcctcaaa tagatcctgt 11040
tcaggaaccg gatcaaagag ttcctccgcc gctggaccta ccaaggcaac gctatgttct 11100
cttgcttttg tcagcaagat agccagatca atgtcgatcg tggctggctc gaagatacct 11160
gcaagaatgt cattgcgctg ccattctcca aattgcagtt cgcgcttagc tggataacgc 11220
cacggaatga tgtcgtcgtg cacaacaatg tgacttcta cagcgcggag aatctcgctc 11280
tctccagggg aagccgaagt ttccaaaagg tcgttgatca aagctcgccg cgttgtttca 11340
tcaagccttta cagtcaccgt aaccagcaaa tcaatatcac tgtgtggctt caggccgcca 11400
tccactgcgg agccgtacaa atgtacggcc agcaacgtcg gttcgagatg cgctcgatg 11460
acgccaacta cctctgatag ttgagtcgat acttcgtggc tcctcatgatg 11520
tttaactcct gaattaagcc gcgccgcgaa gcggtgtcgg cttgaatgaa ttgttaggcg 11580
tcatcctgtg ctcccgagaa ccagtaccag tacatcgctg tttcgttcga gacttgaggt 11640
ctagttttat acgtgaacag gtcaatgccg ccgagagtaa agccacattt tgcgtacaaa 11700
ttgcaggcag gtacattgtt cgtttgtgtc tctaatcgta tgccaaggag ctgtctgctt 11760
agtgcccact ttttcgcaaa ttcgatgaga ctgtgcgcga ctcctttgcc tcggtgcgtg 11820
```

-continued

```
tgcgacacaa caatgtgttc gatagaggct agatcgttcc atgttgagtt gagttcaatc   11880
ttccccgacaa gctcttggtc gatgaatgcg ccatagcaag cagagtcttc atcagagtca   11940
tcatccgaga tgtaatcctt ccggtagggg ctcacacttc tggtagatag ttcaaagcct   12000
tggtcggata ggtgcacatc gaacacttca cgaacaatga aatggttctc agcatccaat   12060
gtttcgcgcca cctgctcagg gatcaccgaa atcttcatat gacgcctaac gcctggcaca   12120
gcggatcgca aacctggcgc ggcttttggc acaaaaggcg tgacaggttt gcgaatccgt   12180
tgctgccact tgttaaccct tttgccagat ttggtaacta taatttatgt tagaggcgaa   12240
gtcttggta aaaactggcc taaaattgct ggggatttca ggaaagtaaa catcaccttc   12300
cggctcgatg tctattgtag atatatgtag tgtatctact tgatcggggg atctgctgc   12360
tcgcgcgttt cggtgatgac ggtgaaaacc tctgacacat gcagctcccg gagacggtca   12420
cagcttgtct gtaagcggat gccgggagca gacaagcccg tcagggcgcg tcagcgggtg   12480
ttggcgggtg tcgggcgca gccatgaccc agtcacgtag cgatagcgga gtgtatactg   12540
gcttaactat gcggcatcag agcagattgt actgagagtg caccatatgc ggtgtgaaat   12600
accgcacaga tgcgtaagga gaaaataccg catcaggcgc tcttccgctt cctcgctcac   12660
tgactcgctg cgctcggtcg ttcggctgcg cgagcggta tcagctcact caaaggcggt   12720
aatacggtta tccacagaat caggggataa cgcaggaaag aacatgtgag caaaaggcca   12780
gcaaaaggcc aggaaccgta aaaaggccgc gttgctggcg ttttttccata ggctccgccc   12840
ccctgacgag catcacaaaa atcgacgctc aagtcagagg tggcgaaacc cgacaggact   12900
ataaagatac caggcgtttc ccctggaag ctccctcgtg cgctctcctg ttccgaccct   12960
gccgcttacc ggatacctgt ccgcctttct cccttcggga agcgtggcgc tttctcatag   13020
ctcacgctgt aggtatctca gttcggtgta ggtcgttcgc tccaagctgg gctgtgtgca   13080
cgaaccccc gttcagcccg accgctgcgc cttatccggt aactatcgtc ttgagtccaa   13140
cccggtaaga cacgacttat cgccactggc agcagccact ggtaacagga ttagcagagc   13200
gaggtatgta ggcggtgcta cagagttctt gaagtggtgg cctaactacg gctacactag   13260
aaggacagta tttggtatct gcgctctgct gaagccagtt accttcggaa aaagagttgg   13320
tagctcttga tccggcaaac aaaccaccgc tggtagcggt ggtttttttg tttgcaagca   13380
gcagattacg cgcagaaaaa aaggatctca agaagatcct ttgatctttt ctacggggtc   13440
tgacgctcag tggaacgaaa actcacgtta agggattttg gtcatgagat tatcaaaaag   13500
gatcttcacc tagatccttt taaattaaaa atgaagtttt aaatcaatct aaagtatata   13560
tgagtaaact tggtctgaca gttaccaatg cttaatcagt gaggcaccta tctcagcgat   13620
ctgtctattt cgttcatcca tagttgcctg actcccgtc gtgtagataa ctacgatacg   13680
ggagggctta ccatctggcc ccagtgctgc aatgataccg cgagacccac gctcaccggc   13740
tccagattta tcagcaataa accagccagc cggaagggcc gagcgcagaa gtggtcctgc   13800
aactttatcc gcctccatcc agtctattaa ttgttgccgg gaagctagag taagtagttc   13860
gccagtaat agtttgcgca acgttgttgc cattgctgca gggggggggg gggggggga   13920
cttccattgt tcattccacg gacaaaaaca gagaaaggaa acgacagagg ccaaaaagcc   13980
tcgctttcag cacctgtcgt ttcctttctt ttcagagggt atttaaata aaaacattaa   14040
gttatgacga agaagaacgg aaacgcctta aaccggaaaa ttttcataaa tagcgaaaac   14100
ccgcgaggtc gccgcccgt aacctgtcgg atcaccgaa aggacccgta aagtgataat   14160
gattatcatc tacatatcac aacgtgcgtg gaggccatca aaccacgtca ataatcaat   14220
tatgacgcag gtatcgtatt aattgatctg catcaactta acgtaaaaac aacttcagac   14280
aatacaaatc agcgacactg aatacggggc aacctcatgt cccccccccc ccccccctg   14340
caggcatcgt ggtgtcacgc tcgtcgtttg gtatggcttc attcagctcc ggttcccaac   14400
gatcaaggcg agttacatga tcccccatgt tgtgcaaaaa agcggttagc tccttccggtc   14460
ctccgatcgt tgtcagaagt aagttggccg cagtgttatc actcatggtt atggcagcac   14520
tgcataattc tcttactgtc atgccatccg taagatgctt ttctgtgact ggtgagtact   14580
caaccaagtc attctgagaa tagtgtatgc ggcgaccgag ttgctcttgc ccggcgtcaa   14640
cacgggataa taccgcgcca catagcagaa ctttaaaagt gctcatcatt ggaaaacgtt   14700
cttcggggcg aaaactctca aggatcttac cgctgttgag atccagttcg atgtaaccca   14760
ctcgtgcacc caactgatct tcagcatctt ttactttcac cagcgtttct gggtgagcaa   14820
aaacaggaag gcaaaatgcc gcaaaaaagg gaataagggc gacacggaaa tgttgaatac   14880
tcatactctt cctttttcaa tattattgaa gcatttatca gggttattgt ctcatgagcg   14940
gatacatatt tgaatgtatt tagaaaaata aacaaatagg ggttccgcgc acatttcccc   15000
gaaaagtgcc acctgacgtc taagaaacca ttattatcat gacattaacc tataaaaata   15060
ggcgtatcac gaggcccttt cgtcttcaag aattggtcga cgatcttgct gcgttcggat   15120
attttcgtgg agttcccgcc acagacccgg attgaaggcg agatccagca actcgcgcca   15180
gatcatcctg tgacggaact ttggcgcgtg atgactggcc aggacgtcgg ccgaaagagc   15240
gacaagcaga tcacgctttt cgacagcgtc ggatttgcga tcgaggattt tcggcgctg   15300
cgctacgtcc gcgaccggt tgagggatca agccacagca gcccactcga ccttctagcc   15360
gacccagacg agccaaggga tcttttttgga atgctgctcc gtcgtcaggc tttccgacgt   15420
ttgggtggtt gaacagaagt cattatcgta cggaatgcca agcactcccg aggggaaccc   15480
tgtggttggc atgcacatac aaatggacga acggataaac cttttcacgc ccttttaaat   15540
atccgttatt ctaataaacg ctcttttctc ttag                                  15574
```

SEQ ID NO: 105         moltype = DNA   length = 15585
FEATURE                Location/Qualifiers
misc_feature           1..15585
                       note = synthetic construct; plasmid PHP44779
source                 1..15585
                       mol_type = other DNA
                       organism = synthetic construct

SEQUENCE: 105

```
gtttacccgc caatatatcc tgtcaaacac tgatagttta aactgaaggc gggaaacgac   60
aatctgatca tgagcggaga attaagggag tcacgttatg accccgccg atgacgcggg   120
acaagccgtt ttacgtttgg aactgacaga accgcaacgt tgaaggagcc actcagcaag   180
ctggtacgat tgtaatacga ctcactatag ggcgaattga gcgctgttta acgctcttc   240
aactggaaga gcgttactta ccggctggat ggcgggcct tgatcgtgca ccgcggcgt   300
ccggactaac taactagtcg agctagttac cctatgaggt gacatgaagc gctcacggtt   360
actatgacgg ttagcttcac gactgttggt ggcagtagcg tacgacttag ctatagttcc   420
```

```
ggacttaccc ttaagataac ttcgtatagc atacattata cgaagttatg ggcccaccgg   480
tggtaccgag ctcgtttaaa cgctcttcaa ctgaagagc  ggttaccaga gctggtcacc   540
tttgtccacc aagatggaac tggcgcgcct cattaattaa gtcagcggcc gctctagttg   600
aagacacgtt catgtcttca tcgtaagaag acactcagta gtcttcggcc agaatggcca   660
tctggattca gcaggcctag aaggccattt aaatcctgag gatctggtct tcctaaggac   720
ccgggatatc ggaccgaagc ttgcatgcct gcagtgcagc gtgacccggt cgtgcccctc   780
tctagagata atgagcattg catgtctaag ttataaaaaa ttaccacata ttttttttgt   840
cacacttgtt tgaagtgcag tttatctatc tttatacata tatttaaact ttactctacg   900
aataatataa tctatagtac tacaataata tcagtgtttt agagaatcat ataaatgaac   960
agttagacat ggtctaaagg acaattgagt attttgacaa caggactcta cagttttatc  1020
tttttagtgt gcatgtgttc tccttttttt ttgcaaatag cttcacctat ataatacttc  1080
atccatttta ttagtacatc catttagggt ttagggttaa tggtttttat agactaattt  1140
ttttagtaca tctattttat tctattttag cctctaaatt aagaaaacta aaactctatt  1200
ttagtttttt tatttaataa tttagatata aaatagaata aaataaagtg actaaaaatt  1260
aaacaaatac cctttaagaa attaaaaaaa ctaaggaaac attttttctg tttcgagtag  1320
ataatgccag cctgttaaac gccgtcgacg agtctaacgg acaccaacca gcgaaccagc  1380
agcgtcgcgt cgggccaagc gaagcagaca gcacggcatc tctgtcgctg cctctggacc  1440
cctctcgaga gttccgctcc accgttggac ttgctccgct gtcggcatcc agaaattgcg  1500
tggcggagcg gcagacgtga gccggcacgg caggcggcct cctcctcctc tcacggcacc  1560
ggcagctacg ggggattcct ttcccaccgc tccttcgctt tccttcctc  gcccgccgta  1620
ataaatagac accccctcca caccctcttt ccccaaccct gtgttgttcg gagcgcacac  1680
acacacaacc agatctcccc caaatccacc cgtcggcacc tccgcttcaa ggtacgccgc  1740
tcgtcctccc cccccccct  ctctaccttc tctagatcgg cgttccggtc catgcatggt  1800
tagggcccgg tagttctact tctgttcatg tttgtgttag atccgtgttt gtgttagatc  1860
cgtgctgcta gcgttcgtac acggatgcga cctgtacgtc agacacgttc tgattgctaa  1920
cttgccagtg tttctctttg gggaatcctg gatggctct  agccgttccg cagacgggat  1980
cgatttcatg attttttttg tttcgttgca tagggtttgg tttgcccttt tcctttattt  2040
caatatatgc cgtgcacttg tttgtcgggt catcttttca tgcttttttt tgtcttggtt  2100
gtgatgatgt ggtctggttg ggcggtcgtt ctagatcgga gtagaattct gtttcaaact  2160
acctggtgga tttattaatt ttggatctgt atgtgtgtgc catacatatt catagttacg  2220
aattgaagat gatggatgga aatatcgatc taggataggt atacatgttg atgcgggttt  2280
tactgatgca tatacagaga tgcttttttgt tcgcttggtt gtgatgatgt ggtgtggttg  2340
ggcggtcgtt cattcgttct agatcggagt agaatactgt ttcaaactac ctggtgtatt  2400
tattaatttt ggaactgtat gtgtgtgtca tacatcttca tagttacgag tttaagatgg  2460
atggaaatat cgatctagga taggtataca tgttgatgtg ggttttactg atgcatatac  2520
atgatggcat atgcagcatc tattcatatg ctctaacctt gagtacctat ctattataat  2580
aaacaagtat gttttataat tattttgatc ttgatatact tggatgatgg catatgcagc  2640
agctatatgt ggattttttt agccctgcct tcatacgcta tttatttgct tggtactgtt  2700
tcttttgtcg atgctcaccc tgttgtttgg tgttacttct gcaggtcgac tctagaggat  2760
ccatggcacc gaagaagaag cgcaaggtgc atatgaacac caagtacaac aaggagttcc  2820
tgctctacct ggccggcttc gtggacggcg acggctccat catcgcgcag atcaagccga  2880
accagtccta caagttcaag caccagctca tgctgaccct taccgtgacc cagaagacgc  2940
agaggcgctg gttcctcgac aagctggtcg acgagatcgg ggtgggcaag gtccgcgacc  3000
gcggtcggt  gtccgactac atcctctccc agatcaagcc cctgcacaac ttcctcaccc  3060
agctccagcc gttcctcaag ctgaagcaga gcaggcgaa  cctcgtcctg aagatcatcg  3120
agcagctccc ctcggccaag gagtcccgg  acaagttcct ggaggtgtgc acgtgggtcg  3180
accagatcgc ggccctcaac gacagcaaga cccgcaagac gacctcggag acggtgcggg  3240
cggtcctgga ctccctccca ggatccgtgg gaggtctatc gccatctcag gcatccagcg  3300
ccgcatcctc ggcttcctca agcccggggtt cagggatctc cgaagcactc agagctggag  3360
caactaagtc caaggaattc ctgctctacc tggccggctt cgtggacggc gacggctcca  3420
tcatcgcgca gatcaagccg aaccagtcct acaagttcaa gcaccagctc tccctgacct  3480
tcaccgtgac ccagaagacg cagaggcgct ggttcctcga caagctggtc gacgagatcg  3540
gggtgggcta cgtccgcgac caggggtcgg tgtcccacta ccagctctcc cagatcaagc  3600
ccctgcacaa cttcctcacc cagctccagc cgttcctcaa gctgaagcag aagcaggcga  3660
acctcgtcct gaagatcatc gagcagctcc cctcggccaa ggagtccccg gacaagttcc  3720
tggaggtgtg cacgtgggtc gaccagatcc cggccctcaa cgacagcaag acccgcaaga  3780
cgacctcgga gacggtgcgg gcggttctag actccctcag cgagaagaag aagtcgtccc  3840
cctgaggtac cacatggtta acctagactt gtccatcttc tggattggcc aacttaatta  3900
atgtatgaaa taaaaggatg cacacatagt gacatgctaa tcactataat gtgggcatca  3960
aagttgtgtg ttatgtgtaa ttactagtta tctgaataaa agagaaagag atcatccata  4020
tttcttatcc taaatgaatg tcacgtgtct ttataattct ttgatgaacc agatgcattt  4080
cattaaccaa atccatatac atataaatat taatcatata taattaatat caattgggtt  4140
agcaaaacaa atctagtcta ggtgtgtttt gcgaatgcgg ccgccaccgc ggtggagctc  4200
gaattccggt ccgataactt cgtatagcat acattatacg aagttatacc tggtggcgtc  4260
actttccccc ctatttttct ccctattttt tcatctcccg cagcggttcc ccctaaatat  4320
tcctatatac cccaatacaa ctataaaata tcattttcta tatcaactat caatttttta  4380
tctactaaca attactcgtg gacccacatc acaatgttta gggtgatgaa cagtgacacg  4440
ctagatctga ggggagagag aaaagggtcg gcgcgtaggg ggcgctgtag ggggcaccgc  4500
tgcggctgtg gagtgccccc tacagcccccc atgcaagggg aggggatac  tgaggggct   4560
gcgttgcgta cagcctgaca ggctctcctt cgcatttgcg cgggacagaa atgacttgcc  4620
gaggatggaa gcagagagac ggatttggcc gagcgcacag cagctcgcca aagacggcgt  4680
cgaagcagca gtgaccgcgg tcgagtgagg gagtcatcct ggattcgcgg tttatcgact  4740
cggcacgggg gcaaccatgg cgttgaaggt aggcaacatg aggagccatc gattgacacc  4800
gtcttcgga  atcgacggat ctcgacgatg gtgacaagga aagcgtcgtc  4860
gagcagagcg cgacaagcaa atcgagtcgg ccacgagcgt ggatttggat ctgaccccca  4920
agttttgta  tggatcctat tccccaattt gtagatcttc aatttcctta ctttaatttt  4980
ccatagcaca aacgatgttt gcatgcacga ttcggacaat cttgacttgt tcgtccacgt  5040
ttggagttta gggttggaat gtgtaaaaca cgtgataaac tgtgtacaac tcgagaacta  5100
gataattcat tttggattgt aatatgtgta cctcatgcta tagttttggt taaatctgac  5160
```

```
gtgaaagggc gaattcgccg ctagcctgca gtgcagcgtg acccggtcgt gcccctctct    5220
agagataatg agcattgcat gtctaagtta taaaaaatta ccacatattt tttttgtcac    5280
acttgtttga agtgcagttt atctatcttt atacatatat ttaaacttta ctctacgaat    5340
aatataatct atagtactac aataaatca gtgtttttaga gaatcatata aatgaacagt    5400
tagacatggt ctaaaggaca attgagtatt ttgacaacag gactctacag tttttatcttt   5460
ttagtgtgca tgtgttctcc ttttttttg caaatagctt cacctatata tacttcatc     5520
catttttatta gtacatccat ttagggttta gggttaatgg tttttataga ctaatttttt   5580
tagtacatct attttattct attttagcct ctaaattaag aaaactaaaa ctctatttta    5640
gttttttat ttaataattt agatatataaa tagaataaaa taaagtgact aaaaaattaaa   5700
caaatacccct ttaagaaatt aaaaaaacta aggaaacatt tttcttgttt cgagtagata   5760
atgccagcct gttaaacgcc gtcgacgagt ctaacggaca ccaaccagcg aaccagcagc    5820
gtcgcgtcgg gccaagcgaa gcagacggca cggcatctct gtcgctgcct ctggaccccct   5880
ctcgagagtt ccgctccacc gttggacttg ctccgctgtc ggcatccaga aattgcgtgg    5940
cggagcggca gacgtgagcc ggcacggcag gcggcctcct cctcctctca cggacaccggc   6000
agctacgggg gattcctttc ccaccgctcc ttcgctttcc cttcctcgcc cgccgtaata    6060
aatagacacc ccctccacac cctctttccc caacctcgtg ttgttcggag cgcacacaca    6120
cacaaccaga tctcccccaa atccaccgt cggcacctcc gcttcaaggt acgccgctcg     6180
tcctccccc cccccctc taccttctct agatcggcgt tccggtccat gcatggttag       6240
ggccggtag ttctacttct gttcatgttt gtgttagatc cgtgtttgtg ttagatccgt     6300
gctgctagcg ttcgtacacg gatgcgacct gtacgtcaga cacgttctga ttgctaactt    6360
gccagtgttt ctctttgggg aatcctggga tggctctagc cgttccgcag acgggatcga    6420
tttcatgatt ttttttgttt cgttgcatag ggtttggttt gcctttttcc tttatttcaa    6480
tatatgccgt gcacttgttt gtcgggtcat cttttcatgc tttttttttgt cttggttgtg   6540
atgatgtggt ctggttgggc ggtcgttcta gatcggagta gaattctgtt tcaaactacc    6600
tggtggattt attaattttg gatctgtatg tgtgtgccat acatattcat agttacgaat    6660
tgaagatgat ggatggaaat atcgatctag gataggtata catgttgatg cgggttttac    6720
tgatgcatat acagagatgc ttttttgttcg cttggttgtg atgatgtggt gtggttgggc    6780
ggtcgttcat tcgttctaga tcggagtaga atactgtttc aaactacctg gtgtatttat    6840
taattttgga actgtatgtg tgtgtcatac atcttcatag ttacgagttt aagatggatg    6900
gaaatatcga tctaggatag gtatacatgt tgatgtgggt tttactgatg catatacatg    6960
atggcatatg cagcatctat tcatatgctc taaccttgag tacctatcta ttataataaa    7020
caagtatgtt ttataattat tttgatcttg atatacttgg atgatggcat atgcagcagc    7080
tatatgtgga tttttttagc cctgccttca tacgctattt atttgcttgg tactgtttct    7140
tttgtcgatg ctcaccctgt tgtttggtgt tacttctgca ggtcgactct agaggatcaa    7200
ttcgctagcg aagttcctat tccgaagttc ctattctcta gaaagtatag gaacttcaga    7260
tccaccggga tccacacgac accatgtccc ccgagcgccg ccccgtcgag atccgccgg     7320
ccaccgccgc cgacatggcc gccgtgtgcg acatcgtgaa ccactacatc gagacctcca    7380
ccgtgaactt ccgcaccgag ccgcagaccc gcaggagtg gatcgacgac ctggagcgcc    7440
tccaggaccg ctaccgtggg ctcgtgccg aggtggaggg cgtggtggcc ggcatcgcct    7500
acgccggccc gtggaaggcc cgcaacgcct acgactggaa cgtggagtcc accgtgtacg   7560
tgtcccaccg ccaccagcgc ctcggcctcg gctccaccct ctacacccac ctcctcaaga   7620
gcatggaggc ccagggcttc aagtccgtgg tggccgtgat cggcctcccg aacgacccgt   7680
gcgtgccgct ccacgaggcc ctcggctaca ccgcccgcag cacccctccgc gccgccggct   7740
acaagcacgg cggctggcac gacgtcggct tctggcagcg cgacttcgag ctgccggccc   7800
cgccgcgccc ggtgcgcccg gtgacgcaga tctgagtcga aacctagact tgtccatctt    7860
ctggattggc caacttaatt aatgtatgaa ataaaaggat gcacacatag tgacatgcta    7920
atcactataa tgtgggcatc aaagttgtgt gttatgtgta attactagtt atctgaataa    7980
aagagaaaga gatcatccat atttcttatc ctaaatgaat gtcacgtgtc tttataattc    8040
tttgatgaac cagatgcatt tcattaacca aatccatata catataaata ttaatcatat    8100
ataattaata tcaattgggt tagcaaaaca aatctagtct aggtgtgttt tgcgaatgcg    8160
gccctagcgt atacgaagtt cctattccga agttcctat ctccagaaag tataggaact    8220
tctgtacacc tgagctgatt ccgatgactt cgtaggttcc tagctcaagc cgctcgtgtc    8280
caagcgtcac ttacgattag ctaatgatta cggcatctag gaccgactag ctaactaact    8340
agtacaattc gcccttgtga atctgttgg aattgaaaaa caagtgcttc cttttataca    8400
ccactatgtc gcttcaatgt ttgcgaacca aggtaaagaa atgtaaaatc ttacaatttc    8460
cgtgcatccg acataaatct gtggtcacat agctattgtt aaacggttgc aaatcctaag    8520
gaggaccatt attgtgcaac aactacatat ggtagaagcg cttgttttga tgtgtgcaca    8580
ttttgttgct aaaaggatca cgatgcccaa gagggggtg aattgggctt ttctaaaaat    8640
caacactaat taaaacctaa gcaagagccc aacttcacgc cgacaactag caataagaga    8700
atatgaaagg gaaataggat caaaccttt cctaaatgat tttggtggtt gaattgccca    8760
acacaaataa ttggactaac tagtttgctc tagatcatac atttctacagg tgccaaaggt    8820
tcaacacaaa ccaatcaaaa gaacaagtta ggcttcaaaa gaaggagca aaaaggaaac    8880
cgaagtgtgc ctggtctggc gcaccgggct gtccggtgtg ccaccagaca gtgtccggtg    8940
caccagggtg aatcagctca agctcctcaa ctttcgggttt cccagacgca gctccactat    9000
aattcattgg actgtccggt gcaccgcag agcaacggct acttgcgcgc aacggtcgac    9060
tctgcaaagt gaacagtgca attcagaagt cagagcagat ggtcagaggg gcaccggatt    9120
gtccggtgta gcaccggact gtccggtgcc gcatgaggac aaaagcctcca acggtcgacc    9180
agctccaagc cctaactaca agatgacgtg gcggcgcacc ggacactgtc cggtggtgca    9240
ccggactgtt cggtgcgccc atcgccagta gccttctcca acggctacaa tttggttggt    9300
ggctataaat accaccccaa ccggccactt taaggtgtgg gagcccaagc aacattccaa    9360
gtcatatagt tgacatattc aagccatccc aaccaccgta gaattaattc attccgatta    9420
atcgtggcct cttgctcttc aggatgaaga gctatgttta aacgtgcaag cgctactaga    9480
caattcagta cattaaaaac gtccgcaatg tgttattaag ttgtctaagc gtcaatttgt    9540
ttacaccaca atatatcctg ccaccagcca gccaacagct cccgacccgg cagctcggca    9600
caaaatcacc actcgataca ggcagcccat cagtccggga cggcgtcagc gggagagcca    9660
ttgtaaggcg gcagactttg ctcatgttac cgatgctatt cggaagaacg gcaactaagc    9720
tgccgggttt gaaacacgga tgatctcgcg gagggtagca tgttgattgt aacgatgaca    9780
gagcgttgct gcctgtgatc aaaatatcatc tccctgcgag agatccgaat tatcagcctt    9840
cttattcatt tctcgcttaa ccgtgacagg ctgtcgatct tgagaactat gccgacataa    9900
```

```
taggaaatcg ctggataaag ccgctgagga agctgagtgg cgctatttct ttagaagtga  9960
acgttgacga tcgtcgaccg taccccgatg aattaattcg gacgtacgtt ctgaacacag 10020
ctggatactt acttgggcga ttgtcataca tgacatcaac aatgtacccg tttgtgtaac 10080
cgtctcttgg aggttcgtat gacactagtg gttcccctca gcttgcgact agatgttgag 10140
gcctaacatt ttattagaga gcaggctagt tgcttagata catgatcttc aggccgttat 10200
ctgtcagggc aagcgaaaat tggccattta tgacgaccaa tgccccgcag aagctcccat 10260
cttttgccgcc atagacgccg cgccccccctt tggggtgta gaacatcctt ttgccagatg 10320
tggaaaagaa gttcgttgtc ccattgttgg caatgacgta gtagccggcg aaagtgcgag 10380
acccatttgc gctatatata agcctacgat ttccgttgcg actattgtcg taattggatg 10440
aactattatc gtagttgctc tcagagttgt cgtaatttga tggactattg tcgtaattgc 10500
ttatggagtt gtcgtagttg cttggagaaa tgtcgtagtt ggatggggag tagtcatagg 10560
gaagacgagc ttcatccact aaaacaattg gcaggtcagc aagtgcctgc cccgatgcca 10620
tcgcaagtac gaggcttaga accaccttca acagatcgcg catagtcttc cccagctctc 10680
taacgcttga gttaagccgc gccgcgaagc ggcgtcggct tgaacgaatt gttagacatt 10740
atttgccgac tacctggtg atctcgcctt tcacgtagtg aacaaattct tccaactgat 10800
ctgcgcgcga ggccaagcga tcttcttgtc caagataagc ctgcctagct tcaagtatga 10860
cgggctgata ctgggccggc aggcgctcca ttgcccagtc ggcagcgaca tccttcggcg 10920
cgattttgcc ggttactgcg ctgtaccaaa tgcgggacaa cgtaagcact acatttcgct 10980
catcgccagc ccagtcgggc ggcgagttcc atagcgttaa ggtttcattt agcgcctcaa 11040
atagatcctg ttcaggaacc ggatcaaaga gttcctccgc cgctggacct accaaggcaa 11100
cgctatgttc tcttgctttt gtcagcaaga tagccagatc aatgtcgatc gtggctggct 11160
cgaagatacc tgcaagaatg tcattgcgct gccattctcc aaattgcagt tcgcgcttag 11220
ctggataacg ccacggaatg atgtcgtcgt gcacaacaat ggtgacttct acagcgcgga 11280
gaatctcgct ctcccagggg gaagccaagg tttccaaaag gtcgttgatc aaagctcgcc 11340
gcgttgtttc atcaagcctt acagtcaccg taaccagcaa atcaatatca ctgtgtggct 11400
tcaggccgcc atccactgcg gagccgtaca aatgtacgcg cagcaacgtc ggttcgagat 11460
ggcgctcgat gacgccaact acctctgata gttgagtcga tacttcggcg atcaccgctt 11520
ccctcatgat gtttaactcc tgaattaagc cgcgccgcga agcggtgtcg gcttgaatga 11580
attgttaggc gtcatcctgt gctcccgaga accagtacca gtacatcgct gtttcgttcg 11640
agacttgagg tctagtttta tacgtgaaca ggtcaatgcc gccgagagta aagccacatt 11700
ttgcgtacaa attgcaggca ggtacattgt tcgtttgtgt ctctaatcgt atgccaagga 11760
gctgtctgct tagtgcccac tttttcgcaa attcgatgag actgtgcgcg actcctttgc 11820
ctcggtgcgt gtgcgacaca acaatgtgtt cgatagaggc tagatcgttc catgttgagt 11880
tgagttcaat cttcccgaca agctcttggt cgatgaatgc gccatagcaa gcagagtctt 11940
catcagagtc atcatccgag atgtaatcct tccggtaggg gctcacactt ctggtagata 12000
gttcaaagcc ttggtcggat aggtgcacat cgaacacttc acgaacaatg aaatggttct 12060
cagcatccaa tgtttccgcc acctgctcag ggatcaccga aatcttcata tgacgcctaa 12120
cgcctggcac agcggatcgc aaacctggcg cggcttttgg cacaaaaggc gtgacaggtt 12180
tgcgaatccg ttgctgccac ttgttaaccc ttttgccaga tttggtaact ataatttatg 12240
ttagaggcga agtcttgggt aaaaactggc ctaaaattgc tggggatttc aggaaagtaa 12300
acatcacctt ccggctcgat gtctattgta gatatatgta gtgtatctac ttgatcgggg 12360
gatctgctgc ctcgcgcgtt tcggtgatga cggtgaaaac ctctgacaca tgcagctccc 12420
ggagacggtc acagcttgtc tgtaagcgga tgccgggacg agacaagccc gtcagggcgc 12480
gtcagcgggt gttggcgggt gtcggggcgc agccatgacc cagtcacgta gcgatagcgg 12540
agtgtatact ggcttaacta tgcggcatca gagcagattg tactgagagt gcaccatatg 12600
cggtgtgaaa taccgcacag atgcgtaagg agaaaatacc gcatcaggcg ctcttccgct 12660
tcctcgctca ctgactcgct gcgctcggtc gttcggctgc ggcgagcggt atcagctcac 12720
tcaaaggcgg taatacggtt atccacagaa tcagggata acgcaggaaa gaacatgtga 12780
gcaaaaggcc agcaaaaggc caggaaccgt aaaaaggccg cgttgctggc gtttttccat 12840
aggctccgcc cccctgacga gcatcacaaa aatcgacgct caagtcagag gtggcgaaac 12900
ccgacaggac tataaagata ccaggcgttt cccctgaaga ctcccctcgt gcgctctcct 12960
gttccgaccc tgccgcttac cggatacctg tccgcctttc tcccttcggg aagcgtggcg 13020
ctttctcata gctcacgctg taggtatctc agttcggtgt aggtcgttcg ctccaagctg 13080
ggctgtgtgc acgaacccc cgttcagccc gaccgctgcg ccttatccgg taactatcgt 13140
cttgagtcca acccggtaag acacgactta tcgccactgg cagcagccac tggtaacagg 13200
attagcagag cgaggtatgt aggcggtgct acagagttct tgaagtggtg gcctaactac 13260
ggctacacta aaggacagt atttggtatc tgcgctctgc tgaagccagt taccttcgga 13320
aaaagagttg gtagctcttg atccggcaaa caaaccaccg ctggtagcgg tggtttttt 13380
gtttgcaagc agcagattac gcgcagaaaa aaaggatctc aagaagatcc tttgatcttt 13440
tctacggggt ctgacgctca gtggaacgaa aactcacgtt aagggatttt ggtcatgaga 13500
ttatcaaaaa ggatcttcac ctagatcctt ttaaattaaa aatgaagttt taaatcaatc 13560
taaagtatat atgagtaaac ttggtctgac agttaccaat gcttaatcag tgaggcacct 13620
atctcagcga tctgtctatt tcgttcatcc atagttgcct gactcccgt cgtgtagata 13680
actacgatac gggagggctt accatctggc cccagtgctg caatgatacc gcgagaccca 13740
cgctcaccgg ctccagattt atcagcaata aaccagccag ccggaagggc cgagcgcaga 13800
agtggtcctg caactttatc cgcctccatc cagtctatta attgttgccg ggaagctaga 13860
gtaagtagtt cgccagttaa tagtttgcgc aacgttgttg ccattgctgc aggggggggg 13920
ggggggggg acttccattg ttcattccac ggacaaaaac agagaaagga aacgacagag 13980
gccaaaaagc ctcgcttttca gcacctgtcg tttcctttct tttcagagtg tattttaaat 14040
aaaaacatta agttatgacg aagaagaacg gaaacgcctt aaaccggaaa attttcataa 14100
atagcgaaaa cccgcgaggt cgccgcccg taacctgtcg gatcaccgga aaggacccgt 14160
aaagtgataa tgattatcat ctacatatca caacgtgcgt ggaggccatc aaaccacgtc 14220
aaataatcaa ttatgacgca ggtatcgtat taattgatct gcatcaactt aacgtaaaaa 14280
caacttcaga caatacaaat cagcgacact gaatacgggg caacctcatg tcccccccc 14340
cccccccct gcaggcatcg tggtgtcacg ctcgtcgttt ggtatggctt cattcagctc 14400
cggttcccaa cgatcaaggc gagttacatg atccccatg ttgtgcaaaa aagcggttag 14460
ctccttcggt cctccgatcg ttgtcagaag taagttggcc gcagtgttat cactcatggt 14520
tatggcagca ctgcataatt ctcttactgt catgccatcc gtaagatgct tttctgtgac 14580
tggtgagtac tcaaccaagt cattctgaga atagtgtatg cggcgaccga gttgctcttg 14640
```

```
cccggcgtca acacgggata ataccgcgcc acatagcaga actttaaaag tgctcatcat    14700
tggaaaacgt tcttcgggc gaaaactctc aaggatctta ccgctgttga gatccagttc     14760
gatgtaaccc actcgtgcac ccaactgatc ttcagcatct tttactttca ccagcgtttc    14820
tgggtgagca aaaacaggaa ggcaaaatgc cgcaaaaaag gaataaggg cgacacggaa     14880
atgttgaata ctcatactct tccttttca atattattga agcatttatt agggttattg    14940
tctcatgagc ggatacatat ttgaatgtat ttagaaaaat aaacaaatag gggttccgcg    15000
cacatttccc cgaaaagtgc cacctgacgt ctaagaaacc attattatca tgacattaac    15060
ctataaaaat aggcgtatca cgaggccctt tcgtcttcaa gaattggtcg acgatcttgc    15120
tgcgttcgga tattttcgtg gagttcccgc cacagacccg gattgaaggc gagatccagc    15180
aactcgcgcc agatcatcct gtgacggaac tttggcgcgt gatgactggc caggacgtcg    15240
gccgaaagag cgacaagcag atcacgcttt tcgacagcgt cggatttgcg atcgaggatt    15300
tttcggcgct gcgctacgtc cgcgaccgcg ttgagggatc aagccacagc agcccactcg    15360
accttctagc cgacccagac gagccaaggg atcttttttgg aatgctgctc cgtcgtcagg    15420
ctttccgacg tttgggtggt tgaacagaag tcattatcgt acggaatgct aagcactccc    15480
gaggggaacc ctgtgggttgg catgcacata caaatggacg aacggataaa cctttttcacg    15540
cccttttaaa tatccgttat tctaataaac gctcttttct cttag                    15585

SEQ ID NO: 106          moltype = DNA   length = 18
FEATURE                 Location/Qualifiers
misc_feature            1..18
                        note = synthetic construct; MHP14TS probe
source                  1..18
                        mol_type = other DNA
                        organism = synthetic construct
SEQUENCE: 106
cagattcacg tcagattt                                                    18

SEQ ID NO: 107          moltype = DNA   length = 26
FEATURE                 Location/Qualifiers
misc_feature            1..26
                        note = synthetic construct; MHPTS14_Forward_MGB primer
source                  1..26
                        mol_type = other DNA
                        organism = synthetic construct
SEQUENCE: 107
agcgacatag tggtgtataa aaggaa                                           26

SEQ ID NO: 108          moltype = DNA   length = 27
FEATURE                 Location/Qualifiers
misc_feature            1..27
                        note = synthetic construct; MHPTS14_Reverse_MGB primer
source                  1..27
                        mol_type = other DNA
                        organism = synthetic construct
SEQUENCE: 108
tggattgtaa tatgtgtacc tcatgct                                          27

SEQ ID NO: 109          moltype = DNA   length = 27
FEATURE                 Location/Qualifiers
misc_feature            1..27
                        note = synthetic construct; primer 146775
source                  1..27
                        mol_type = other DNA
                        organism = synthetic construct
SEQUENCE: 109
gctttctatt ttgtggcact attgtgg                                          27

SEQ ID NO: 110          moltype = DNA   length = 31
FEATURE                 Location/Qualifiers
misc_feature            1..31
                        note = synthetic construct; primer 146773
source                  1..31
                        mol_type = other DNA
                        organism = synthetic construct
SEQUENCE: 110
gctcgtgtcc aagcgtcact tacgattagc t                                     31

SEQ ID NO: 111          moltype = DNA   length = 23
FEATURE                 Location/Qualifiers
misc_feature            1..23
                        note = synthetic construct; primer 146772
source                  1..23
                        mol_type = other DNA
                        organism = synthetic construct
SEQUENCE: 111
accgctacca gcaacaatcg tct                                              23

SEQ ID NO: 112          moltype = DNA   length = 21
FEATURE                 Location/Qualifiers
```

```
misc_feature           1..21
                       note = synthetic construct; primer 146778
source                 1..21
                       mol_type = other DNA
                       organism = synthetic construct
SEQUENCE: 112
tcacgctgca ctgcaggcta g                                          21

SEQ ID NO: 113         moltype = DNA  length = 27
FEATURE                Location/Qualifiers
misc_feature           1..27
                       note = synthetic construct; primer mopatF2
source                 1..27
                       mol_type = other DNA
                       organism = synthetic construct
SEQUENCE: 113
tcagatctgc gtcaccgggc gcaccgg                                    27

SEQ ID NO: 114         moltype = DNA  length = 27
FEATURE                Location/Qualifiers
misc_feature           1..27
                       note = synthetic construct; primer mopatR2
source                 1..27
                       mol_type = other DNA
                       organism = synthetic construct
SEQUENCE: 114
ccgccgtgtg cgacatcgtg aaccact                                    27

SEQ ID NO: 115         moltype = DNA  length = 16
FEATURE                Location/Qualifiers
misc_feature           1..16
                       note = synthetic construct; MHP55TS probe
source                 1..16
                       mol_type = other DNA
                       organism = synthetic construct
SEQUENCE: 115
aaccgtcgtg agacct                                                16

SEQ ID NO: 116         moltype = DNA  length = 17
FEATURE                Location/Qualifiers
misc_feature           1..17
                       note = synthetic construct; MHPTS55_Forward_MGB primer
source                 1..17
                       mol_type = other DNA
                       organism = synthetic construct
SEQUENCE: 116
aaggcgcagc cgttgag                                               17

SEQ ID NO: 117         moltype = DNA  length = 20
FEATURE                Location/Qualifiers
misc_feature           1..20
                       note = synthetic construct; MHP55TS_Reverse_MGB primer
source                 1..20
                       mol_type = other DNA
                       organism = synthetic construct
SEQUENCE: 117
ctaccggttt cgcgtgctct                                            20

SEQ ID NO: 118         moltype = DNA  length = 21
FEATURE                Location/Qualifiers
misc_feature           1..21
                       note = synthetic construct; MHP77TS probe
source                 1..21
                       mol_type = other DNA
                       organism = synthetic construct
SEQUENCE: 118
tagtatgaca tacataccgc c                                          21

SEQ ID NO: 119         moltype = DNA  length = 23
FEATURE                Location/Qualifiers
misc_feature           1..23
                       note = synthetic construct; MHP77TS_Forward_MGB primer
source                 1..23
                       mol_type = other DNA
                       organism = synthetic construct
SEQUENCE: 119
tccttagggc ggtatgtatg tca                                        23

SEQ ID NO: 120         moltype = DNA  length = 26
```

```
FEATURE              Location/Qualifiers
misc_feature         1..26
                     note = synthetic construct; MHP77TS_Reverse_MGB primer
source               1..26
                     mol_type = other DNA
                     organism = synthetic construct
SEQUENCE: 120
catcggtcaa aaacacata aacttt                                              26

SEQ ID NO: 121       moltype = DNA  length = 105
FEATURE              Location/Qualifiers
source               1..105
                     mol_type = genomic DNA
                     organism = Glycine max
SEQUENCE: 121
tcttaaagaa gatacactgt gtaaatgtgt aatggcactg gcactctcgt gtgtgattaa        60
agtcatatat ggtttaagat acttttttt ataaagatag tagtg                       105

SEQ ID NO: 122       moltype = DNA  length = 52
FEATURE              Location/Qualifiers
source               1..52
                     mol_type = genomic DNA
                     organism = Glycine max
SEQUENCE: 122
tcttaaagaa gatacactgt gtaaatgtgt aatggcactg gcactctcgt gt                52

SEQ ID NO: 123       moltype = DNA  length = 28
FEATURE              Location/Qualifiers
source               1..28
                     mol_type = genomic DNA
                     organism = Glycine max
SEQUENCE: 123
gatactttt tttataaaga tagtagtg                                            28

SEQ ID NO: 124       moltype = DNA  length = 100
FEATURE              Location/Qualifiers
source               1..100
                     mol_type = genomic DNA
                     organism = Glycine max
SEQUENCE: 124
taatgatcac attttttttt tctcacactc acctaagtgc acgagtacac acgtaagtct        60
taggttaaag tttcatgccc cccccccccc cccccaaaa                              100

SEQ ID NO: 125       moltype = DNA  length = 54
FEATURE              Location/Qualifiers
source               1..54
                     mol_type = genomic DNA
                     organism = Glycine max
SEQUENCE: 125
taatgatcac attttttttt tctcacactc acctaagtgc acgagtacac acgt              54

SEQ ID NO: 126       moltype = DNA  length = 100
FEATURE              Location/Qualifiers
source               1..100
                     mol_type = genomic DNA
                     organism = Glycine max
SEQUENCE: 126
taatgatcac attttttttt tctcacactc acctaagtgc acgagtacac acgtaagtct        60
taggttaaag tttcatgccc cccccccccc cccccaaaa                              100

SEQ ID NO: 127       moltype = DNA  length = 45
FEATURE              Location/Qualifiers
source               1..45
                     mol_type = genomic DNA
                     organism = Glycine max
SEQUENCE: 127
taatgatcac attttttttt tctcacactc acctaagtgc acgag                        45

SEQ ID NO: 128       moltype = DNA  length = 104
FEATURE              Location/Qualifiers
source               1..104
                     mol_type = genomic DNA
                     organism = Glycine max
SEQUENCE: 128
taatgatcac attttttttt tctcacactc acctaagtgc agacgtacgc aagtagcttt        60
gttactttcg tattgacaat tcaaaatcgt cttttatttt tatt                        104

SEQ ID NO: 129       moltype = DNA  length = 102
FEATURE              Location/Qualifiers
```

```
misc_feature       47..48
                   note = 115 bp insertion between position 47 and position 48
                    omitted below and in the alignment in Figure 4B
source             1..102
                   mol_type = genomic DNA
                   organism = Glycine max
SEQUENCE: 129
taatgatcac attttttttt tctcacactc acctaagtgc agacgtacaa gtagctttgt   60
tactttcgta ttgacaattc aaaatcgtct tttatttta tt                      102
```